United States Patent
Luo et al.

(10) Patent No.: US 11,505,532 B2
(45) Date of Patent: Nov. 22, 2022

(54) SSAO INHIBITOR

(71) Applicant: SHANDONG DANHONG PHARMACEUTICAL CO., LTD., Heze (CN)

(72) Inventors: Zhi Luo, Shanghai (CN); Xiaolin Li, Shanghai (CN); Yaxun Yang, Shanghai (CN); Lele Yang, Shanghai (CN); Peng Li, Shanghai (CN); Haiying He, Shanghai (CN); Jian Li, Shanghai (CN); Shuhui Chen, Shanghai (CN)

( * ) Notice: Subject to any disclaimer, the term of this patent is extended or adjusted under 35 U.S.C. 154(b) by 139 days.

(21) Appl. No.: 17/191,161

(22) Filed: Mar. 3, 2021

(65) Prior Publication Data

US 2021/0198220 A1   Jul. 1, 2021

Related U.S. Application Data

(60) Division of application No. 16/714,690, filed on Dec. 14, 2019, now Pat. No. 11,001,563, which is a continuation of application No. PCT/CN2018/092003, filed on Jun. 20, 2018.

(30) Foreign Application Priority Data

| Jun. 20, 2017 | (CN) | 201710470167.8 |
| Aug. 4, 2017 | (CN) | 201710661017.5 |
| Nov. 29, 2017 | (CN) | 201711229457.X |
| Jun. 7, 2018 | (CN) | 201810582595.4 |

(51) Int. Cl.
| C07D 271/10 | (2006.01) |
| A61P 1/16 | (2006.01) |
| C07D 231/12 | (2006.01) |
| C07D 235/18 | (2006.01) |
| C07D 239/08 | (2006.01) |
| C07D 239/26 | (2006.01) |
| C07D 249/08 | (2006.01) |
| C07D 257/04 | (2006.01) |
| C07D 261/08 | (2006.01) |
| C07D 261/20 | (2006.01) |
| C07D 263/57 | (2006.01) |
| C07D 271/06 | (2006.01) |
| C07D 277/24 | (2006.01) |
| C07D 405/04 | (2006.01) |
| C07D 413/04 | (2006.01) |
| C07D 417/04 | (2006.01) |

(52) U.S. Cl.
CPC ........... *C07D 271/10* (2013.01); *A61P 1/16* (2018.01); *C07D 231/12* (2013.01); *C07D 235/18* (2013.01); *C07D 239/08* (2013.01); *C07D 239/26* (2013.01); *C07D 249/08* (2013.01); *C07D 257/04* (2013.01); *C07D 261/08* (2013.01); *C07D 261/20* (2013.01); *C07D 263/57* (2013.01); *C07D 271/06* (2013.01); *C07D 277/24* (2013.01); *C07D 405/04* (2013.01); *C07D 413/04* (2013.01); *C07D 417/04* (2013.01)

(58) Field of Classification Search
CPC .................................................... C07D 271/10
See application file for complete search history.

(56) References Cited

U.S. PATENT DOCUMENTS

| 7,678,820 B2 | 3/2010 | Harada et al. |
| 8,426,587 B2 | 4/2013 | McDonald et al. |
| 9,302,986 B2 | 4/2016 | Deodhar et al. |
| 11,001,563 B2 * | 5/2021 | Luo ............. C07D 249/08 |
| 2006/0025438 A1 | 2/2006 | Salter-Cid |
| 2007/0293548 A1 | 12/2007 | Wang et al. |
| 2009/0203764 A1 | 8/2009 | Wang et al. |
| 2010/0168159 A1 | 7/2010 | Harada et al. |
| 2010/0298330 A1 | 11/2010 | McDonald et al. |
| 2015/0056612 A1 | 2/2015 | Shen et al. |
| 2016/0168096 A1 | 6/2016 | Kim et al. |
| 2019/0071396 A1 | 3/2019 | Deodhar et al. |

(Continued)

FOREIGN PATENT DOCUMENTS

| CN | 1921841 A | 2/2007 |
| CN | 101917845 A | 12/2010 |
| CN | 104520268 A | 4/2015 |

(Continued)

OTHER PUBLICATIONS

Office Action of Chinese Application No. 201880037601.6, dated Oct. 18, 2021.

(Continued)

*Primary Examiner* — Golam M Shameem

(74) *Attorney, Agent, or Firm* — W&K IP

(57) ABSTRACT

The present invention provides an SSAO inhibitor and an application thereof in preparing a drug for treating a disease related to SSAO. In particular, the present invention provides a compound shown in formula (IV) and a pharmaceutically acceptable salt thereof.

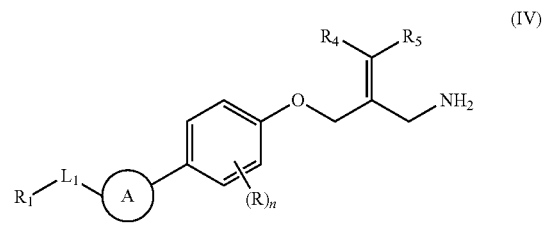

9 Claims, 1 Drawing Sheet

(56) References Cited

U.S. PATENT DOCUMENTS

2020/0087248 A1 3/2020 Zhu et al.

FOREIGN PATENT DOCUMENTS

| EP | 3617186 | A1 | 3/2020 |
|---|---|---|---|
| JP | 2011504485 | A | 2/2011 |
| JP | 2015521167 | A | 7/2015 |
| JP | 2016523902 | A | 8/2016 |
| WO | 2007116866 | A1 | 10/2007 |
| WO | 2007120528 | A2 | 10/2007 |
| WO | 2009066152 | A2 | 5/2009 |
| WO | 2013163675 | A1 | 11/2013 |
| WO | 2018196677 | A1 | 11/2018 |

OTHER PUBLICATIONS

Office Action of European Application No. 18820595.9 Form Epo, dated Mar. 16, 2020.
Office Action of Chinese Application No. 201880037601.6, dated Apr. 3, 2022.
Office Action of EPO Application No. 18820595.9, dated Feb. 24, 2022.
Internatinal Search Report and Written Opinion of PCT/CN2018/092003, dated Sep. 21, 2018.
"Research progress of SSAO inhibitors" J of Nanhua Univ. 2008 1. v 36 No. 1 pp. 129-131.
"VAP-1: an adhesin and an enzyme" Trends in Immunology vol. 22 No. 4 Apr. 2001. pp. 211-216.
"Semicarbazide Sensitive Amine Oxidase and Vascular Adhesion Protein-1: One Protein Being Validated as a Therapeutic Target for Inflammatory Diseases" Annual Reports in Medicinal Chemistry, vol. 42.
"Targeting Vascular Adhesion Protein-1 to Treat Autoimmune and Inflammatory Diseases" Ann. N.Y. Acad Sci. 1110: 382-388 (2007).
Supplementary European Search Report of Application No. 18820595.9.
First Office Action of Australian Application No. 2018287777.
First Office Action of Korean Application No. 10-2020-7001569.
First Office Action of European Application No. 18820595.9 Form EPO, dated Aug. 5, 2020.
Refusal Decision of Korean Application No. 10-2020-7001569, dated Sep. 25, 2020.
First Office Action of Japanese Application No. 2019-570384 dated Dec. 15, 2020.

* cited by examiner

SSAO INHIBITOR

CROSS REFERENCE TO RELATED APPLICATIONS

This application is a divisional application of U.S. utility application Ser. No. 16/714,690, filed Dec. 14, 2019, now pending, which is a continuation application of International Patent Application No. PCT/CN2018/092003 with an international filing date of Jun. 20, 2018, designating the United States, now expired, and further claims priority benefits to Chinese Patent Application No. CN201710470167.8, filed on Jun. 20, 2017; Chinese Patent Application No. CN201710661017.5, filed on Aug. 4, 2017; Chinese Patent Application No. CN201711229457.X, filed on Nov. 29, 2017; and Chinese Patent Application No. CN201810582595.4, filed on Jun. 7, 2018. The contents of all of the aforementioned applications are incorporated herein by reference.

TECHNICAL FIELD

The present disclosure relates to an SSAO inhibitor and use thereof in the preparation of a medicament for the treatment of diseases related to SSAO. Specifically, the present disclosure relates to a compound of a formula (IV) and a pharmaceutically acceptable salt thereof.

BACKGROUND

In most organisms including humans, two families of mammalian metabolize various monoamine-, diamine-, and polyamines that are endogenously produced or absorbed from exogenous sources through amine oxidases. These include monoamine oxidases (MAO-A and MAO-B) present in mitochondria of most cell types and using covalently bound flavin adenine dinucleotide (FAD) as a cofactor. Polyamine oxidase is another FAD-dependent amine oxidase that oxidizes deaminospermine and spermidine. SSAO/VAP-1 belongs to the second family that is copper-dependent and uses other cofactors such as oxidative tyrosine residues (abbreviated as TPQ or LTQ) in addition to FAD. MAO and SSAO/VAP-1 oxidative deamination includes some common substrates of monoamines such as dopamine, tyramine, and benzylamine. SSAO/VAP-1 also oxidizes endogenous methylamine and aminoacetone.

Semicarbazide-sensitive amine oxidase (SSAO), also known as primary amine oxidase, plasma amine oxidase, and benzylamine oxidase, is structurally identical to vascular adhesion protein-1 (VAP-1). SSAO/VAP-1 is used to describe the protein. Please see the following literature reviews for the role of this protein in inflammatory diseases (Smith D. J. and Vaino P. J., Targeting Vascular Adhesion Protein-1 to Treat Autoimmune and Inflammatory Diseases. Ann. N.Y. Acad. Sci. 2007, 1110, 382-388; and McDonald I. A. et al., Semicarbazide Sensitive Amine Oxidase and Vascular Adhesion Protein-1: One Protein Being Validated as a Therapeutic Target for Inflammatory Diseases. Annual Reports in Medicinal Chemistry, 2008, 43, 229-241).

Some of these enzymes are initially defined by the ability of some compounds to inhibit their enzymatic activity. For example, MAO-A is selectively inhibited by clorgiline, and MAO-B is selectively inhibited by L-deprenyl, although neither clorgiline nor L-deprenyl inhibits the amine oxidase activity of SSAO/VAP-1. SSAO/VAP-1 can be inhibited by semicarbazide, hence semicarbazide-sensitive amine oxidase is named.

SSAO/VAP-1 is an extracellular enzyme comprising a very short cytoplasmic tail, a single transmembrane domain and a large hyperglycosylated extracellular domain comprising an active center for amine oxidase activity. SSAO/VAP-1 is also present in a dissolved form that circulates in the plasma of some animals This form has been shown to be a cleavage product of membrane-bound SSAO/VAP-1.

SSAO/VAP-1 appears to have two physiological functions: the first is the above amine oxidase activity and the second is cell adhesion activity. Both activities are related to the inflammatory process. SSAO/VAP-1 has been shown to play an important role in extravasation of circulating inflammatory cells from the site of inflammation (Salmi M and Jalkanen S., VAP-1: adhesins and enzymes. Trends Immunol. 2001, 22, 211-216). The VAP-1 antibody has been shown to attenuate the inflammatory process by blocking the site of adhesion of the SSAO/VAP-1 protein and provides a large amount of evidences for in vitro and in vivo knockout. It is now clear that SSAO/VAP-1 is an important cellular mediator of inflammation.

WO2013163675 discloses a compound PXS-4728A, which has a structure as follows:

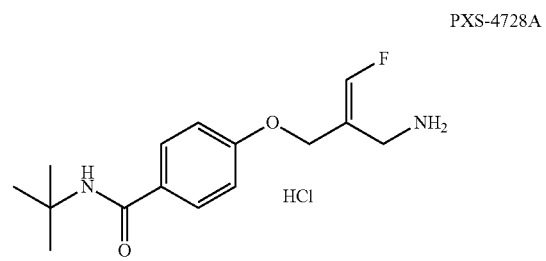

PXS-4728A

SUMMARY

The present disclosure provides a compound of a formula (IV) or a pharmaceutically acceptable salt thereof,

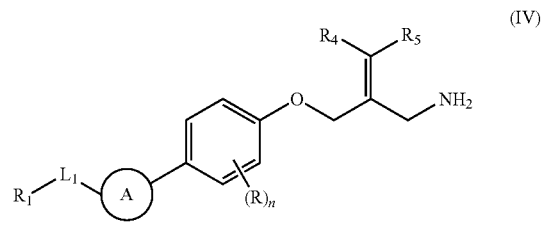

(IV)

wherein, one of $R_4$ and $R_5$ is H, and the other is selected from the group consisting of F, Cl, Br and I;

the ring A is selected from the group consisting of phenyl or 5-9 membered heteroaryl, wherein each is optionally substituted by a R group;

$R_1$ is selected from the group consisting of H, halogen, OH, $NH_2$, CN, COOH, and —C(=O)$NH_2$; or is selected from the group consisting of $C_{1-6}$ alkyl, $C_{1-6}$ heteroalkyl, $C_{3-6}$ cycloalkyl, 5-6 membered heterocycloalkyl, phenyl and 5-6 membered heteroaryl, wherein each is optionally substituted by one, two or three R groups;

$L_1$ is selected from the group consisting of a single bond, —(CRR)$_{1-3}$—,

 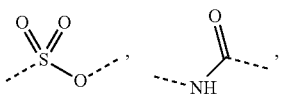

and —NH—;

n is selected from 0, 1, 2 or 3;

R is selected from the group consisting of H, F, Cl, Br, I, OH, $NH_2$, and $C(=O)NH_2$; or is selected from the group consisting of $C_{1-6}$ alkyl, $C_{1-6}$ heteroalkyl, $C_{3-6}$ cycloalkyl and $C_{3-6}$ cycloalkyl-NH—, wherein each is optionally substituted by one, two or three R' groups;

R' is selected from the group consisting of H, F, Cl, Br, I, OH, CN, $NH_2$, COOH, Me, Et, $CF_3$, $CHF_2$, $CH_2F$, $NHCH_3$ and $N(CH_3)_2$;

the "hetero" of the 5-9 membered heteroaryl, 5-10 membered heterocycloalkyl, $C_{1-6}$ heteroalkyl, 5-6 membered heterocycloalkyl and 5-6 membered heteroaryl represents a heteroatom or a heteroatom group, and is selected from the group consisting of —C(=O)NH—, —NH—, —C(=NH)—, —S(=O)$_2$NH—, —S(=O)NH—, —O—, —S—, N, =O, =S, —C(=O)O—, —C(=O)—, —S(=O)— and —S(=O)$_2$—; and in any one of the above cases, the number of the heteroatom or the heteroatom group is independently selected from 1, 2 or 3.

In some embodiments of the present disclosure, the above compound or the pharmaceutically acceptable salt thereof is selected from the group consisting of

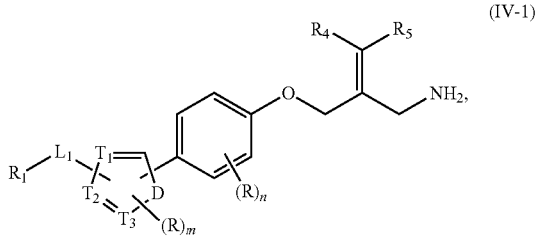

(IV-1)

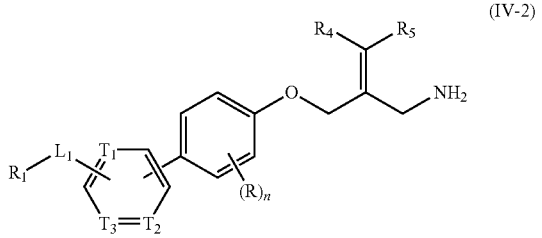

(IV-2)

wherein, n is selected from 0, 1, 2 or 3;

m is selected from 0 or 1;

$T_1$ is selected from N or CH;

$T_2$ is selected from N or CH;

$T_3$ is selected from N or CH;

D is selected from O, S or NH;

$R_1$ is selected from the group consisting of H, halogen, OH, $NH_2$, CN, COOH, and —C(=O)$NH_2$; or is selected from the group consisting of $C_{1-6}$ alkyl, $C_{1-6}$ heteroalkyl, $C_{3-6}$ cycloalkyl, 5-6 membered heterocycloalkyl and phenyl, wherein each is optionally substituted by one, two or three R groups;

$L_1$ is selected from the group consisting of a single bond, —(CRR)$_{1-3}$—, and —NH—;

one of $R_4$ and $R_5$ is selected from H, and the other is selected from F, Cl, Br and I;

R is selected from the group consisting of H, F, Cl, Br, I, OH, $NH_2$, and $C(=O)NH_2$; or is selected from the group consisting of $C_{1-6}$ alkyl, $C_{1-6}$ heteroalkyl, $C_{3-6}$ cycloalkyl and $C_{3-6}$ cycloalkyl-NH—, wherein each is optionally substituted by one, two or three R' groups;

R' is selected from the group consisting of H, F, Cl, Br, I, OH, CN, $NH_2$, COOH, Me, Et, $CF_3$, $CHF_2$, $CH_2F$, $NHCH_3$ and $N(CH_3)_2$;

the "hetero" of the 5-9 membered heteroaryl, 5-10 membered heterocycloalkyl, $C_{1-6}$ heteroalkyl, 5-6 membered heterocycloalkyl and 5-6 membered heteroaryl represents a heteroatom or a heteroatom group, and is selected from the group consisting of —C(=O)NH—, —NH—, —C(=NH)—, —S(=O)$_2$NH—, —S(=O)NH—, —O—, —S—, N, =O, =S, —C(=O)O—, —C(=O)—, —S(=O)— and —S(=O)$_2$—; and in any one of the above cases, the number of the heteroatom or the heteroatom group is independently selected from 1, 2 or 3.

In some embodiments of the present disclosure, the above R is selected from the group consisting of H, F, Cl, Br, I, OH, $NH_2$, and $C(=O)NH_2$, or is selected from the group consisting of Me, Et,

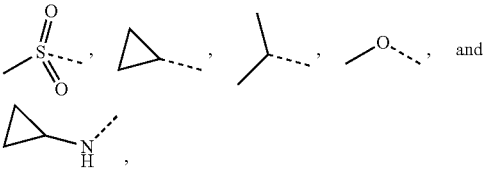

wherein each is optionally substituted by one, two or three R' groups. Other variables are as defined by the present disclosure.

In some embodiments of the present disclosure, the above R is selected from the group consisting of H, F, Cl, Br, I, OH, $NH_2$, Me, Et, $CF_3$, $C(=O)NH_2$,

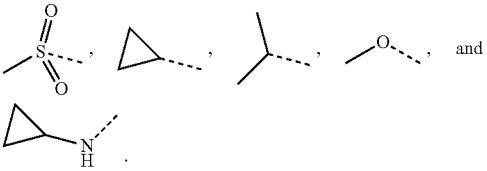

Other variables are as defined by the present disclosure.

In some embodiments of the present disclosure, the above ring A is selected from the group consisting of 1,3,4-oxadiazolyl, 1,2,4-oxadiazolyl, 1H-1,2,4-triazolyl, thiazolyl, isothiazolyl, 1,2,4-thiadiazolyl, oxazolyl, isoxazolyl, 1H-tetrazolyl, pyridyl, pyrimidinyl, pyridazinyl, indolyl, benzoxazolyl, benzisoxazolyl, 4,5,6,7-tetrahydro-1H-benzimidazolyl, 2H-1,2,3-triazolyl, benzo[d]thiazolyl, 2H-benzo[d]imidazolyl, indoline-2,3-diketo, 4,5-dihydro-1H-imidazolyl and 1,3-dihydro-1H-pyrrole, wherein each is optionally substituted by a R group. Other variables are as defined by the present disclosure.

In some embodiments of the present disclosure, the above ring A is selected from the group consisting of

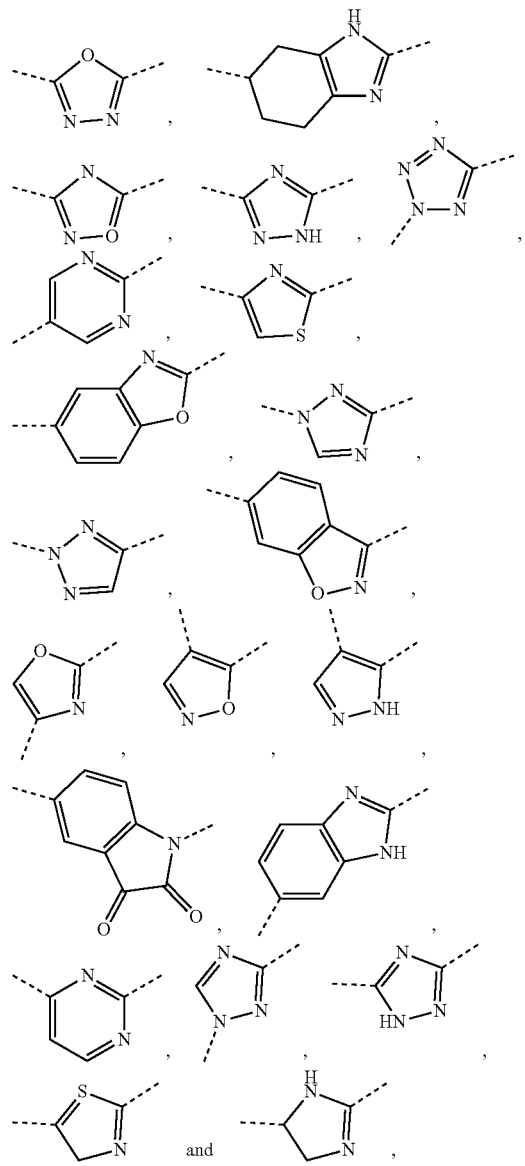

wherein each is optionally substituted by a R group. Other variables are as defined by the present disclosure.

In some embodiments of the present disclosure, the compound or the pharmaceutically acceptable salt thereof is disclosed, wherein the ring A is selected from the group consisting of

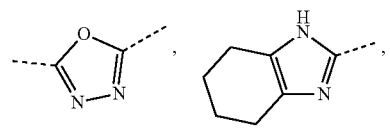

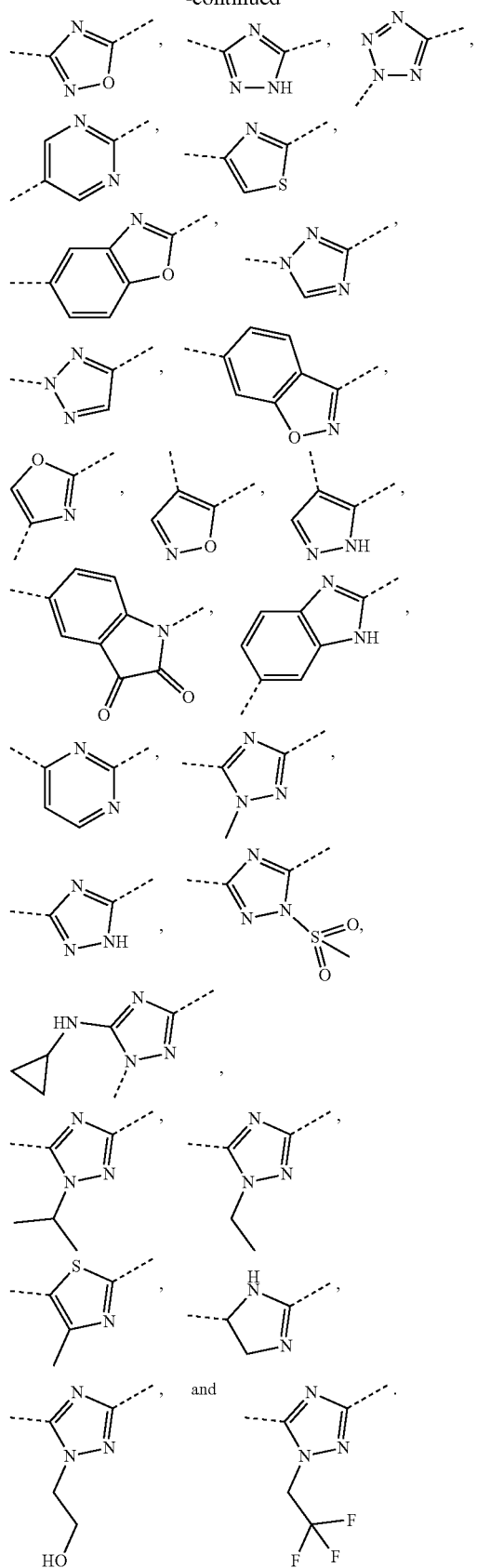

Other variables are as defined by the present disclosure.

In some embodiments of the present disclosure, the compound or the pharmaceutically acceptable salt thereof is disclosed, wherein the structural unit

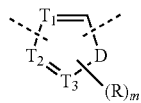

is selected from

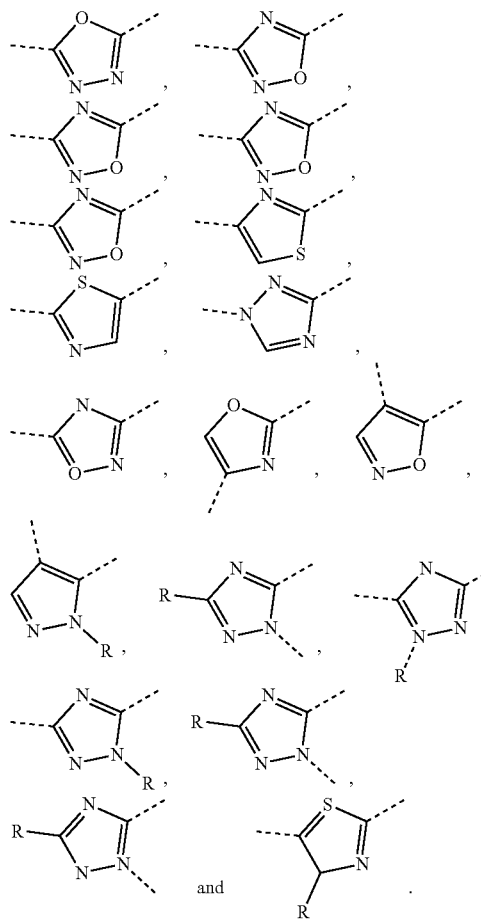

Other variables are as defined by the present disclosure.

In some embodiments of the present disclosure, the compound or the pharmaceutically acceptable salt thereof is disclosed, wherein the structural unit

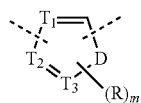

is selected from

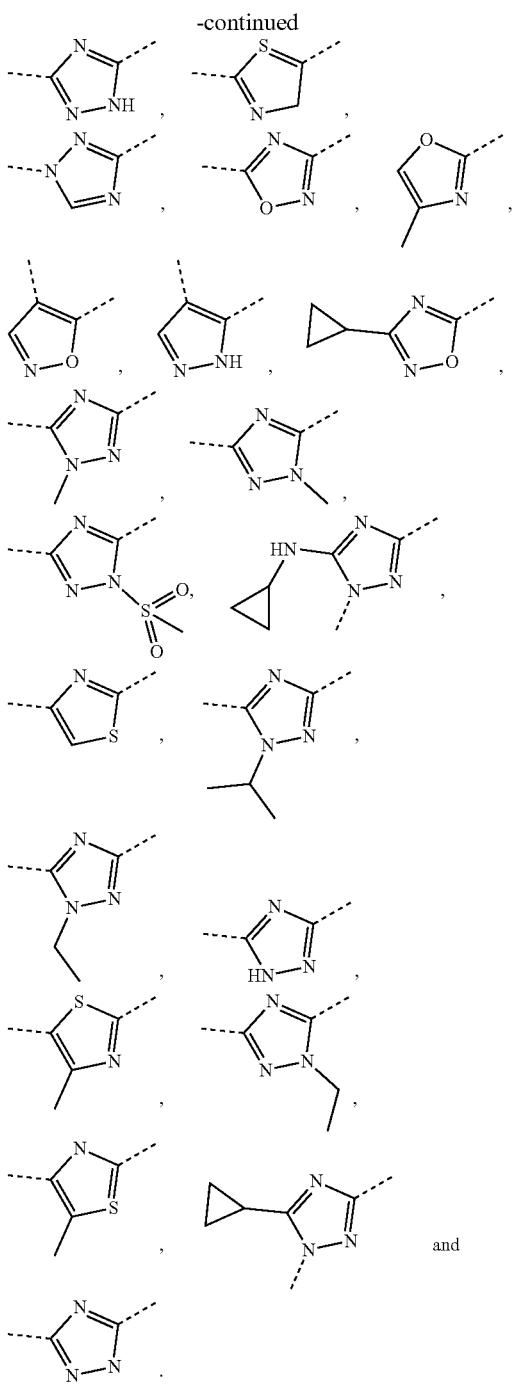

Other variables are as defined by the present disclosure.

In some embodiments of the present disclosure, the above $R_1$ is selected from the group consisting of H, halogen, OH, $NH_2$, CN, COOH, and —C(=O)$NH_2$, or is selected from the group consisting of $C_{1-3}$ alkyl, $C_{1-3}$ heteroalkyl, phenyl, cyclopropyl, cyclopentyl, cyclohexyl, morpholinyl, cyclobutyl and tetrahydro-2H-pyranyl, wherein each is optionally substituted by one, two or three R groups. Other variables are as defined by the present disclosure.

In some embodiments of the present disclosure, the above $R_1$ is selected from the group consisting of H, F, Cl, Br, I, OH, $NH_2$, CN, COOH, —C(=O)$NH_2$, Me, $CF_3$, Et,

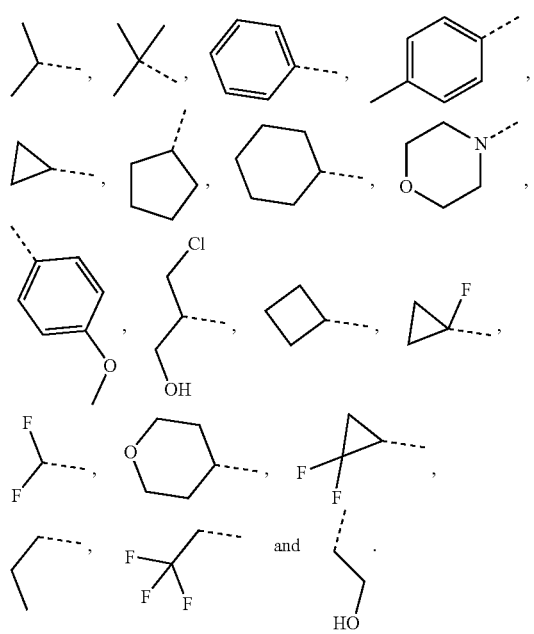

Other variables are as defined by the present disclosure.

In some embodiments of the present disclosure, the above $L_1$ is selected from the group consisting of a single bond, —$CH_2$—, —$CH_2CH_2$—,

and —NH—. Other variables are as defined by the present disclosure.

In some embodiments of the present disclosure, the above structural unit

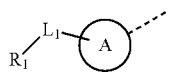

is selected from the group consisting of H, $NH_2$, COOH, —C(=O)$NH_2$, Me, $CF_3$, Et,

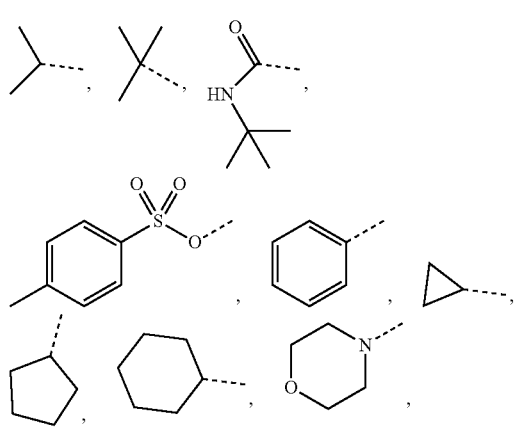

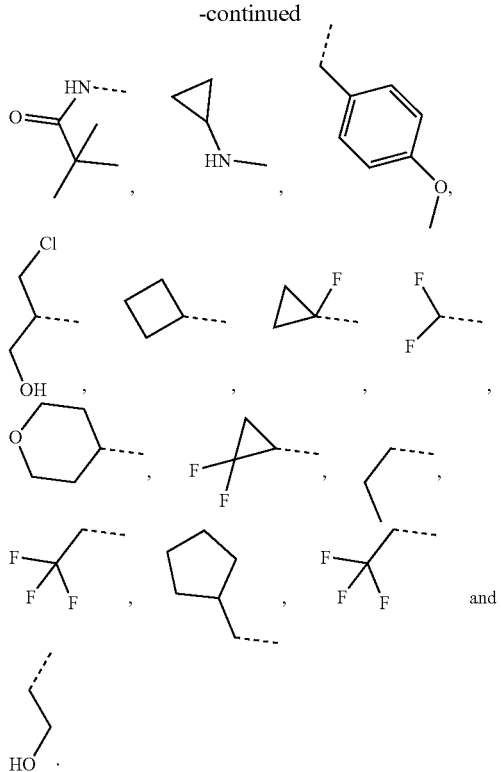

Other variables are as defined by the present disclosure.

In some embodiments of the present disclosure, the above structural unit

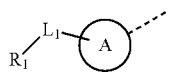

is selected from the group consisting of

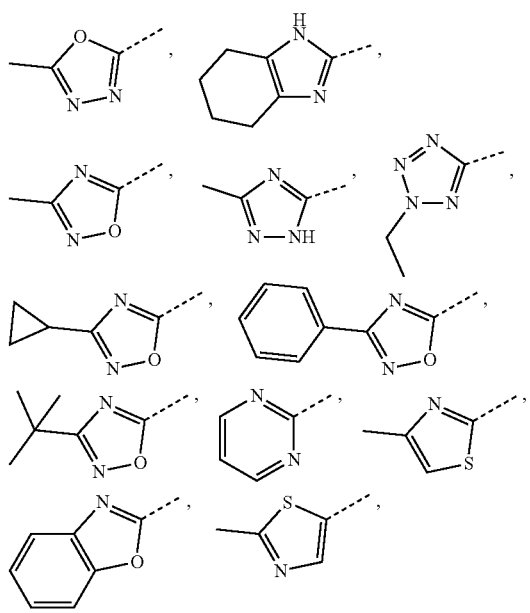

-continued
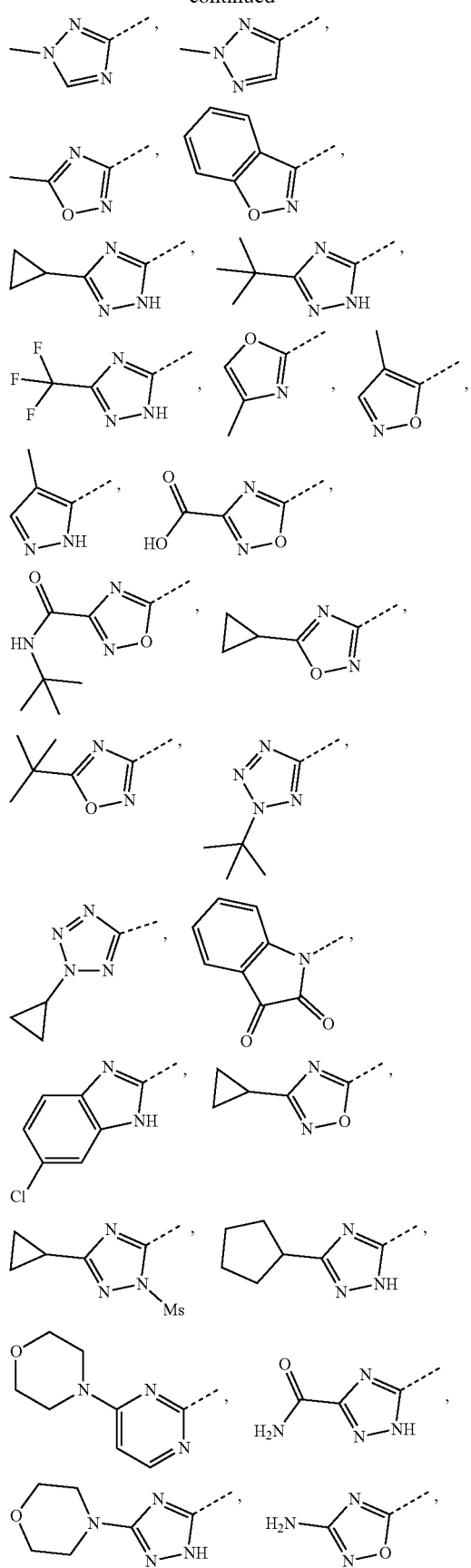
-continued
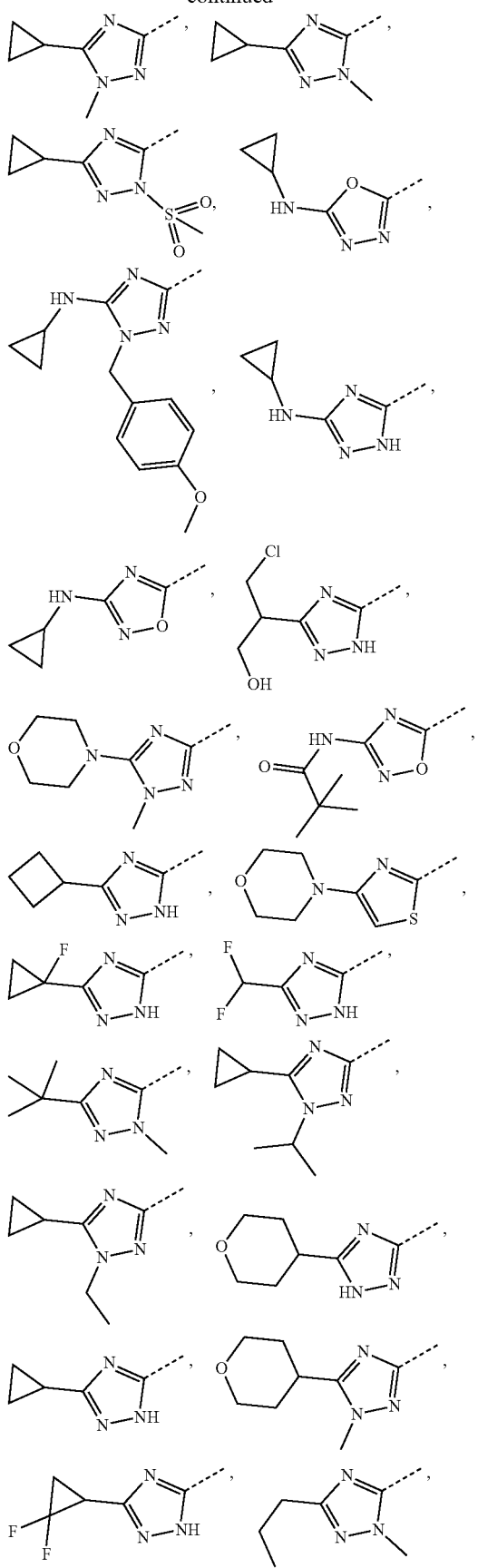

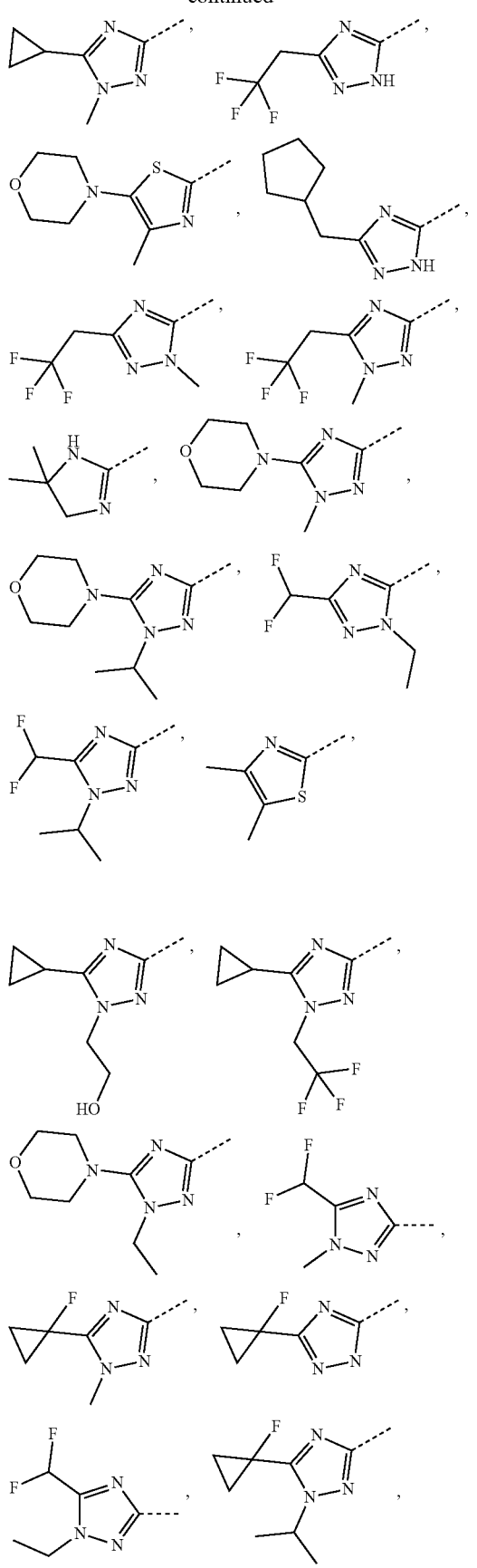
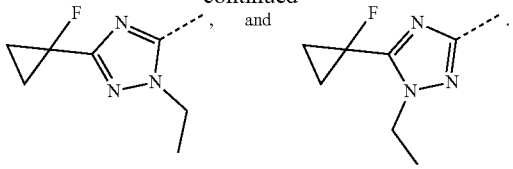
Other variables are as defined by the present disclosure.
In some embodiments of the present disclosure, the above structural unit
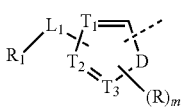
is selected from the group consisting of
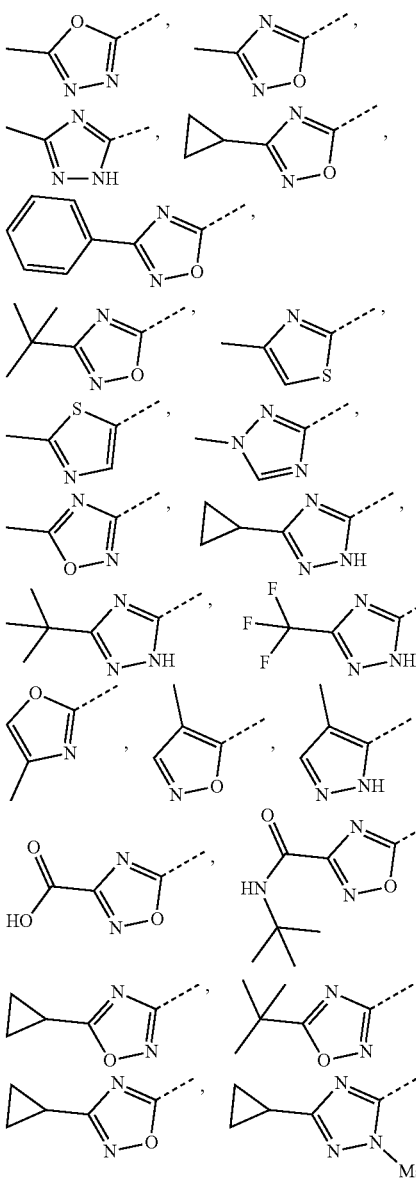

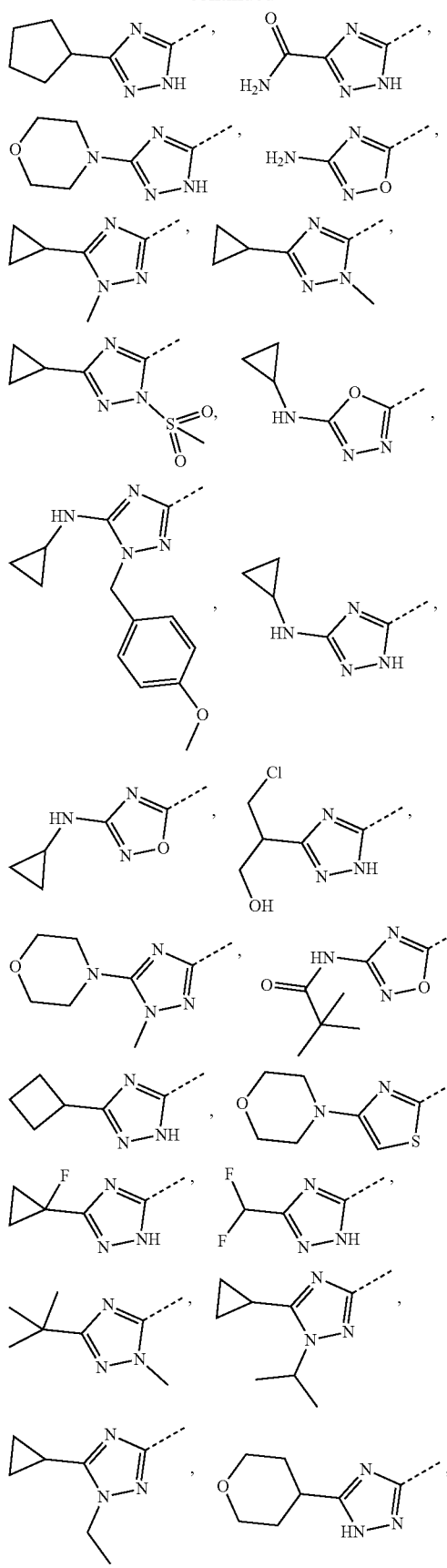
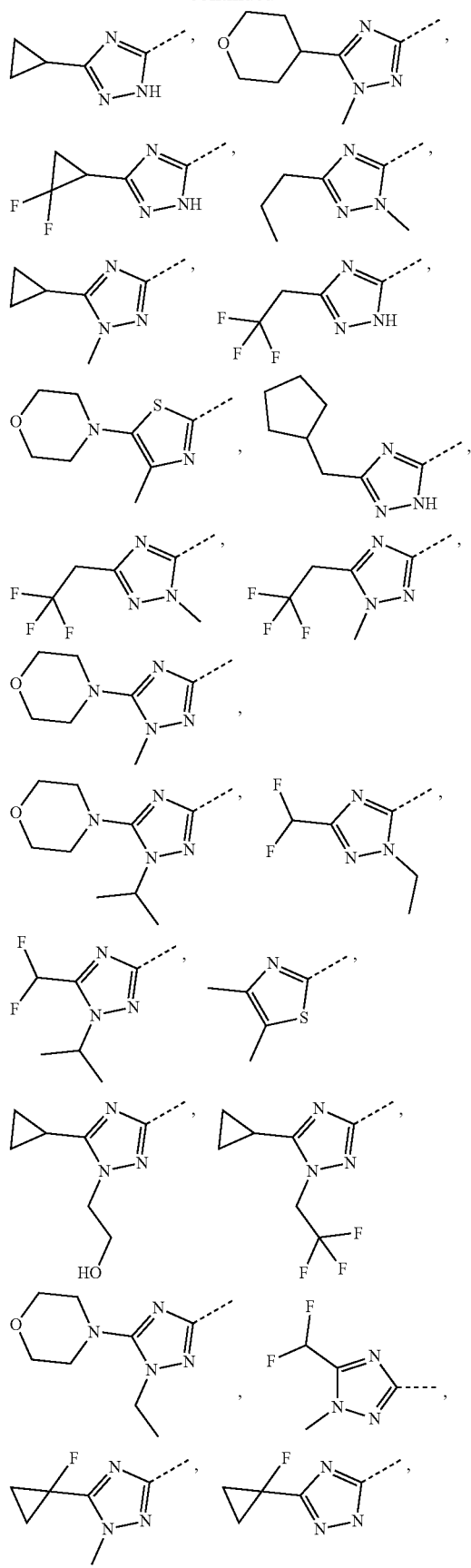

-continued

[chemical structures with F, cyclopropyl, triazole, ethyl, isopropyl groups]

Other variables are as defined by the present disclosure.

In some embodiments of the present disclosure, the above compound or the pharmaceutically acceptable salt thereof is selected from (IV-1a)

[structure with R, L1, R1, triazole, phenyl, O, F, NH2]

(IV-1b)

[structure with R, L1, R1, triazole, phenyl, O, F, NH2]

(IV-1c)

[structure with R, L1, R1, oxadiazole, phenyl, O, F, NH2]

wherein,
$R_1$, $L_1$ and R are as defined above.

The present disclosure provides a compound of a formula (III) or a pharmaceutically acceptable salt thereof, (III)

[structure M-O-CH2-C(=CR4R5)-CH2-NH2]

wherein,
one of $R_4$ and $R_5$ is H, and the other is selected from the group consisting of F, Cl, Br and I;

M is selected from

[structure R1-L1-A-C]

;

the ring A is selected from the group consisting of 4,5-dihydro-1H-imidazolyl, phenyl or 5-9 membered heteroaryl, wherein each is optionally substituted by a R group;

the ring C is selected from phenyl that is optionally substituted by one, two or three R groups;

$R_1$ is selected from the group consisting of H, halogen, OH, $NH_2$, CN, COOH, and —C(=O)$NH_2$, or is selected from the group consisting of $C_{1-6}$ alkyl, $C_{1-6}$ heteroalkyl, $C_{3-6}$ cycloalkyl, 5-6 membered heterocycloalkyl, phenyl and 5-6 membered heteroaryl, wherein each is optionally substituted by one, two or three R groups;

$L_1$ is selected from the group consisting of a single bond, —(CRR)$_{1-3}$—,

[—S(=O)2—O—, —C(=O)—NH—]

and —NH—;

R is selected from the group consisting of H, F, Cl, Br, I, OH, $NH_2$, and C(=O)$NH_2$, or is selected from the group consisting of $C_{1-6}$ alkyl, $C_{1-6}$ heteroalkyl, $C_{3-6}$ cycloalkyl and $C_{3-6}$ cycloalkyl-NH—, wherein each is optionally substituted by one, two or three R' groups;

R' is selected from the group consisting of H, F, Cl, Br, I, OH, CN, $NH_2$, COOH, Me, Et, $CF_3$, $CHF_2$, $CH_2F$, $NHCH_3$ and $N(CH_3)_2$;

the "hetero" of the 5-9 membered heteroaryl, 5-10 membered heterocycloalkyl, $C_{1-6}$ heteroalkyl, 5-6 membered heterocycloalkyl and 5-6 membered heteroaryl represents a heteroatom or a heteroatom group, and is selected from the group consisting of —C(=O)NH—, —NH—, —C(=NH)—, —S(=O)$_2$NH—, —S(=O)NH—, —O—, —S—, N, =O, =S, —C(=O)O—, —C(=O)—, —S(=O)— and —S(=O)$_2$—; and in any one of the above cases, the number of the heteroatom or the heteroatom group is independently selected from 1, 2 or 3.

In some embodiments of the present disclosure, the above compound or the pharmaceutically acceptable salt thereof is selected from (I)

[structure R1-L1-A-C-O-CH2-C(=CHF)-CH2-NH2]

wherein, the ring A is selected from the group consisting of 4,5-dihydro-1H-imidazolyl, phenyl or 5-9 membered heteroaryl, wherein each is optionally substituted by a R group;

the ring C is selected from phenyl that is optionally substituted by one, two or three R groups;

$R_1$ is selected from the group consisting of H, halogen, OH, $NH_2$, CN, COOH, and —C(=O)$NH_2$, or is selected from the group consisting of $C_{1-6}$ alkyl, $C_{1-6}$ heteroalkyl, $C_{3-6}$ cycloalkyl, 5-6 membered heterocycloalkyl and phenyl, wherein each is optionally substituted by one, two or three R groups;

$L_1$ is selected from the group consisting of a single bond, —(CRR)$_{1-3}$—,

and —NH—;

R is selected from the group consisting of H, F, Cl, Br, I, OH, $NH_2$, and C(=O)$NH_2$, or is selected from the group consisting of $C_{1-6}$ alkyl, $C_{1-6}$ heteroalkyl, $C_{3-6}$ cycloalkyl and $C_{3-6}$ cycloalkyl-NH—, wherein each is optionally substituted by one, two or three R' groups;

R' is selected from the group consisting of H, F, Cl, Br, I, OH, CN, $NH_2$, COOH, Me, Et, $CF_3$, $CHF_2$, $CH_2F$, $NHCH_3$ and $N(CH_3)_2$;

the "hetero" of the 5-9 membered heteroaryl, 5-10 membered heterocycloalkyl, $C_{1-6}$ heteroalkyl, 5-6 membered heterocycloalkyl and 5-6 membered heteroaryl represents a heteroatom or a heteroatom group, and is selected from the group consisting of —C(=O)NH—, —NH—, —C(=NH)—, —S(=O)$_2$NH—, —S(=O)NH—, —O—, —S—, N, =O, =S, —C(=O)O—, —C(=O)—, —S(=O)— and —S(=O)$_2$—; and in any one of the above cases, the number of the heteroatom or the heteroatom group is independently selected from 1, 2 or 3.

In some embodiments of the present disclosure, the above R is selected from the group consisting of H, F, Cl, Br, I, OH, $NH_2$, and C(=O)$NH_2$; or is selected from the group consisting of Me, Et,

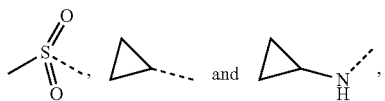

wherein each is optionally substituted by one, two or three R' groups, and R' is as defined by the present disclosure.

In some embodiments of the present disclosure, the above R is selected from the group consisting of H, F, Cl, Br, I, OH, $NH_2$, Me, Et, $CF_3$, C(=O)$NH_2$,

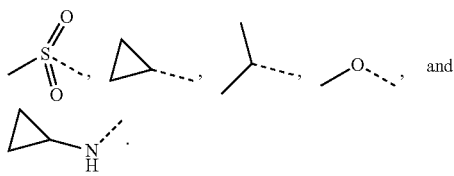

In some embodiments of the present disclosure, the above ring A is selected from the group consisting of 1,3,4-oxadiazolyl, 1,2,4-oxadiazolyl, 1H-1,2,4-triazolyl, thiazolyl, isothiazolyl, 1,2,4-thiadiazolyl, oxazolyl, isoxazolyl, 1H-tetrazolyl, pyridyl, pyrimidinyl, pyridazinyl, indolyl, benzoxazolyl, benzisoxazolyl, 4,5,6,7-tetrahydro-1H-benzimidazolyl, 2H-1,2,3-triazolyl, benzo[d]thiazolyl, 2H-benzo[d]imidazolyl, indoline-2,3-diketo and 4,5-dihydro-1H-imidazolyl, wherein each is optionally substituted by a R group, and R is as defined by the present disclosure.

In some embodiments of the present disclosure, the above ring A is selected from the group consisting of

wherein each is optionally substituted by a R group, and R is as defined by the present disclosure.

In some embodiments of the present disclosure, the above ring A is selected from the group consisting of

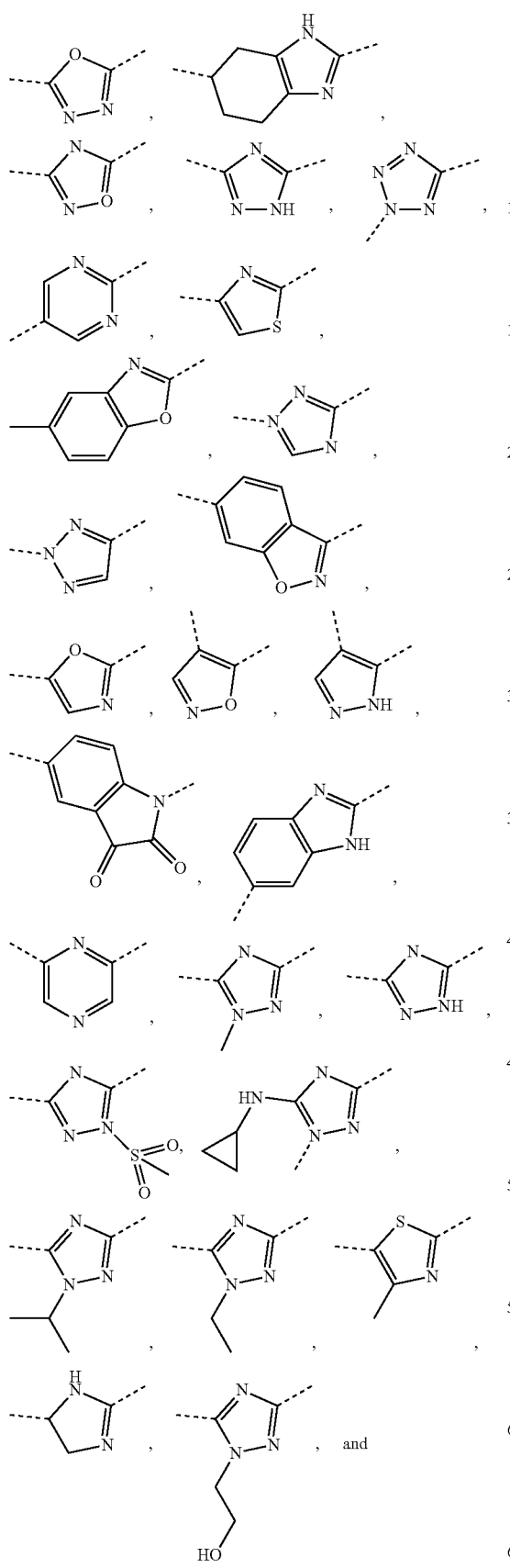

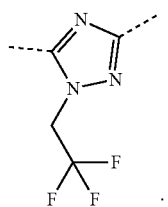

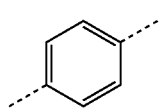

-continued

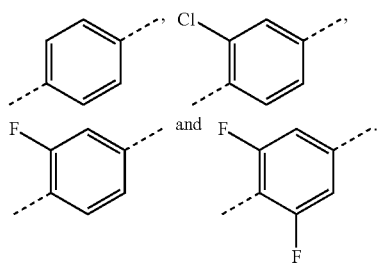

In some embodiments of the present disclosure, the above ring C is selected from

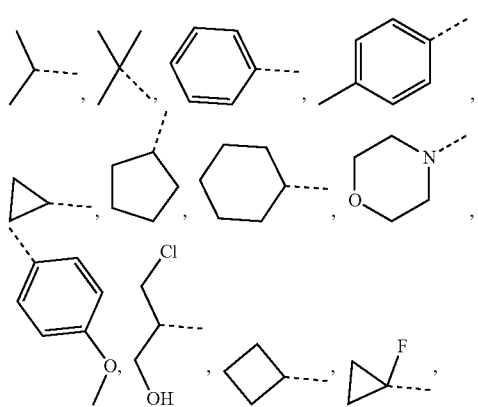

that is optionally substituted by one, two or three F, Cl, Br, I, OH or $NH_2$.

In some embodiments of the present disclosure, the above ring C is selected from the group consisting of In some embodiments of the present disclosure, the above $R_1$ is selected from the group consisting of H, halogen, OH, $NH_2$, CN, COOH, and —C(=O)$NH_2$, or is selected from the group consisting of $C_{1-3}$ alkyl, $C_{1-3}$ heteroalkyl, phenyl, cyclopropyl, cyclopentyl, cyclohexyl, morpholinyl, cyclobutyl and tetrahydro-2H-pyranyl, wherein each is optionally substituted by one, two or three R groups, and R is as defined in the present disclosure.

In some embodiments of the present disclosure, the above $R_1$ is selected from the group consisting of H, F, Cl, Br, I, OH, $NH_2$, CN, COOH, —C(=O)$NH_2$, Me, $CF_3$, Et, -continued

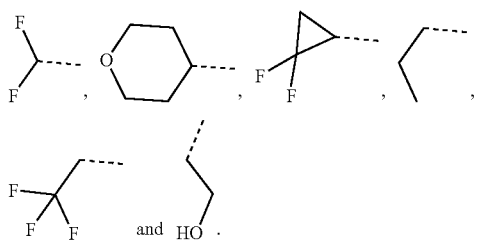

In some embodiments of the present disclosure, the above L₁ is selected from the group consisting of a single bond, —CH₂—, —CH₂CH₂—,

and —NH—.

In some embodiments of the present disclosure, the above structural unit

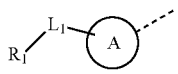

is selected from the group consisting of H, NH₂, COOH, —C(=O)NH₂, Me, CF₃, Et,

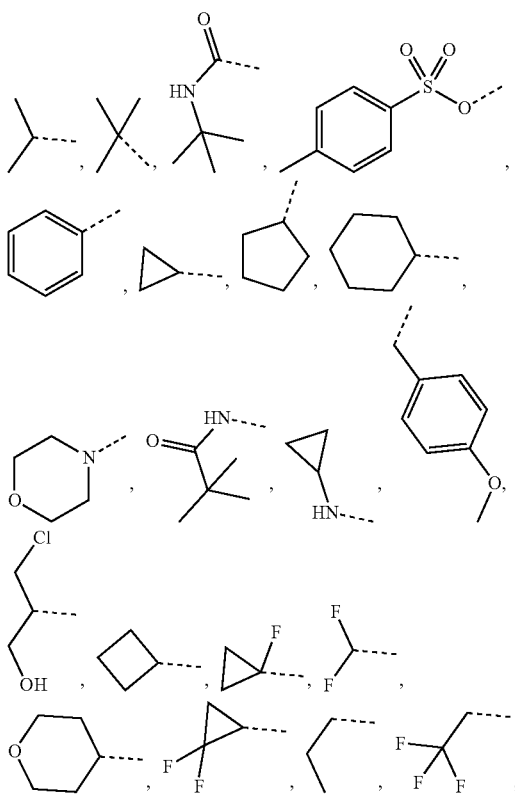

-continued

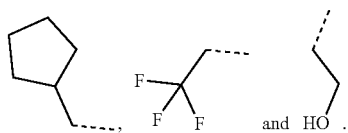

In some embodiments of the present disclosure, the above structural unit $$R_1 \diagup {}^{L_1} \diagup A \diagdown$$

is selected from the group consisting of

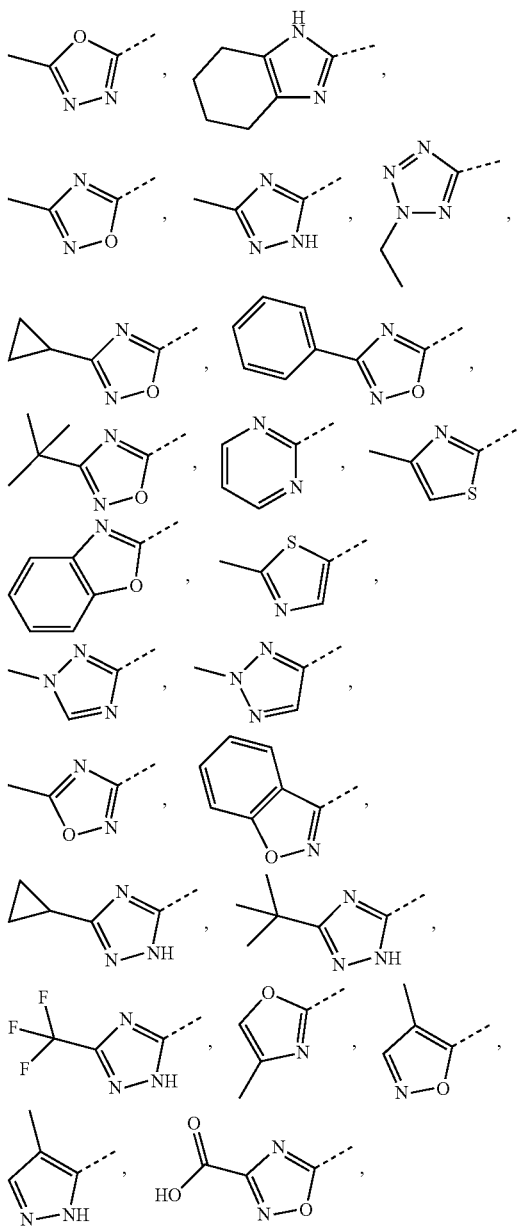

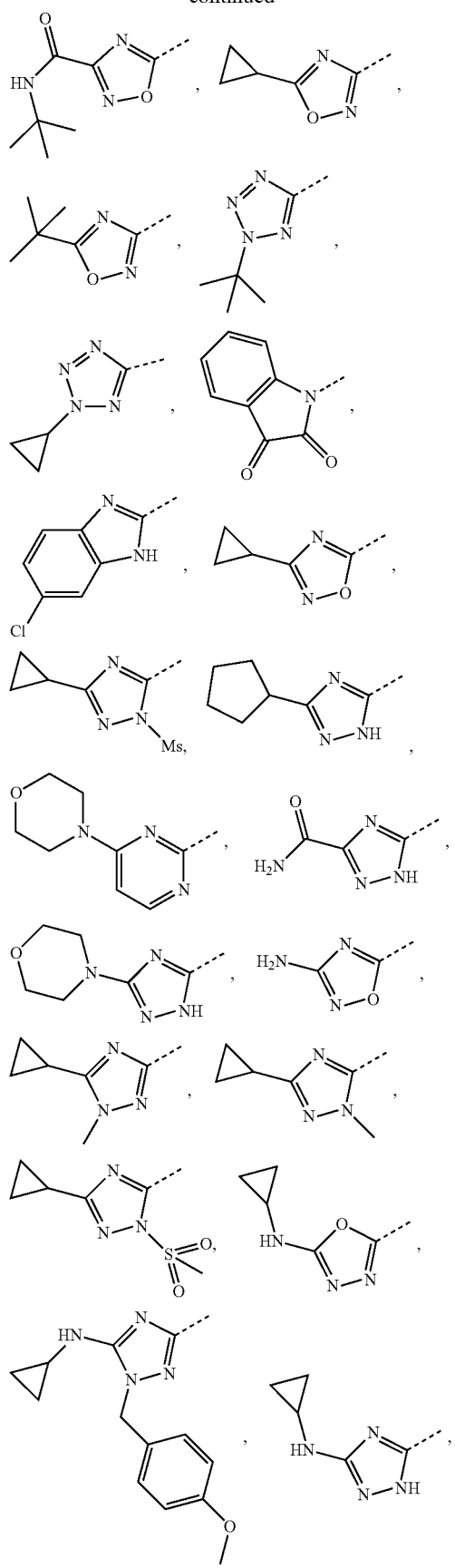
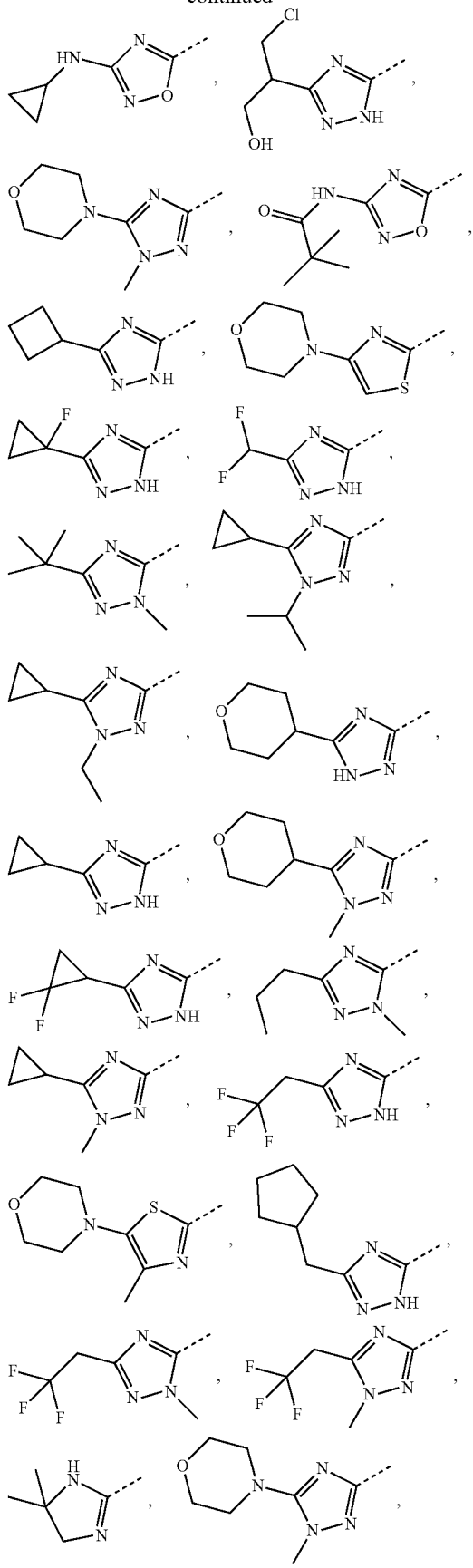

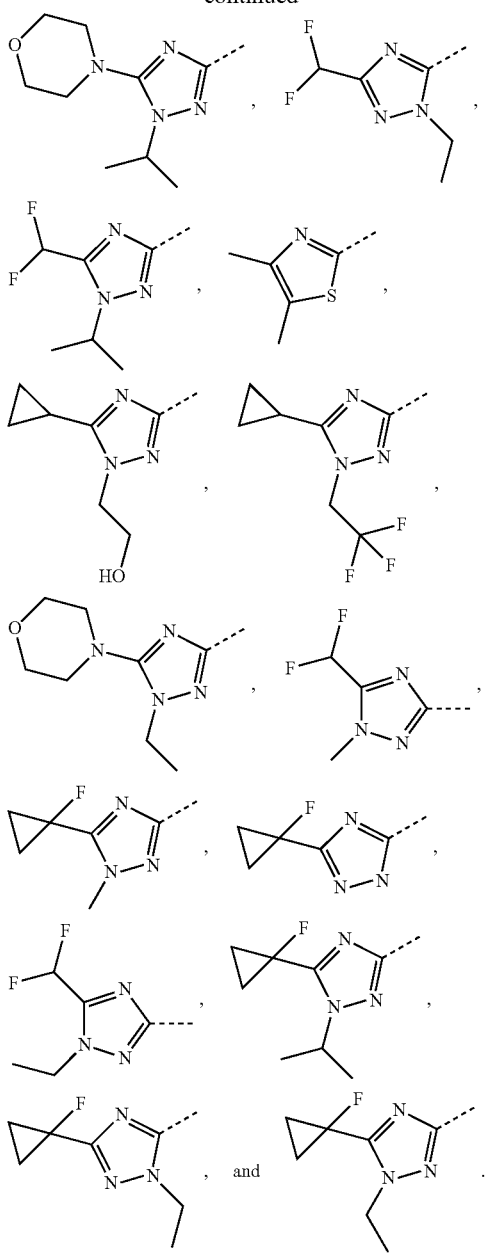

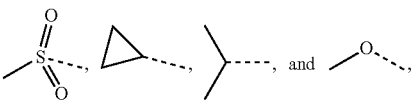

and other variables are as defined above.

In some embodiments of the present disclosure, the above ring A is selected from the group consisting of 1,3,4-oxadiazolyl, 1,2,4-oxadiazolyl, 1H-1,2,4-triazolyl, thiazolyl, isothiazolyl, 1,2,4-thiadiazolyl, oxazolyl, isoxazolyl, 1H-tetrazyl, pyridyl, pyrimidinyl, pyridazinyl, indolyl, benzoxazolyl, benzisoxazolyl, 4,5,6,7-tetrahydro-1H-benzimidazolyl, 2H-1,2,3-triazolyl, benzo[d]thiazolyl, 2H-benzo[d]imidazolyl, indoline-2,3-diketo and 4,5-dihydro-1H-imidazolyl, wherein each is optionally substituted by a R group, and other variables are as defined above.

In some embodiments of the present disclosure, the above ring A is selected from the group consisting of

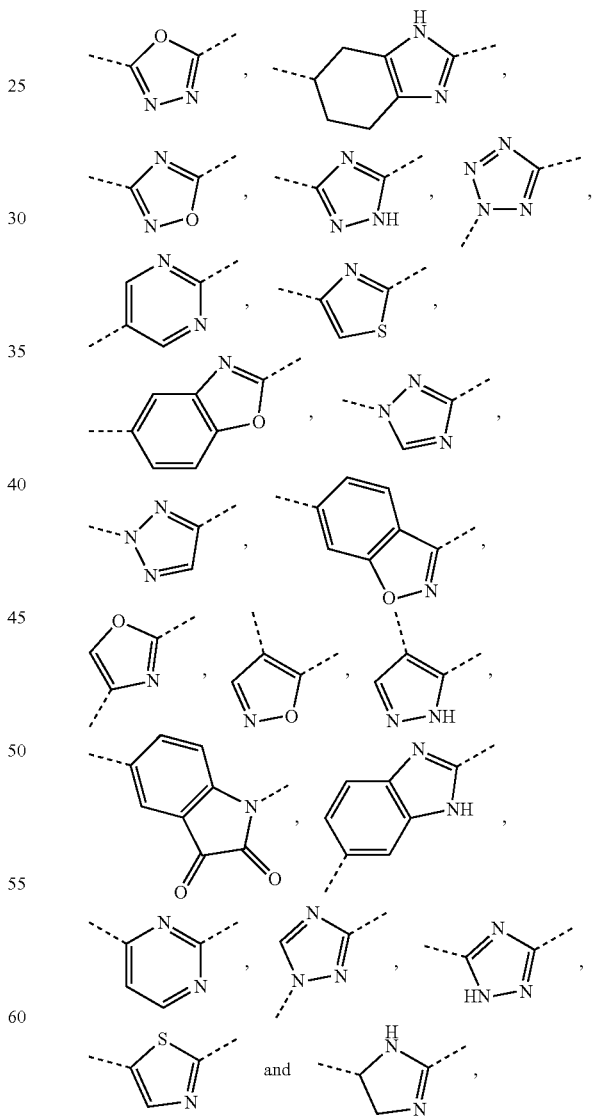

wherein each is optionally substituted by a R group, and other variables are as defined above.

In some embodiments of the present disclosure, the above R is selected from the group consisting of H, F, Cl, Br, I, OH, NH$_2$, and C(=O)NH$_2$, or is selected from the group consisting of Me, Et,

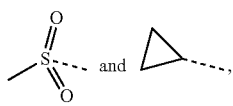

wherein each is optionally substituted by one, two or three R' groups, and other variables are as defined above.

In some embodiments of the present disclosure, the above R is selected from the group consisting of H, F, Cl, Br, I, OH, NH$_2$, Me, Et, CF$_3$, C(=O)NH$_2$, In some embodiments of the present disclosure, the above ring A is selected from the group consisting of

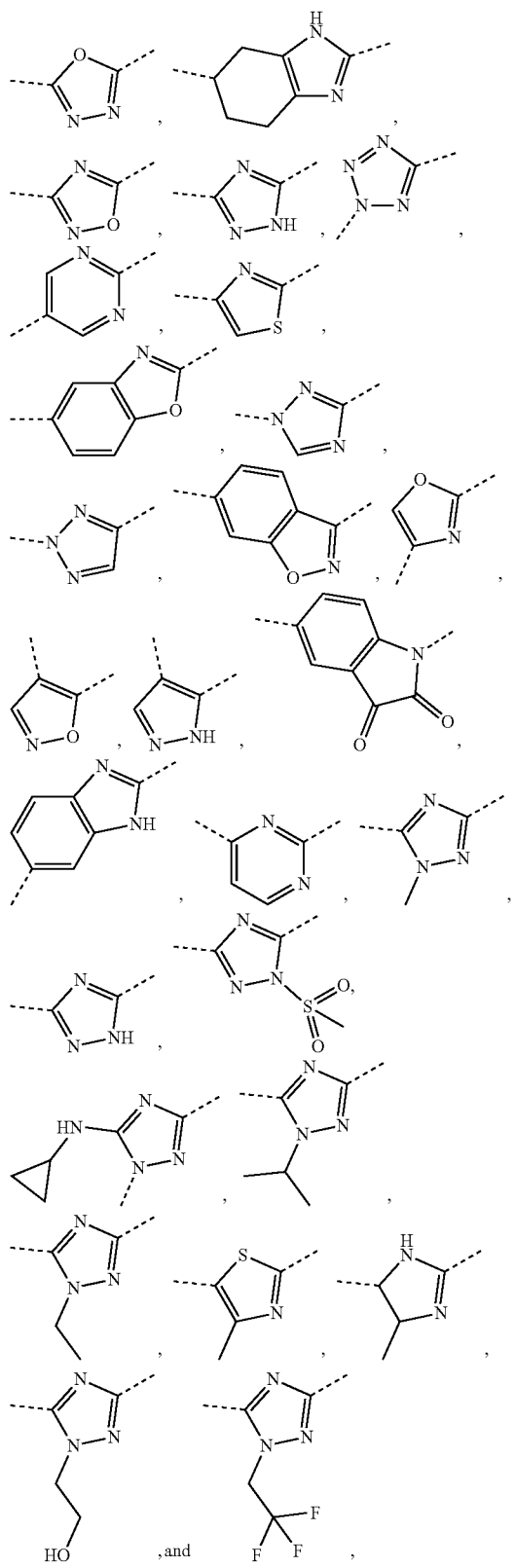

and other variables are as defined above.

In some embodiments of the present disclosure, the above ring C is selected from

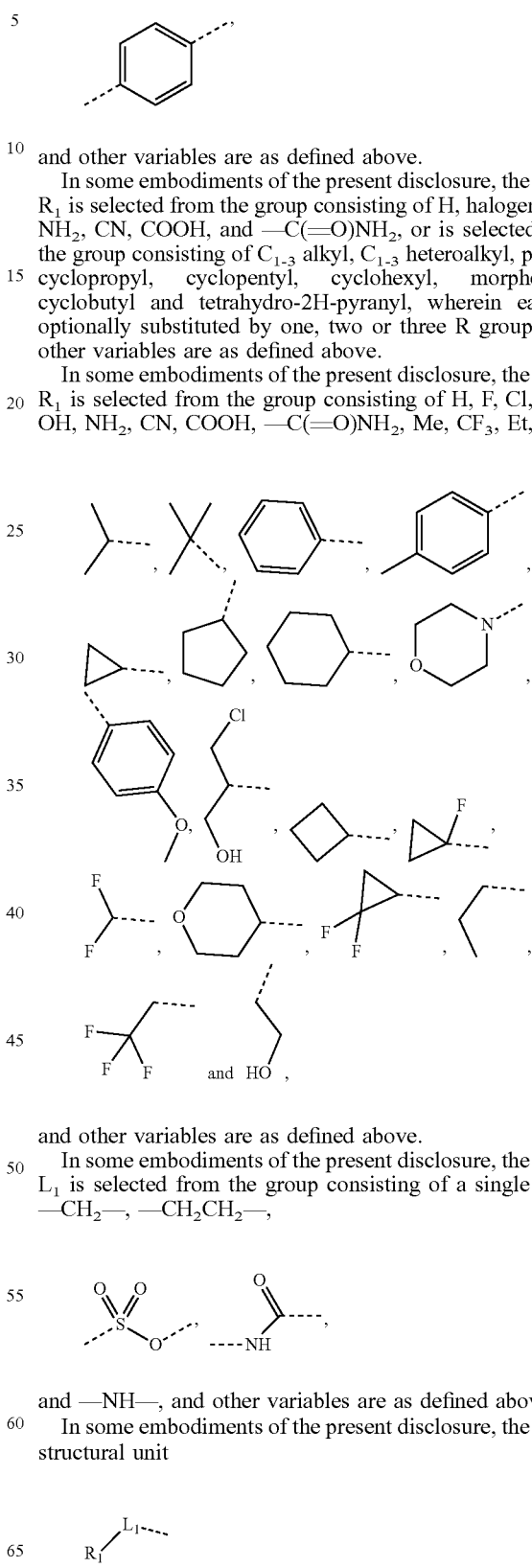

and other variables are as defined above.

In some embodiments of the present disclosure, the above $R_1$ is selected from the group consisting of H, halogen, OH, $NH_2$, CN, COOH, and —C(=O)$NH_2$, or is selected from the group consisting of $C_{1-3}$ alkyl, $C_{1-3}$ heteroalkyl, phenyl, cyclopropyl, cyclopentyl, cyclohexyl, morpholinyl, cyclobutyl and tetrahydro-2H-pyranyl, wherein each is optionally substituted by one, two or three R groups, and other variables are as defined above.

In some embodiments of the present disclosure, the above $R_1$ is selected from the group consisting of H, F, Cl, Br, I, OH, $NH_2$, CN, COOH, —C(=O)$NH_2$, Me, $CF_3$, Et, and other variables are as defined above.

In some embodiments of the present disclosure, the above $L_1$ is selected from the group consisting of a single bond, —$CH_2$—, —$CH_2CH_2$—, and —NH—, and other variables are as defined above.

In some embodiments of the present disclosure, the above structural unit is selected from the group consisting of H, NH₂, COOH, —C(=O)NH₂, Me, CF₃, Et,
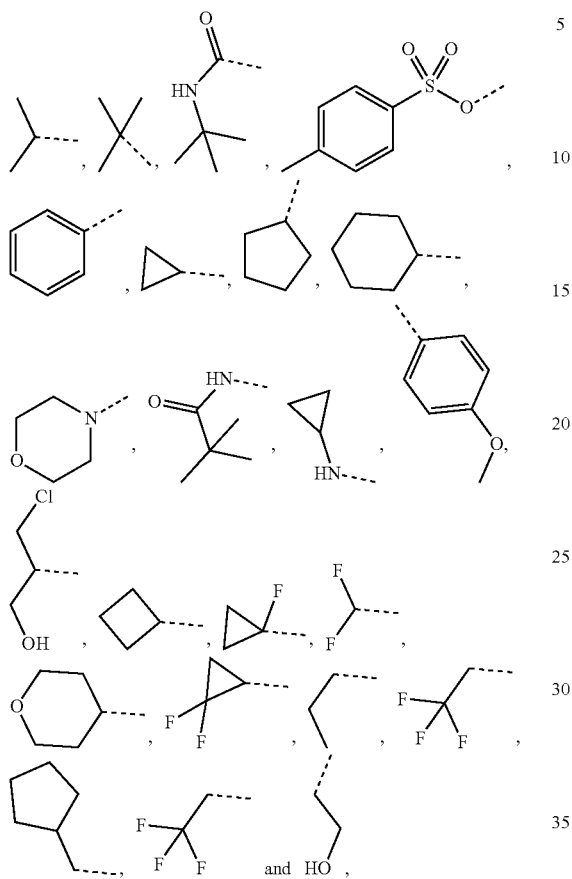
and other variables are as defined above.
In some embodiments of the present disclosure, the above structural unit
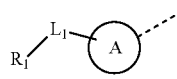
is selected from the group consisting of
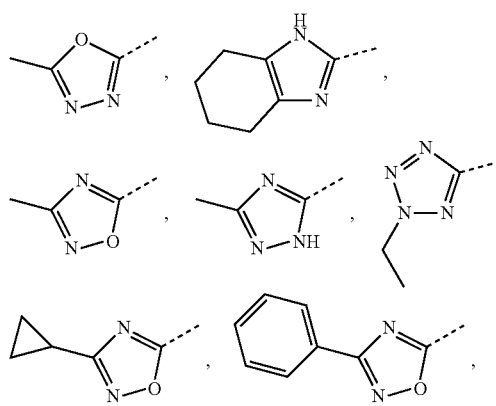
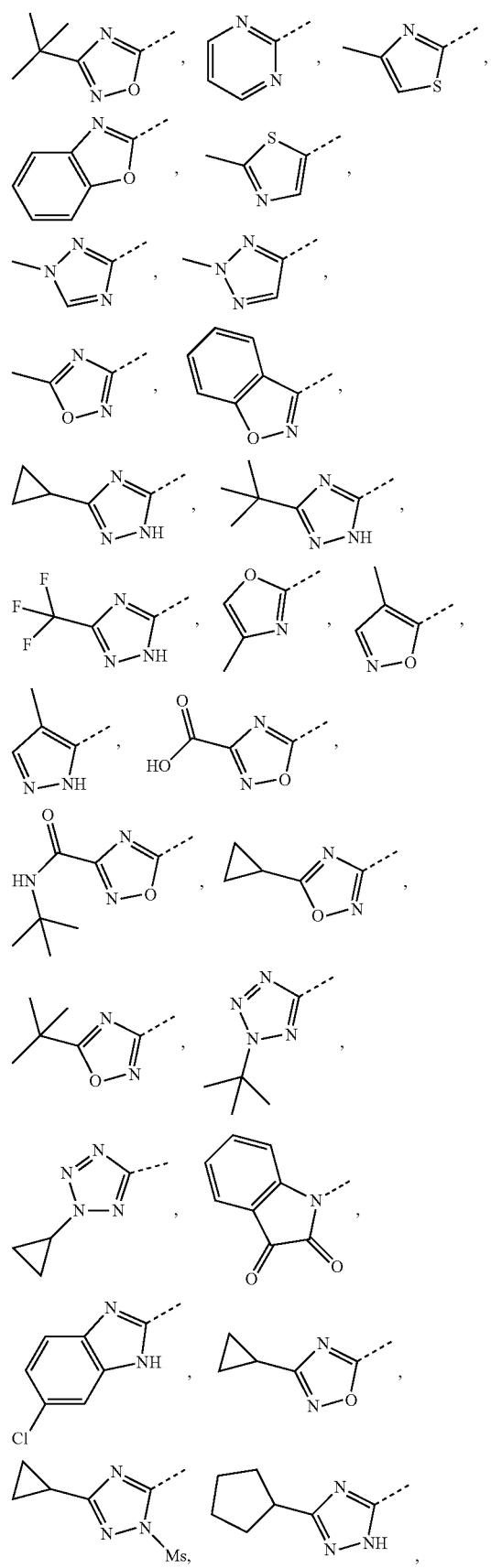

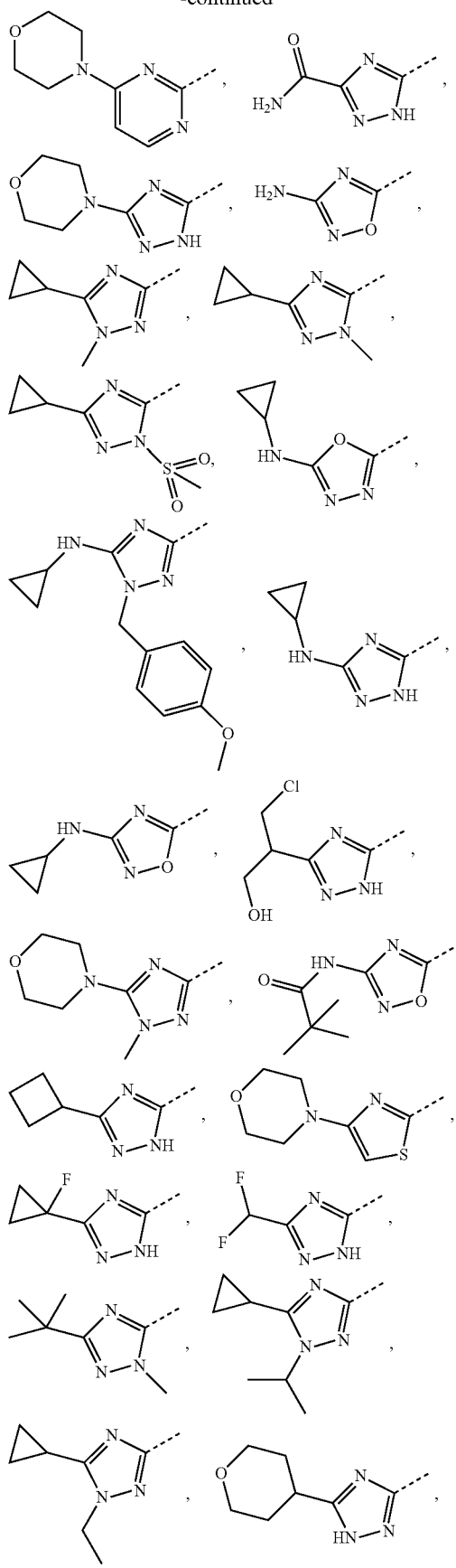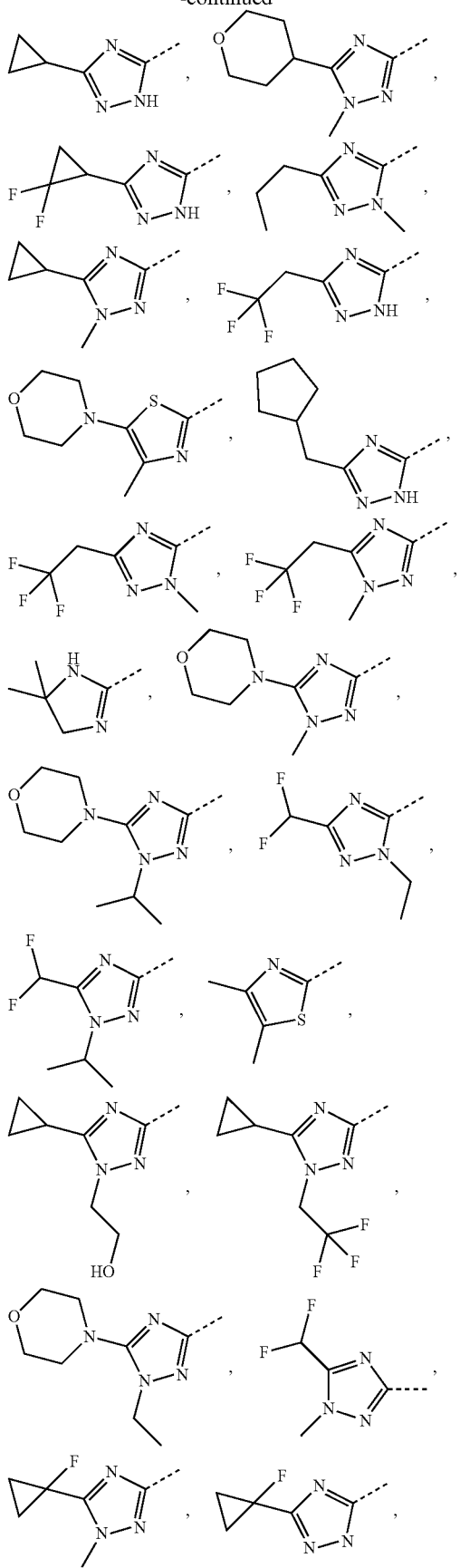

-continued

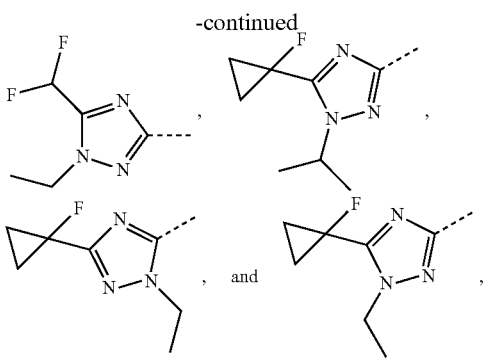

and other variables are as defined above.

In some embodiments of the present disclosure, the above compound or the pharmaceutically acceptable salt thereof is selected from

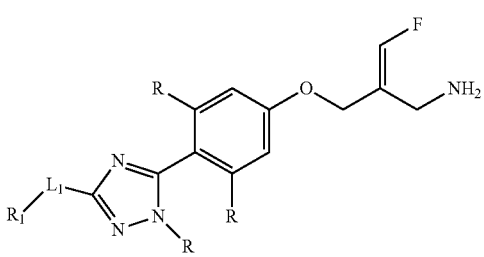
(II-1)

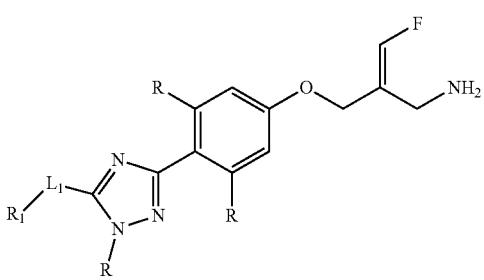
(II-2)

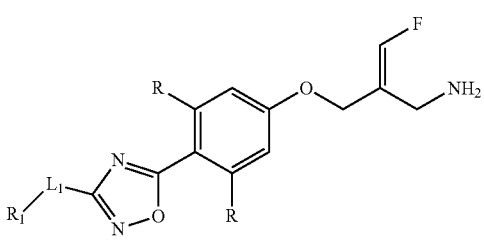
(II-3)

wherein $R_1$, $L_1$ and R are as defined above.

The present disclosure provides a compound of a formula (III) or a pharmaceutically acceptable salt thereof,

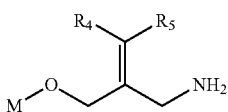
(III)

wherein,
one of $R_4$ and $R_5$ is H, and the other is selected from the group consisting of F, Cl, Br and I;
M is selected from

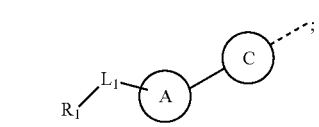

the ring A is selected from the group consisting of phenyl or 5-9 membered heteroaryl, wherein each is optionally substituted by a R group;
the ring C is selected from phenyl;
$R_1$ is selected from the group consisting of H, halogen, OH, $NH_2$, CN, COOH, and —C(=O)$NH_2$, or is selected from the group consisting of $C_{1-6}$ alkyl, $C_{1-6}$ heteroalkyl, $C_{3-6}$ cycloalkyl, 5-6 membered heterocycloalkyl, phenyl and 5-6 membered heteroaryl, wherein each is optionally substituted by one, two or three R groups;
$L_1$ is selected from the group consisting of a single bond and —(CRR)$_{1-3}$—;
R is selected from the group consisting of H, F, Cl, Br, I, OH, $NH_2$, and C(=O)$NH_2$, or is selected from the group consisting of $C_{1-6}$ alkyl, $C_{1-6}$ heteroalkyl and $C_{3-6}$ cycloalkyl, wherein each is optionally substituted by one, two or three R' groups;
R' is selected from the group consisting of H, F, Cl, Br, I, OH, CN, $NH_2$, COOH, Me, Et, $CF_3$, $CHF_2$, $CH_2F$, $NHCH_3$ and $N(CH_3)_2$;
the "hetero" of the 5-9 membered heteroaryl, 5-10 membered heterocycloalkyl, $C_{1-6}$ heteroalkyl, 5-6 membered heterocycloalkyl and 5-6 membered heteroaryl represents a heteroatom or a heteroatom group, and is selected from the group consisting of —C(=O)NH—, —NH—, —C(=NH)—, —S(=O)$_2$NH—, —S(=O)NH—, —O—, —S—, N, =O, =S, —C(=O)O—, —C(=O)—, —S(=O)— and —S(=O)$_2$—; and
in any one of the above cases, the number of the heteroatom or the heteroatom group is independently selected from 1, 2 or 3.

In some embodiments of the present disclosure, the above compound or the pharmaceutically acceptable salt thereof is selected from

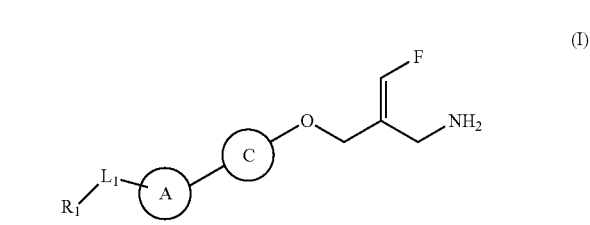
(I)

wherein,
the ring A is selected from the group consisting of phenyl or 5-9 membered heteroaryl, wherein each is optionally substituted by a R group;
the ring C is selected from phenyl;
$R_1$ is selected from the group consisting of H, halogen, OH, $NH_2$, CN, COOH, and —C(=O)$NH_2$, or is selected from the group consisting of $C_{1-6}$ alkyl, $C_{1-6}$ heteroalkyl, $C_{3-6}$ cycloalkyl, 5-6 membered heterocycloalkyl and phenyl, wherein each is optionally substituted by one, two or three R groups;

$L_1$ is selected from the group consisting of a single bond and —(CRR)$_{1-3}$—;

R is selected from the group consisting of H, F, Cl, Br, I, OH, NH$_2$, and C(=O)NH$_2$, or is selected from the group consisting of C$_{1-6}$ alkyl, C$_{1-6}$ heteroalkyl and C$_{3-6}$ cycloalkyl, wherein each is optionally substituted by one, two or three R' groups;

R' is selected from the group consisting of H, F, Cl, Br, I, OH, CN, NH$_2$, COOH, Me, Et, CF$_3$, CHF$_2$, CH$_2$F, NHCH$_3$ and N(CH$_3$)$_2$;

the "hetero" of the 5-9 membered heteroaryl, 5-10 membered heterocycloalkyl, C$_{1-6}$ heteroalkyl, 5-6 membered heterocycloalkyl and 5-6 membered heteroaryl represents a heteroatom or a heteroatom group, and is selected from the group consisting of —C(=O)NH—, —NH—, —C(=NH)—, —S(=O)$_2$NH—, —S(=O)NH—, —O—, —S—, N, =O, =S, —C(=O)O—, —C(=O)—, —S(=O)— and —S(=O)$_2$—; and in any one of the above cases, the number of the heteroatom or the heteroatom group is independently selected from 1, 2 or 3.

In some embodiments of the present disclosure, the above R is selected from the group consisting of F, Cl, Br, I, OH, NH$_2$, and C(=O)NH$_2$, or is selected from the group consisting of Me, Et,

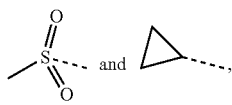

wherein each is optionally substituted by one, two or three R' groups, and R' is as defined by the present disclosure.

In some embodiments of the present disclosure, the above R is selected from the group consisting of H, Me, Et, CF$_3$, C(=O)NH$_2$,

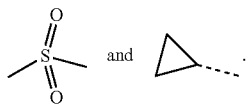

In some embodiments of the present disclosure, the above ring A is selected from the group consisting of 1,3,4-oxadiazolyl, 1,2,4-oxadiazolyl, 1H-1,2,4-triazolyl, thiazolyl, isothiazolyl, 1,2,4-thiadiazolyl, oxazolyl, isoxazolyl, 1H-tetrazolyl, pyridyl, pyrimidinyl, pyridazinyl, indolyl, benzoxazolyl, benzisoxazolyl, 4,5,6,7-tetrahydro-1H-benzimidazolyl, 2H-1,2,3-triazolyl, benzo[d]thiazolyl, 2H-benzo[d]imidazolyl and indoline-2,3-diketo, wherein each is optionally substituted by a R group, and R is as defined by the present disclosure.

In some embodiments of the present disclosure, the above ring A is selected from the group consisting of

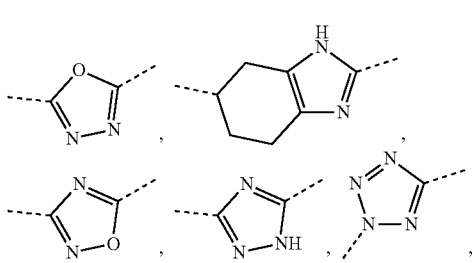

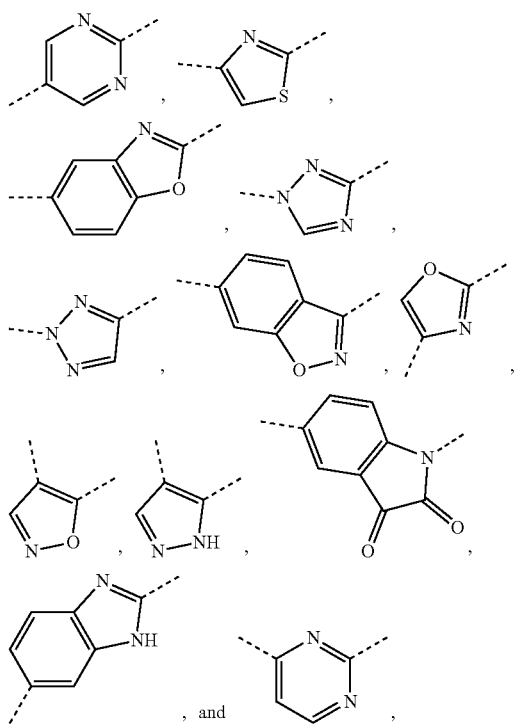

wherein each is optionally substituted by a R group, and R is as defined by the present disclosure.

In some embodiments of the present disclosure, the above ring A is selected from the group consisting of

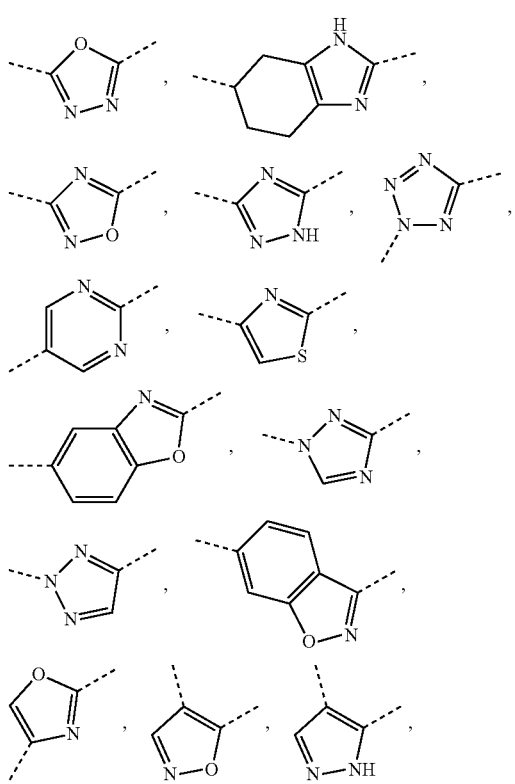

-continued

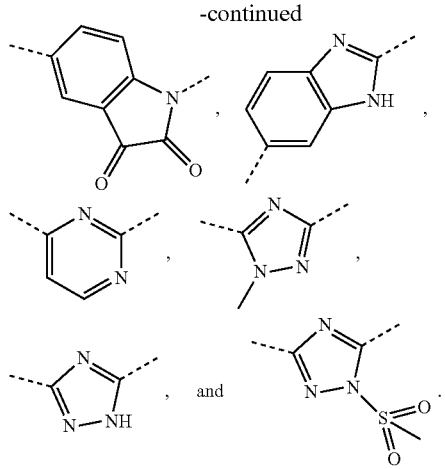

In some embodiments of the present disclosure, the above ring C is selected from

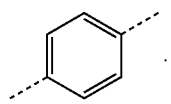

In some embodiments of the present disclosure, the above $R_1$ is selected from the group consisting of H, halogen, OH, $NH_2$, CN, COOH, and $—C(=O)NH_2$, or is selected from the group consisting of $C_{1-3}$ alkyl, $C_{1-3}$ heteroalkyl, phenyl, cyclopropyl, cyclopentyl, cyclohexyl and morpholinyl, wherein each is optionally substituted by one, two or three R groups, and R is as defined in the present disclosure.

In some embodiments of the present disclosure, the above $R_1$ is selected from the group consisting of H, F, Cl, Br, I, OH, $NH_2$, CN, COOH, $—C(=O)NH_2$, Me, $CF_3$, Et,

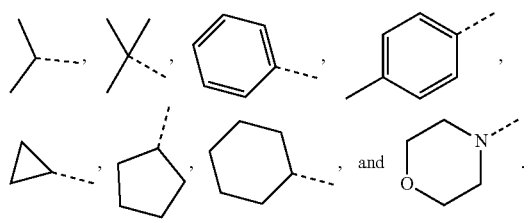

In some embodiments of the present disclosure, the above $L_1$ is selected from the group consisting of a single bond, $—CH_2—$, $—CH_2CH_2—$,

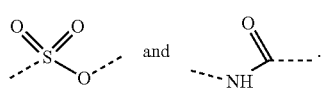

In some embodiments of the present disclosure, the above structural unit

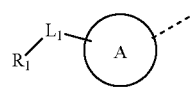

is selected from the group consisting of H, $NH_2$, COOH, $—C(=O)NH_2$, Me, $CF_3$, Et,

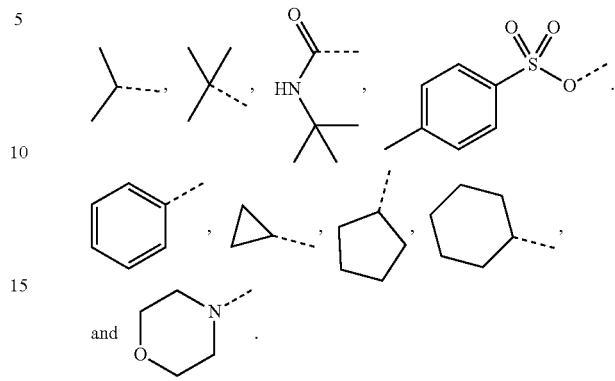

In some embodiments of the present disclosure, the above structural unit

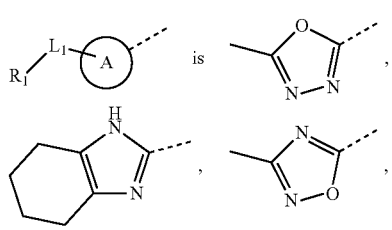

is selected from the group consisting of

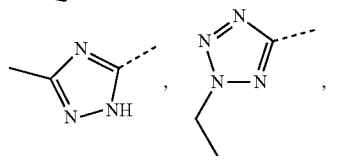

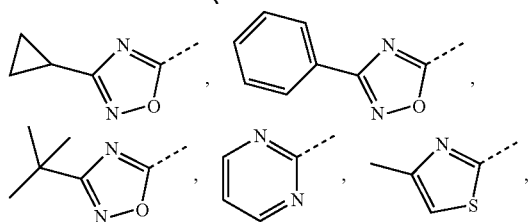

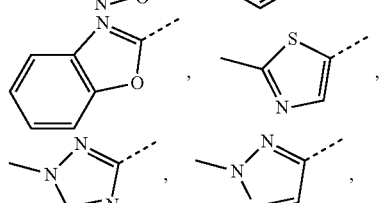

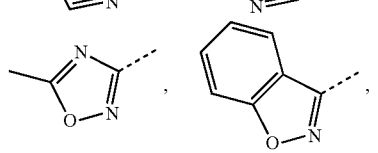

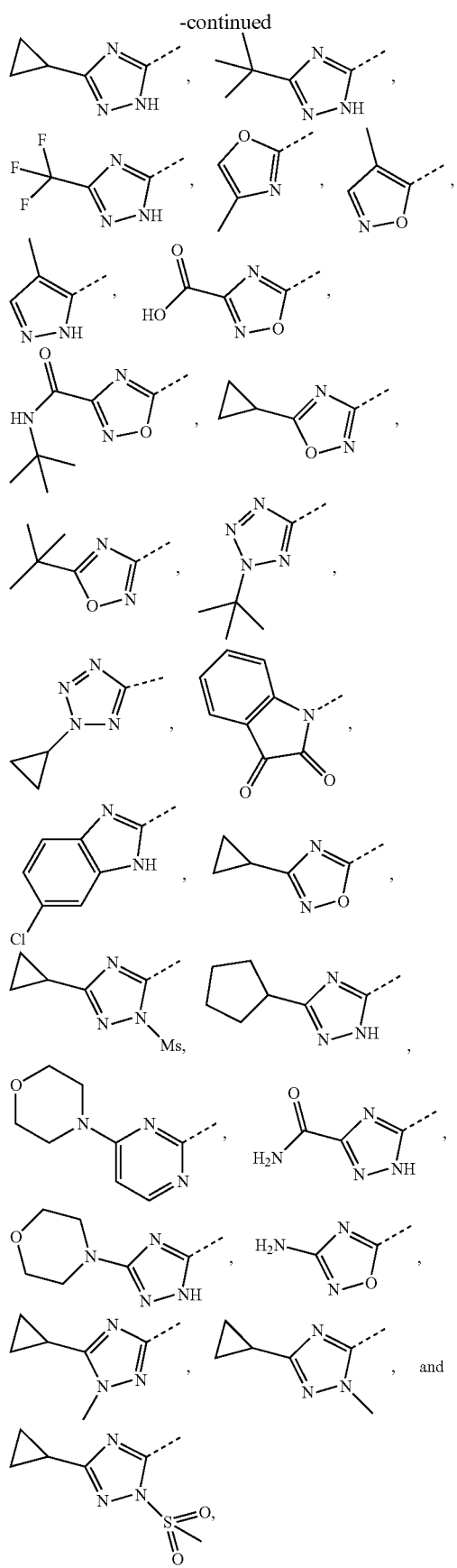

In some embodiments of the present disclosure, the above R is selected from the group consisting of F, Cl, Br, I, OH, NH$_2$, and C(=O)NH$_2$, or is selected from the group consisting of Me, Et,

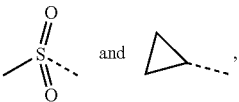

wherein each is optionally substituted by one, two or three R' groups, and other variables are as defined above.

In some embodiments of the present disclosure, the above R is selected from the group consisting of H, Me, Et, CF$_3$, C(=O)NH$_2$,

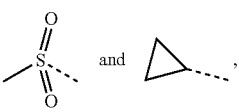

and other variables are as defined above.

In some embodiments of the present disclosure, the above ring A is selected from the group consisting of 1,3,4-oxadiazolyl, 1,2,4-oxadiazolyl, 1H-1,2,4-triazolyl, thiazolyl, isothiazolyl, 1,2,4-thiadiazolyl, oxazolyl, isoxazolyl, 1H-tetrazyl, pyridyl, pyrimidinyl, pyridazinyl, indolyl, benzoxazolyl, benzisoxazolyl, 4,5,6,7-tetrahydro-1H-benzimidazolyl, 2H-1,2,3-triazolyl, benzo[d]thiazolyl, 2H-benzo[d]imidazolyl and indoline-2,3-diketo, wherein each is optionally substituted by a R group, and other variables are as defined above.

In some embodiments of the present disclosure, the above ring A is selected from the group consisting of

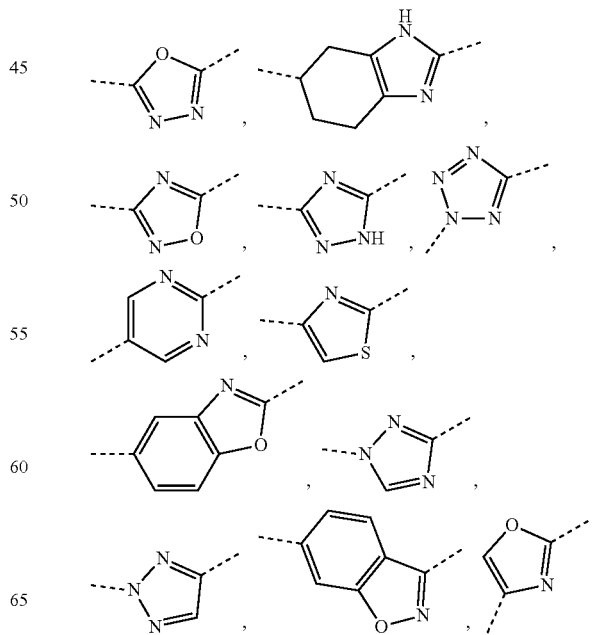

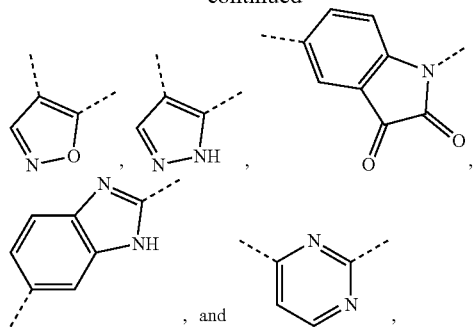

wherein each is optionally substituted by a R group, and other variables are as defined above.

In some embodiments of the present disclosure, the above ring A is selected from the group consisting of

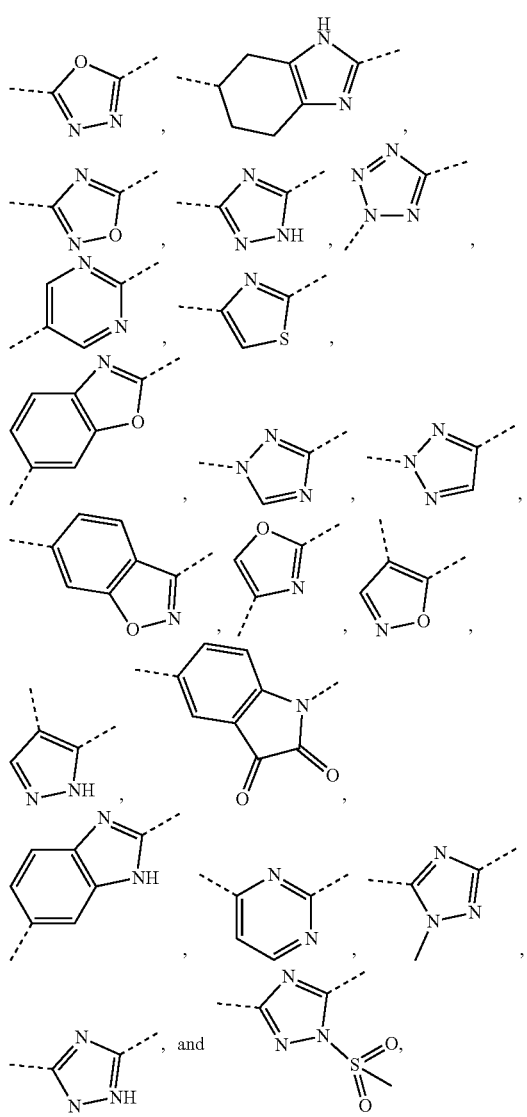

and other variables are as defined above.

In some embodiments of the present disclosure, the above ring C is selected from

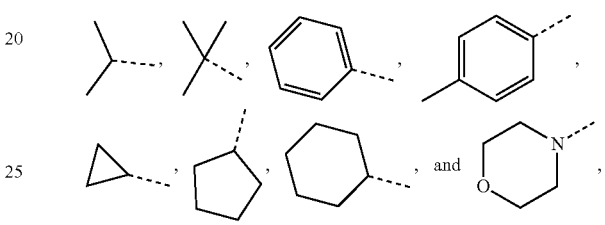

and other variables are as defined above.

In some embodiments of the present disclosure, the above $R_1$ is selected from the group consisting of H, halogen, OH, $NH_2$, CN, COOH, and —C(=O)$NH_2$, or is selected from the group consisting of $C_{1-3}$ alkyl, $C_{1-3}$ heteroalkyl, phenyl, cyclopropyl, cyclopentyl, cyclohexyl and morpholinyl, wherein each is optionally substituted by one, two or three R groups, and other variables are as defined above.

In some embodiments of the present disclosure, the above $R_1$ is selected from the group consisting of H, F, Cl, Br, I, OH, $NH_2$, CN, COOH, —C(=O)$NH_2$, Me, $CF_3$, Et,

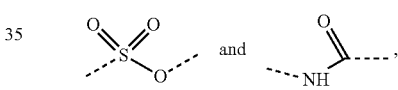

and other variables are as defined above.

In some embodiments of the present disclosure, the above $L_1$ is selected from the group consisting of a single bond, —$CH_2$—, —$CH_2CH_2$—,

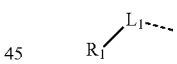

and other variables are as defined above.

In some embodiments of the present disclosure, the above structural unit $R_1 \diagup ^{L_1 ---}$ is selected from the group consisting of H, $NH_2$, COOH, —C(=O)$NH_2$, Me, $CF_3$, Et,

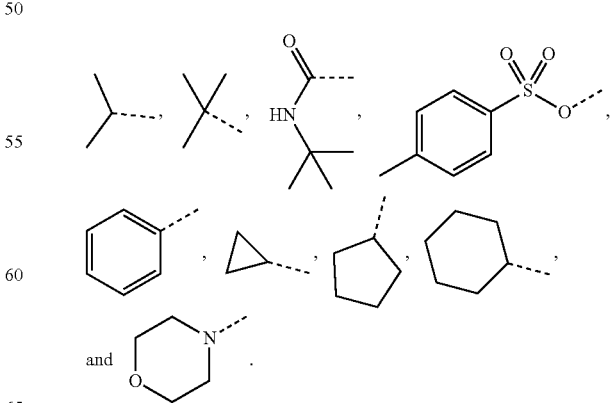

and other variables are as defined above.

In some embodiments of the present disclosure, the above structural unit

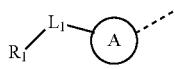

is selected from the group consisting of

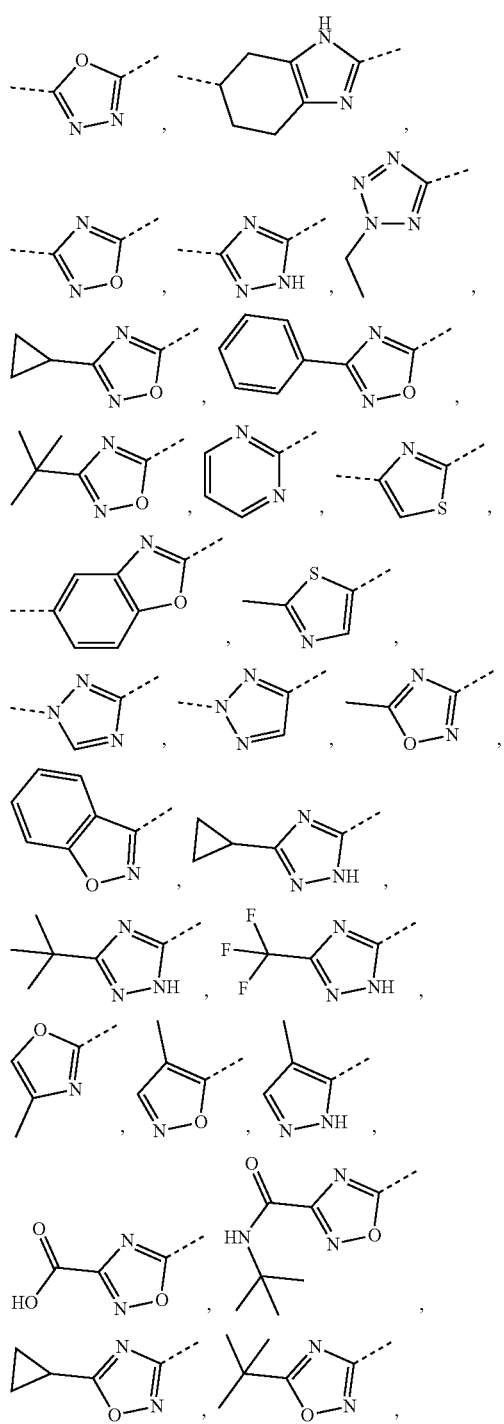

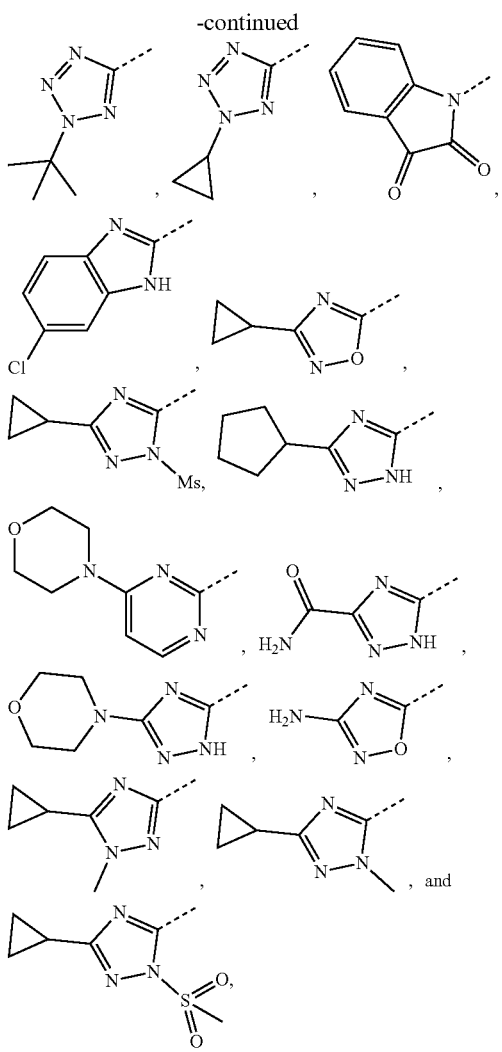

and other variables are as defined above.

Some embodiments of the present disclosure are derived from any combination of the above variables. The present disclosure provides the compound of the following formula or the pharmaceutically acceptable salt thereof, selected from the group consisting of

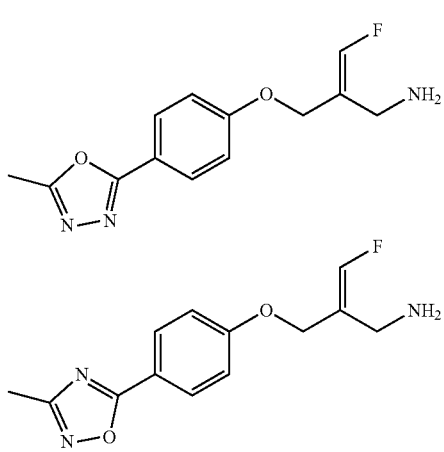

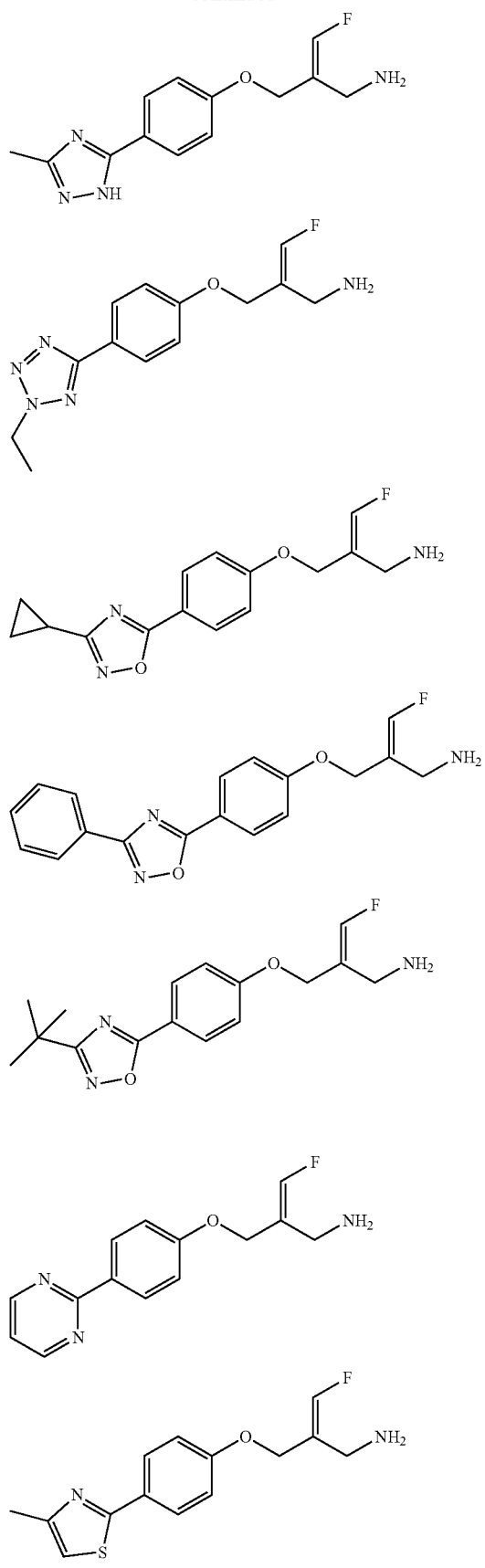
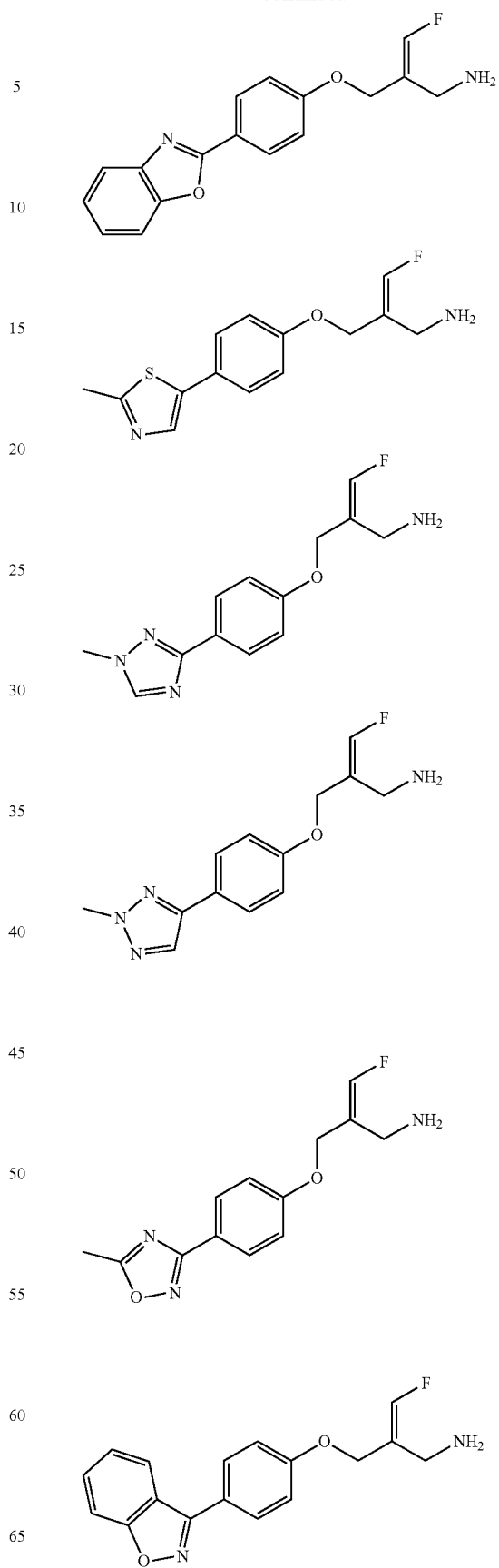

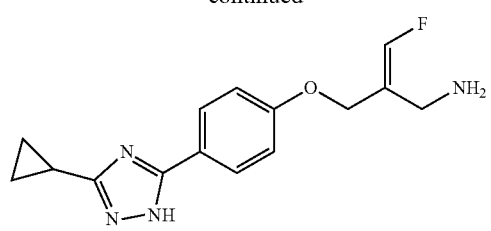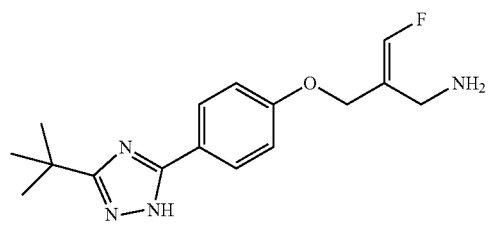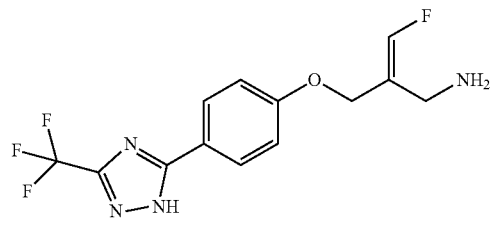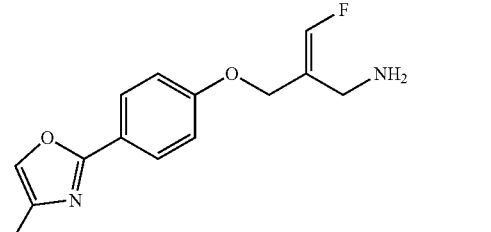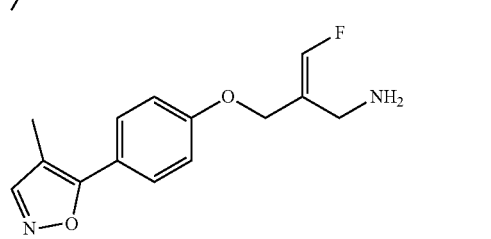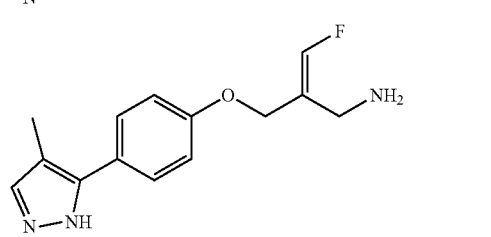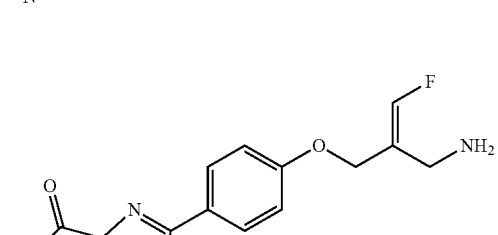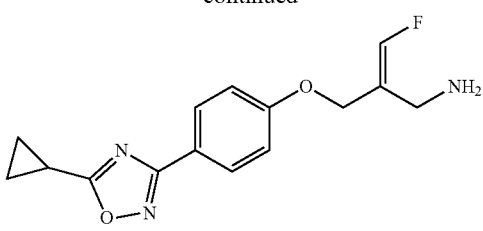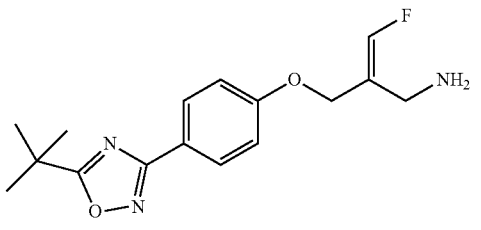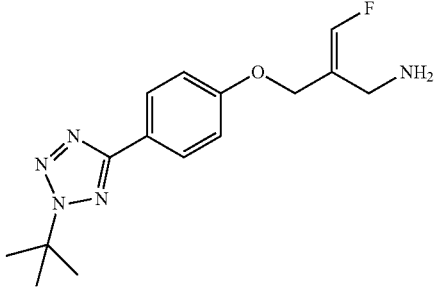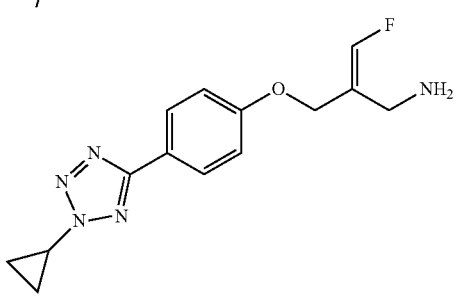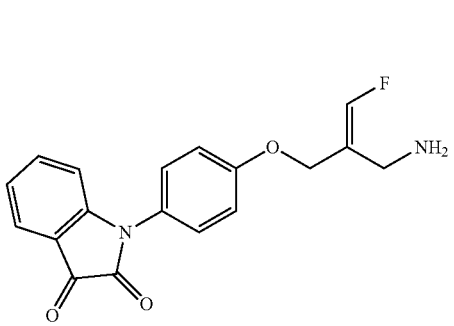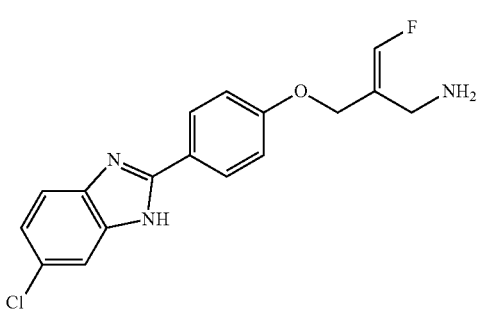

51
-continued
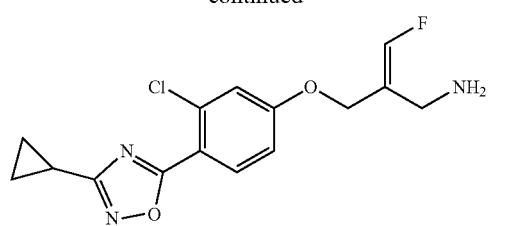
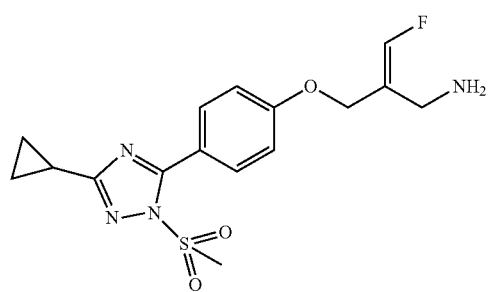
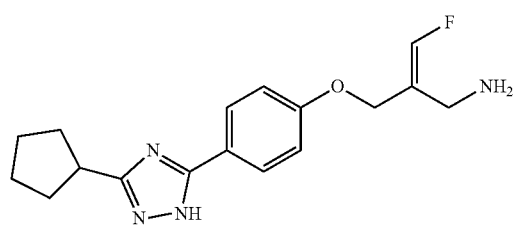
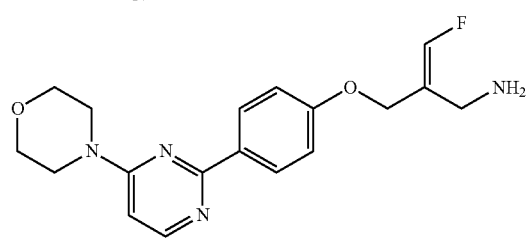
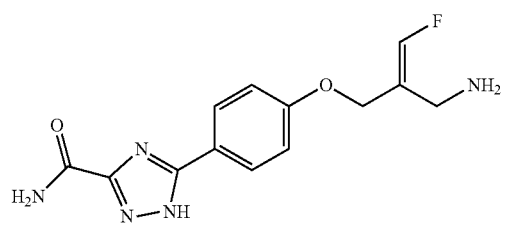
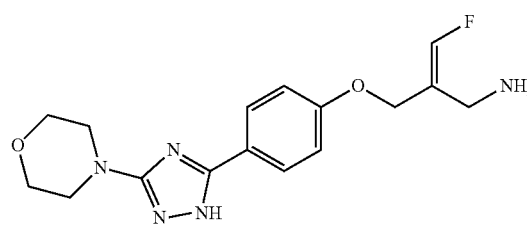
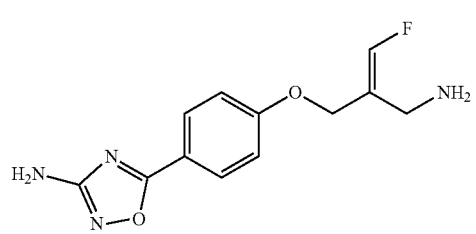
52
-continued
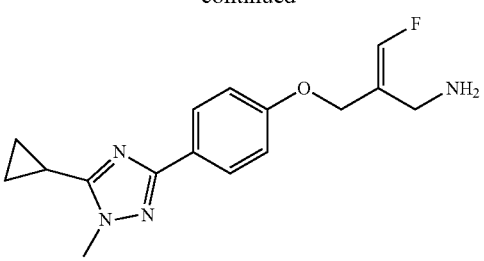
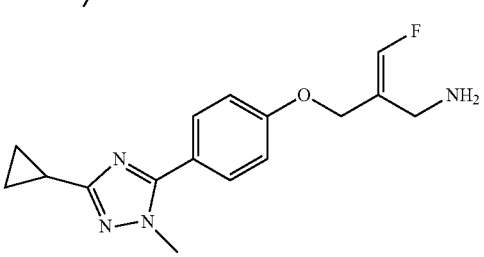
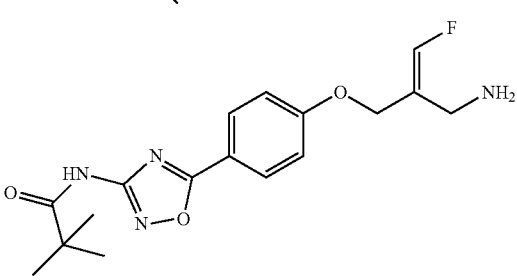
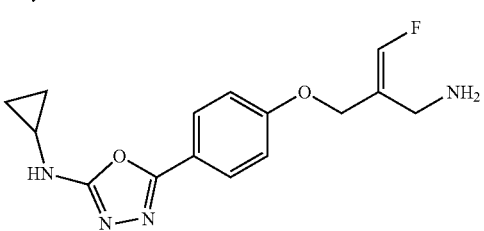
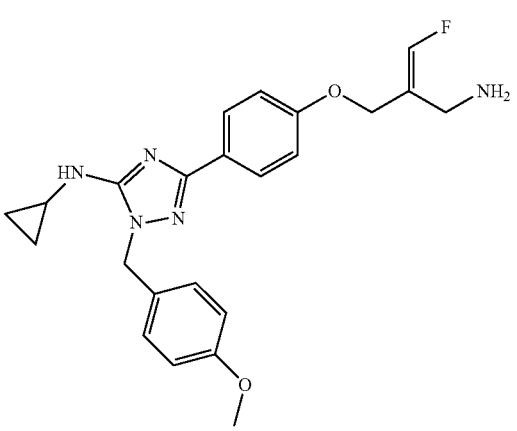
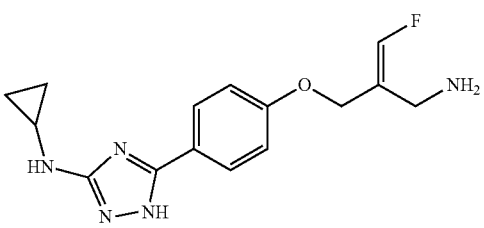

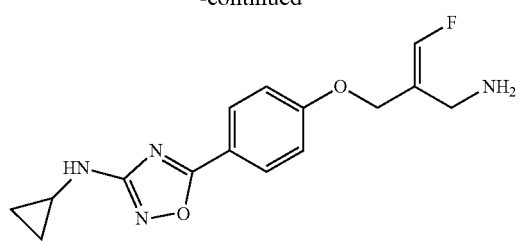
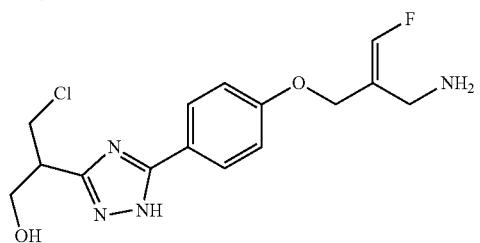
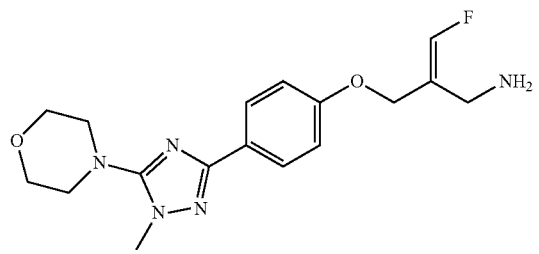
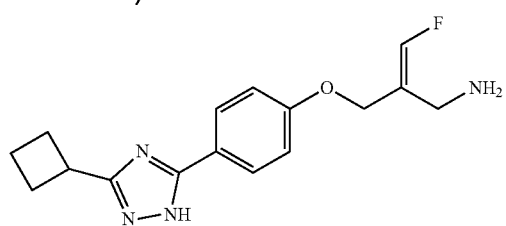
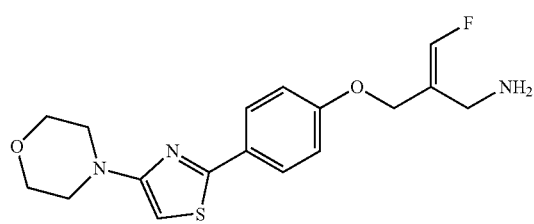
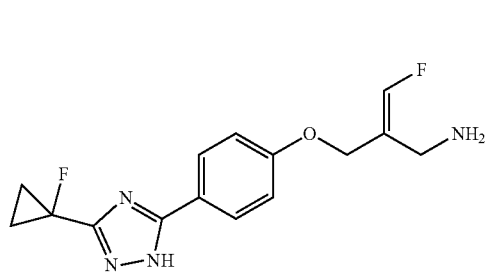
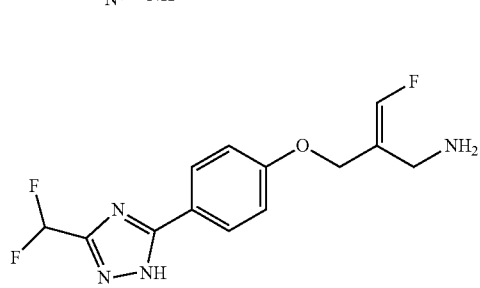
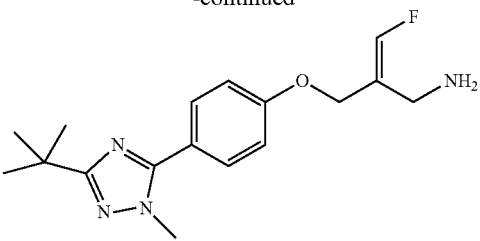
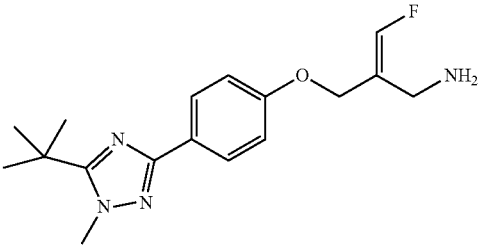
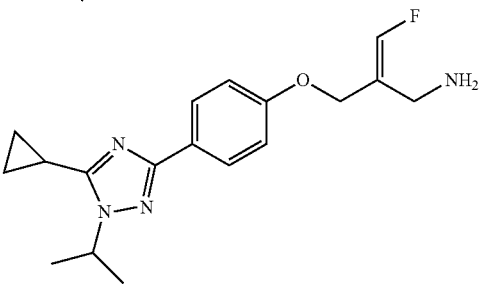
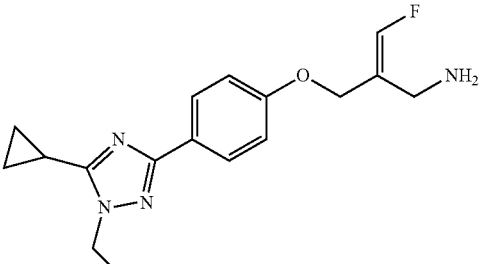
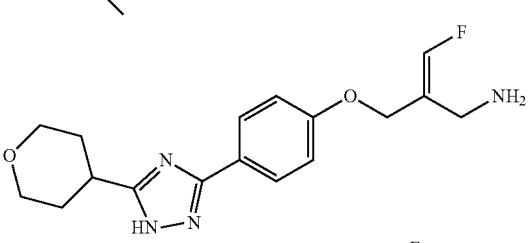
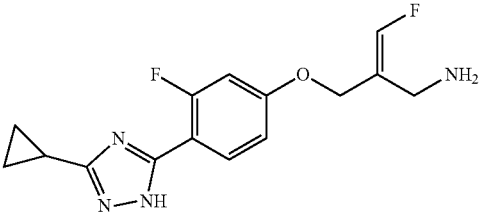
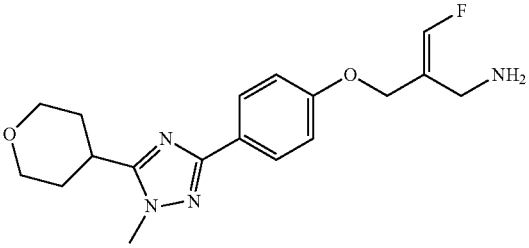

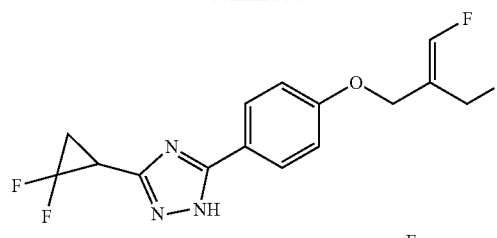
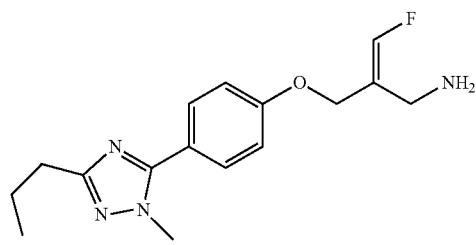
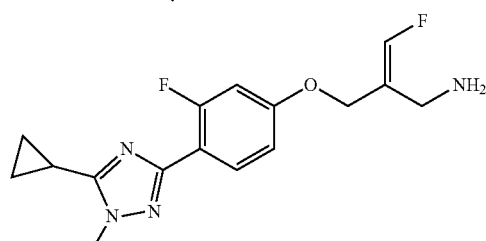
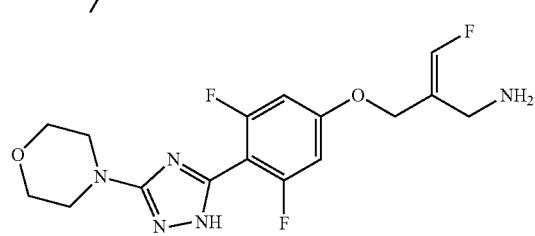
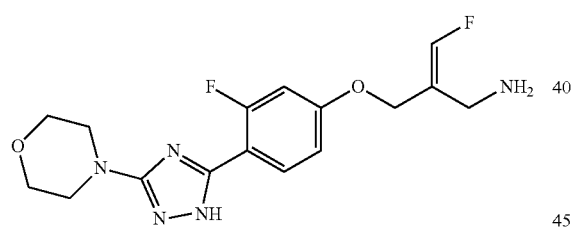
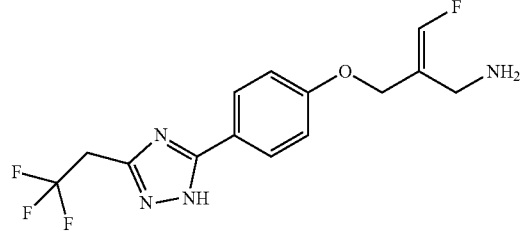
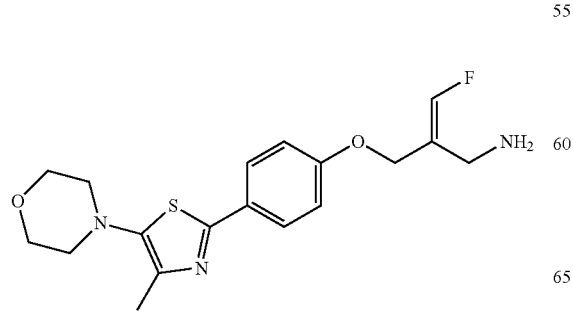
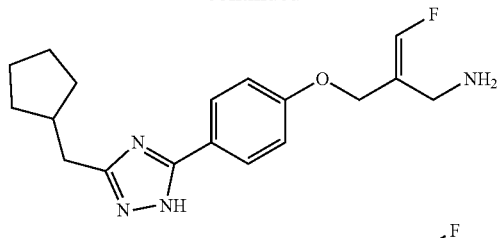
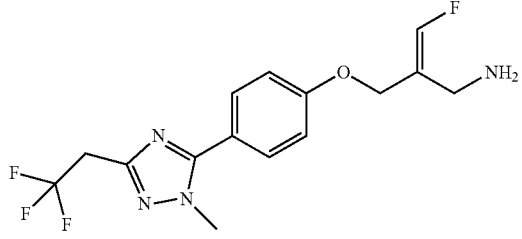
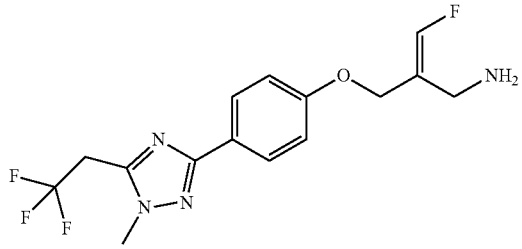
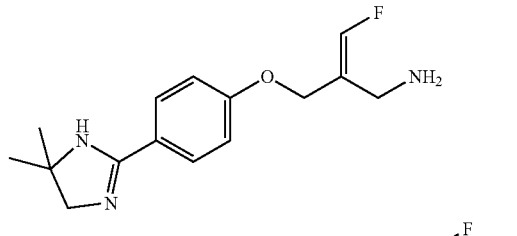
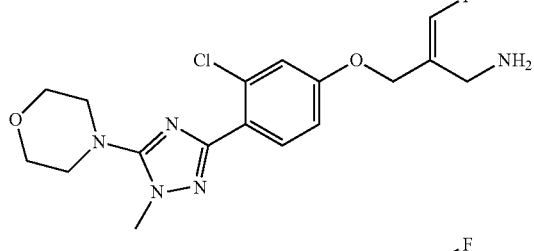
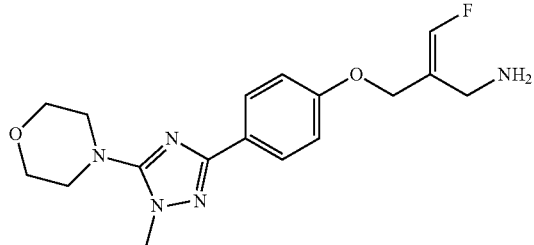
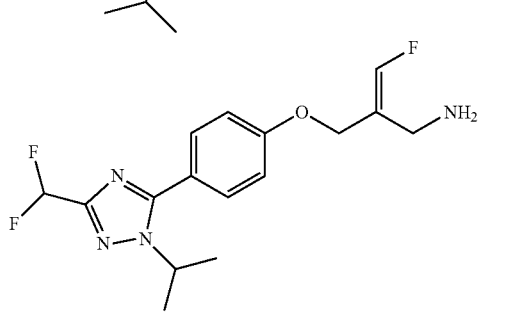

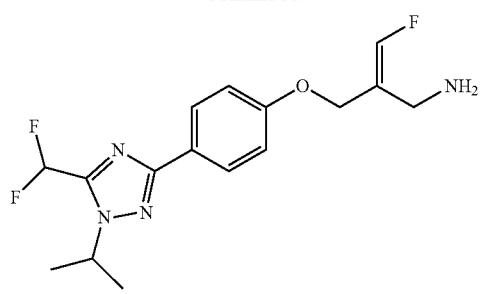
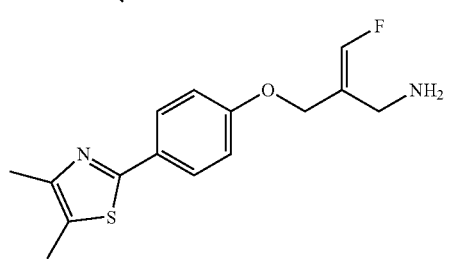
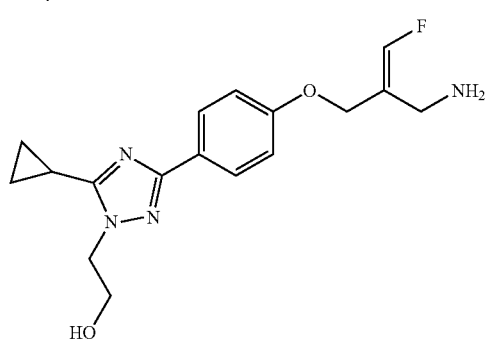
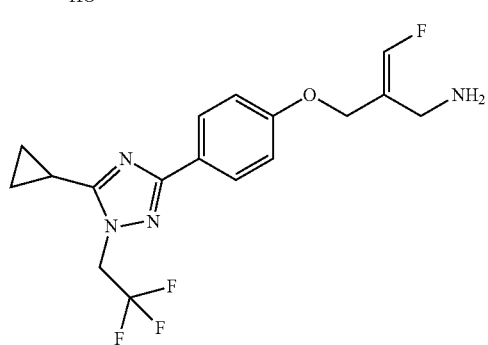
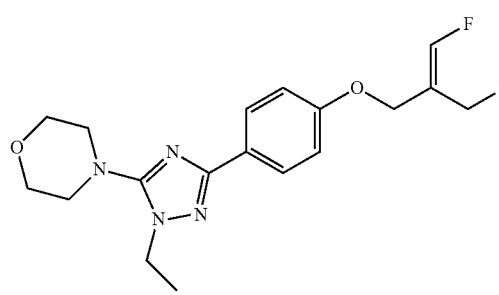
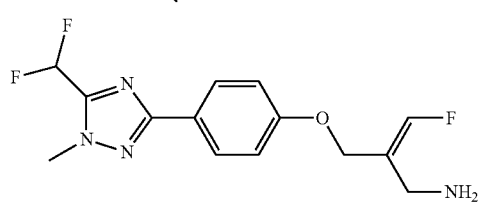
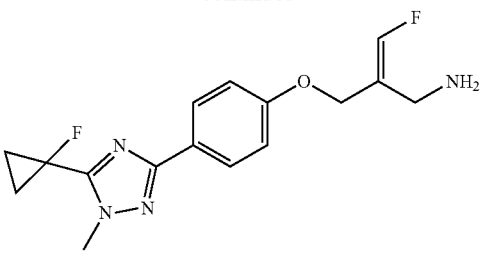
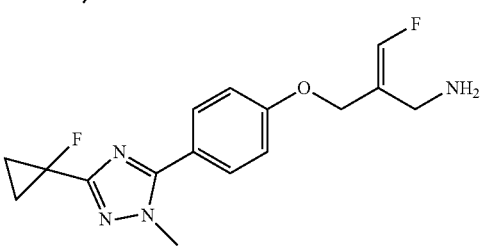
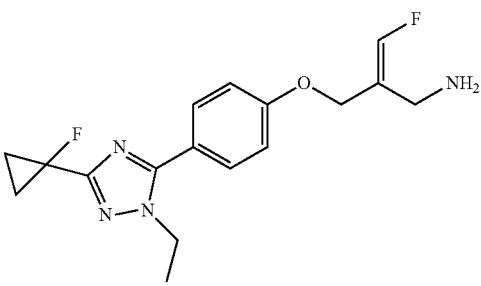
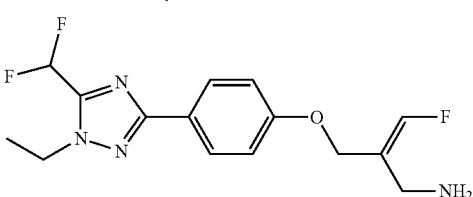
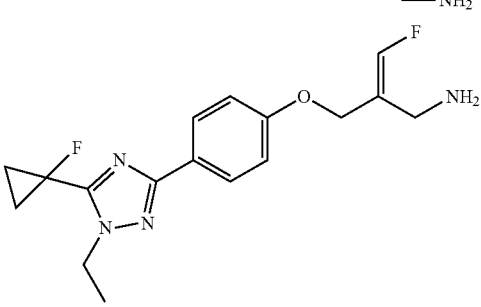
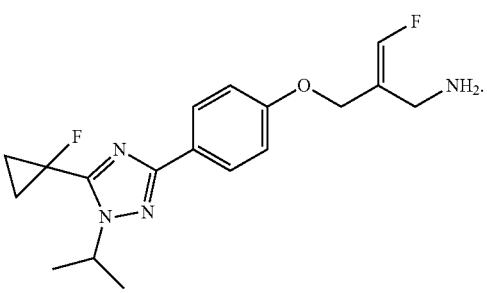
In some embodiments of the present disclosure, the above compound or the pharmaceutically acceptable salt thereof is selected from the group consisting of

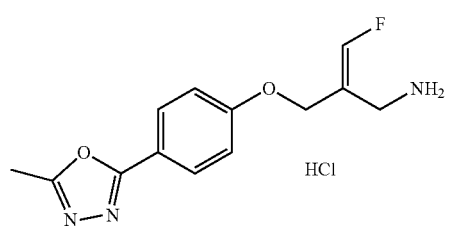
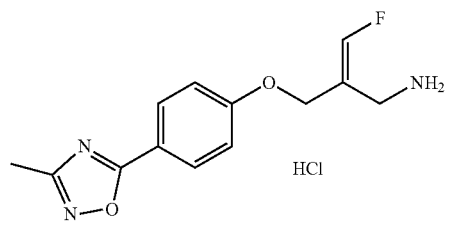
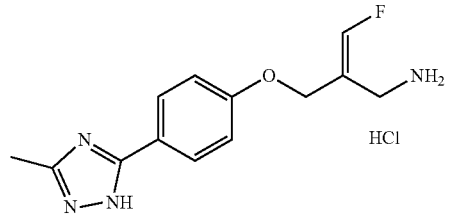
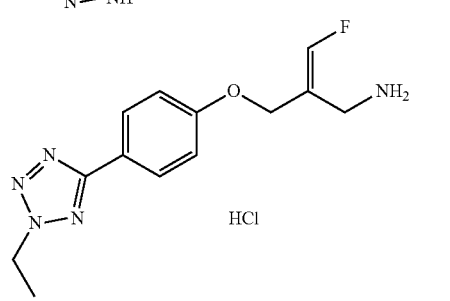
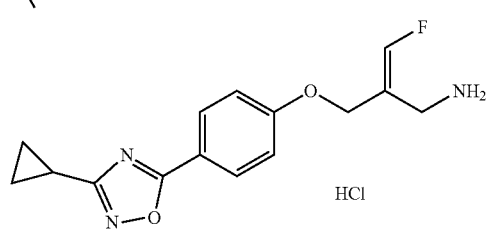
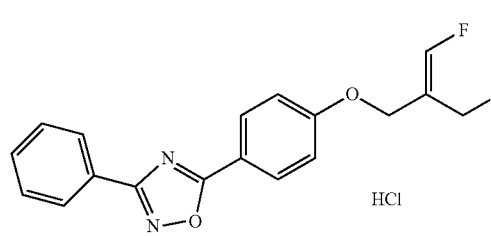
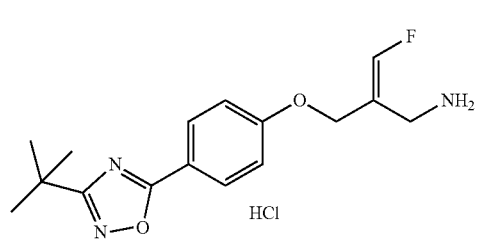
-continued
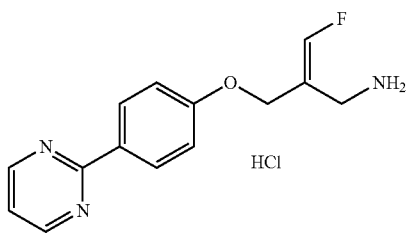
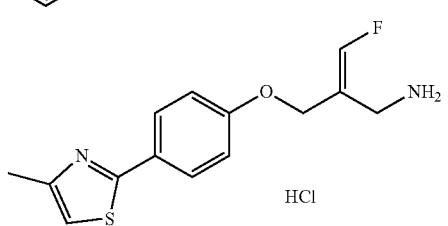
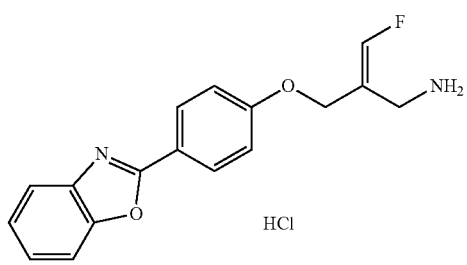
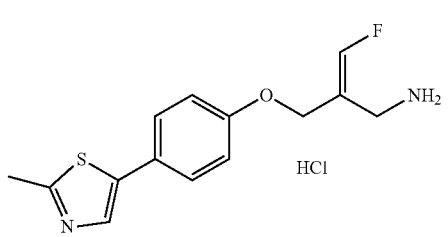
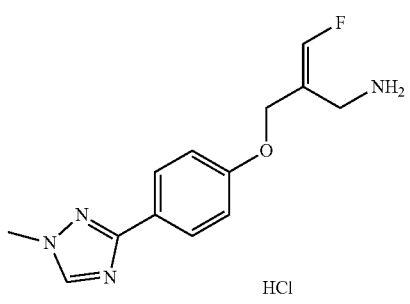
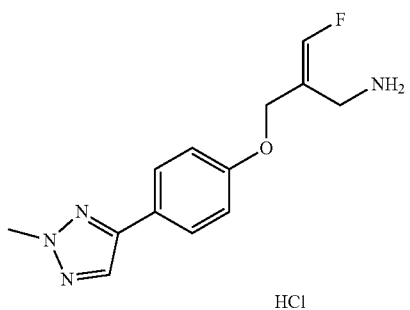

-continued
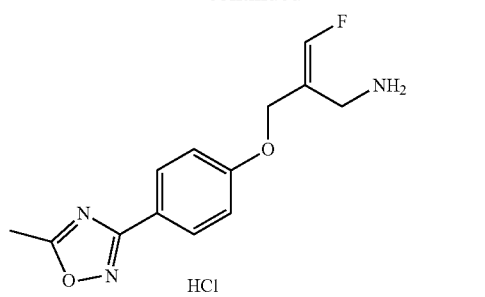
HCl
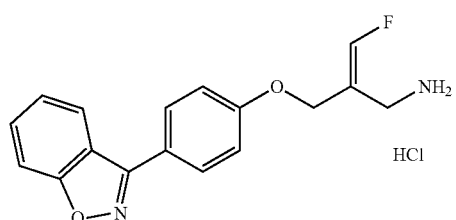
HCl
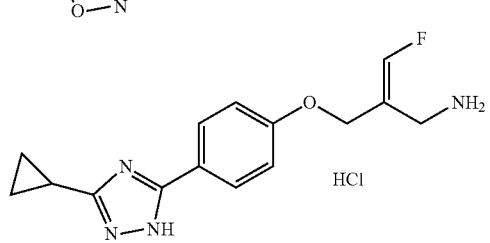
HCl
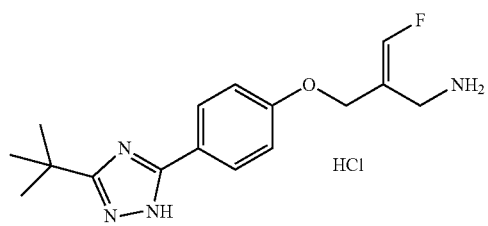
HCl
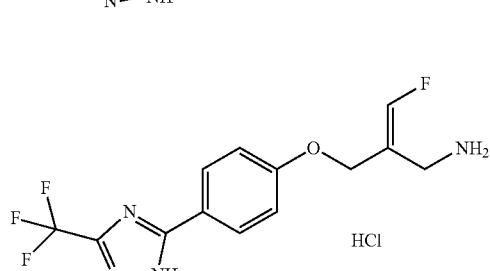
HCl
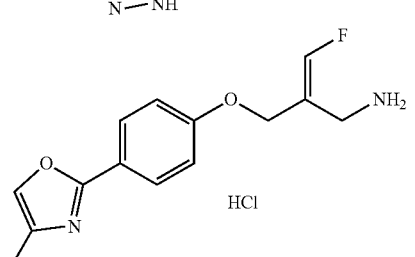
HCl
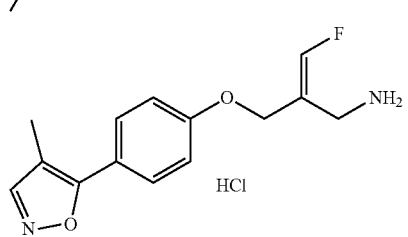
HCl
-continued
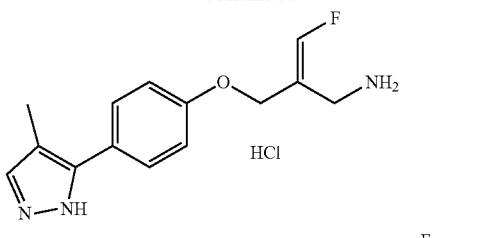
HCl
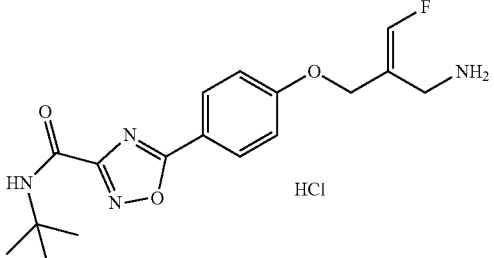
HCl
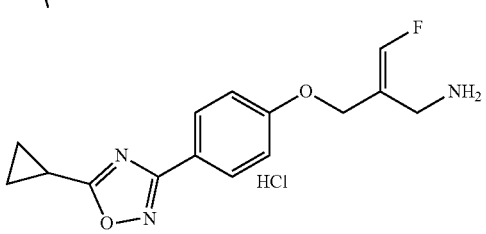
HCl
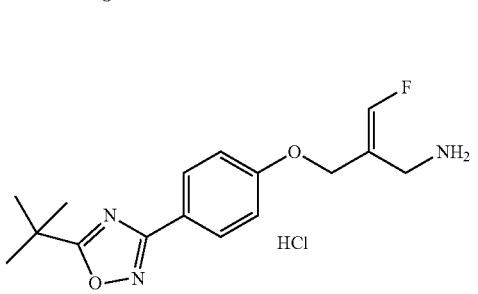
HCl
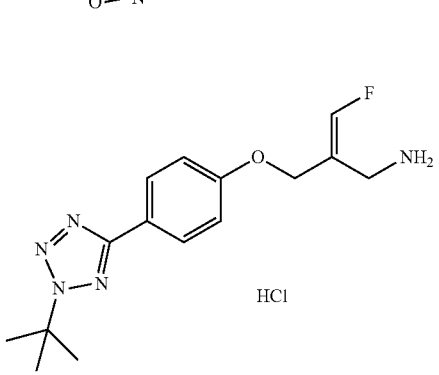
HCl
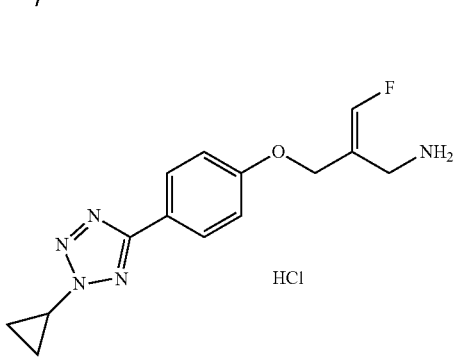
HCl 63
-continued
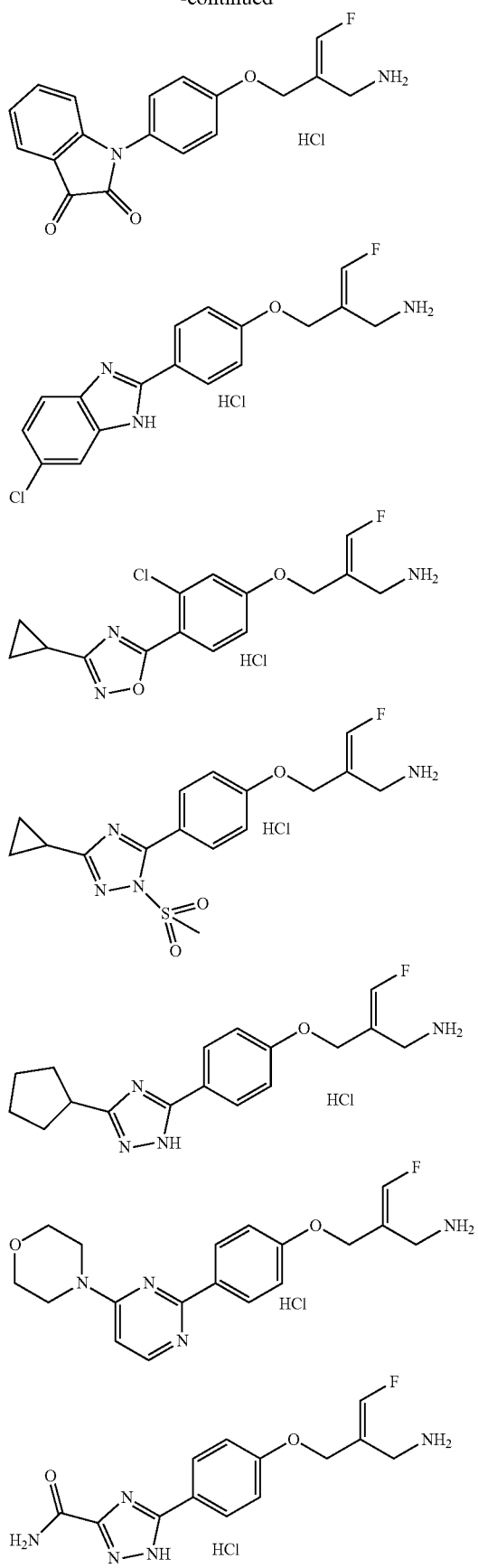
64
-continued
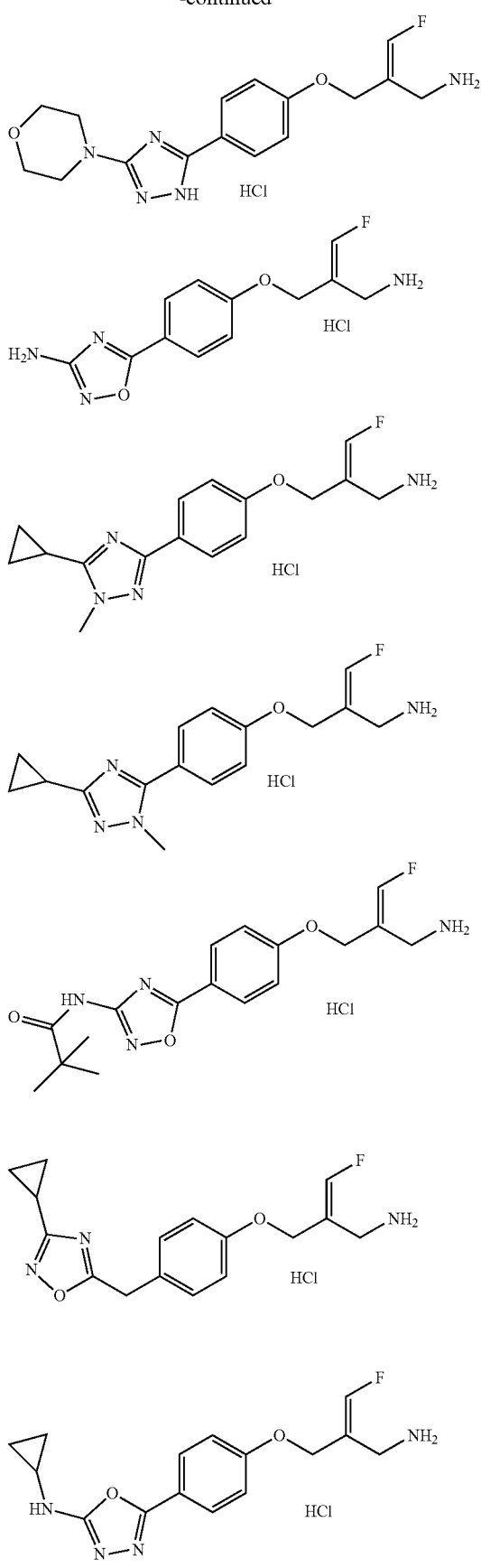

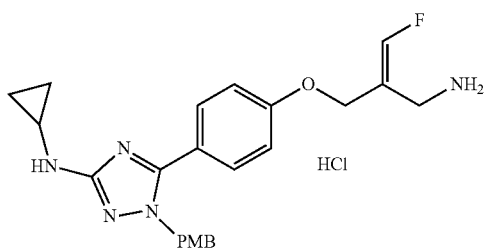
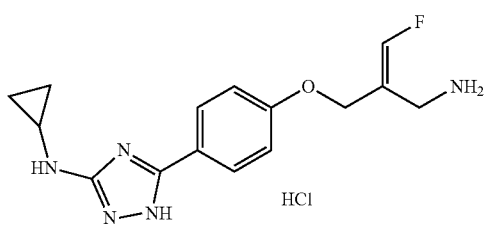
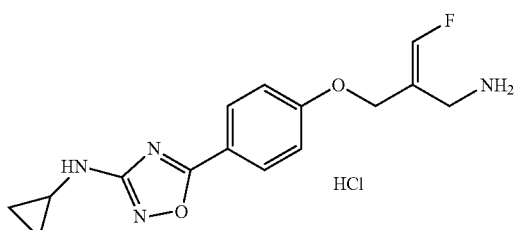
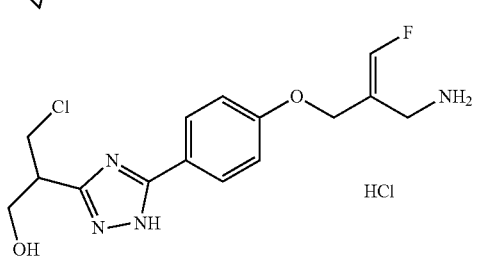
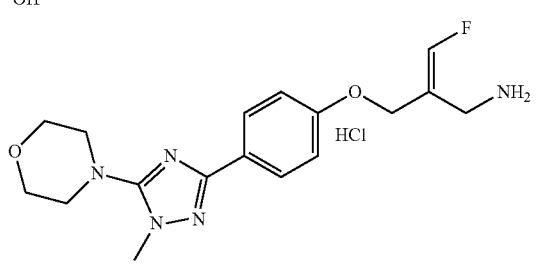
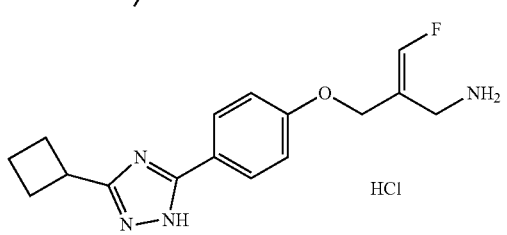
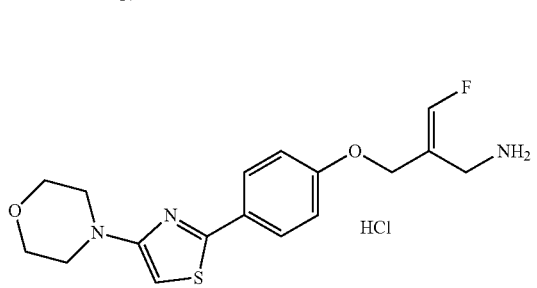
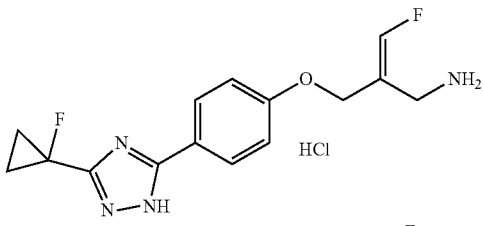
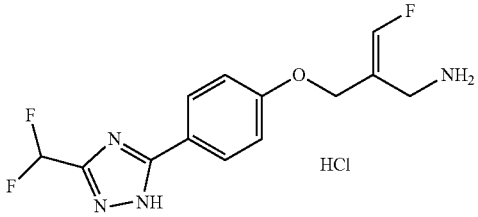
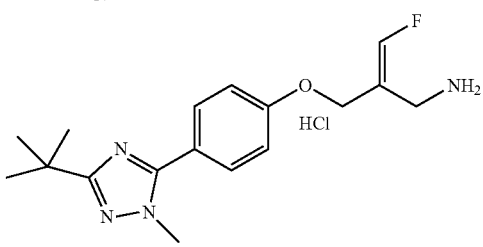
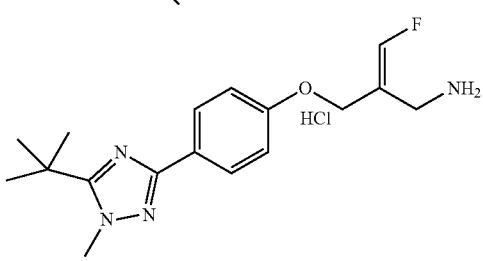
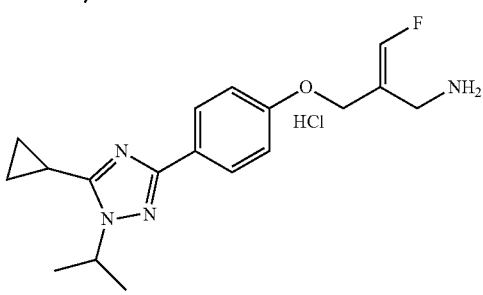
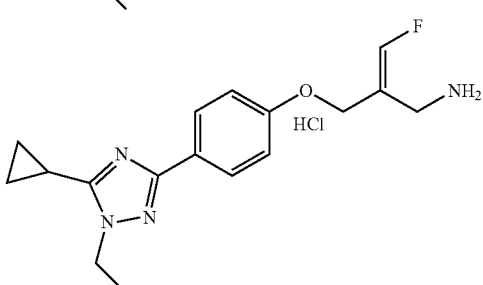
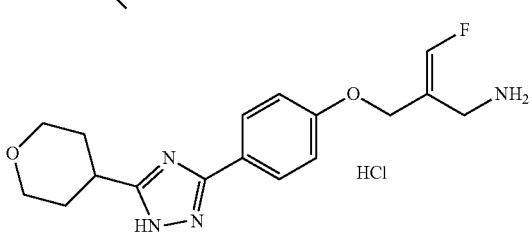

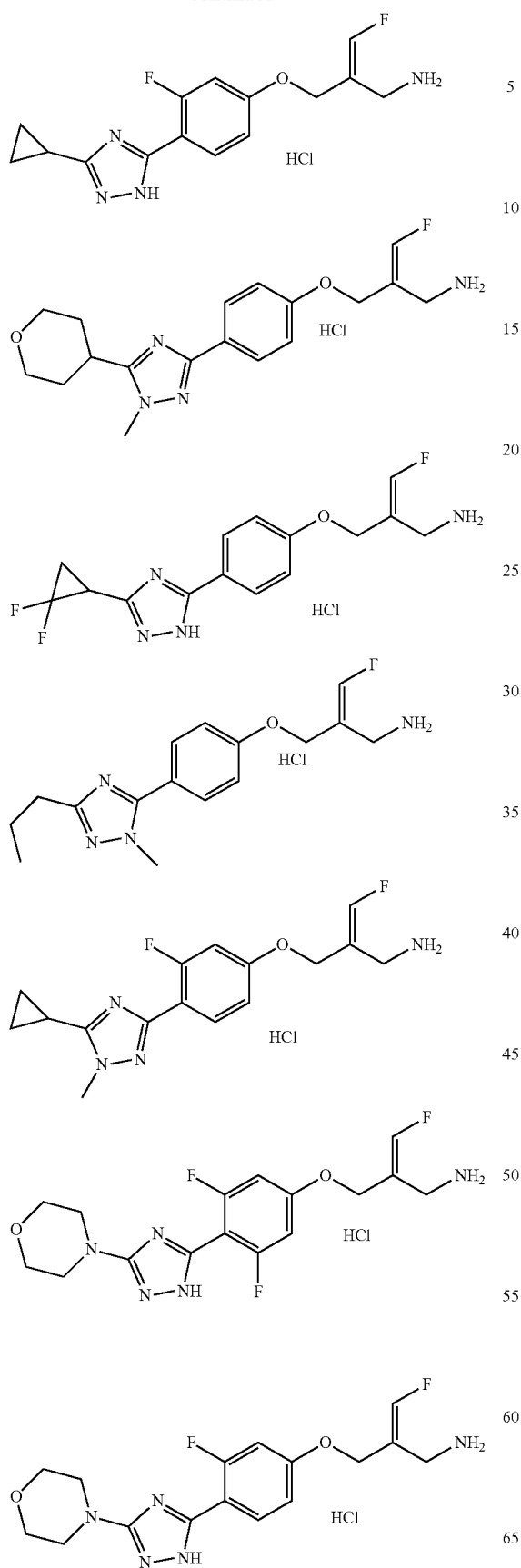
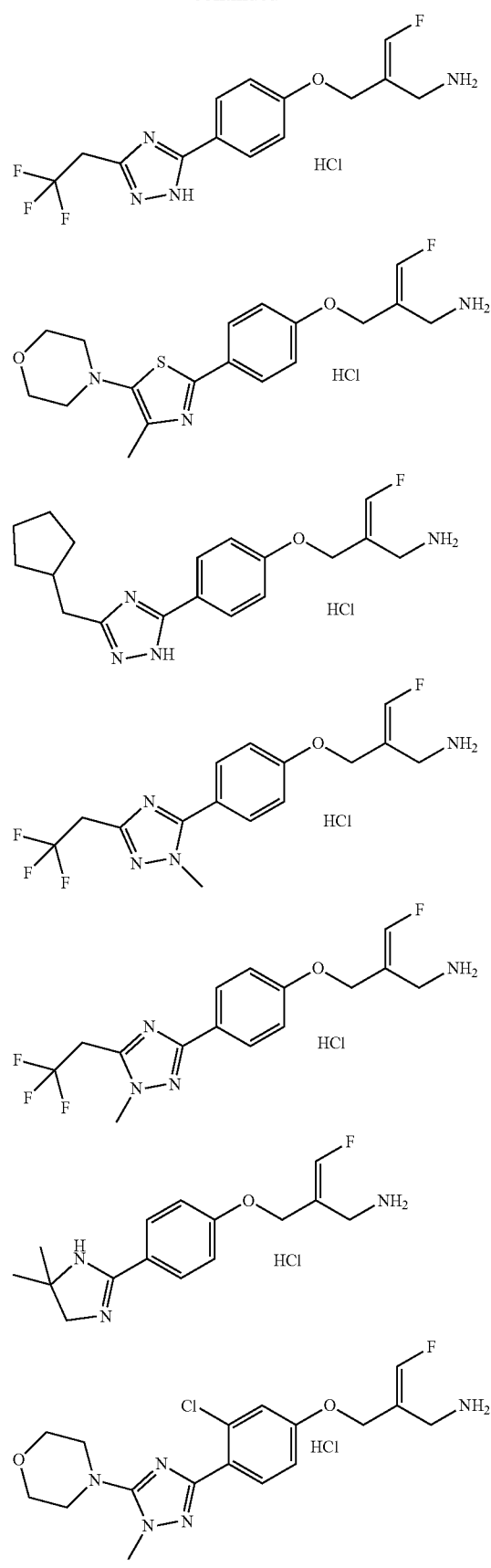

69
-continued
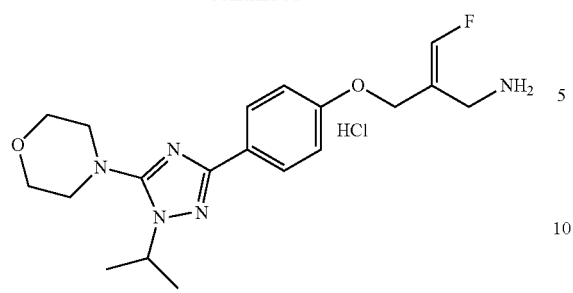
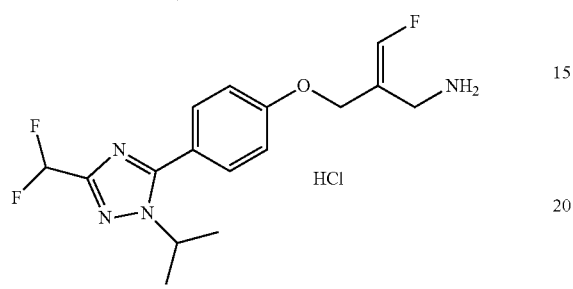
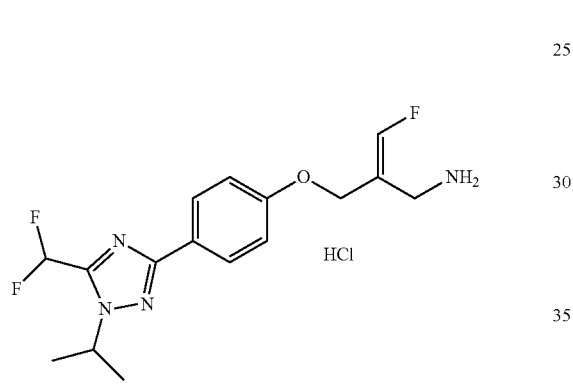
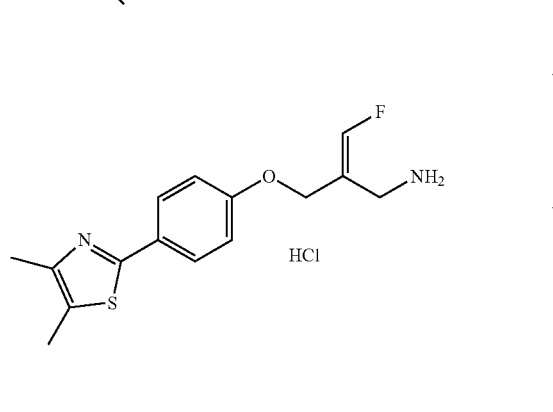
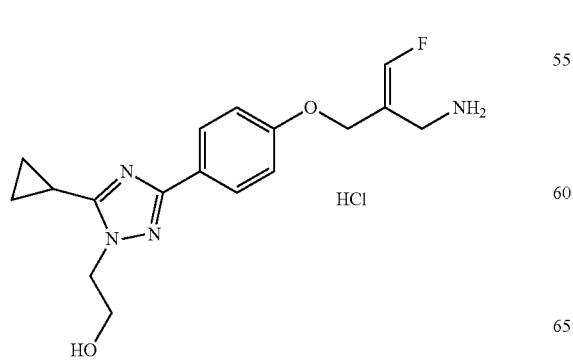
70
-continued
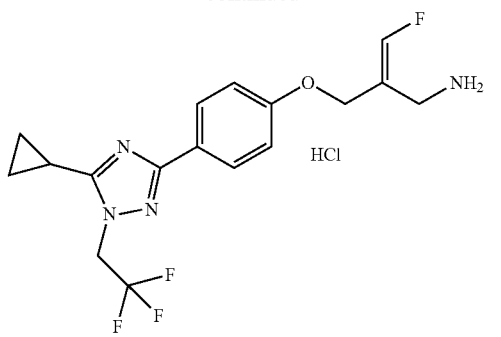
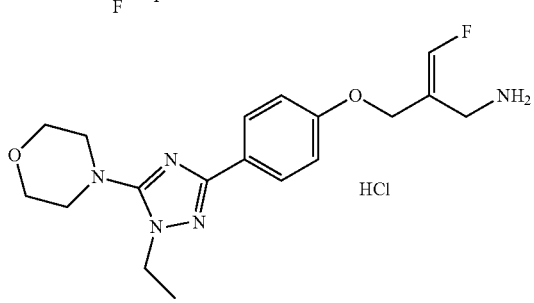
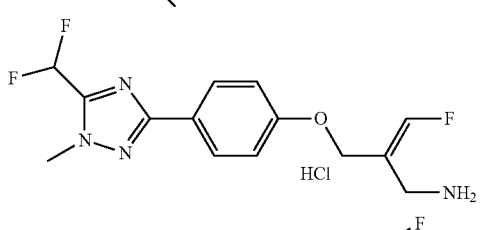
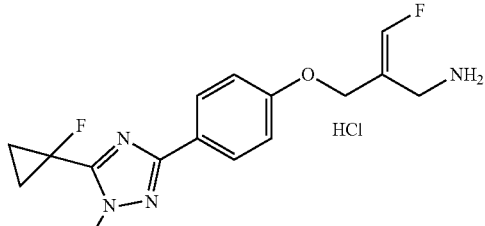
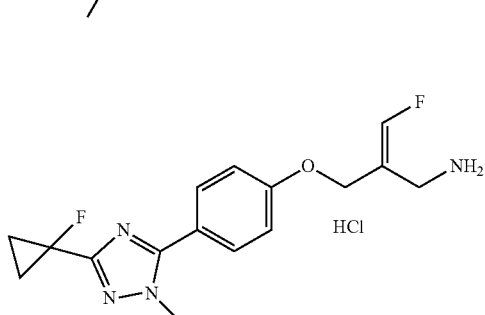
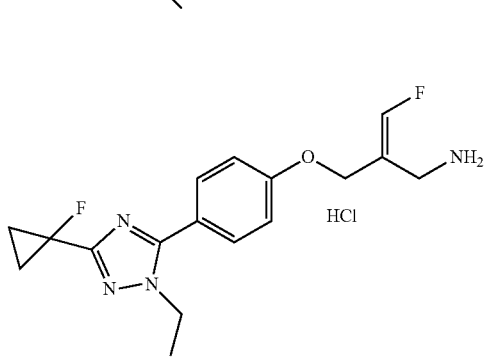

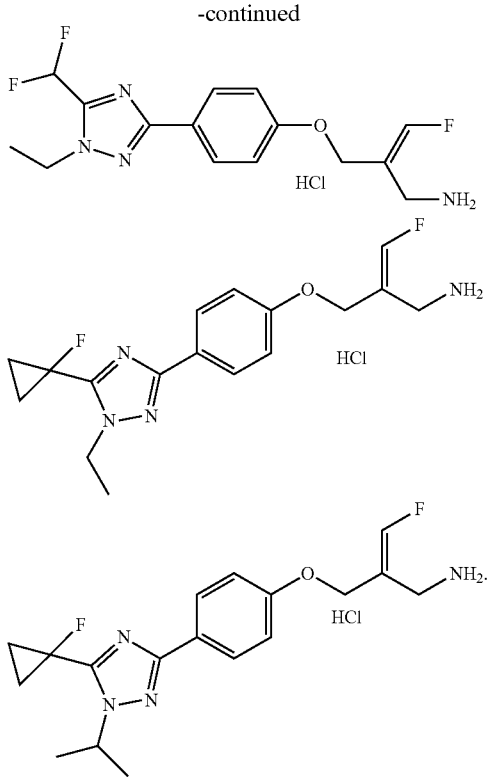

The present disclosure also provides use of the above compound or the pharmaceutically acceptable salt thereof and a tautomer thereof in the manufacture of a medicament for diseases related to SSAO.

In some embodiments of the present disclosure, the disease related to SSAO is nonalcoholic steatohepatitis.

Related Definition

Unless otherwise stated, the following terms and phrases as used herein are intended to have the following meanings. A particular term or phrase should not be considered undefined or unclear without a particular definition, but should be understood in the ordinary sense. When a trade name appears herein, it is intended to refer to its corresponding commodity or its active ingredient. The term "pharmaceutically acceptable" as used herein is intended to mean that those compounds, materials, compositions and/or dosage forms are within the scope of sound medical judgment and are suitable for use in contact with human and animal tissues without excessive toxicity, irritation, allergic reactions or other problems or complications, and commensurate with a reasonable benefit/risk ratio.

The term "pharmaceutically acceptable salt" refers to a salt of the compound of the present disclosure, prepared from a compound having a particular substituent found in the present disclosure and a relatively non-toxic acid or base. When a relatively acidic functional group is contained in the compound of the present disclosure, a base addition salt can be obtained by contacting a neutral form of such a compound with a sufficient amount of a base in a pure solution or a suitable inert solvent. Pharmaceutically acceptable base addition salts include sodium salts, potassium salts, calcium salts, ammonium salts, organic amine salts or magnesium salts or similar salts. When a relatively basic functional group is contained in the compound of the present disclosure, an acid addition salt can be obtained by contacting a neutral form of such a compound with a sufficient amount of an acid in a pure solution or a suitable inert solvent. Examples of pharmaceutically acceptable acid addition salts include inorganic acid salts, wherein the inorganic acid includes, for example, hydrochloric acid, hydrobromic acid, nitric acid, carbonic acid, hydrogen carbonate, phosphoric acid, monohydrogen phosphate, dihydrogen phosphate, sulfuric acid, hydrogen sulfate, hydroiodic acid, and phosphorous acid; and organic acid salts, wherein the organic acid includes, for example, acetic acid, propionic acid, isobutyric acid, maleic acid, malonic acid, benzoic acid, succinic acid, suberic acid, fumaric acid, lactic acid, mandelic acid, phthalic acid, benzenesulfonic acid, p-toluenesulfonic acid, citric acid, tartaric acid, and methanesulfonic acid; and further include salts of amino acids (such as arginine, etc.), and salts of organic acids such as glucuronic acid (see Berge et al., "Pharmaceutical Salts", *Journal of Pharmaceutical Science* 66: 1-19 (1977)). Certain specific compounds of the present disclosure contain both basic and acidic functional groups and thus can be converted to any base or acid addition salts.

Preferably, the salt is contacted with a base or an acid in a conventional manner, and the parent compound is separated, thereby regenerating the neutral form of the compound. The parent form of the compound differs from the form of its various salts in certain physical properties, such as differences in solubility in polar solvents.

As used herein, a "pharmaceutically acceptable salt" is a derivative of the compound of the present disclosure, wherein the parent compound is modified by salt formation with an acid or with a base. Examples of pharmaceutically acceptable salts include, but are not limited to, inorganic or organic acid salts of bases such as amines, alkali metal or organic salts of acid groups such as carboxylic acids, etc. Pharmaceutically acceptable salts include the conventional non-toxic salts or quaternary ammonium salts of the parent compound, for example salts formed from non-toxic inorganic or organic acids. Conventional non-toxic salts include, but are not limited to, those derived from inorganic acids and organic acids selected from the group consisting of 2-acetoxybenzoic acid, 2-hydroxyethanesulfonic acid, acetic acid, ascorbic acid, benzenesulfonic acid, benzoic acid, hydrogen carbonate, carbonic acid, citric acid, edetic acid, ethane disulfonic acid, ethanesulfonic acid, fumaric acid, glucoheptose, gluconic acid, glutamic acid, glycolic acid, hydrobromic acid, hydrochloric acid, hydriodate, hydroxyl, hydroxynaphthalene, isethionic acid, lactic acid, lactose, dodecylsulfonic acid, maleic acid, malic acid, mandelic acid, methanesulfonic acid, nitric acid, oxalic acid, pamoic acid, pantothenic acid, phenylacetic acid, phosphoric acid, polygalacturonic acid, propionic acid, salicylic acid, stearic acid, folinic acid, succinic acid, sulfamic acid, p-aminobenzenesulfonic acid, sulfuric acid, tannin, tartaric acid and p-toluenesulfonic acid.

The pharmaceutically acceptable salts of the present disclosure can be synthesized from the parent compound containing an acid group or a base by conventional chemical methods. In general, such salts are prepared by reacting these compounds via a free acid or base form with a stoichiometric amount of the appropriate base or acid in water or an organic solvent or a mixture of the two. Generally, a nonaqueous medium such as ether, ethyl acetate, ethanol, isopropanol or acetonitrile is preferred.

The compounds of the present disclosure may exist in specific geometric or stereoisomeric forms. The present disclosure contemplates all such compounds, including the cis and trans isomers, the (−)- and (+)-enantiomers, the (R)- and (S)-enantiomers, and the diastereoisomer, a (D)-isomer, a (L)-isomer, and a racemic mixture thereof, and other mixtures such as the mixtures enriched in enantiomer and diastereoisomer, all of which are within the scope of the present disclosure. Additional asymmetric carbon atoms may be present in the substituents such as alkyl groups. All such isomers as well as mixtures thereof are included within the scope of the present disclosure.

Unless otherwise indicated, the term "enantiomer" or "optical isomer" refers to a stereoisomer that is a mirror image of each other.

Unless otherwise indicated, the terms "cis-trans isomer" or "geometric isomer" are caused by the fact that double bonds or single bonds of ring-forming carbon atoms cannot rotate freely.

Unless otherwise indicated, the term "diastereomer" refers to a stereoisomer in which a molecule has two or more chiral centers and a nonmirror image relationship exists between the molecules.

Unless otherwise indicated, "(D)" or "(+)" means dextrorotation, "(L)" or "(−)" means levorotation, "(DL)" or "(±)" means racemization Unless otherwise stated, the solid wedge bond ( ⌁ ) and the wedge dashed bond ( ⌁ ) represent the absolute configuration of a stereocenter, the straight solid bond ( ⌁ ) and the straight dashed bond ( ⌁ ) represent the relative configuration of a stereocenter, the wavy line ( ⌁ ) represents the solid wedge bond ( ⌁ ) or the wedge dashed bond ( ⌁ ), the wavy line ( ⌁ ) represents the straight solid bond ( ⌁ ) and the straight dashed bond ( ⌁ ).

The compounds of the present disclosure may be present in particular. Unless otherwise indicated, the terms "tautomer" or "tautomeric form" mean that the different functional isomers are in dynamic equilibrium at room temperature and can be rapidly converted into each other. If tautomers are possible (such as in a solution), the chemical equilibrium of the tautomers can be achieved. For example, proton tautomer (also known as prototropic tautomer) includes interconversions by proton transfer, such as ketoenol isomerization and imine-enamine isomerization. The valence tautomer includes mutual transformation through the recombination of some of the bonding electrons. A specific example of keto-enol tautomerization is the interconversion between two tautomers pentane-2,4-dione and 4-hydroxypent-3-en-2-one.

Unless otherwise indicated, the terms "Being rich in one isomer", "isomer enriched", "being rich in one enantiomer" or "enantiomer enriched" refer to the content of one of the isomers or enantiomers is smaller than 100%, and the content of the isomer or enantiomer is greater than or equal to 60%, or greater than or equal to 70%, or greater than or equal to 80%, or greater than or equal to 90%, or greater than or equal to 95%, or greater than or equal to 96%, or greater than or equal to 97%, or greater than or equal to 98%, or greater than or equal to 99%, or greater than or equal to 99.5%, or greater than or equal to 99.6%, or greater than or equal to 99.7%, or greater than or equal to 99.8%, or greater than or equal to 99.9%.

Unless otherwise indicated, the term "isomer excess" or "enantiomeric excess" refers to the relative percentage difference between two isomers or two enantiomers. For example, if one of the isomers or enantiomers is present in an amount of 90% and the other isomer or enantiomer is present in an amount of 10%, the isomer or enantiomeric excess (ee value) is 80%.

The optically active (R)- and (S)-isomers as well as the D and L isomers can be prepared by chiral synthesis or chiral reagents or other conventional techniques. If an enantiomer of the compound of the present disclosure is desired, it can be prepared by asymmetric synthesis or by derivatization with a chiral auxiliary, wherein the resulting mixture of diastereomers is separated and the auxiliary group is cleaved to provide the desired pure enantiomer. Alternatively, when a molecule contains a basic functional group (e.g., an amino group) or an acidic functional group (e.g., a carboxyl group), a diastereomeric salt is formed with a suitable optically active acid or base, and then the diastereomers are resolved by conventional methods well known in the art, and the pure enantiomer is recovered. Furthermore, the separation of enantiomers and diastereomers is generally accomplished by the use of chromatography using a chiral stationary phase optionally combined with chemical derivatization (eg, formation of carbamate from an amine). The compounds of the present disclosure may contain an unnatural proportion of atomic isotopes on one or more of the atoms constituting the compound. For example, a compound can be labeled with a radioisotope such as tritium ($^3H$), iodine-125 ($^{125}I$) or C-14 ($^{14}C$). Alterations of all isotopes of the compounds of the present disclosure, whether radioactive or not, are included within the scope of the present disclosure.

The term "pharmaceutically acceptable carrier" refers to any formulation or carrier medium that is capable of delivering an effective amount of an active substance of the present disclosure, does not interfere with the biological activity of the active substance, and has no toxic and side effects on the host or patient, and the representative carrier includes water, oil, vegetables and minerals, cream bases, lotion bases, ointment bases, etc. These bases include suspending agents, tackifiers, transdermal enhancers and the like. Their formulations are well known to those skilled in the cosmetic or topical pharmaceutical arts.

The term "excipient" generally refers to a carrier, a diluent and/or a medium required to prepare an effective pharmaceutical composition.

The term "effective amount" or "therapeutically effective amount", with respect to a pharmaceutical or pharmacologically active agent, refers to a sufficient amount of a drug or agent that is non-toxic but that achieves the desired effect. For oral dosage forms in the present disclosure, an "effective amount" of an active substance in a composition refers to the amount required to achieve the desired effect when used in combination with another active substance in the composition. The determination of the effective amount will vary from person to person, depending on the age and general condition of the recipient, and also depending on the particular active substance, and a suitable effective amount in an individual case can be determined by one skilled in the art based on routine experimentation.

The term "active ingredient", "therapeutic agent", "active substance" or "active agent" refers to a chemical entity that is effective in treating a target disorder, disease or condition.

"Optional" or "optionally" means that the subsequently described event or condition may, but is not necessarily, occur, and the description includes instances in which the event or condition occurs and instances in which the event or condition does not occur.

The term "substituted" means that any one or more hydrogen atoms on a particular atom are replaced by a substituent, and may include variants of heavy hydrogen and hydrogen, as long as the valence of the particular atom is normal and the substituted compound is stable. When the substituent is a keto group (ie, =O), it means that two hydrogen atoms are substituted. Keto substitution does not occur on the aryl group. The term "optionally substituted" means that it may or may not be substituted, and unless otherwise specified, the type and number of substituents may be arbitrary as long as it is chemically achievable.

When any variable (eg, R) occurs one or more times in the composition or structure of a compound, its definition in each case is independent. Thus, for example, if a group is substituted by 0-2 R groups, the group may optionally be substituted at most by two R groups, and R has an independent option in each case. Furthermore, combinations of substituents and/or variants thereof are permissible only if such combinations result in stable compounds.

When the number of one linking group is 0, such as —(CRR)$_0$—, it indicates that the linking group is a single bond.

When one of the variables is selected from a single bond, it means that the two groups to which it is attached are directly linked. For example, when L represents a single bond in A-L-Z, the structure is actually A-Z.

When a substituent is vacant, it means that the substituent is absent. For example, when X is vacant in A-X, the structure is actually A. When a substituent may be attached to one or more atoms on a ring, the substituent may be bonded to any atom on the ring. For example, the structural unit

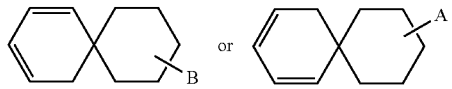

indicates that the substituent R can replace at any position in the cyclohexyl or cyclohexadiene. When the substituents listed do not indicate which atom is attached to the substituted group, such a substituent may be bonded through any atom thereof. For example, as a substituent, pyridyl can be attached to the substituted group through any carbon atom in the pyridine ring. When the listed linking group does not indicate its attachment direction, its attachment direction is arbitrary. For example, the linking group L in

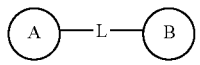

is -M-W—, and at this time -M-W— may connect the ring A and ring B to form

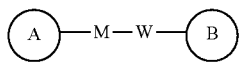

according to the direction the same as the reading direction of from left to right, or -M-W— may connect the ring A and ring B to form

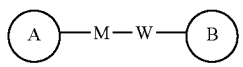

according to the direction opposite to the reading direction of from left to right. The combination of the linking groups, substituents and/or variants thereof is permitted only if such combination produces a stable compound.

Unless otherwise specified, the term "hetero" denotes a heteroatom or a heteroatom group (ie, a radical containing a heteroatom), including atoms other than carbon (C) and hydrogen (H), and radicals containing such heteroatoms, including, for example, oxygen (O), nitrogen (N), sulfur (S), silicon (Si), germanium (Ge), aluminum (Al), boron (B), —O—, —S—, =O, =S, —C(=O)O—, —C(=O)—, —C(=S)—, —S(=O), —S(=O)$_2$—, and optionally substituted —C(=O)N(H)—, —N(H)—, —C(=NH)—, —S(=O)$_2$N(H)— or —S(=O)N(H)—.

Unless otherwise specified, the term "heteroaryl" means a stable 5, 6, 7 membered monocyclic or bicyclic or 7, 8, 9 or 10 membered bicyclic heterocyclyl aromatic ring containing carbon atoms and 1, 2, 3 or 4 heterocyclic atoms independently selected from N, O and S. The nitrogen atom may be substituted or unsubstituted (i.e., N or NR, wherein R is H or other substituents as already defined herein). The nitrogen and sulfur heteroatoms may be optionally oxidized (i.e., NO and S(O)p, and p is 1 or 2). It is worth noting that the total number of S and O atoms on the aromatic heterocycle does not exceed one. Unless otherwise specified, the term "hydrocarbyl" or its specific term (such as alkyl, alkenyl, alkynyl, aryl, etc.), by itself or as a part of another substituent, is meant to be straight-chain, branched or cyclic hydrocarbon atom group or a combination thereof, may be fully saturated (such as an alkyl), monounsaturated or polyunsaturated (such as alkenyl, alkynyl, aryl), may be monosubstituted or polysubstituted, may be monovalent (such as methyl), divalent (such as methylene) or polyvalent (such as methine), may include divalent or multivalent radicals with a specified number of carbon atoms (eg, $C_1$-$C_{12}$ represents 1 to 12 carbons, $C_{1-12}$ is selected from the group consisting of $C_1$, $C_2$, $C_3$, $C_4$, $C_5$, $C_6$, $C_7$, $C_8$, $C_9$, $C_{10}$, $C_{11}$ and $C_{12}$; $C_{3-12}$ is selected from $C_3$, $C_4$, $C_5$, $C_6$, $C_7$, $C_8$, $C_9$, $C_{10}$, $C_{11}$ and $C_{12}$). "Hydrocarbyl" includes, but is not limited to, aliphatic hydrocarbyl and aromatic hydrocarbyl, wherein the aliphatic hydrocarbyl includes chained aliphatic hydrocarbyl and cyclic aliphatic hydrocarbyl, specifically including but not limited to alkyl, alkenyl, and alkynyl, and the aromatic hydrocarbyl includes but not limited to, 6-12 membered aromatic hydrocarbyl such as benzene, naphthalene or the like. In some embodiments, the term "hydrocarbyl" means a straight or branched chain radical or a combination thereof, which may be fully saturated, monounsaturated or polyunsaturated, and may include divalent and multivalent radicals. Examples of saturated hydrocarbon radicals include, but are not limited to, a homolog or isomer of radicals such as methyl, ethyl, n-propyl, isopropyl, n-butyl, t-butyl, isobutyl, sec-butyl, isobutyl, cyclohexyl, (cyclohexyl)methyl, cyclopropylmethyl, and n-pentyl, n-hexyl, n-heptyl and n-octyl. The unsaturated hydrocarbyl has one or more double or triple bonds, and examples thereof include, but are not limited to, vinyl, 2-propenyl, butenyl, crotyl, 2-isopentenyl, 2-(butadienyl), 2,4-pentadienyl, 3-(1,4-pentadienyl), ethynyl, 1- and 3-propynyl, 3-butynyl, and higher homologs and isomers.

Unless otherwise specified, the term "heterohydrocarbyl" or its specific term (such as heteroalkyl, heteroalkenyl, heteroalkynyl, heteroaryl, etc.), by itself or in combination with another term, means a stable straight-chain, branched, or cyclic hydrocarbon radical or a combination thereof having a certain number of carbon atoms and at least one heteroatom. In some embodiments, the term "heteroalkyl", by itself or in conjunction with another term, refers to a stable straight-chain or branched hydrocarbon radical or a combination thereof having a certain number of carbon atoms and at least one heteroatom. In a typical embodiment, the heteroatoms are selected from the group consisting of B, O, N, and S, wherein the nitrogen and sulfur atoms are optionally oxidized, and the nitrogen heteroatoms are optionally quaternized. The heteroatom or heteroatom group may be located at any internal position of the heterohydrocarbyl, including a position where the hydrocarbyl is attached to the rest of the molecule, but the terms "alkoxyl", "alkylamino" and "alkylthio" (or thioalkoxy) belong to a customary expression, and refer to those alkyl groups which are attached to the remainder of the molecule through an oxygen atom, an amino group or a sulfur atom, respectively. Examples include, but are not limited to, —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$—S(O)—CH$_3$, —CH$_2$—CH$_2$—S(O)$_2$—CH$_3$, —CH=CH—O—CH$_3$, —CH$_2$—CH=N—OCH$_3$ and —CH=CH—N(CH$_3$)—CH$_3$. At most two heteroatoms can be continuous, such as —CH$_2$—NH—OCH$_3$.

Unless otherwise specified, the term "alkyl" is used to denote a straight or branched saturated hydrocarbon group, which may be monosubstituted (eg, —CH$_2$F) or polysubstituted (eg, —CF$_3$), and may be monovalent (eg, methyl), divalent (such as methylene) or polyvalent (such as methine). Examples of the alkyl group include methyl (Me), ethyl (Et), propyl (e.g., n-propyl and isopropyl), butyl (e.g., n-butyl, isobutyl, s-butyl, and t-butyl), pentyl (eg, n-pentyl, isopentyl, and neopentyl) and the like.

Unless otherwise specified, a cycloalkyl group includes any stable cyclic or polycyclic hydrocarbon group, wherein any carbon atom is saturated, and may be monosubstituted or polysubstituted, and may be monovalent, divalent or multivalent. Examples of these cycloalkyl groups include, but are not limited to, cyclopropyl, norbornyl, [2.2.2]bicyclooctane, [4.4.0]bicyclodecane, etc.

Unless otherwise specified, "C$_{3-6}$ cycloalkyl" means a cyclic hydrocarbon group consisting of 3 to 6 carbon atoms which is a monocyclic and bicyclic system, and the C$_{3-6}$ cycloalkyl group includes C$_{3-5}$, C$_{4-5}$ and C$_{5-6}$ cycloalkyl, etc, which may be monovalent, divalent or multivalent. Examples of C$_{3-6}$ cycloalkyl groups include, but are not limited to, cyclopropyl, cyclobutyl, cyclopentyl, cyclohexyl, and the like.

Unless otherwise specified, the term "5-6 membered heterocycloalkyl", by itself or in combination with other terms, denotes a saturated cyclic group consisting of 5 to 6 ring atoms, respectively, having 1, 2, 3 or 4 ring atoms independently selected from O, S and N heteroatoms, the remainder being carbon atoms, wherein the nitrogen atom is optionally quaternized, and the nitrogen and sulfur heteroatoms are optionally oxidized (ie NO and S(O)$_p$, p is 1 or 2). It includes both monocyclic and bicyclic systems, wherein the bicyclic system includes a spiro ring, a fused ring, and a bridge ring. Further, in the case of the "5-6 membered heterocycloalkyl", a heteroatom may occupy a position where a heterocycloalkyl is bonded to the rest of the molecule. The 5-6 membered heterocycloalkyl includes 5-membered and 6-membered heterocycloalkyl. Examples of 5-6 membered heterocycloalkyl include, but are not limited to, pyrrolidinyl, pyrazolidinyl, imidazolidinyl, tetrahydrothiophenyl (including tetrahydrothiophen-2-yl and tetrahydrothiophen-3-yl, etc.), tetrahydrofuranyl (including tetrahydrofuran-2-yl, etc.), tetrahydropyranyl, piperidinyl (including 1-piperidinyl, 2-piperidinyl and 3-piperidinyl, etc.), piperazinyl (including 1-piperazinyl and 2-piperazinyl, etc.), morpholinyl (including 3-morpholinyl and 4-morpholinyl, etc.), dioxanyl, dithianyl, isoxazolidinyl, isothiazolidinyl, 1,2-oxazinyl, 1,2-thiazinyl, hexahydropyridazinyl, homopiperazinyl or homopiperidinyl and the like.

Unless otherwise specified, the term "halo" or "halogen", by itself or as a part of another substituent, refers to a fluorine, chlorine, bromine or iodine atom. Further, the term "haloalkyl" is intended to include both monohaloalkyl and polyhaloalkyl. For example, the term "halo(C$_1$-C$_4$)alkyl" is intended to include, but is not limited to, trifluoromethyl, 2,2,2-trifluoroethyl, 4-chlorobutyl, 3-bromopropyl, etc. Unless otherwise specified, examples of haloalkyl include, but are not limited to, trifluoromethyl, trichloromethyl, pentafluoroethyl and pentachloroethyl.

"Alkoxyl" represents the above alkyl group having a specified number of carbon atoms attached through an oxygen bridge, and unless otherwise specified, C$_{1-6}$ alkoxyl includes C$_1$, C$_2$, C$_3$, C$_4$, C$_5$ and C$_6$ alkoxyl. Examples of alkoxyl include, but are not limited to, methoxy, ethoxy, n-propoxy, isopropoxy, n-butoxy, sec-butoxy, tert-butoxy, n-pentyloxy and S-pentyloxy.

Unless otherwise specified, the term "aryl" denotes a polyunsaturated aromatic hydrocarbon substituent which may be monosubstituted or polysubstituted, may be monovalent, divalent or polyvalent, and may be monocyclic or polycyclic (for example, 1 to 3 rings; at least one of which is aromatic), they are fused together or covalently linked. The term "heteroaryl" refers to an aryl (or ring) containing one to four heteroatoms. In an illustrative example, the heteroatoms are selected from the group consisting of B, N, O, and S, wherein the nitrogen and sulfur atoms are optionally oxidized, and the nitrogen atom is optionally quaternized. Heteroaryl may be attached to the remaining part of the molecule through a heteroatom. Non-limiting examples of aryl or heteroaryl include phenyl, naphthyl, biphenyl, pyrrolyl, pyrazolyl, imidazolyl, pyrazinyl, oxazolyl, phenyloxazolyl, isoxazolyl, thiazolyl, furyl, thienyl, pyridyl, pyrimidinyl, benzothiazolyl, purinyl, benzimidazolyl, indolyl, isoquinolyl, quinoxalinyl, quinolyl, 1-naphthyl, 2-naphthyl, 4-biphenylyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidinyl, 4-pyrimidinyl, 5-benzothiazolyl, purinyl, 2-benzimidazolyl, 5-indolyl, 1-isoquinolinyl, 5-isoquinolinyl, 2-quinoxalinyl, 5-quinoxalinyl, 3-quinolyl and 6-quinolyl. The substituents of any of the above aryl and heteroaryl ring systems are selected from the group of acceptable substituents described below.

Unless otherwise specified, aryl, when used in conjunction with other terms (e.g., aryloxyl, arylthio, and aralkyl), include aryl and heteroaryl rings as defined above. Thus, the term "aralkyl" is intended to include those atomic groups (eg, benzyl, phenethyl, pyridylmethyl, etc.) in which an aryl group is attached to an alkyl group, including alkyl of which the carbon atom (eg, methylene) has been substituted by such as an oxygen atom, for example, phenoxymethyl, 2-pyridyloxymethyl 3-(1-naphthyloxy)propyl, etc.

The term "leaving group" refers to a functional group or atom which may be substituted by another functional group or atom by a substitution reaction (for example, a nucleophilic substitution reaction). For example, representative leaving groups include triflate; chlorine, bromine, and iodine; sulfonate groups such as methanesulfonate, tosylate, p-bromobenzene sulfonate, p-tosylate and the like; acyloxyl such as acetoxyl, trifluoroacetoxyl and the like.

The compounds of the present disclosure may be prepared by a variety of synthetic methods well known to those skilled in the art, including the specific embodiments set forth below, embodiments formed through combinations thereof with other chemical synthetic methods, and those equivalent alternatives well known to those skilled in the art, and preferred embodiments include, but are not limited to, embodiments of the present disclosure.

The solvent used in the present disclosure is commercially available. The present disclosure employs the following abbreviations: aq stands for water; HATU stands for O-(7-azabenzotriazol-1-yl)-N,N,N',N'-tetramethyl urea hexafluorophosphate; EDC stands for N-(3-dimethylaminopropyl)-N'-ethylcarbodiimide hydrochloride; m-CPBA stands for 3-chloroperoxybenzoic acid; eq stands for equivalent weight, and equal weight; CDI stands for carbonyl diimidazole; DCM stands for dichloromethane; PE stands for petroleum ether; DIAD stands for diisopropyl azodicarboxylate; DMF stands for N,N-dimethylformamide; DMSO stands for dimethyl sulfoxide; EtOAc represents ethyl acetate; EtOH represents ethanol; MeOH represents methanol; CBz represents benzyloxycarbonyl, an amine protecting group; BOC represents t-butylcarbonyl which is an amine protecting group; HOAc represents acetic acid; NaCNBH$_3$ represents sodium cyanoborohydride; r.t. represents room temperature; O/N stands for overnight; THF stands for tetrahydrofuran; Boc$_2$O stands for di-tert-butyldicarbonate; TFA stands for trifluoroacetic acid; DIPEA stands for diisopropylethylamine; SOCl$_2$ stands for thionyl chloride; CS$_2$ stands for carbon disulfide; TsOH stands for p-toluenesulfonic acid; NFSI stands for N-fluoro-N-(phenylsulfonyl)benzenesulfonamide; NCS stands for 1-chloropyrrolidine-2,5-dione; n-Bu$_4$NF stands for tetrabutylammonium fluoride; iPrOH stands for 2-propanol; mp stands for a melting point; LDA stands for lithium diisopropylamide; TBAF stands for tetrabutylammonium fluoride.

Compounds are named by hand or by ChemDraw® software, and commercial compounds are based on supplier catalog names.

Technical Effect

The compounds of the present disclosure were all tested for human recombinant VAP-1 enzyme activity, and the data showed that the activity of the compound was less than 1 nM, which was much better than the current clinical compound PXS-4728A; the PK results showed that the bioavailability of the compound of the present disclosure was close to 100%. It is a good molecule that can be developed for oral administration, and because of the high distribution of compounds in the liver, the liver/blood ratio is high, which is the advantage of developing liver drugs.

The compounds of the present disclosure exhibit excellent anti-inflammatory and anti-fibrotic pharmaceutical effects in the carbon tetrachloride model of mice, and have good pharmaceutical effects at low doses.

DETAILED DESCRIPTION

Figure 1:
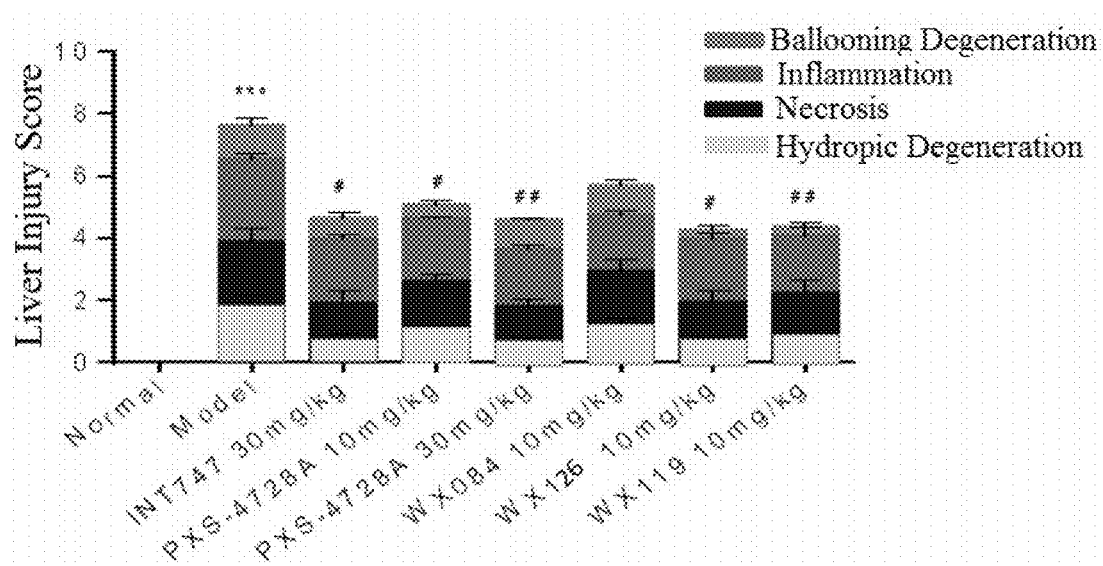
FIG. 1: Results of liver injury scores.

The present disclosure is described in detail below by the examples, but is not intended to adversely limit the present disclosure. The present disclosure has been described in detail herein, the embodiments of the present disclosure are disclosed herein, and various modifications and changes may be made to the embodiments of the present disclosure without departing from the spirit and scope of the present disclosure, which is obvious for those skilled in the art.

Reference Example 1: Fragment BB-1

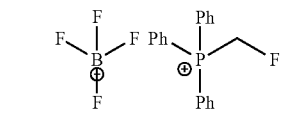

Synthesis Route:

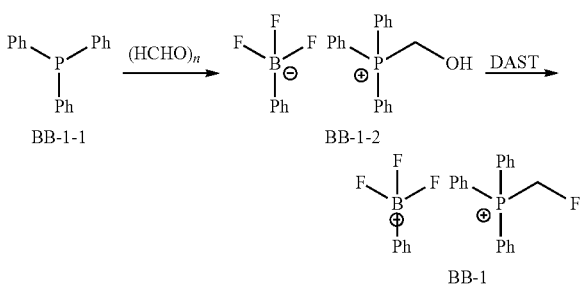

Step 1: Synthesis of Compound BB-1-2

Boron trifluoride hydrofluorate (274.11 g, 1.25 mol, 194.40 mL, 40% purity) was slowly added dropwise to a diethyl ether solution (700 mL) of a compound BB-1-1 (131.00 g, 499.47 mmol) and paraformaldehyde (44.99 g, 499.47 mmol). After the addition was completed, the reaction solution was stirred at 15° C. for 72 hours. After completion of the reaction, the reaction solution was filtered and washed with 200 mL of diethyl ether to give the compound BB-1-2. $^1$H NMR (400 MHz, CDCl$_3$) δ: 7.78-7.87 (m, 3H), 7.64-7.73 (m, 12H), 5.36 (s, 2H), 4.79 (br.s., 1H), 31P NMR (162 MHz, CHLOROFORM-d) δ 17.55 (s, 1P).

Step 2: Synthesis of Compound BB-1

DAST (37.85 g, 234.79 mmol, 31.02 mL) was slowly added dropwise to a dichloromethane (400 mL) solution of the compound BB-1-2 (85.00 g, 223.61 mmol) at 0° C. After the addition was completed, the reaction solution was stirred at 20° C. for 20 hours. After the completion of the reaction, the reaction was quenched with water (250 mL), the system was stirred at 0° C. for 15 minutes, the organic layer was separated, washed with 250 mL 5% sodium bicarbonate aqueous solution, and concentrated under reduced pressure to obtain a crude product, and the crude product was recrystallized with diethyl ether:dichloromethane=1:1 (600 mL) to obtain the target product BB-1. $^1$H NMR (400 MHz, CDCl$_3$) δ: 7.83-7.94 (m, 2H), 7.66-7.79 (m, 9H), 7.41-7.57 (m, 2H), 7.08-7.22 (m, 2H), 6.22-6.40 (m, 1H), 3.65-3.73 (m, 1H).

Reference Example 2: Fragment BB-2

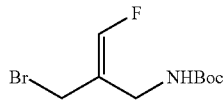

Synthesis Route:

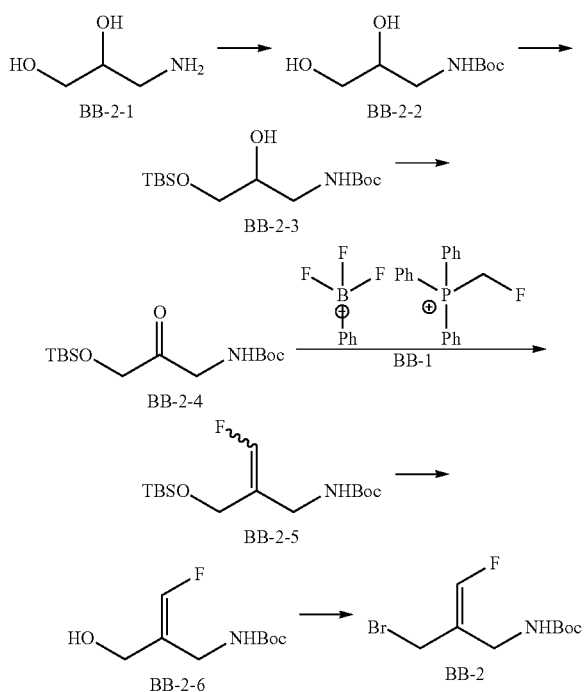

Step 1: Synthesis of Compound BB-2-2

Triethylamine (134.16 g, 1.33 mol, 183.78 mL) and Boc$_2$O (210.80 g, 965.87 mmol, 221.89 mL) were added to a methanol (1.60 L) solution of a compound BB-2-1 (80.00 g, 878.06 mmol, 67.80 mL), and the reaction solution was stirred at 15° C. for 12 hours. After the reaction was completed, the solvent was removed under reduced pressure to obtain the compound BB-2-2. The product did not need to be purified and was directly used for the next step. 1H NMR (400 MHz, CHLOROFORM-d) δ 5.32 (br s, 1H), 3.69-3.79 (m, 2H), 3.51-3.63 (m, 2H), 3.24 (td, J=5.80, 15.00 Hz, 2H), 1.44 (s, 9H).

Step 2: Synthesis of Compound BB-2-3

Imidazole (79.04 g, 1.16 mol) and TBSCl (160.40 g, 1.06 mol, 130.41 ml) were added to a dichloromethane (2.40 L) solution of the compound BB-2-2 (185.00 g, 967.47 mmol) at 0° C., and the reaction solution was stirred at 0° C. for 2 hours. After the reaction was completed, 1.50 L of water was added to quench the reaction. The system was extracted with dichloromethane (500 mL×3), and the organic layer was washed with water (200 mL×2) and dried with anhydrous sodium sulfate, and after the drying agent was filtered and removed, the filtrate was decompressed to remove the solvent to obtain the target compound BB-2-3. 1H NMR (400 MHz, CHLOROFORM-d) δ 5.05 (br s, 1H), 3.71 (br s, 1H), 3.45-3.65 (m, 2H), 3.30 (br s, 1H), 3.04-3.15 (m, 1H), 2.98 (br s, 1H), 1.42 (br s, 9H), 0.83-0.97 (m, 9H), 0.05 (s, 6H).

Step 3: Synthesis of Compound BB-2-4

A dichloromethane (300 mL) solution of the compound BB-2-3 (30.00 g, 98.21 mmol) and DMP (62.48 g, 147.31 mmol) was stirred at 20° C. for 20 hours. After the reaction was completed, a sodium sulfite aqueous solution (350 mL) was added to quench the reaction, and the organic layer was separated. The organic layer was washed with a saturated sodium bicarbonate solution (350 mL), and concentrated under reduced pressure. The resulting residue was separated by a chromatography column (eluent: petroleum ether/ethyl acetate=10:1-8:1) to obtain the target compound BB-2-4. 1H NMR (400 MHz, CHLOROFORM-d) δ 5.01-5.23 (m, 1H), 4.15 (s, 4H), 1.36 (s, 9H), 0.83 (s, 9H), 0.00 (s, 6H).

Step 4: Synthesis of Compound BB-2-5

NaHMDS (1M, 4.95 mL) was slowly added dropwise to a tetrahydrofuran (20.00 mL) solution of the compound BB-2-4 (1.89 g, 4.95 mmol) under nitrogen protection at −78° C., and the reaction system was stirred for 1 hour at −78° C. At this temperature, the compound BB-1 (1.00 g, 3.30 mmol) was added to the system, and the system was slowly heated up to 20° C. after 1 hour, and the reaction solution was stirred at 20° C. for 18 hours. After the reaction was completed, a saturated ammonium chloride solution (20 mL) was used to quench the reaction, extraction was performed with ethyl acetate (30 mL), the organic layer was separated, and the organic phase was washed with water (20.0 mL), and concentrated under reduced pressure, and the resulting residue was separated by a chromatography column (eluent: petroleum ether/ethyl acetate=20:1-10:1) to obtain the target compound BB-2-5. 1H NMR (400 MHz, CHLOROFORM-d) δ 6.38-6.69 (m, 1H), 4.84 (br s, 1H), 4.02 (dd, J=1.00, 4.52 Hz, 2H), 3.81 (br d, J=3.76 Hz, 2H), 1.36 (s, 9H), 0.81-0.84 (m, 9H), 0.00 (s, 6H).

Step 5: Synthesis of Compound BB-2-6

The compound BB-2-5 (310.00 mg, 970.30 μmop was dissolved in tetrahydrofuran (3.00 mL), and stirred for 10 minutes at 0° C., and TBAF (1 M, 1.16 mL) was slowly added to the system. After the addition was completed, the reaction solution was stirred at 20° C. for 16 hours.

After the reaction was completed, the reaction solution was concentrated under reduced pressure, and the resulting residue was separated by a chromatography column (eluent: petroleum ether/ethyl acetate=3:1-2:1) to obtain the target compound BB-2-6. 1H NMR (400 MHz, CHLOROFORM-d) δ 6.43-6.82 (m, 1H), 4.94 (br s, 1H), 3.90-4.02 (m, 4H), 3.74 (br s, 1H), 1.45 (s, 9H).

Step 6: Synthesis of Compound BB-2

An acetone (10.00 mL) solution of the compound BB-2-6 (120.00 mg, 584.71 μmol), methane sulfonyl chloride (300.00 mg, 2.62 mmol, 202.70 μL) and triethylamine (295.83 mg, 2.92 mmol, 405.25 μL) was stirred at 20° C. for 1 hour, and the precipitate was filtered and washed with an acetone (10.00 mL) solution. The solution was stirred at 20° C. for 5 minutes, then lithium bromide (253.91 mg, 2.92 mmol) was added to the system, and the reaction solution was continuously stirred at 20° C. for 20 hours. After the reaction was completed, the reaction solution was concentrated under reduced pressure, and the resulting residue was separated by a chromatography column (developing solvent: ethyl acetate/petroleum ether=1:10) to obtain the target compound BB-2. 1H NMR (400 MHz, CHLOROFORM-d) δ 6.60-6.90 (m, 1H), 4.63-4.85 (m, 1H), 3.92-4.11 (m, 4H), 1.45 (s, 9H).

Reference Example 3: Fragment BB-3

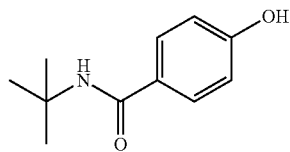

Synthesis Route:

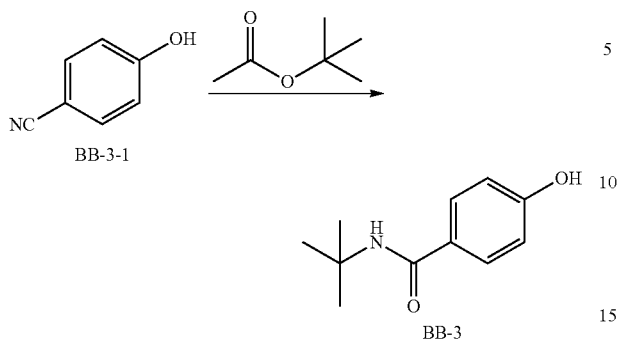

Step 1: Synthesis of Compound BB-3

The reaction system of a compound BB-3-1 (20.00 g, 167.90 mmol), tert-butyl acetate (19.50 g, 167.90 mmol), acetic acid (175.03 g, 2.91 mol) and sulfuric acid (29.64 g, 302.22 mmol) was stirred for 20 hours at room temperature. After the reaction was completed, 200 mL of water and 400 mL of ethyl acetate were added into the reaction system, and the organic layer was separated. The organic layer was washed with 200 mL of water and 200 mL of a saturated sodium bicarbonate aqueous solution, respectively. Then the organic layer was decompressed to remove the solvent to obtain the target compound BB-3. 1H NMR (400 MHz, DMSO-d6) δ 9.40-10.42 (m, 1H), 7.69 (d, J=8.53 Hz, 2H), 7.46 (s, 1H), 6.77 (d, J=8.53 Hz, 2H), 1.37 (s, 9H), MS m/z: 194.2 [M+H]$^+$.

Reference Example 4: Fragment BB-4

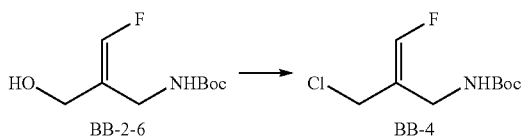

Synthesis Route:

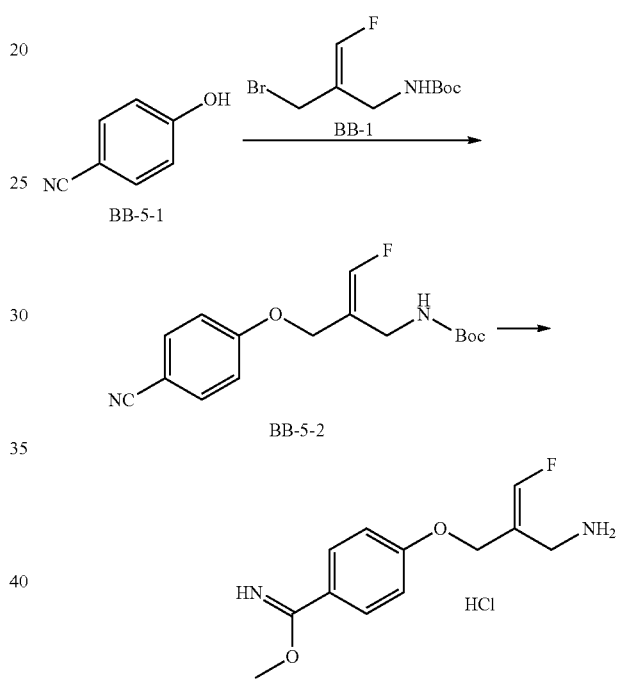

Step 1: Synthesis of Compound BB-4

A dichloromethane (25.00 mL) solution of the compound BB-2-6 (5.00 g, 24.36 mmol), methane sulfonyl chloride (3.0 g, 26.19 mmol) and triethylamine (3.70 g, 36.54 mmol, 5.07 mL) was stirred at 20° C. for 6 hours. After the reaction was completed, water (50 mL) was added to quench the reaction, the reaction solution was extracted with methyl tert-butyl ether (60 mL×2), washed with salt water (50 mL×2), dried with anhydrous Na$_2$SO$_4$, filtered, and concentrated under reduced pressure, and the obtained crude product was crystallized with (methyl tert-butyl ether/petroleum ether=1:1, 30 mL) to obtain the target compound BB-2. $^1$H NMR (400 MHz, CHLOROFORM-d) δ=6.88-6.62 (m, 1H), 4.76 (br s, 1H), 4.07 (d, J=3.3 Hz, 2H), 4.01 (br d, J=3.9 Hz, 2H), 1.47 (s, 9H).

Reference Example 5: Fragment BB-5

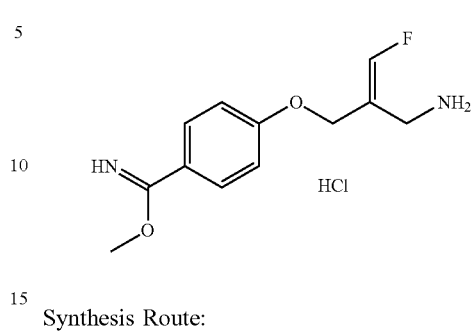

Synthesis Route:

Step 1: Synthesis of Compound BB-5-2

A compound BB-5-1 (3.00 g, 11.19 mmol, 1.00 eq) and a compound BB-1 (1.33 g, 11.19 mmol, 1.00 eq) were dissolved in N,N-dimethylformamide (30.00 mL), then potassium carbonate (2.32 g, 16.79 mmol, 1.50 eq) was added at 25° C., and the system was stirred at 25° C. for 5 hours. Sodium hydroxide (1M, 40 ml) and ethyl acetate (20 ml) were added to the system, and the organic phase was washed with saturated salt water (10 ml×3). The system was concentrated to be dry through a water pump to obtain a crude product WX035-2. MS m/z: 307.1 [M+H]

Step 2: Synthesis of Compound BB-5

BB-5-2 (500.00 mg, 1.63 mmol, 1.00 eq) was dissolved in methanol (10.00 mL) and cooled to −60° C. Hydrogen chloride gas was introduced for 1 hour, and then the system was stirred at 20° C. for 2 hours. The system was concentrated to be dry through a water pump to obtain a crude product WX035-3 (500.00 mg, crude product) which was yellow and oily. 1H NMR (400 MHz, DMSO).

Reference Example 6: Fragment BB-6

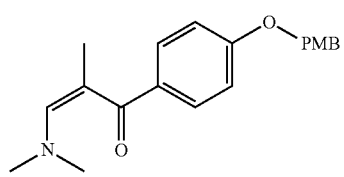

Synthesis Route:

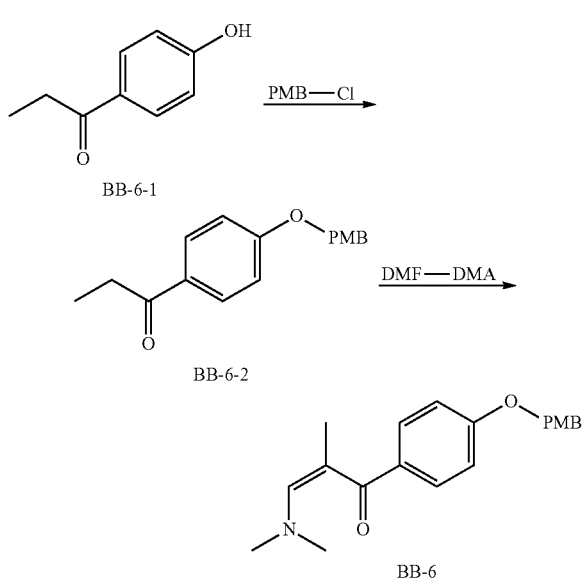

Step 1: Synthesis of Compound BB-6-2

PMB-Cl (5.48 g) was added to a DMF (10 mL) mixture of a compound BB-6-1 (5 g) and potassium carbonate (9.2 g) and a reaction was carried out at 40° C. under the protection of nitrogen for 12 hours. The reaction liquid was poured into water (200 mL) and the solid was collected to obtain the compound BB-6-2.

1H NMR (400 MHz, CHLOROFORM-d) δ=7.99-7.92 (m, 2H), 7.37 (d, J=8.7 Hz, 2H), 7.03-6.91 (m, 4H), 5.06 (s, 2H), 3.83 (s, 3H), 2.96 (d, J=7.3 Hz, 1H), 2.99-2.92 (m, 1H), 1.22 (t, J=7.2 Hz, 3H)

Step 2: Synthesis of Compound BB-6

A DMF-DMA solution (5.00 mL) of the compound BB-6-2 was stirred at 100° C. for 36 hours under nitrogen protection. The reaction solution was spin-dried to be used directly for the next step.

$^1$H NMR (400 MHz, CHLOROFORM-d) δ=7.43-7.31 (m, 4H), 7.00-6.83 (m, 6H), 5.01 (s, 2H), 3.82 (s, 3H), 3.05 (s, 6H), 2.29-2.25 (m, 2H), 2.13 (s, 3H)

Reference Example 7: Fragment BB-7

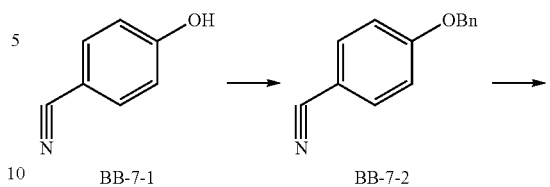

Step 1: Synthesis of Compound BB-7-2

Benzyl bromide (4.74 g, 27.70 mmol, 3.29 mL, 1.1 eq) was added to an acetone solution (50 mL) of a compound BB-7-1 (3.00 g, 25.18 mmol, 1 eq) and potassium carbonate (13.92 g, 100.74 mmol, 4 eq) at 0° C. The mixture was stirred at 40° C. for 3 hours. The reaction solution was poured into 100 mL of water, was extracted by ethyl acetate (50 mL×4) and concentrated to obtain the target compound BB-7-2.

Step 2: Synthesis of Compound BB-7

Hydrogen chloride gas was introduced into a methanol solution (2.00 mL) of the compound BB-7-2 (1.00 g, 4.78 mmol, 1 eq) at −30° C. for half an hour. The obtained mixture was reacted at 25° C. for 2 hours. The reaction solution was spin-dried to obtain the target compound BB-7.

Example 1: WX004

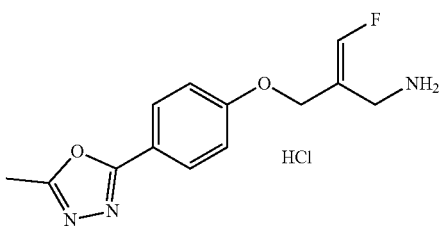 [SMILES: Cc1nnc(-c2ccc(OC/C(=C/F)CN)cc2)o1 ; Cl]

Synthesis Route:

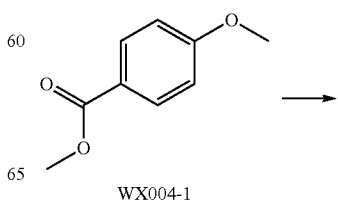

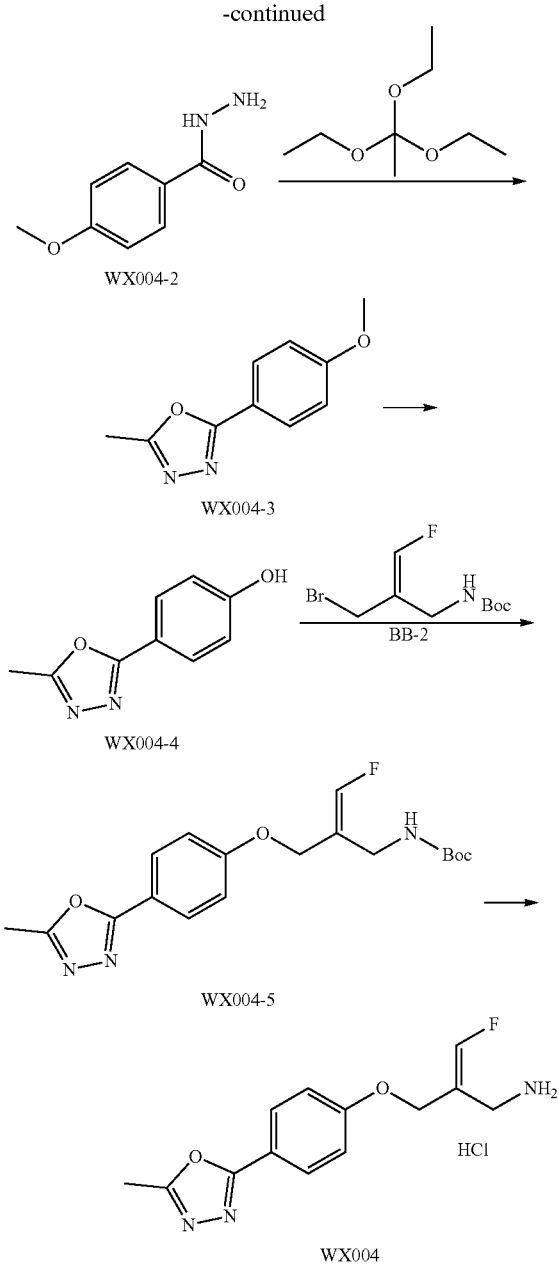

δ 7.95-8.00 (m, 2H), 6.99-7.04 (m, 2H), 3.89 (s, 3H), 2.58-2.64 (m, 3H), MS m/z: 191.2 [M+H]$^+$.

Step 3: Synthesis of Compound WX004-4

The compound WX004-3 (200.00 mg, 1.05 mmol) was dissolved in a dichloromethane (10.00 mL) solution, and boron tribromide (526.09 mg, 2.10 mmol, 202.34 μL) was added at 0° C., and the mixture was heated to 20° C. and stirred for 16 hours. After the reaction was completed, the reaction was quenched with 10 mL of a saturated sodium bicarbonate solution, the reaction solution was extracted with ethyl acetate (50 mL), and concentrated to obtain WX004-4, MS m/z: 177.2 [M+H]$^+$.

Step 4: Synthesis of Compound WX004-5

The compound WX004-4 (150.00 mg, 851.45 μmop was dissolved in anhydrous DMF (10.00 mL), then potassium carbonate (176.52 mg, 1.28 mmol) and the compound BB-2 (228.29 mg, 851.45 μmol) were added sequentially. The suspension solution was stirred at 20° C. for 20 hours, and the LCMS was used to test the completion of the reaction. 50 mL of water and 150 mL of ethyl acetate were added to quench the reaction, the organic phase was separated and washed with 50 mL of water, and then spin-dried to get a crude product. The crude product was purified by column chromatography (developing solvent: petroleum ether/ethyl acetate=1:1) to obtain the target compound WX004-5. 1H NMR (400 MHz, CHLOROFORM-d) δ 7.95-7.98 (m, 2H), 6.98-7.03 (m, 2H), 6.65-6.89 (m, 1H), 4.76 (br d, J=2.51 Hz, 1H), 4.51 (d, J=3.51 Hz, 2H), 4.02 (br d, J=4.52 Hz, 2H), 2.60 (s, 3H), 1.41 (s, 9H), 19F NMR (377 MHz, CHLOROFORM-d) δ -128.22 (br s, 1F), MS m/z: 364.4 [M+H]$^+$.

Step 5: Synthesis of Compound WX004

The compound WX004-5 (200.00 mg, 550.39 μmop was dissolved in ethyl acetate (4.00 mL), and ethyl acetate hydrochloride (4 M, 137.60 μL) was added at 0° C. The reaction was stirred at 20° C. for 1 hour. After the reaction was completed, the solvent was removed under reduced pressure, and the resulting residue was separated by preparative chromatography (HCl system) to obtain the target compound WX004.

1H NMR (400 MHz, DMSO-d6) δ 8.42 (br s, 3H), 7.93 (br d, J=8.53 Hz, 2H), 7.24-7.48 (m, 1H), 7.20 (br d, J=8.78 Hz, 2H), 4.76 (br d, J=2.76 Hz, 2H), 3.61 (br s, 2H), 2.56 (s, 3H), 19F NMR (376 MHz, DMSO-d6) δ -122.43 (br s, 1F), MS m/z: 264.4 [M+H]$^+$.

Example 2: WX008

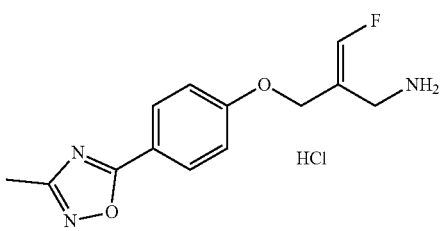 [SMILES: Cc1noc(-c2ccc(OC/C(=C/F)CN)cc2)n1 ; Cl]

Step 1: Synthesis of Compound WX004-2

A liquid mixture of a compound WX004-1 (4.70 g, 28.28 mmol) and hydrazine hydrate (20.00 ml) was stirred at 120° C. for 2 hours. After the reaction was completed, the reaction solution was concentrated under reduced pressure to obtain the target compound WX004-2 which was directly used in the next reaction step without purification, MS m/z: 167.2 [M+H]$^+$.

Step 2: Synthesis of Compound WX004-3

A solution of the compound WX004-2 (3.20 g, 19.26 mmol) and triethyl orthoacetate (32.08 g, 197.76 mmol, 36.05 mL) was stirred at 120° C. for 2 hours. After the reaction was completed, the reaction solution was concentrated under reduced pressure, and the resulting residue was separated by a chromatography column (developing agent: petroleum ether/ethyl acetate=2:1) to obtain the target compound WX004-3. 1H NMR (400 MHz, CHLOROFORM-d)

Synthesis Route:

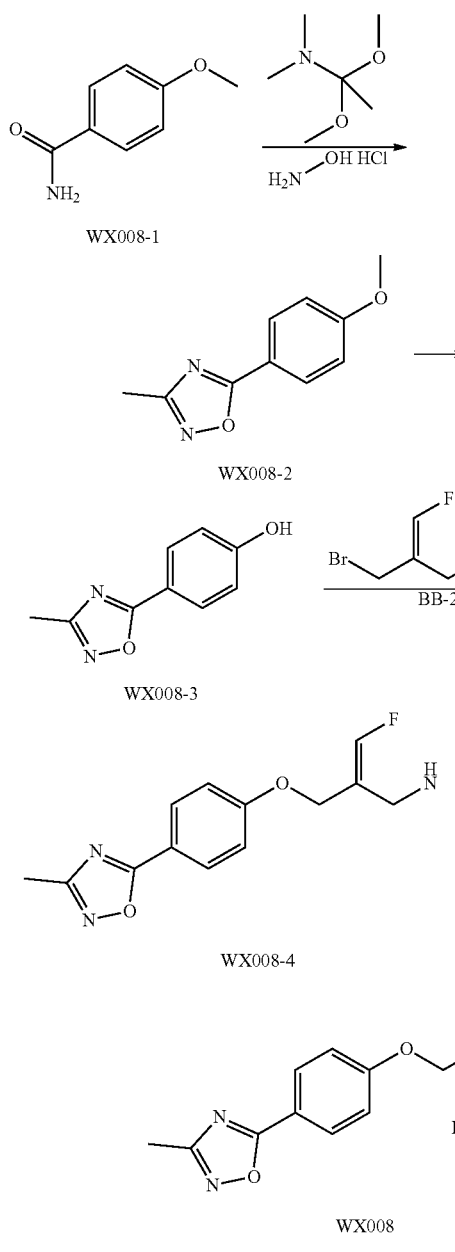

Step 1: Synthesis of Compound WX008-2

A solution of a compound WX008-1 (2.00 g, 13.23 mmol) and 1,1-dimethoxy-N,N-dimethylethylamine (8.81 g, 66.15 mmol, 9.68 mL) was reacted at 120° C. for 3 hours. After the mixture was concentrated under reduced pressure, the residue was dissolved in 20.00 mL of dioxane and 25.00 mL of acetic acid. Sodium hydroxide (1 M, 18.52 mL) and hydroxylamine hydrochloride (1.29 g, 18.52 mmol) were added to the system. The reaction mixture was reacted for 3 hours at 20° C. and for 16 hours at 90° C. After the reaction was completed, 80.00 mL of water was added to extract the reaction, and 250.00 mL of ethyl acetate was used for extraction, the organic layer was separated and concentrated under reduced pressure. The crude product was purified by column chromatography (petroleum ether/ethyl acetate=10:1) to obtain the compound WX008-2. 1H NMR (400 MHz, CHLOROFORM-d) δ 8.05 (d, J=9.03 Hz, 2H), 6.74-7.10 (m, 2H), 3.73-3.97 (m, 3H), 2.45 (s, 3H).

Step 2: Synthesis of Compound WX008-3

The synthesis of the compound WX008-3 referred to the synthesis method of the step 3 in Example 1. $^1$H NMR (400 MHz, CHLOROFORM-d) δ 8.37-8.25 (m, 2H), 7.33-7.27 (m, 2H), 7.12 (d, J=8.8 Hz, 1H), 7.15-7.09 (m, 1H), 4.05-3.90 (m, 1H), 3.74 (br d, J=4.0 Hz, 1H), 3.62 (br d, J=15.3 Hz, 1H), 3.26-3.04 (m, 1H), 2.78 (br d, J=3.8 Hz, 2H), 2.60 (br d, J=14.6 Hz, 2H), 1.91-1.72 (m, 4H), 1.57 (s, 9H), 1.43 (s, 9H), MS m/z: 177.2 [M+H]$^+$.

Step 3: Synthesis of Compound WX008-4

The synthesis of the compound WX008-4 referred to the synthesis method of the step 4 in Example 1, MS m/z: 364.4 [M+H]$^+$.

Step 4: Synthesis of Compound WX008

The synthesis of the compound WX008 referred to the synthesis method of the step 5 in Example 1. 1H NMR (400 MHz, DEUTERIUM OXIDE) δ 7.75 (br d, J=9.03 Hz, 2H), 7.06 (6, J=84.00 Hz, 1H), 6.96 (br d, J=8.53 Hz, 2H), 4.58 (br d, J=2.51 Hz, 2H), 3.78 (br s, 2H), 2.24 (s, 3H), 19F NMR (377 MHz, DEUTERIUM OXIDE) δ −120.31 (s, 1F), MS m/z: 264.4 [M+H]$^+$.

Example 3: WX009

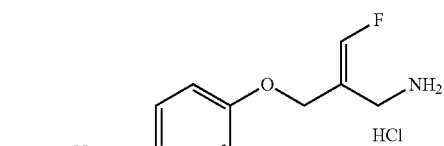

Synthesis Route:

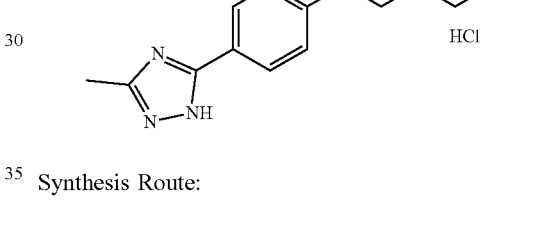

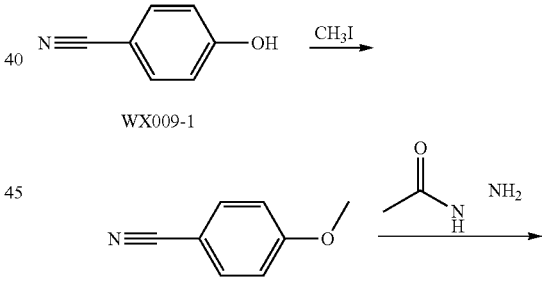

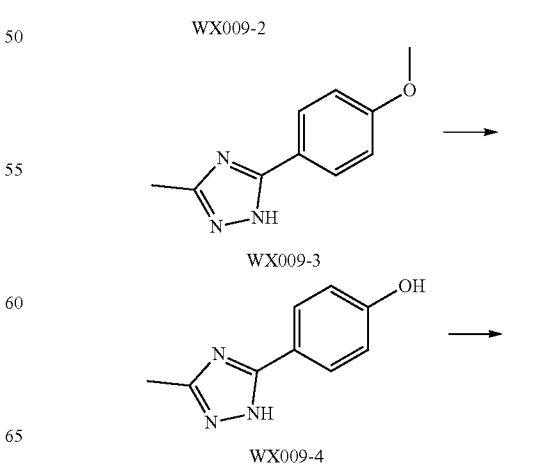

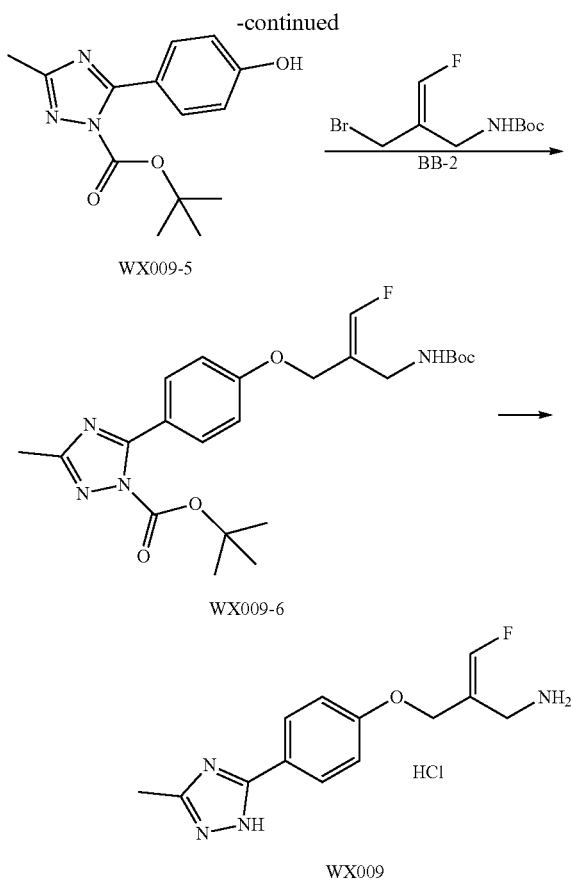

Step 1: Synthesis of Compound WX009-2

A compound WX009-1 (10.00 g, 83.95 mmol) was dissolved in acetone (100.00 mL), and potassium carbonate (23.21 g, 167.90 mmol) and iodomethane (19.44 g, 136.96 mmol, 8.53 ml) were added. The reaction mixture was reacted at 60° C. for 12 hours. After the reaction was completed, the mixture was concentrated under reduced pressure, and the crude product was dissolved in 100.00 mL of ethyl acetate and filtered, and the filtrate was concentrated to obtain the compound WX009-2. $^1$H NMR (400 MHz, CHLOROFORM-d) δ 7.59 (d, J=9.0 Hz, 2H), 7.26 (s, 1H), 6.95 (d, J=9.0 Hz, 2H), 3.86 (s, 3H).

Step 2: Synthesis of Compound WX009-3

Potassium carbonate (1.87 g, 13.50 mmol) was added to a n-butanol (10.00 mL) liquid mixture of the compound WX009-2 (1.80 g, 13.50 mmol) and acetyl hydrazine (1.00 g, 13.50 mmol), and the mixture was subjected to a microwave reaction at 150° C. for 2 hours. After the reaction was completed, 20.00 mL of water was added to quench the reaction, and the reaction solution was extracted with ethyl acetate (20.00 mL×2), and the organic layers were mixed, washed with 20.00 mL of water and 20.00 mL of salt water respectively, dried with anhydrous sodium sulfate, and filtered and concentrated. The crude product was purified by column chromatography (petroleum ether/ethyl acetate=2:1-1:1) to obtain the compound WX009-3. $^1$H NMR (400 MHz, CHLOROFORM-d) δ 8.00-7.89 (m, 2H), 7.79 (d, J=8.8 Hz, 1H), 6.92 (dd, J=2.3, 8.8 Hz, 3H), 6.08 (br s, 1H), 3.85 (s, 2H), 3.83 (s, 3H), 2.53-2.42 (m, 3H).

Step 3: Synthesis of Compound WX009-4

A hydrobromic acid acetic acid (10.00 mL) solution of the compound WX009-3 (200.00 mg, 1.06 mmol) was sealed for a reaction at 100° C. for 12 hours. After the reaction was completed, the reaction solution was concentrated under reduced pressure, and the crude product was purified by column chromatography (dichloromethane/methanol=1:0-10:1) to obtain the compound WX009-4. $^1$H NMR (400 MHz, METHANOL-$d_4$) δ=7.81-7.76 (m, 2H), 6.91-6.85 (m, 2H), 2.57-2.32 (m, 3H).

Step 4: Synthesis of Compound WX009-5

The compound WX009-4 (100.00 mg, 570.81 μmol) was dissolved in anhydrous dichloromethane (10 mL). Triethylamine (173.28 mg, 1.71 mmol) and $Boc_2O$ (149.49 mg, 684.97 μmol) were sequentially added at 25° C., and the reaction was kept to be stirred at 25° C. for 12 hours. TLC (petroleum ether/ethyl acetate=1:3) showed the end of the reaction, and LCMS detected the target molecular weight. After the reaction was quenched with water (100 mL), extraction was performed with dichloromethane (100 mL), and the organic phase was spin-dried to obtain a crude product. The crude product was purified by column chromatography (petroleum ether/ethyl acetate=10:1 to 1:3) to obtain the target product WX009-5. $^1$H NMR (400 MHz, CHLOROFORM-d) δ 7.96 (d, J=8.5 Hz, 2H), 6.81 (d, J=8.5 Hz, 2H), 2.69 (s, 3H), 1.61 (s, 9H), MS m/z: 276.3 $[M+H]^+$.

Step 5: Synthesis of Compound WX009-6

The synthesis of the compound WX009-6 referred to the synthesis method of the step 4 in Example 1, $^1$H NMR (400 MHz, CHLOROFORM-d) δ 8.09 (d, J=9.0 Hz, 2H), 7.02-6.92 (m, 2H), 6.88 (s, 1H), 6.67 (s, 1H), 4.49 (br s, 2H), 4.02 (br s, 2H), 2.77 (s, 3H), 1.69 (s, 9H), 1.42 (s, 9H), MS m/z: 463.5 $[M+H]^+$.

Step 6: Synthesis of Compound WX009

The synthesis of the compound WX009 referred to the synthesis method of the step 5 in Example 1, $^1$H NMR (400 MHz, DEUTERIUM OXIDE) δ 7.79 (d, J=8.8 Hz, 2H), 7.16 (s, 1H), 7.07 (d, J=8.8 Hz, 2H), 6.96 (s, 1H), 4.62 (d, J=3.0 Hz, 2H), 3.80 (s, 2H), 2.43 (s, 3H), MS m/z: 363.5 $[M+H]^+$.

Example 4: WX014

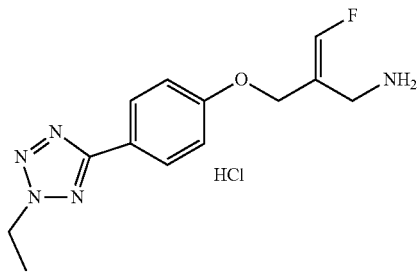 [SMILES: CCn1nnc(-c2ccc(OC/C(=C/F)CN)cc2)n1 ; Cl]

Synthesis Route:

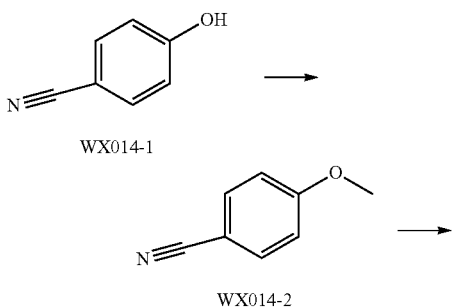

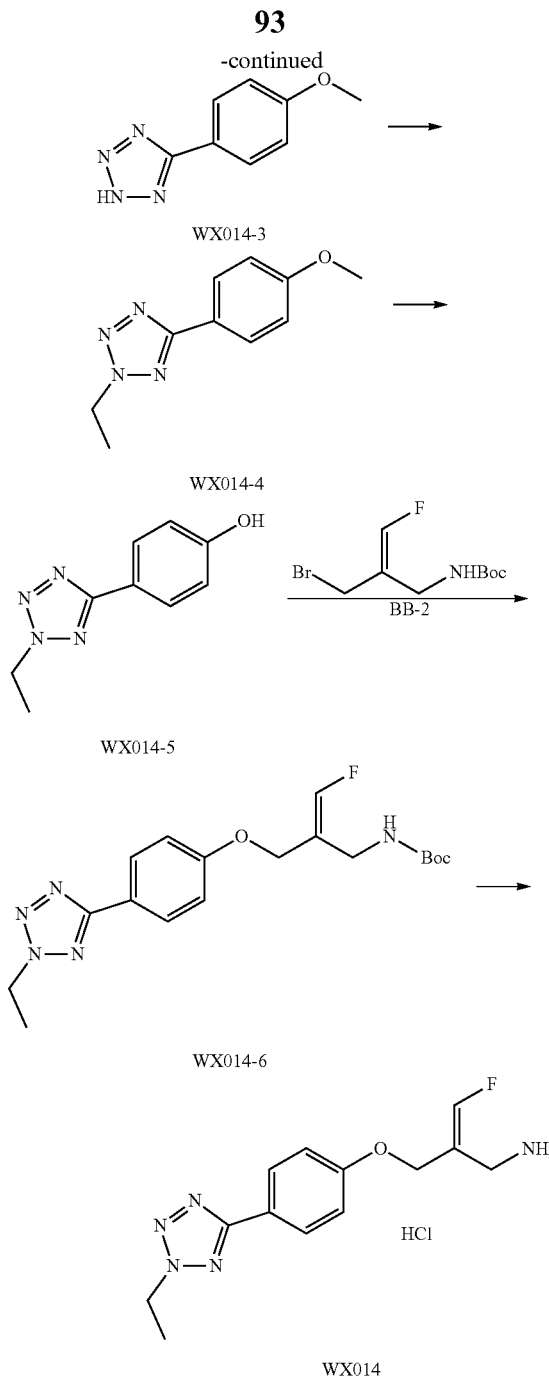

filtered to obtain the compound WX014-3. 1H NMR (400 MHz, DMSO-d6) δ 7.90-8.10 (m, 2H), 7.04-7.27 (m, 2H), 3.84 (s, 3H), 3.42 (br s, 1H).

Step 3: Synthesis of Compound WX014-4

A N,N-dimethylformamide (10.00 mL) solution of the compound WX014-3 (500.00 mg, 2.84 mmol), potassium carbonate (784.48 mg, 5.68 mmol) and bromoethane (463.89 mg, 4.26 mmol, 317.73 μL) was reacted at 20° C. for 16 hours. After the reaction was completed, a saturated ammonium chloride solution (50 mL) and ethyl acetate (100 mL) were added, the organic phase was separated, washed with 50 mL of water, and concentrated under reduced pressure to obtain the compound WX014-4. MS m/z: 205.2 [M+H]⁺.

Step 4: Synthesis of Compound WX014-5

The compound WX014-5 was synthesized according to the synthesis method of the step 3 in Example 1, ¹H NMR (400 MHz, DMSO-d6) δ 7.81-8.00 (m, 2H), 6.84-6.95 (m, 2H), 4.71 (q, J=7.53 Hz, 2H), 1.55 (t, J=7.28 Hz, 3H), MS m/z: 191.2 [M+H]⁺.

Step 5: Synthesis of Compound WX014-6

The synthesis of the compound WX014-6 referred to the synthesis method of the step 4 in Example 1, MS m/z: 378.4 [M+H]+.

Step 6: Synthesis of Compound WX014

The synthesis of the compound WX004 referred to the synthesis method of the step 5 in Example 1, ¹H NMR (400 MHz, DMSO-d6) δ 8.22 (br s, 3H), 8.02 (d, J=8.53 Hz, 2H), 7.25-7.47 (m, 1H), 7.18 (d, J=9.03 Hz, 2H), 4.71-4.78 (m, 2H), 4.71 (d, J=2.51 Hz, 2H), 3.64 (br s, 2H), 1.57 (t, J=7.28 Hz, 3H), MS m/z: 278.3 [M+H]⁺.

Example 5: WX016

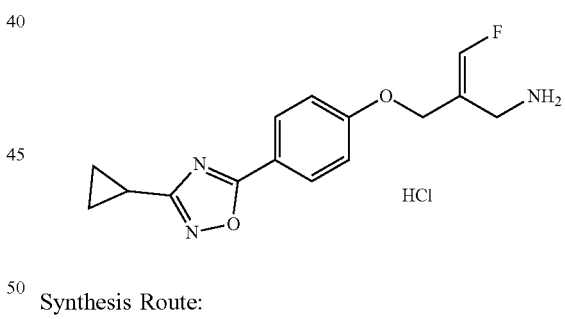

Synthesis Route:

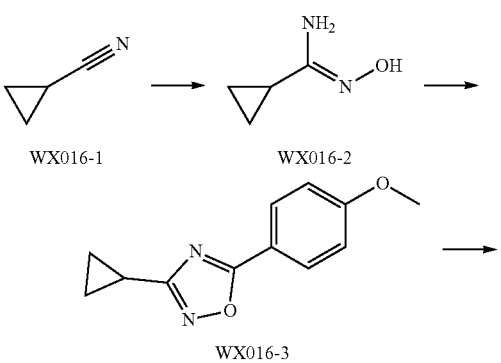

Step 1: Synthesis of Compound WX014-2

The synthesis of the compound WX014-2 was performed according to the synthesis method described in the step 1 of Example 3, ¹H NMR (400 MHz, CHLOROFORM-d) δ 7.96 (d, J=8.5 Hz, 2H), 6.81 (d, J=8.5 Hz, 2H), 2.69 (s, 3H), 1.61 (s, 9H), MS m/z: 276.3 [M+H]⁺.

Step 2: Synthesis of Compound WX014-3

A N,N-dimethylformamide (20.00 mL) liquid mixture of the compound WX014-2 (2.20 g, 16.52 mmol), sodium azide (1.18 g, 18.17 mmol) and ammonium chloride (220.95 mg, 4.13 mmol) was reacted at 110° C. for 16 hours. After the reaction was completed, 150.00 mL of ice water was added to quench the reaction, and the reaction solution was continuously stirred for 15 minutes. 12M of hydrochloric acid was added to adjust the pH to 1-2, and the mixture was -continued

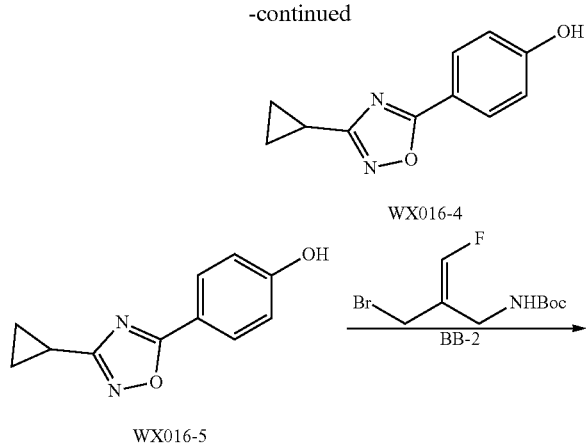

WX016-4

WX016-5

WX016-6

WX016

Step 1: Synthesis of Compound WX016-2

A water (12.00 ml) and ethanol (120.00 ml) solution of a compound cyclopropylacetonitrile (5.00 g, 74.53 mmol), potassium carbonate (10.51 g, 76.02 mmol) and hydroxylamine hydrochloride (5.18 g, 74.53 mmol) was reacted at 25° C. for 20 hours. After the reaction was completed, the reaction solution was concentrated under reduced pressure, and the crude product was dissolved in 200 mL of ethanol to obtain suspension liquid, and the suspension liquid was filtered, and the filtrate was concentrated under reduced pressure to obtain the compound WX016-2, $^1$H NMR (400 MHz, DMSO-d6) δ 8.72 (br s, 1H), 5.12-5.34 (m, 2H), 1.28-1.38 (m, 1H), 0.62-0.67 (m, 2H), 0.55-0.61 (m, 2H).

Step 2: Synthesis of Compound WX016-3

A pyridine (50.00 mL) liquid mixture of compound WX016-2 (1.40 g, 13.98 mmol) and p-methoxybenzoyl chloride (4.77 g, 27.96 mmol) was reacted at 130° C. for 1 hour. After the reaction was completed, 200.00 mL of water and 300.00 mL of ethyl acetate were added to separate the organic phase. The organic phase was washed with 1 M hydrochloric acid (200.00 mL) and 2 M sodium hydroxide (200.00 mL), respectively, and then concentrated under reduced pressure. The organic phase was purified by a column (petroleum ether:ethyl acetate=20:1-10:1) to obtain the compound WX016-3, MS m/z: 217.2 [M+H]$^+$.

Step 3: Synthesis of Compound WX016-4

The synthesis of the compound WX016-4 referred to the synthesis method of the step 3 in Example 1, MS m/z: 203.2 [M+H]$^+$.

Step 4: Synthesis of Compound WX016-5

The synthesis of the compound WX016-5 referred to the synthesis method of the step 4 in Example 1, MS m/z: 390.4 [M+H]$^+$.

Step 5: Synthesis of Compound WX016

The synthesis of the compound WX016 referred to the synthesis method of the step 5 in Example 1, $^1$H NMR (DMSO-d6, 400 MHz): δ=8.32 (br s, 3H), 8.02 (d, J=8.5 Hz, 2H), 7.24-7.46 (m, 1H), 7.21 (d, J=8.5 Hz, 2H), 4.75 (br d, J=2.5 Hz, 2H), 3.62 (s, 2H), 2.12-2.21 (m, 1H), 1.05-1.14 (m, 2H), 0.91-1.02 ppm (m, 2H), 19F NMR (DMSO-d6, 377 MHz) δ −122.09 ppm (s, 1F), MS m/z: 290.4 [M+H]$^+$.

Example 6: WX017

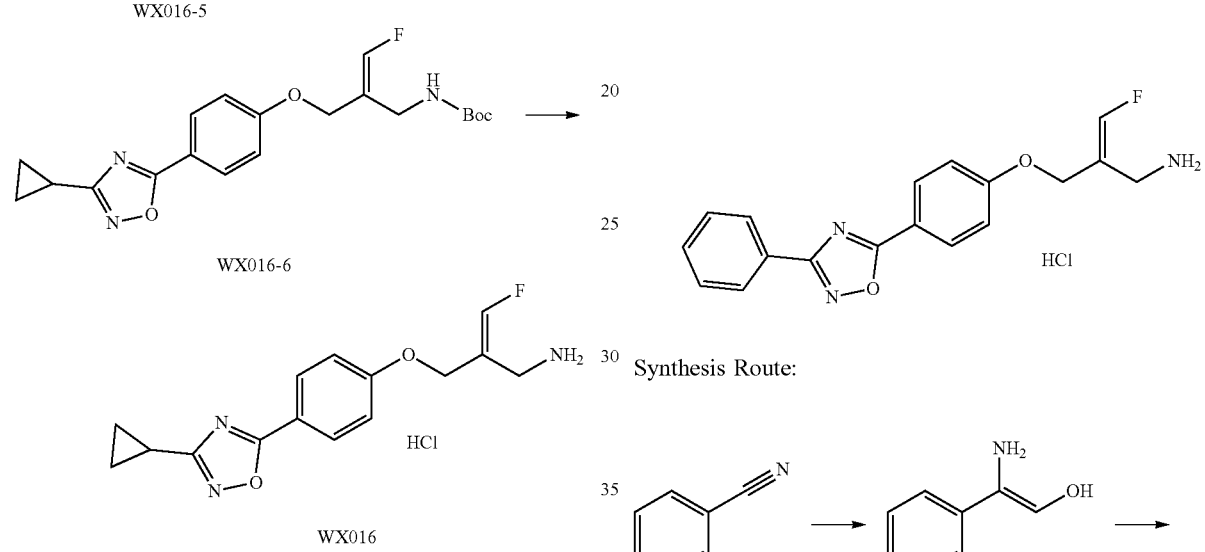

Synthesis Route:

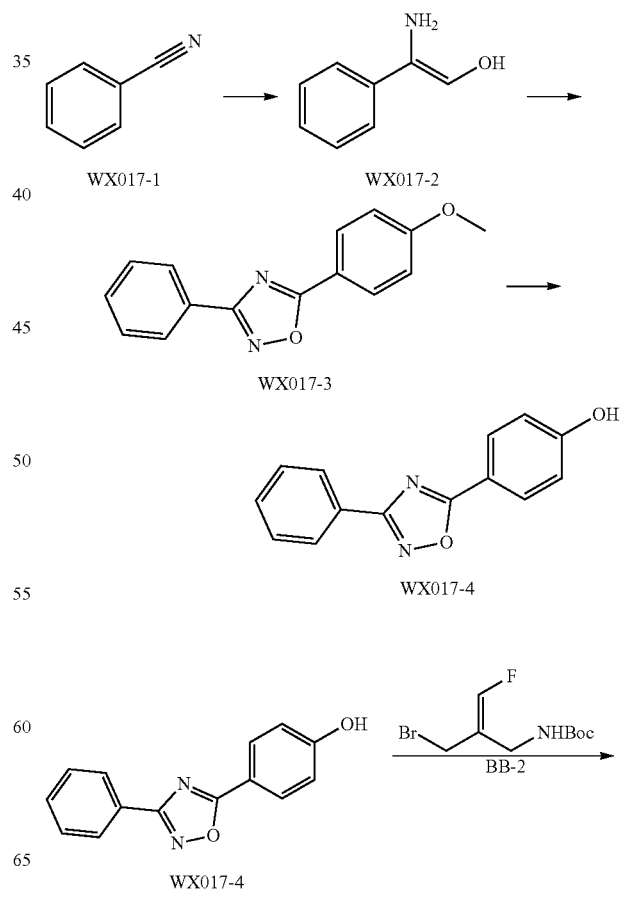

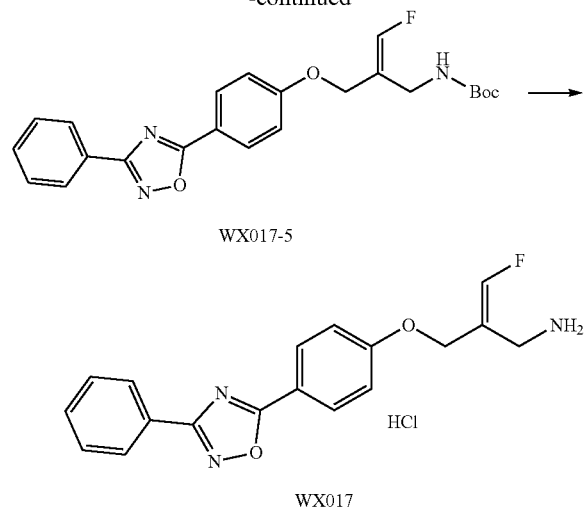

WX017-5

WX017

Step 1: Synthesis of Compound WX017-2

The synthesis of the compound WX017-2 was performed according to the synthesis method described in the step 1 of Example 5, $^1$H NMR (400 MHz, DMSO-d6) δ 9.65 (br s, 1H), 7.65-7.71 (m, 2H), 7.34-7.40 (m, 3H), 5.81 (s, 2H).

Step 2: Synthesis of Compound WX017-3

Synthesis of the compound WX017-3 referred to the synthesis method of the step 2 in Example 5, MS m/z: 252.9 [M+H]$^+$.

Step 3: Synthesis of Compound WX017-4

The synthesis of the compound WX017-4 referred to the synthesis method of the step 3 in Example 1, MS m/z: 238.8 [M+H]$^+$.

Step 4: Synthesis of Compound WX017-5

Synthesis of the compound WX017-5 referred to the synthesis method of the step 4 in Example 1, MS m/z: 370.1 [M−56+H]$^+$.

Step 5: Synthesis of Compound WX017

The synthesis of the compound WX017 referred to the synthesis method of the step 5 in Example 1, $^1$H NMR (DMSO-d6, 400 MHz): δ=8.39 (br s, 3H), 8.17 (br d, J=8.5 Hz, 2H), 8.09 (br d, J=6.0 Hz, 2H), 7.62 (br s, 2H), 7.48 (s, 1H), 7.28 (br d, J=8.0 Hz, 2H), 4.80 (br s, 2H), 3.63 ppm (br s, 2H). 19F NMR (DMSO-d6, 377 MHz): δ=−122.06 ppm (s, 1F). MS m/z: 326.0 [M+H]$^+$.

Example 7: WX019

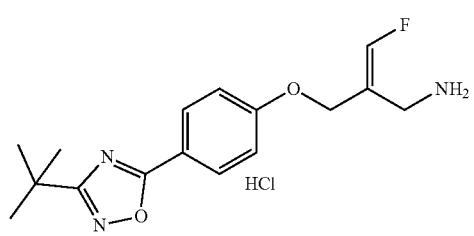 [SMILES: CC(C)(C)c1noc(-c2ccc(OC/C(=C/F)CN)cc2)n1 ; Cl]

Synthesis Route:

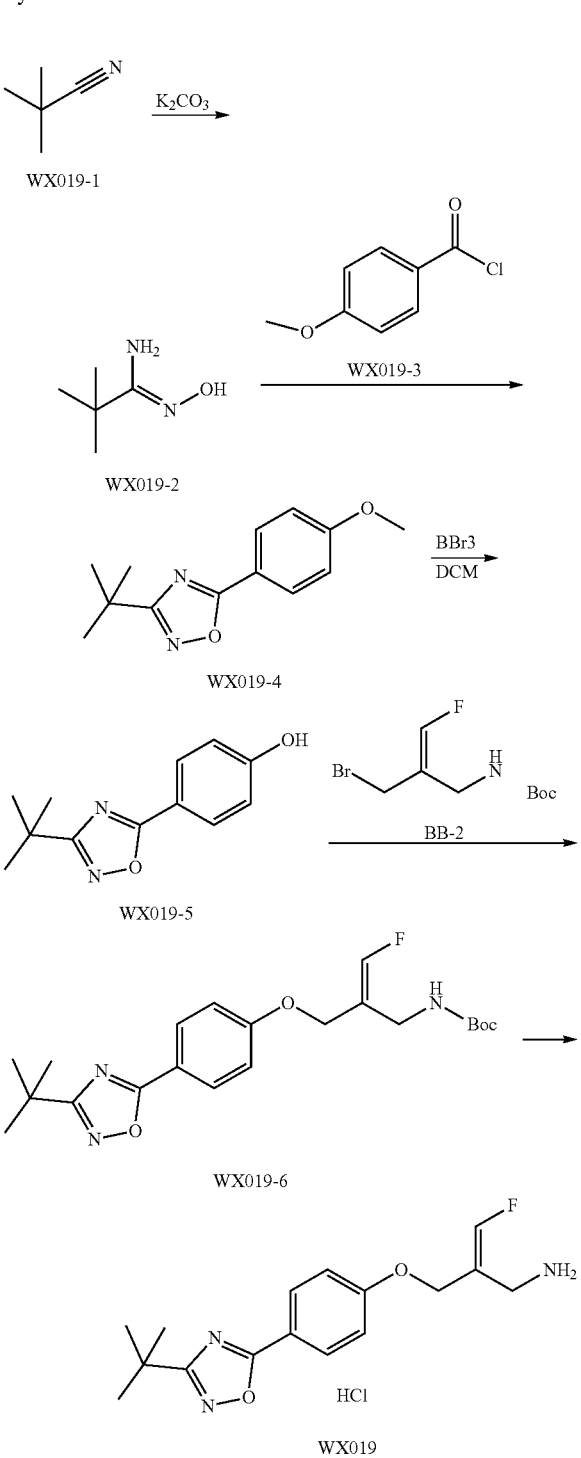

Step 1: Synthesis of Compound WX019-2

The synthesis of the compound WX019-2 referred to the synthesis method of the step 1 in Example 5, 1H NMR (DMSO-d6, 400 MHz): δ=8.89 (br s, 1H), 5.21 (br s, 2H), 1.08 ppm (s, 9H).

Step 2: Synthesis of Compound WX019-4

The synthesis of the compound WX019-4 referred to the synthesis method of the step 2 in Example 5, MS m/z: 232.9 [M+H]$^+$.

Step 3: Synthesis of Compound WX019-5

The synthesis of the compound WX019-5 referred to the synthesis method of the step 3 in Example 1, MS m/z: 218.9 [M+H]$^+$.

Step 4: Synthesis of Compound WX019-6

The synthesis of the compound WX019-6 referred to the synthesis method of the step 4 in Example 1, MS m/z: 350.1 [M+H]$^+$.

Step 5: Synthesis of Compound WX019

The synthesis of the compound WX019 referred to the synthesis method of the step 5 in Example 1, $^1$H NMR (DMSO-d6, 400 MHz): δ=8.30 (br s, 3H), 8.06 (d, J=9.0 Hz, 2H), 7.25-7.48 (m, 1H), 7.22 (d, J=8.5 Hz, 2H), 4.75 (d, J=3.0 Hz, 2H), 3.63 (s, 2H), 1.36 ppm (s, 9H).

Example 8: WX021

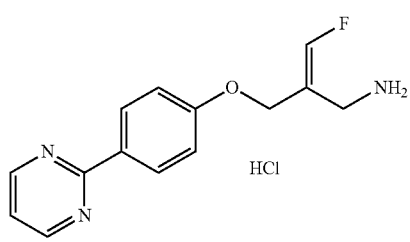 [SMILES: NC/C(=C\F)COc1ccc(-c2ncccn2)cc1 ; Cl]

Synthesis Route:

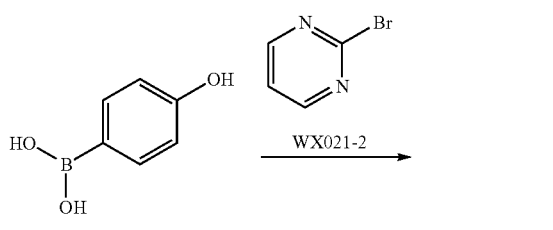

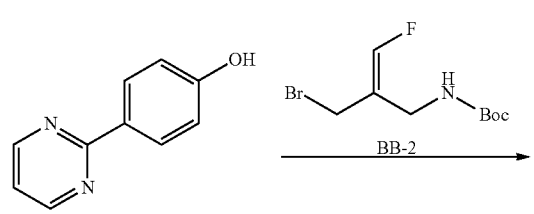

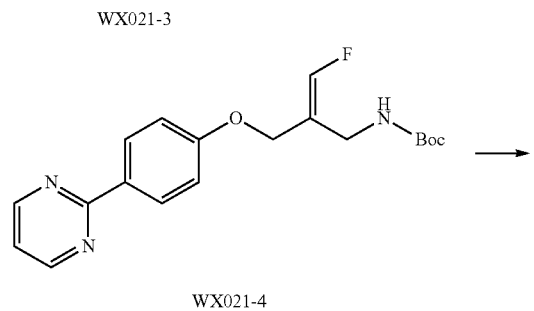

-continued

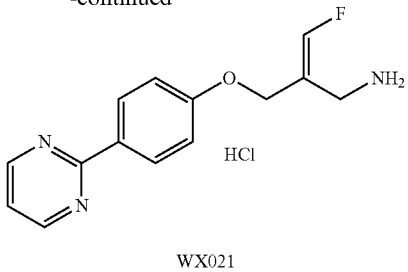

WX021

Step 1: Synthesis of Compound WX021-3

A tetrahydrofuran (5.00 mL) mixture of a compound WX021-1 (206.90 mg, 1.50 mmol), a compound WX021-2 (198.73 mg, 1.25 mmol), tetrakis(triphenylphosphine)palladium (288.90 mg, 250.01 μmol) and potassium carbonate (345.53 mg, 2.50 mmol) was reacted at 85° C. for 3 hours under nitrogen protection. After the reaction was completed, the mixture was cooled down and 1M hydrochloric acid was added to adjust the pH to 6. The mixture was diluted with 20 mL of water, extracted with 20 mL of ethyl acetate twice, and dried and spin-dried to obtain the compound WX021-3. 1H NMR (400 MHz, CHLOROFORM-d) δ=8.77 (d, J=4.8 Hz, 2H), 8.35 (d, J=8.7 Hz, 2H), 7.14 (t, J=4.8 Hz, 1H), 6.93 (d, J=8.7 Hz, 2H), 5.63 (br s, 1H).

Step 2: Synthesis of Compound WX021-4

The synthesis of the compound WX021-4 referred to the synthesis method of the step 4 in Example 1. $^1$H NMR (400 MHz, CHLOROFORM-d) δ=8.77 (d, J=4.7 Hz, 2H), 8.44-8.38 (m, J=8.8 Hz, 2H), 7.14 (t, J=4.8 Hz, 1H), 7.05-6.99 (m, J=8.9 Hz, 2H), 6.94-6.62 (m, 1H), 4.79 (br s, 1H), 4.53 (br d, J=3.3 Hz, 2H), 4.03 (br d, J=4.9 Hz, 2H), 1.43 (s, 9H).

Step 3: Synthesis of Compound WX021

The synthesis of the compound WX021 referred to the synthesis method of the step 5 in Example 1. $^1$H NMR (400 MHz, DMSO-d$_6$) δ=8.85 (d, J=4.8 Hz, 2H), 8.46-8.09 (m, 5H), 7.48-7.23 (m, 2H), 7.14 (d, J=8.9 Hz, 2H), 4.71 (br s, 2H), 3.63 (br s, 2H).

Example 9: WX022

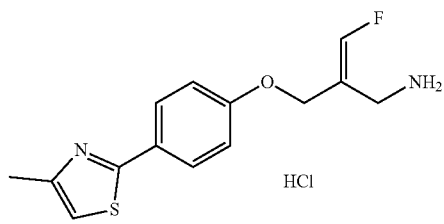 [SMILES: Cc1csc(-c2ccc(OC/C(=C/F)CN)cc2)n1 ; Cl]

Synthesis Route:

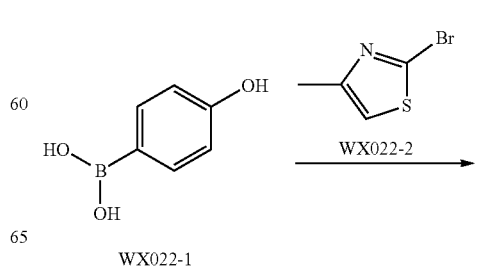

101
-continued

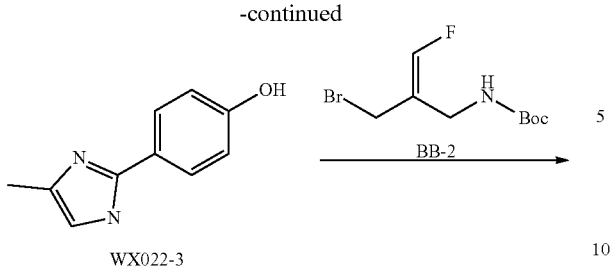

WX022-3

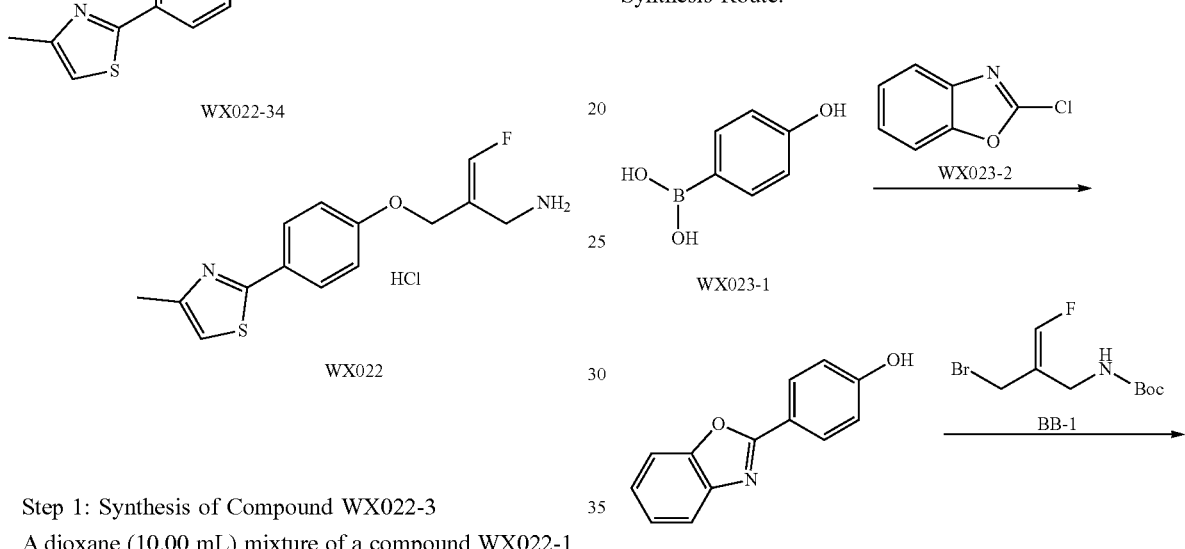

WX022-34

WX022

Step 1: Synthesis of Compound WX022-3

A dioxane (10.00 mL) mixture of a compound WX022-1 (206.90 mg, 1.50 mmol), a compound WX022-2 (222.56 mg, 1.25 mmol), [1,1'-Bis(diphenylphosphino)ferrocene]dichloropalladium(II) (94.16 mg, 0.125 mmol) and sodium carbonate (264.98 mg, 2.50 mmol) was reacted at 85° C. for 3 hours under the protection of nitrogen. After the reaction was completed, the mixture was cooled down and 1M hydrochloric acid was added to adjust the pH to 6. The mixture was diluted with 10 mL of water, and extracted with 20 mL of ethyl acetate twice, and the water phase was adjusted with NaHCO$_3$ (aq) to a pH of 8. Then the mixture was extracted with 20 mL of ethyl acetate twice, dried with anhydrous sodium sulfate and spin-dried to obtain the compound WX022-3. $^1$H NMR (400 MHz, CHLOROFORM-d) δ=7.81 (br d, J=7.8 Hz, 2H), 6.90 (br d, J=8.3 Hz, 1H), 6.94-6.87 (m, 1H), 6.80 (s, 1H), 2.49 (s, 3H).

Step 2: Synthesis of Compound WX022-4

The synthesis of the compound WX022-4 referred to the synthesis method of the step 4 in Example 1. $^1$H NMR (400 MHz, CHLOROFORM-d) δ=7.88 (d, J=8.5 Hz, 2H), 6.95 (d, J=8.7 Hz, 2H), 6.67 (s, 2H), 4.75 (br s, 1H), 4.50 (br d, J=3.4 Hz, 2H), 4.02 (br d, J=4.5 Hz, 2H), 2.50 (s, 3H), 1.43 (s, 9H).

Step 3: Synthesis of Compound WX022

The synthesis of the compound WX022 referred to the synthesis method of the step 5 in Example 1. $^1$H NMR (400 MHz, DMSO-d$_6$) δ=8.24 (br s, 3H), 7.87 (d, J=8.8 Hz, 2H), 7.47-7.20 (m, 2H), 7.10 (d, J=8.7 Hz, 2H), 4.68 (br s, 1H), 3.62 (br s, 2H).

102
Example 10: WX023

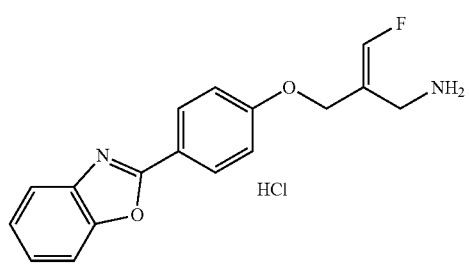 [SMILES: NC/C(=C\F)COc1ccc(-c2nc3ccccc3o2)cc1 ; Cl]

Synthesis Route:

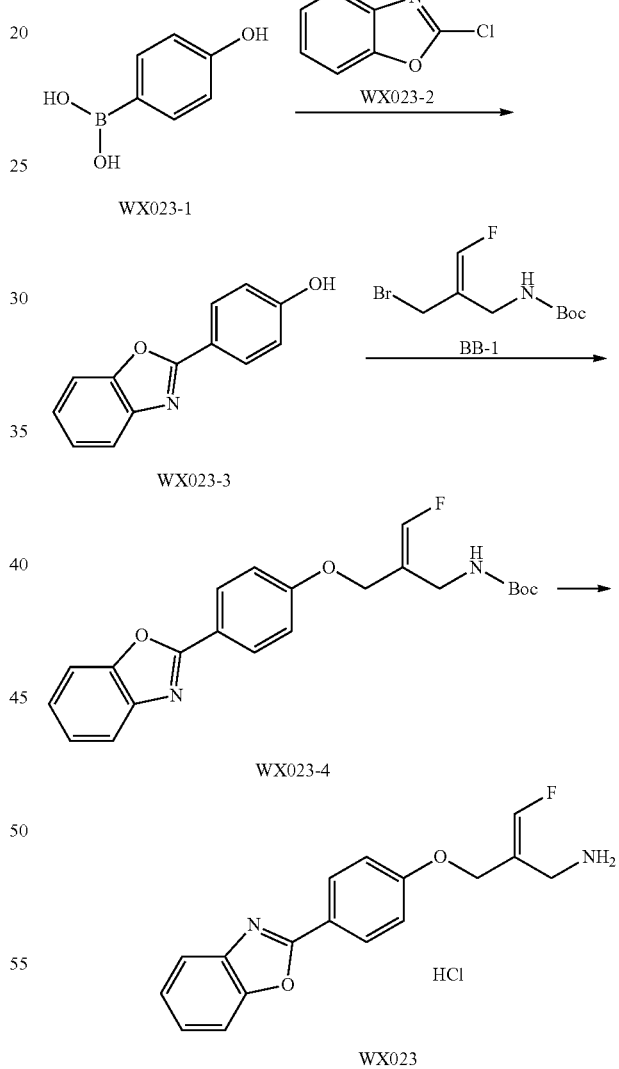

Step 1: Synthesis of Compound WX023-3

A dioxane (15.00 mL) mixture of a compound WX023-1 (322.76 mg, 2.34 mmol), a compound WX023-2 (300.00 mg, 1.95 mmol), tetrakis(triphenylphosphine)palladium (225.33 mg, 195.00 μmol) and potassium carbonate (539.02 mg, 3.90 mmol) was reacted under nitrogen protection for 4 hours at 90° C. After the reaction was completed, the mixture was cooled down and 1M hydrochloric acid was added to adjust the pH to 6. The mixture was diluted with 10 mL of water, extracted with 20 mL of ethyl acetate twice, dried with anhydrous sodium sulfate and spin-dried, and the crude product was allowed to pass through a silica gel column (petroleum ether:ethyl acetate=5:1 to 3:1) to obtain the compound WX023-3. ¹H NMR (400 MHz, CHLOROFORM-d) δ ppm 5.44 (s, 1H) 7.00 (d, J=8.41 Hz, 2H) 7.34-7.37 (m, 2H) 7.59 (br d, J=9.41 Hz, 1H) 7.76 (br d, J=5.77 Hz, 1H), 8.19 (d, J=8.66 Hz, 2H).

Step 2: Synthesis of Compound WX023-4

The synthesis of the compound WX023-4 referred to the synthesis method of the step 4 in Example 1. ¹H NMR (400 MHz, DMSO-d₆) δ ppm 1.36 (s, 9H) 3.39-3.49 (m, 2H) 3.80 (br s, 2H) 4.58 (br d, J=2.76 Hz, 2H) 7.20 (br d, J=8.78 Hz, 3H) 7.39-7.45 (m, 2H) 7.76-7.81 (m, 2H) 8.16 (d, J=8.66 Hz, 2H).

Step 3: Synthesis of Compound WX023

The synthesis of the compound WX023 referred to the synthesis method of the step 5 in Example 1. ¹H NMR (400 MHz, DMSO-d₆) δ ppm 3.65 (br s, 2H) 4.74 (br s, 2H) 7.24 (d, J=8.91 Hz, 2H) 7.28-7.50 (m, 3H) 7.77 (td, J=4.55, 2.82 Hz, 2H) 8.11 (br s, 3H) 8.19 (d, J=8.91 Hz, 2H).

Example 11: WX024

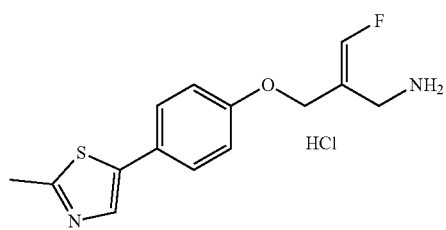 [SMILES: Cc1ncc(-c2ccc(OC/C(=C/F)CN)cc2)s1 ; Cl]

Synthesis Route:

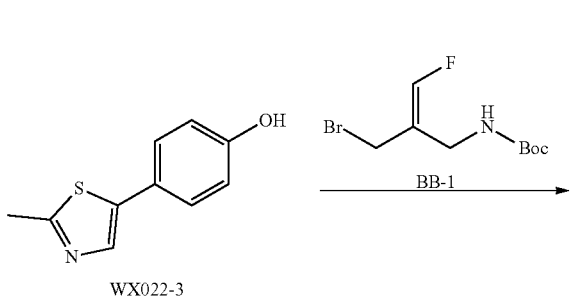

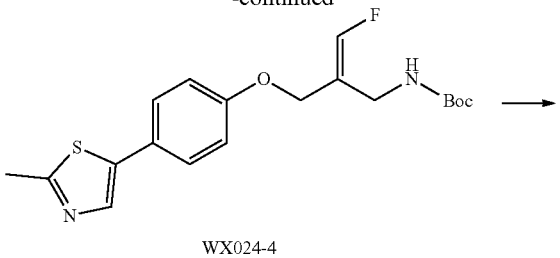

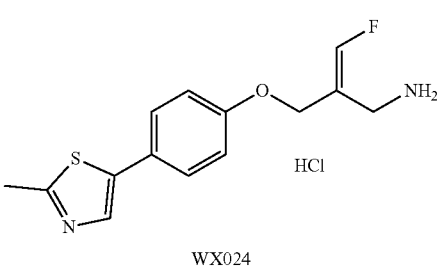

Step 1: Synthesis of Compound WX024-3

The synthesis of the compound WX024-3 referred to the synthesis method of the step 1 in Example 8. ESI, [M+1]⁺=192.

Step 2: Synthesis of Compound WX024-4

The synthesis of the compound WX024-4 referred to the synthesis method of the step 4 in Example 1. ¹H NMR (400 MHz, CHLOROFORM-d) δ=7.69 (s, 1H), 7.45 (d, J=8.8 Hz, 2H), 6.93 (d, J=8.8 Hz, 2H), 6.87 (d, J=2.1 Hz, 1H), 5.54 (s, 1H), 4.48 (br d, J=3.0 Hz, 2H), 4.01 (br d, J=5.6 Hz, 2H), 2.72 (s, 3H), 1.43 (s, 9H).

Step 3: Synthesis of Compound WX024

The synthesis of the compound WX024 referred to the synthesis method of the step 5 in Example 1. ¹H NMR (400 MHz, DMSO-d₆) δ=8.31 (br s, 3H), 8.01-7.92 (m, 1H), 7.60-7.54 (m, 2H), 7.45-7.19 (m, 1H), 7.10-7.04 (m, 2H), 4.67 (br s, 2H), 3.60 (br s, 2H).

Example 12: WX025

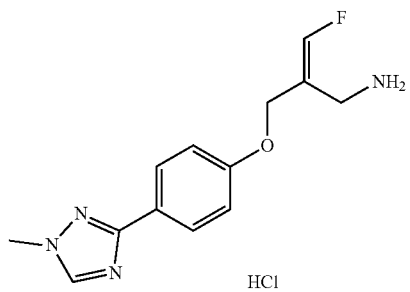 [SMILES: Cn1cnc(-c2ccc(OC/C(=C/F)CN)cc2)n1 ; Cl]

105

Synthesis Route:

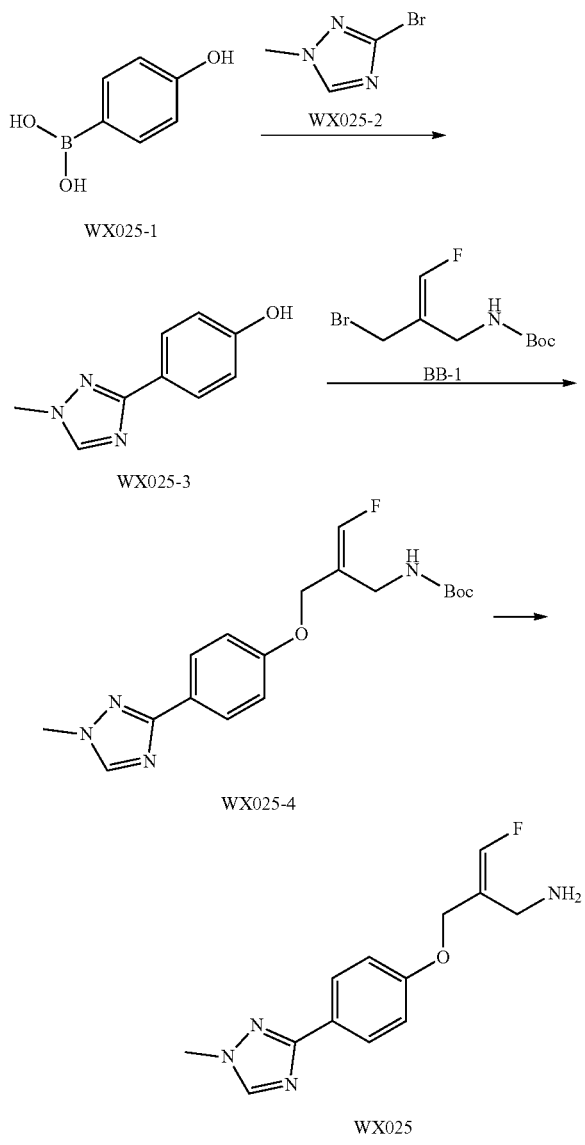

Step 1: Synthesis of Compound WX025-3

The synthesis of the compound WX25-3 referred to the synthesis method of the step 1 in Example 8. 1H NMR (400 MHz, DMSO-d6) δ 9.65 (br s, 1H), 7.65-7.71 (m, 2H), 7.34-7.40 (m, 3H), 5.81 (s, 2H).

Step 2: Synthesis of Compound WX025-4

The synthesis of the compound WX025-4 referred to the synthesis method of the step 4 in Example 1, MS m/z: 363.4 [M+H]$^+$.

Step 3: Synthesis of Compound WX025

The synthesis of the compound WX025 referred to the synthesis method of the step 5 in Example 1, 1H NMR (400 MHz, DMSO) δ 8.47 (s, 1H), 7.91-7.93 (m, 2H), 7.03-7.08 (m, 3H), 4.62 (s, 2H), 3.95 (s, 3H), 3.45 (br, 4H).

106

Example 13: WX026

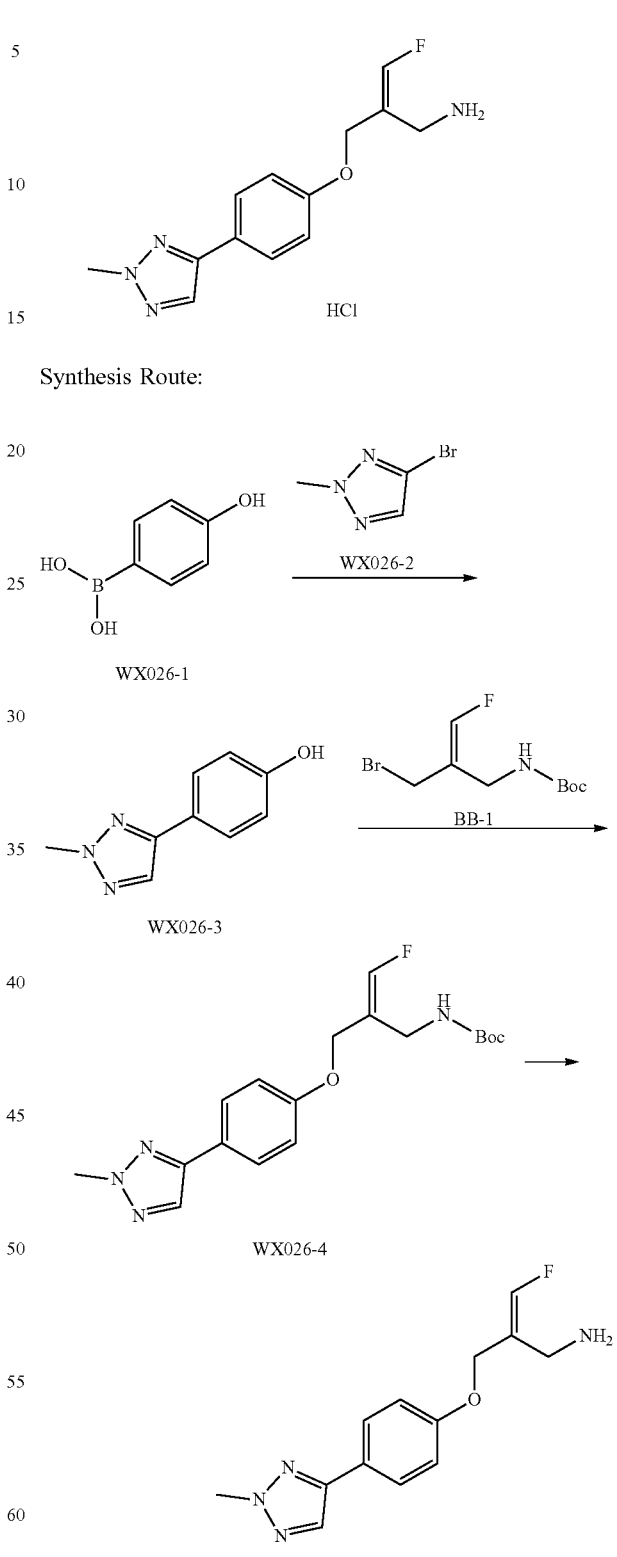

Step 1: Synthesis of Compound WX026-3

The synthesis of the compound WX26-3 referred to the synthesis method of the step 1 in Example 8, 1H NMR (400

MHz, DMSO) δ 8.47 (s, 1H), 7.75-7.77 (m, 2H), 7.06-7.27 (m, 3H), 4.63 (s, 2H), 4.07 (s, 3H), 3.46-3.47 (m, 4H).

Step 2: Synthesis of Compound WX026-4

The synthesis of the compound WX026-4 referred to the synthesis method of the step 4 in Example 1, MS m/z: 363.4 [M+H]+.

Step 3: Synthesis of Compound WX026

The synthesis of the compound WX026 referred to the synthesis method of the step 5 in Example 1, 1H NMR (400 MHz, DMSO) δ 8.47 (s, 1H), 7.75-7.77 (m, 2H), 7.06-7.27 (m, 3H), 4.63 (s, 2H), 4.07 (s, 3H), 3.46-3.47 (m, 4H).

Example 14: WX028

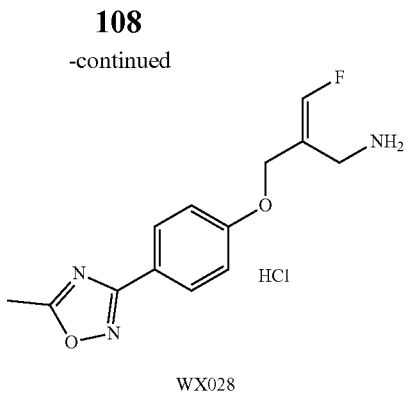

WX028

Synthesis Route:

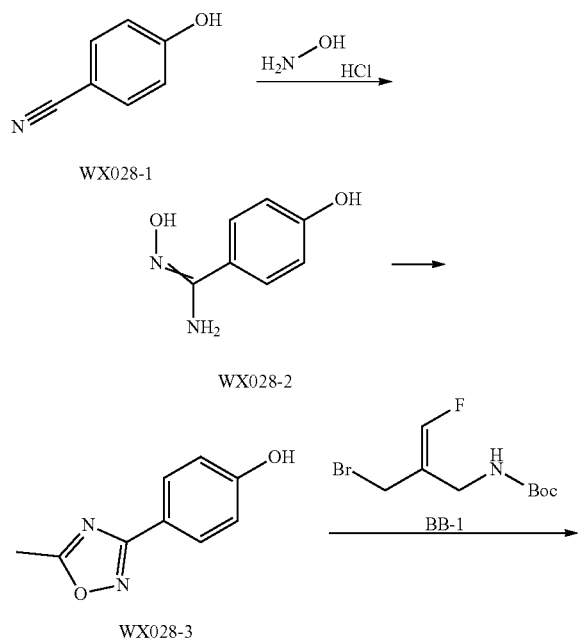

Step 1: Synthesis of Compound WX028-2

A compound WX028-1 (5.00 g, 41.97 mmol, 1.00 eq), hydroxylamine hydrochloride (14.58 g, 209.85 mmol, 5.00 eq) and potassium carbonate (29.01 g, 209.85 mmol, 5.00 eq) were added to EtOH (200.00 mL). Nitrogen replacement was performed for three times. The system was stirred at 80° C. for 12 hours, when the system was cooled, and filtered, and the filter cake was dried to give a crude product WX028-2. 1H NMR (400 MHz, MeOD) δ 7.30-7.35 (m, 2H), 6.61-6.65 (m, 2H)

Step 2: Synthesis of Compound WX028-3

The compound WX028-2 (1.00 g, 6.57 mmol, 1.00 eq) and acetic anhydride (805.18 mg, 7.89 mmol, 1.20 eq) were heated for 10 hours at 120° C. Methanol (20 ml) was added into the system, and then the system was concentrated to be dry with a water pump to get a crude product. And the crude product was purified by a column (petroleum ether:ethyl acetate=1:1) to obtain the compound WX028-3. 1H NMR (400 MHz, CDCl₃) δ 7.94-7.96 (m, 1H), 7.54-7.56 (m, 1H), 6.90-6.94 (m, 2H), 2.64 (s, 3H).

Step 3: Synthesis of Compound WX028-4

The synthesis of the compound WX028-4 referred to the synthesis method of the step 4 in Example 1, 1H NMR (400 MHz, CDCl₃) δ 7.99-8.01 (m, 2H), 7.01-7.03 (m, 2H), 6.68-6.88 (m, 1H), 4.80 (s, 1H), 4.50 (s, 2H), 4.02-4.03 (m, 2H), 2.79 (s, 2H), 2.65 (s, 3H), 1.42 (s, 9H).

Step 4: Synthesis of Compound WX028

The synthesis of the compound WX028 referred to the synthesis method of the step 5 of Example 1, 1H NMR (400 MHz, DMSO) δ 8.14 (s, 3H), 7.95-7.97 (m, 2H), 7.25-7.46 (m, 1H), 7.16-7.18 (m, 2H), 4.69 (s, 2H), 3.63 (s, 2H), 2.64 (s, 3H).

Example 15: WX033

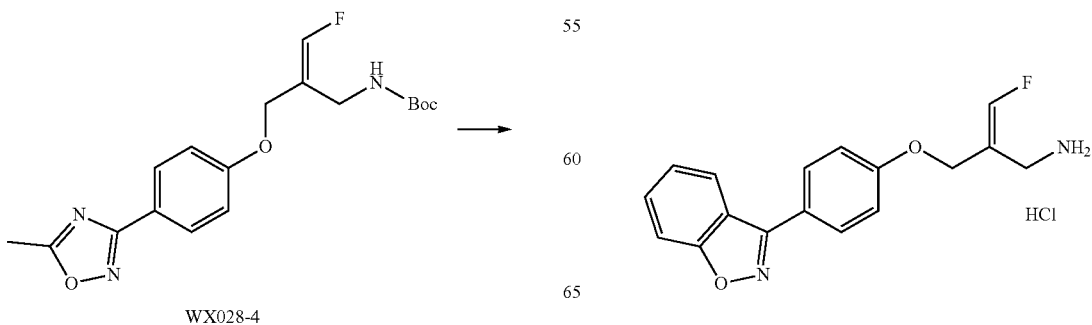

Synthesis Route:

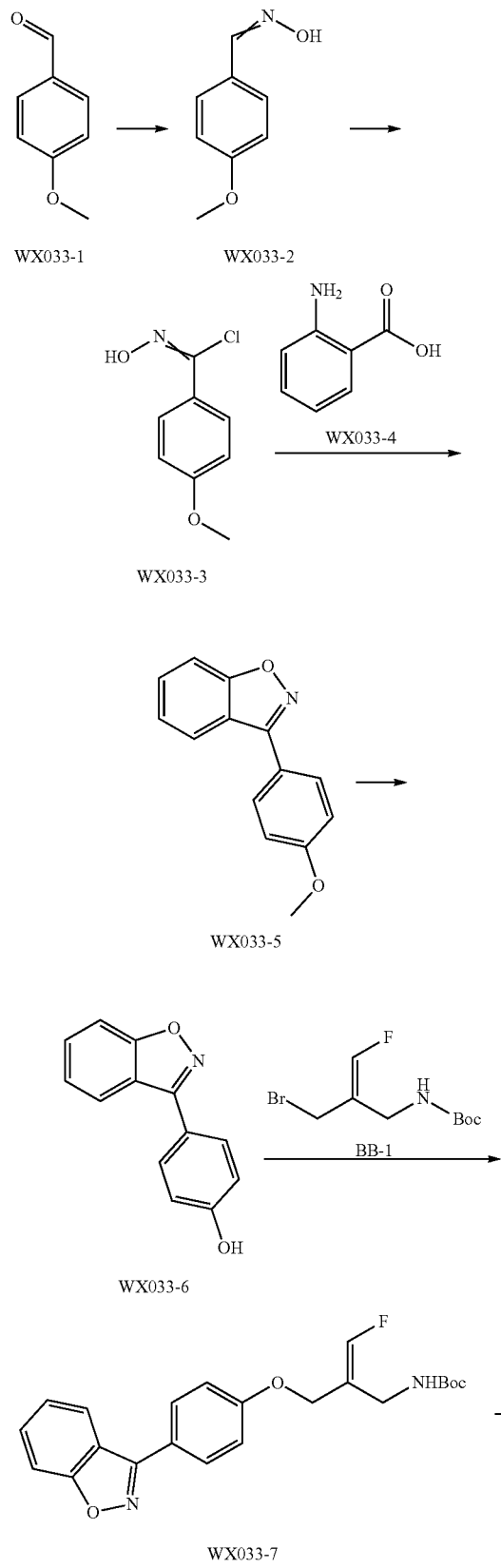

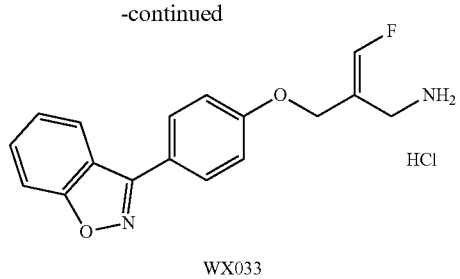

WX033

Step 1: Synthesis of Compound WX033-2

Sodium carbonate (1.05 g, 9.91 mmol, 0.50 eq) was added to a water (10 mL) and methanol (10 mL) mixed solution of a compound WX033-1 (2.70 g, 19.83 mmol, 2.41 mL, 1.00 eq) and hydroxylamine hydrochloride (1.52 g, 21.81 mmol, 1.10 eq). The mixture was stirred at 25° C. for 2 hours. The reaction solution was diluted with water and extracted with ethyl acetate, and the extraction liquid was washed with salt water, dried with anhydrous sodium sulfate, filtered and spin-dried to obtain the compound WX033-2. $^1$H NMR (400 MHz, CHLOROFORM-d) δ=8.10 (s, 1H), 7.93 (d, J=8.9 Hz, 1H), 7.60-7.44 (m, 3H), 6.96-6.89 (m, 2H), 4.13 (q, J=7.2 Hz, 1H), 3.86-3.83 (m, 3H), 2.06 (s, 1H), 1.63 (br s, 3H), 1.27 (t, J=7.2 Hz, 1H).

Step 2: Synthesis of Compound WX033-3

Chlorosuccinimide (2.12 g, 15.88 mmol, 1.20 eq) was added to a dichloromethane solution (20.00 mL) of the compound WX033-2 (2.00 g, 13.23 mmol, 1.00 eq) and pyridine (104.66 mg, 1.32 mmol, 106.79 μL, 0.10 eq), and the reaction solution was stirred at 40° C. for 2 hours. The reaction solution was diluted with dichloromethane, washed with salt water, dried with anhydrous sodium sulfate, filtered and spin-dried to obtain the brown oily compound WX033-3. $^1$H NMR (400 MHz, CHLOROFORM-d) δ=7.80-7.76 (m, 2H), 6.94-6.90 (m, 2H), 3.85 (s, 3H)

Step 3: Synthesis of Compound WX033-5

Potassium carbonate (557.68 mg, 4.04 mmol, 1.50 eq) was added to an acetonitrile solution (30.00 mL) of the compound WX033-3 (500.00 mg, 2.69 mmol, 1.00 eq), a compound WX033-4 (737.81 mg, 5.38 mmol, 2.00 eq) and tert-butyl nitrite (554.79 mg, 5.38 mmol, 637.68 ul, 2.00 eq). The resulting mixture was reacted in an autoclave at 80° C. for one hour. The reaction solution was diluted with water and extracted with ethyl acetate. The extraction solution was washed with salt water, dried with anhydrous sodium sulfate, and then filtered and spin-dried to be allowed to pass through a silica gel column (petroleum ether/ethyl acetate=10:1) to obtain the compound WX033-5. $^1$H NMR (400 MHz, CHLOROFORM-d) δ=7.97-7.89 (m, 3H), 7.68-7.57 (m, 2H), 7.42-7.34 (m, 1H), 7.12-7.04 (m, 2H), 3.91 (s, 3H)

Step 4: Synthesis of Compound WX033-6

The synthesis of the compound WX033-6 referred to the synthesis method of the step 3 of Example 1, $^1$H NMR (400 MHz, METHANOL-d$_4$) δ=8.06-8.01 (m, 1H), 7.86-7.83 (m, 2H), 7.68-7.64 (m, 2H), 7.47-7.41 (m, 1H), 7.03-6.98 (m, 2H).

Step 5: Synthesis of Compound WX033-7

The synthesis of the compound WX033-7 referred to the synthesis method of the step 4 in Example 1, $^1$H NMR (400 MHz, CHLOROFORM-d) δ=8.02-7.90 (m, 3H), 7.67-7.55 (m, 2H), 7.41-7.34 (m, 1H), 7.13-7.04 (m, 2H), 6.91-6.68 (m, 1H), 4.86 (br s, 1H), 4.54 (br d, J=2.9 Hz, 2H), 4.04 (br d, J=5.1 Hz, 2H), 1.42 (s, 9H).

Step 6: Synthesis of Compound WX033

The synthesis of the compound WX033 referred to the synthesis method of the step 5 in Example 1, $^1$H NMR (400 MHz, DMSO-d$_6$) δ=8.37 (br s, 3H), 8.13 (d, J=8.0 Hz, 1H), 8.02 (d, J=8.5 Hz, 2H), 7.84 (d, J=8.4 Hz, 1H), 7.74 (t, J=7.7 Hz, 1H), 7.53-7.24 (m, 4H), 4.77 (br s, 2H), 3.65 (br s, 2H).

Example 16: WX034

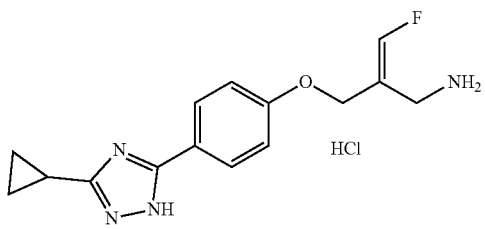 [SMILES: NC/C(=C\F)COc1ccc(-c2nc(C3CC3)n[nH]2)cc1 ; Cl]

Synthesis Route:

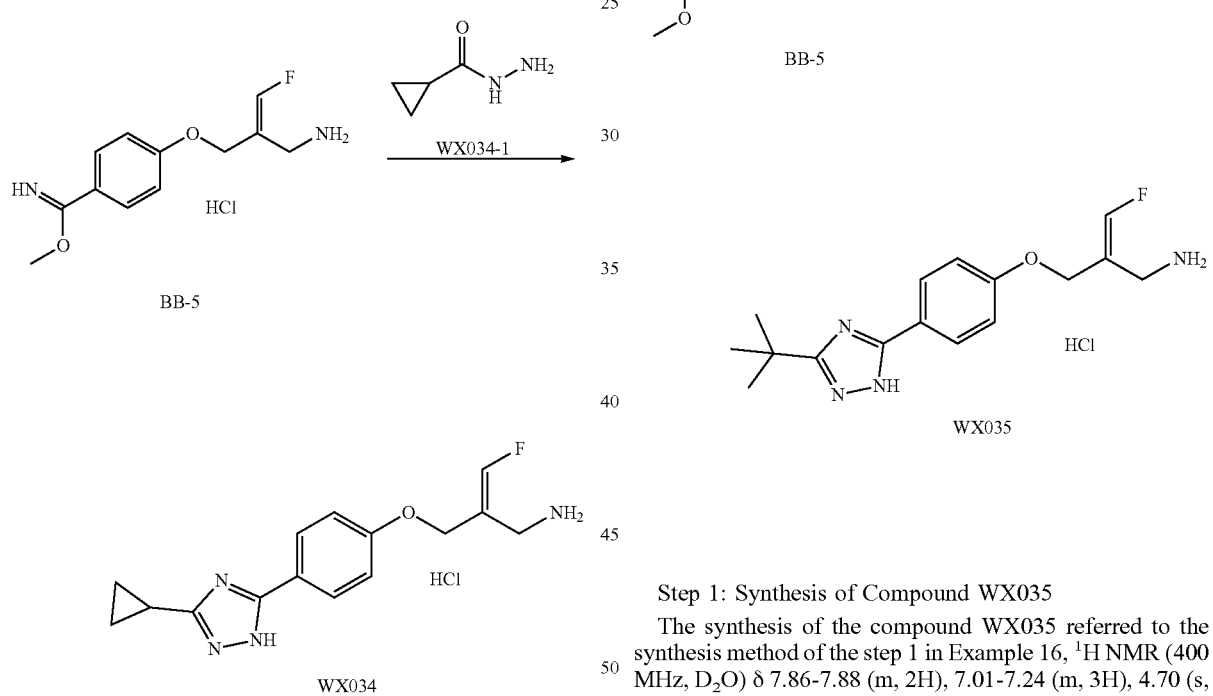

Step 1: Synthesis of Compound WX034

A compound WX034-1 (147.08 mg, 1.47 mmol,) and the compound BB-5 (233.49 mg) were dissolved in methanol (6.00 mL), triethylamine (198.20 mg) was added, and a reaction was carried out at 80° C. for 14 hours. The reaction solution was diluted with water (10 mL) and extracted with ethyl acetate (10 mL×2). Organic phases were mixed, dried and spin-dried. The crude product was purified by preparative HPLC (column: Luna C18 100×30 5μ; mobile phase: [water (0.05% HCl)-ACN]; B %: 10%-35%, 12 min) to obtain the compound WX034. $^1$H NMR (400 MHz, DEUTERIUM OXIDE) δ=7.75 (d, J=8.8 Hz, 2H), 7.20-6.95 (m, 3H), 4.63 (d, J=3.3 Hz, 2H), 3.81 (s, 2H), 2.22-2.15 (m, 1H), 1.30-1.21 (m, 2H), 1.16-1.06 (m, 2H)

Example 17: WX035

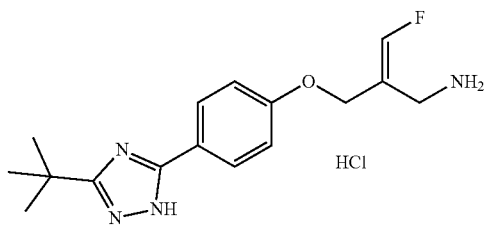 [SMILES: CC(C)(C)c1n[nH]c(-c2ccc(OC/C(=C/F)CN)cc2)n1 ; Cl]

Synthesis Route:

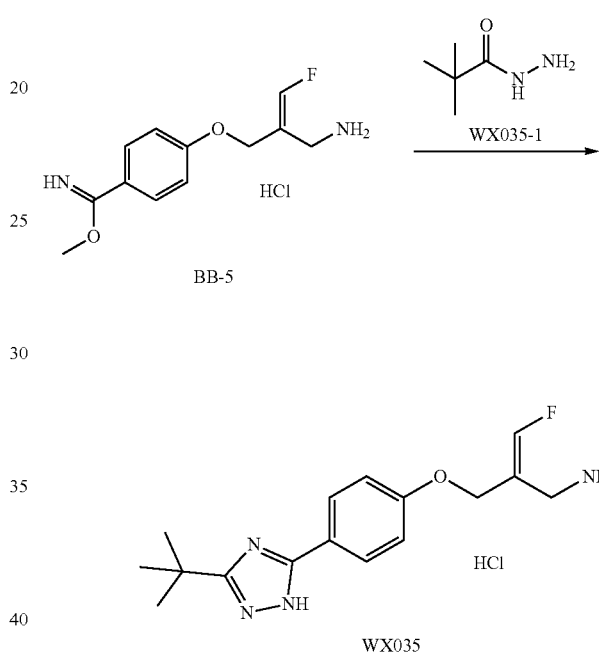

Step 1: Synthesis of Compound WX035

The synthesis of the compound WX035 referred to the synthesis method of the step 1 in Example 16, $^1$H NMR (400 MHz, D$_2$O) δ 7.86-7.88 (m, 2H), 7.01-7.24 (m, 3H), 4.70 (s, 2H), 3.87 (s, 2H), 1.46 (s, 9H).

Example 18: WX036

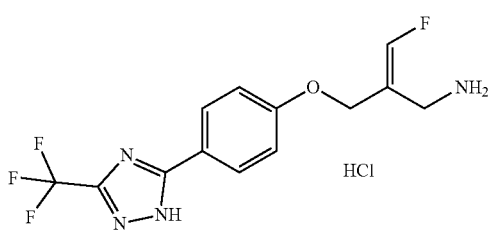 [SMILES: NC/C(=C\F)COc1ccc(-c2nc(C(F)(F)F)n[nH]2)cc1 ; Cl]

Synthesis Route:

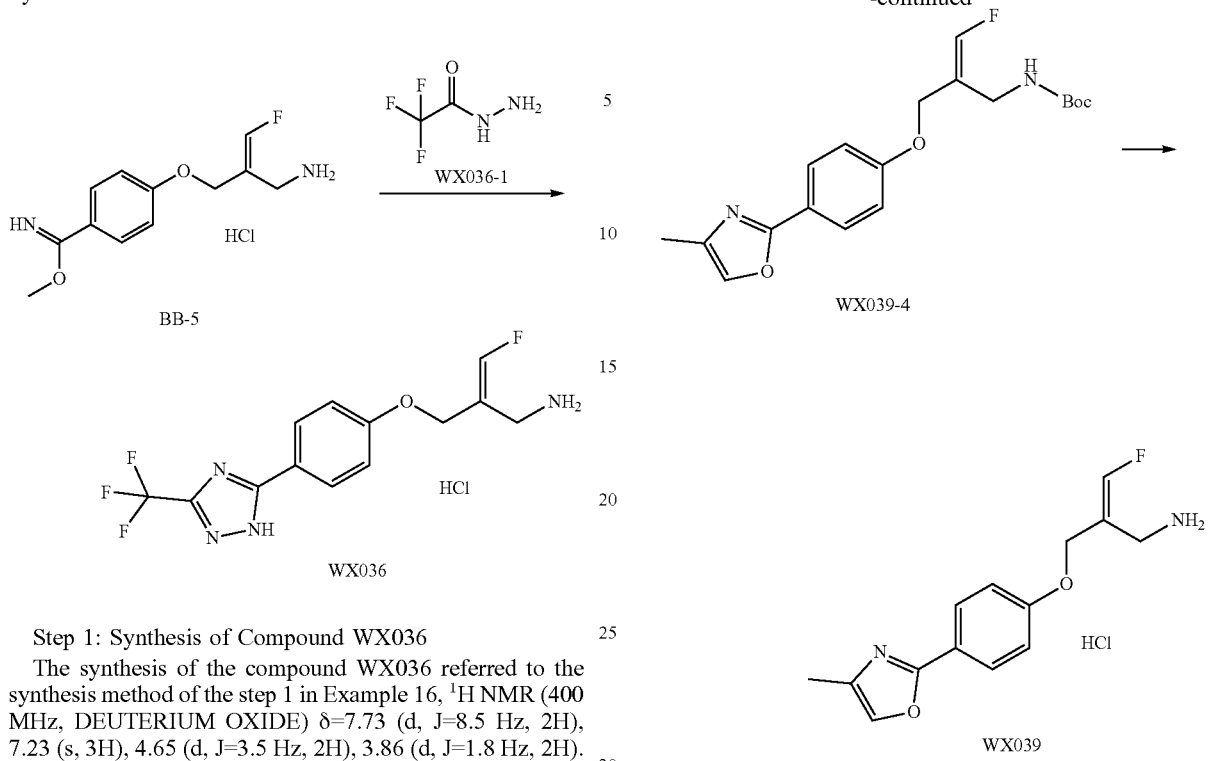

Step 1: Synthesis of Compound WX036

The synthesis of the compound WX036 referred to the synthesis method of the step 1 in Example 16, $^1$H NMR (400 MHz, DEUTERIUM OXIDE) δ=7.73 (d, J=8.5 Hz, 2H), 7.23 (s, 3H), 4.65 (d, J=3.5 Hz, 2H), 3.86 (d, J=1.8 Hz, 2H).

Example 19: WX039

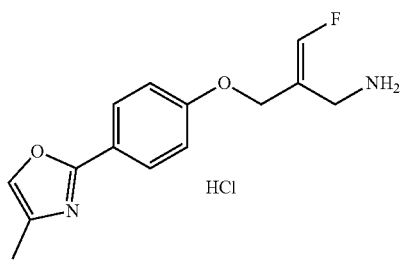 [SMILES: Cc1coc(-c2ccc(OC/C(=C/F)CN)cc2)n1 ; Cl]

Synthesis Route:

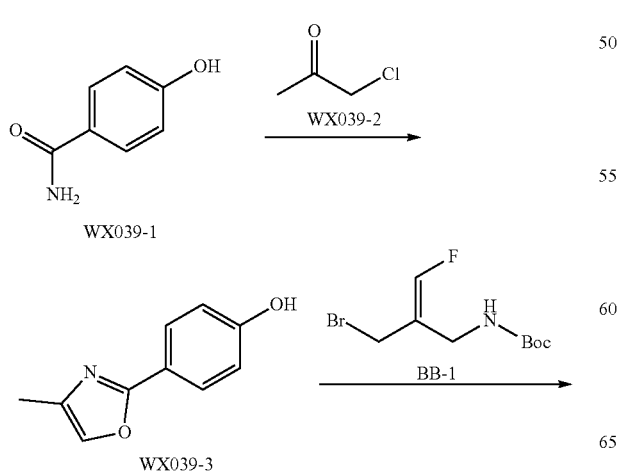

Step 1: Synthesis of Compound WX039-3

A compound WX039-1 (500 mg, 3.65 mmol, 1.0 eq), a compound WX039-2 (337.71 mg, 3.65 mmol, 1.00 eq) and potassium carbonate (504.47 mg, 3.65 mmol, 1.00 eq) were heated for 2 hours at 130° C. Methanol (5 ml) was added, filtering was performed, and the filtrate was concentrated to be dry with a water pump to obtain a crude product which was allowed to pass through a column (petroleum ether: ethyl acetate=10:1 to 2:1) to obtain the compound WX039-3 m/z: 176.2 [M+H].

Step 2: Synthesis of Compound WX039-4

The synthesis of the compound WX039-4 referred to the synthesis method of the step 4 in Example 1. MS m/z: 363.2 [M+H].

Step 3: Synthesis of Compound WX039

Synthesis of the compound WX039 referred to the synthesis method of the step 5 in Example 1. $^1$H NMR (400 MHz, MeOD) 8.02-8.02 (m, 2H), 7.89 (s, 1H), 7.17-7.37 (m, 3H), 4.73-4.74 (m, 2H), 3.84 (s, 2H), 2.31 (s, 3H).

Example 20: WX040

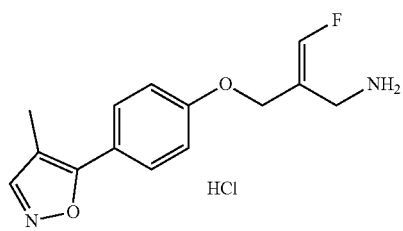 [SMILES: Cc1cnoc1-c1ccc(OC/C(=C/F)CN)cc1 ; Cl]

Synthesis Route:

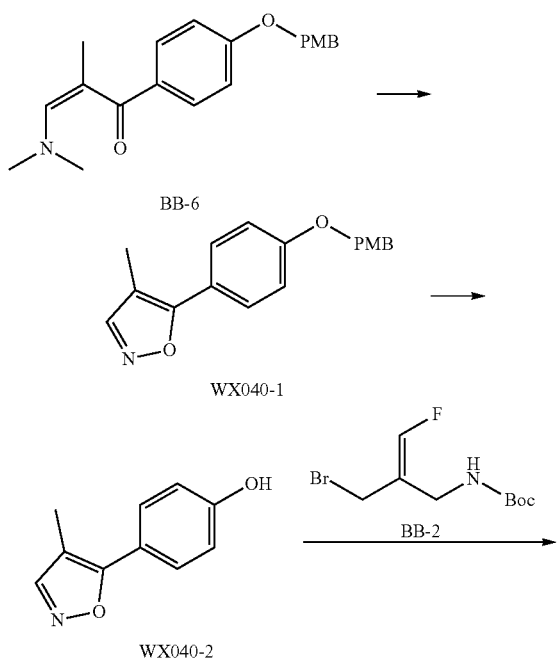

Step 1: Synthesis of Compound WX040-1

An ethanol solution of a compound BB-6 (300.00 mg) and hydroxylamine hydrochloride (96.10 mg) was reacted under nitrogen protection at 85° C. for 5 hours. The reaction solution was spin-dried and purified by a silica gel column (petroleum ether/ethyl acetate=10/1 to 5:1) to obtain the compound WX040-1. $^1$H NMR (400 MHz, CHLOROFORM-d) δ=8.14 (s, 1H), 7.69 (d, J=8.8 Hz, 2H), 7.40 (d, J=8.5 Hz, 2H), 7.09 (d, J=8.8 Hz, 2H), 6.96 (d, J=8.5 Hz, 2H), 5.07 (s, 2H), 4.15 (q, J=7.2 Hz, 1H), 3.85 (s, 3H), 2.26 (s, 3H), 2.07 (s, 2H), 1.28 (t, J=7.2 Hz, 3H).

Step 2: Synthesis of Compound WX040-2

A trifluoroacetic acid solution of the compound WX040-1 (90 mg) was reacted at 25° C. for 14 hours. The reaction solution was spin-dried. The crude product was crystallized by an ethyl acetate solution of hydrogen chloride to obtain the compound WX040-2. $^1$H NMR (400 MHz, CHLOROFORM-d) δ=8.50 (s, 1H), 7.62 (d, J=8.6 Hz, 2H), 6.98 (d, J=8.8 Hz, 2H), 5.90 (s, 1H), 2.23 (s, 3H)

Step 3: Synthesis of Compound WX040-3

The synthesis of the compound WX040-3 referred to the synthesis method of the step 4 in Example 1. $^1$H NMR (400 MHz, CHLOROFORM-d) δ=8.05 (s, 1H), 7.60 (d, J=8.9 Hz, 2H), 6.94 (d, J=8.9 Hz, 2H), 6.86 (br d, J=9.0 Hz, 1H), 4.68 (br d, J=3.8 Hz, 2H), 4.43 (br s, 2H), 3.94 (br s, 2H), 2.17 (s, 3H), 1.35 (s, 9H).

Step 4: Synthesis of Compound WX040

The synthesis of the compound WX040 referred to the synthesis method of the step 5 in Example 1.

$^1$H NMR (400 MHz, DEUTERIUM OXIDE) δ=8.09 (s, 1H), 7.44 (d, J=8.6 Hz, 2H), 7.10-6.86 (m, 3H), 4.47 (d, J=3.3 Hz, 2H), 3.72 (s, 2H), 1.96 (s, 3H).

Example 21: WX041

Synthesis Route:

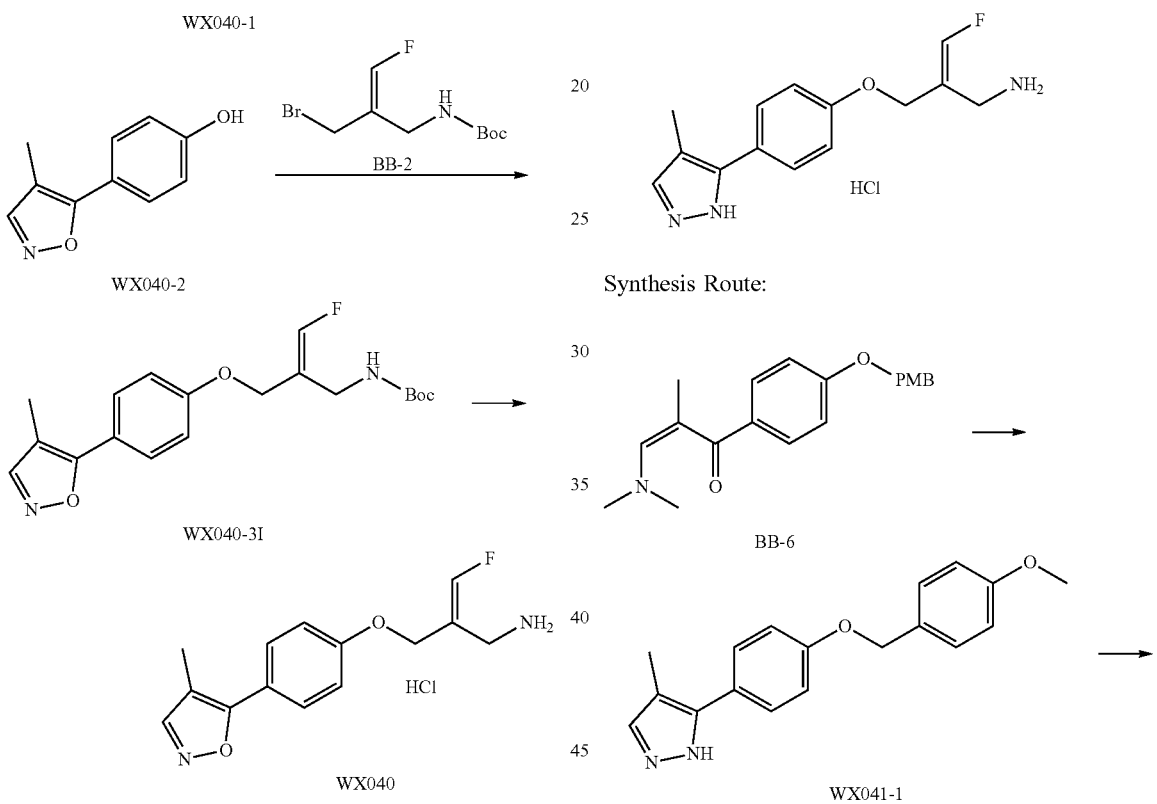

-continued

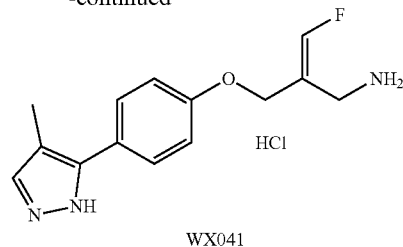

WX041

Step 1: Synthesis of Compound WX041-1

The synthesis of the compound WX041-1 referred to the synthesis method of the step 1 in Example 20. $^1$H NMR (400 MHz, CHLOROFORM-d) δ=7.49-7.26 (m, 5H), 6.97 (d, J=8.7 Hz, 2H), 6.86 (d, J=8.7 Hz, 2H), 4.96 (s, 2H), 3.75 (s, 3H), 2.14 (s, 3H).

Step 2: Synthesis of Compound WX041-2

The synthesis of the compound WX041-2 referred to the synthesis method of the step 2 in Example 20. $^1$H NMR (400 MHz, CHLOROFORM-d) δ=7.72 (br s, 1H), 7.55-7.43 (m, 2H), 7.03-6.82 (m, 2H), 2.22 (s, 3H).

Step 3: Synthesis of Compound WX041-3

The synthesis of the compound WX041-3 referred to the synthesis method of the step 4 in Example 1. $^1$H NMR (400 MHz, CHLOROFORM-d) δ=7.57-7.36 (m, 3H), 6.97 (br d, J=8.6 Hz, 2H), 6.87-6.83 (m, 1H), 4.47 (br s, 2H), 4.00 (br s, 2H), 3.20 (s, 2H), 2.21-2.19 (m, 3H), 1.41 (s, 9H).

Step 4: Synthesis of Compound WX041

The synthesis of the compound WX041 referred to the synthesis method of the step 5 in Example 1. $^1$H NMR (400 MHz, DMSO-d$_6$) δ=7.99 (br s, 3H), 7.87 (d, J=8.8 Hz, 2H), 7.45-7.22 (m, 1H), 6.91 (d, J=8.8 Hz, 2H), 4.60 (d, J=3.0 Hz, 2H), 3.64 (s, 2H).

Example 22: WX042

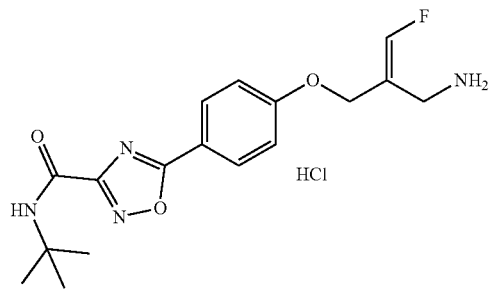 [SMILES: CC(C)(C)NC(=O)c1noc(-c2ccc(OC/C(=C/F)CN)cc2)n1 ; Cl]

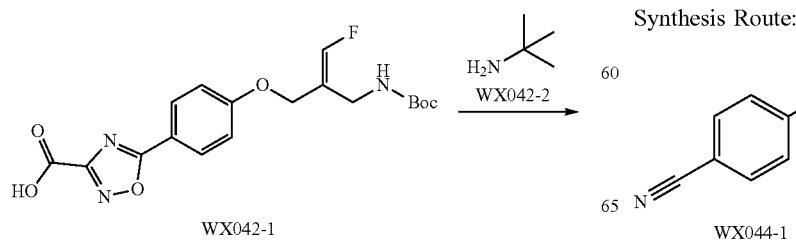

-continued

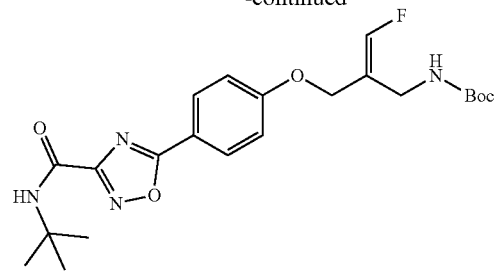

WX042-3

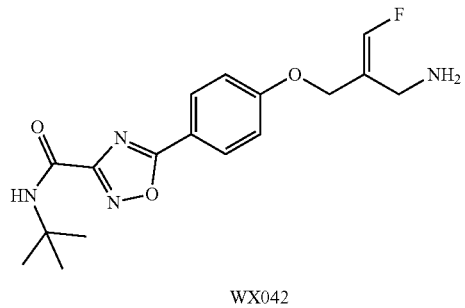

WX042

Step 1: Synthesis of Compound WX042-3

A compound WX042-1 (20.00 mg, 50.84 μmol, 1.00 eq) was dissolved in dichloromethane (1.00 mL), and then triethylamine (7.72 mg, 76.29 μmol, 10.58 μL, 1.50 eq) and HATU (23.20 mg, 61.01 umol, 1.20 eq) were added. The system was stirred at 20° C. for 5 hours, and dichloromethane (5 ml) and water (5 ml) were added into the system. The organic phase was concentrated to be dry with a water pump to obtain the compound WX042-3. MS m/z: 471.1 [M+Na].

Step 2: Synthesis of Compound WX042

The synthesis of the compound WX042 referred to the synthesis method of the step 5 in Example 1. $^1$H NMR (400 MHz, D$_2$O) δ 8.04-8.07 (m, 2H), 7.01-7.21 (m, 3H), 3.84 (s, 2H), 1.39 (s, 9H).

Example 23: WX044

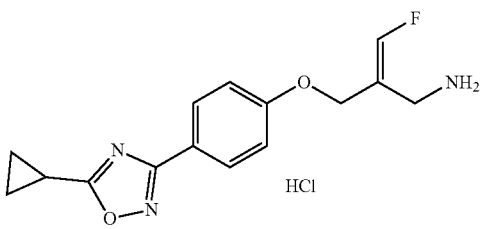 [SMILES: NC/C(=C\F)COc1ccc(-c2noc(C3CC3)n2)cc1 ; Cl]

Synthesis Route:

-continued

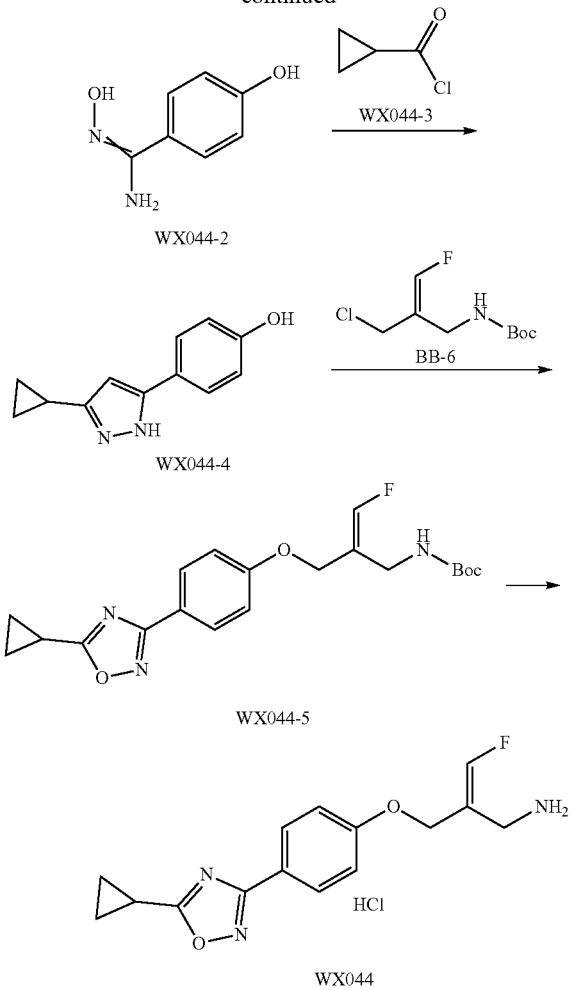

Step 1: Synthesis of Compound WX044-2

An ethanol mixture of a compound WX044-1 (5.00 g, 41.97 mmol), hydroxylamine hydrochloride (14.58 g, 209.85 mmol) and potassium carbonate (29.01 g, 209.85 mmol) was reacted at 80° C. for 12 hours under the protection of nitrogen. The reaction solution was spin-dried, diluted with water (100 mL), adjusted to a pH of 8, and extracted with ethyl acetate (100 mL×6), dried with anhydrous sodium sulfate and spin-dried to obtain the compound WX044-2. $^1$H NMR (400 MHz, DMSO-d$_6$) δ=9.58 (br s, 1H), 7.44 (d, J=7.8 Hz, 2H), 6.70 (d, J=7.8 Hz, 2H), 5.62 (s, 2H).

Step 2: Synthesis of Compound WX044-4

A compound WX044-3 (412.21 mg, 3.94 mmol, 358.44 μL) was added to a tetrahydrofuran (10.00 mL) mixture of N,N-diisopropyl ethylamine (509.21 mg, 3.94 mmol, 688.12 μL) and the compound WX044-2 (599.47 mg, 3.94 mmol) at 0° C., and the obtained mixture was reacted at 80° C. for 4 hours under the protection of nitrogen. The reaction solution was diluted with 20 mL of water and extracted with ethyl acetate (20 mL×2), dried with anhydrous sodium sulfate, filtered and spin-dried. The resulting product was added into 15 mL of toluene and reacted at 80° C. for 12 hours. The reaction solution was spin-dried, diluted with ethyl acetate (50 mL), washed with water (20 mL×2), dried with anhydrous sodium sulfate, filtered and spin-dried, and the crude product was separated by a column to obtain the compound WX044-4. 1H NMR (400 MHz, DMSO-d6) δ=10.09 (s, 1H), 7.79 (d, J=8.8 Hz, 2H), 6.89 (d, J=8.7 Hz, 2H), 2.46-2.26 (m, 1H), 1.32-1.10 (m, 4H), 0.98-0.71 (m, 1H).

Step 3: Synthesis of Compound WX044-5

The synthesis of the compound WX044-5 referred to the step 4 in Example 1. 1H NMR (400 MHz, CHLOROFORM-d) δ=7.96 (d, J=8.8 Hz, 2H), 6.99-6.92 (m, 2H), 6.87-6.63 (m, 1H), 4.85-4.61 (m, 1H), 4.47 (br d, J=3.1 Hz, 2H), 4.09-3.89 (m, 2H), 3.88-3.66 (m, 1H), 2.26-2.14 (m, 1H), 1.39 (s, 9H), 1.29-1.26 (m, 2H), 1.25-1.22 (m, 2H).

Step 4: Synthesis of Compound WX044

The synthesis of the compound WX044 referred to the synthesis method of the step 5 in Example 1. 1H NMR (400 MHz, DMSO-d6) δ=8.39 (br s, 3H), 7.92 (d, J=8.9 Hz, 2H), 7.48-7.23 (m, 1H), 7.16 (d, J=8.9 Hz, 2H), 4.73 (br d, J=3.1 Hz, 2H), 3.61 (br s, 2H), 2.47-2.31 (m, 1H), 1.34-1.12 (m, 4H).

Example 24: WX045

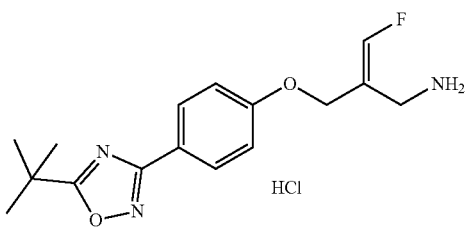 [SMILES: CC(C)(C)c1nc(-c2ccc(OC/C(=C/F)CN)cc2)no1 ; Cl]

Synthesis Route:

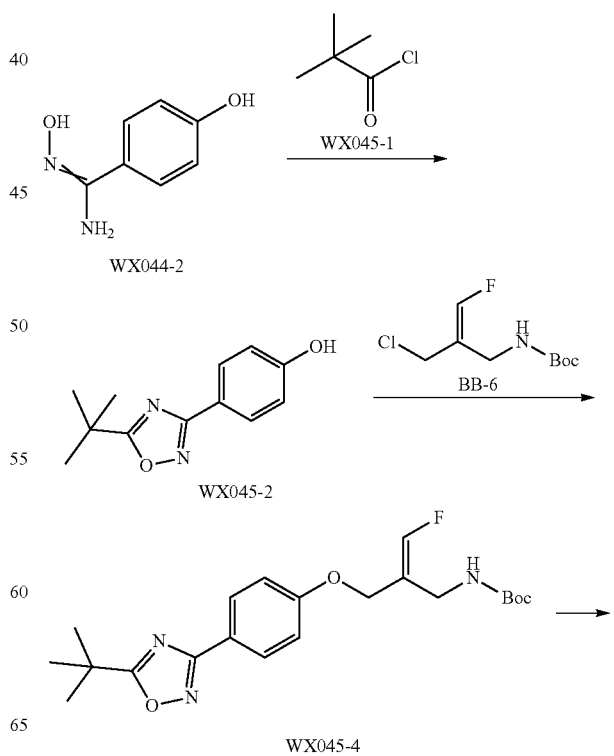

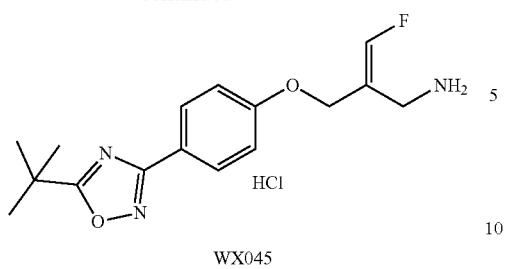

WX045

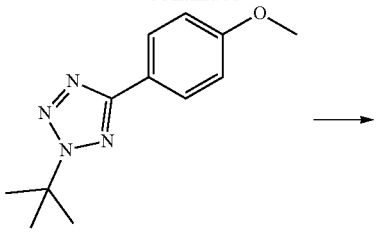

WX048-1

Step 1: Synthesis of Compound WX045-2

The synthesis of the compound WX045-2 referred to the synthesis method of the step 2 in Example 23. 1H NMR (400 MHz, DMSO-d6) δ=10.10 (s, 1H), 7.88-7.77 (m, J=8.7 Hz, 2H), 6.96-6.86 (m, J=8.7 Hz, 2H), 1.43 (s, 9H).

Step 2: Synthesis of Compound WX045-3

The synthesis of the compound WX044-5 referred to the synthesis method of the step 4 in Example 1. $^1$H NMR (400 MHz, CHLOROFORM-d) δ=8.03-7.98 (m, 2H), 7.00-6.93 (m, 2H), 6.65 (s, 1H), 4.74 (br s, 1H), 4.48 (br d, J=3.5 Hz, 2H), 4.00 (br d, J=5.3 Hz, 2H), 2.16 (s, 1H), 1.47 (s, 9H), 1.39 (s, 9H).

Step 3: Synthesis of Compound WX045

The synthesis of the compound WX045 referred to the synthesis method of the step 5 in Example 1. $^1$H NMR (400 MHz, DMSO-d$_6$) δ=8.31 (br s, 3H), 8.03-7.91 (m, 2H), 7.47-7.24 (m, 1H), 7.22-7.13 (m, 2H), 4.78-4.68 (m, 2H), 3.63 (br s, 2H), 3.34 (s, 1H), 2.57-2.52 (m, 1H), 1.47-1.38 (m, 9H).

Example 25: WX048

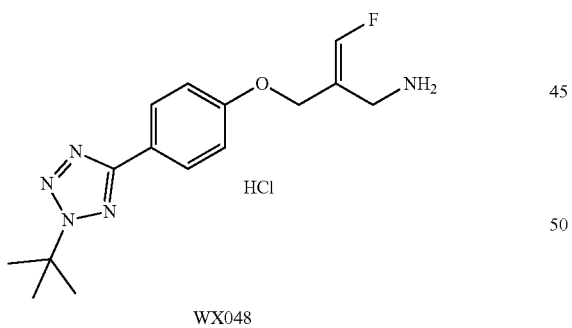

WX048

Synthesis Route:

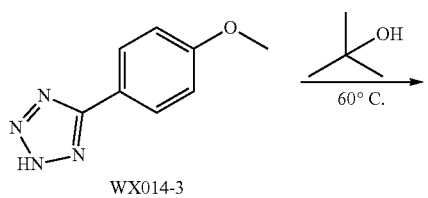

WX014-3

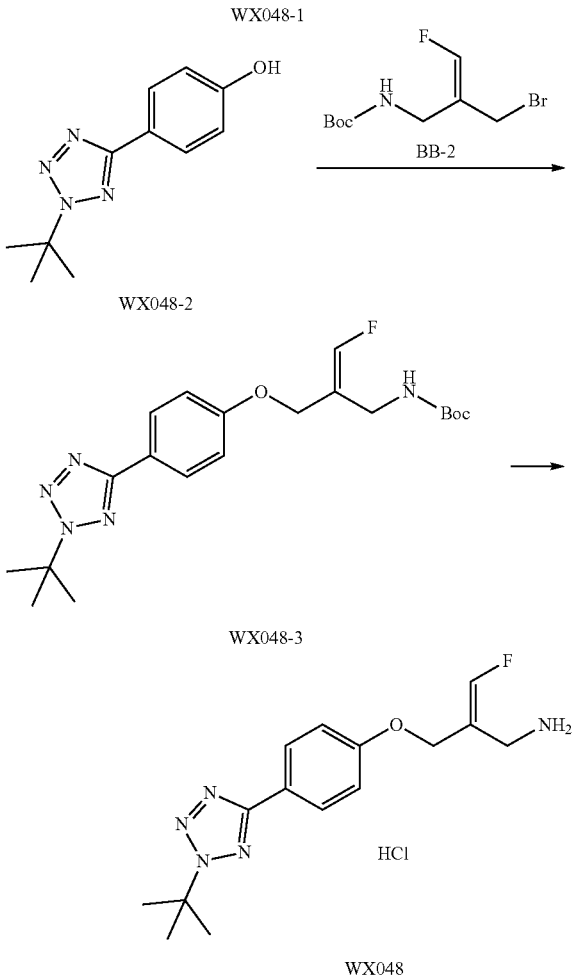

WX048-2

WX048-3

WX048

Step 1: Synthesis of Compound WX048-1

A trifluoroacetic acid mixture of the compound WX014-3 (352.36 mg, 2.00 mmol, 1.00 eq), sulfuric acid (196.16 mg, 2.00 mmol, 106.61 μL, 1.00 eq) and tert-butanol (296.48 mg, 4.00 mmol, 380.10 μL, 2.00 eq) was reacted at 60° C. for 12 hours under nitrogen protection. The reaction solution was spin-dried, diluted with 100 mL of water and extracted with ethyl acetate (100 mL×3). And the organic phase was washed with saturated sodium bicarbonate (100 mL×2), dried with anhydrous sodium sulfate, filtered and spin-dried to obtain the compound WX048-1. ESI m/z: [M+H]$^+$=233.1.

Step 2: Synthesis of Compound WX048-2

The synthesis of the compound WX048-2 referred to the synthesis method of the step 3 of Example 1. ESI m/z: [M−H]$^-$=217.2.

Step 3: Synthesis of Compound WX048-3

The synthesis of the compound WX048-3 referred to the synthesis method of the step 4 of Example 1. ESI m/z: [M-tBu+H]$^+$=350.2.

Step 4: Synthesis of Compound WX048

The synthesis of the compound WX048 referred to the synthesis method of the step 5 in Example 1. $^1$H NMR (400 MHz, DMSO-d$_6$) δ=8.25 (br s, 3H), 8.02 (d, J=8.8 Hz, 2H), 7.48-7.24 (m, 1H), 7.18 (d, J=8.8 Hz, 2H), 4.76-4.66 (m, 2H), 3.34 (s, 2H), 1.74 (s, 9H).

Example 26: WX049

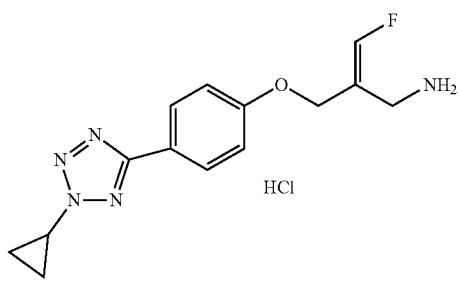 [SMILES: NC/C(=C\F)COc1ccc(-c2nnn(C3CC3)n2)cc1 ; Cl]

Synthesis Route:

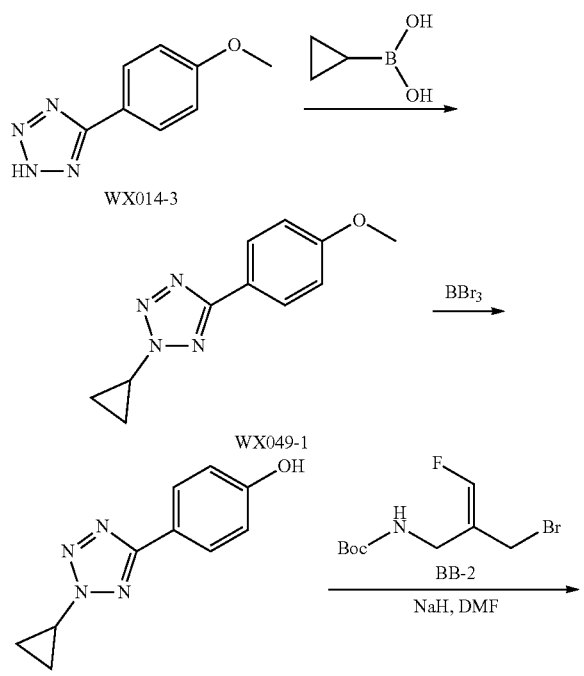

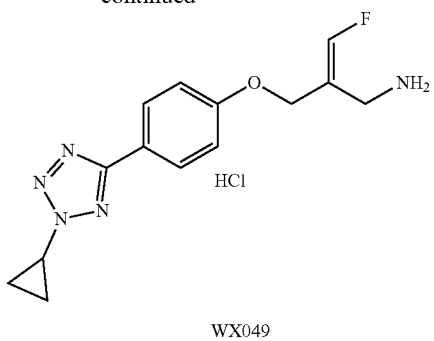

WX049

Step 1: Synthesis of Compound WX049-1

A 1,2-dichloroethane (20 mL) mixture of the compound WX014-3 (600 mg, 3.41 mmol, 1 eq), cyclopropyl boric acid (585.08 mg, 6.81 mmol, 2 eq), copper acetate (618.58 mg, 3.41 mmol, 2 eq), sodium carbonate (721.94 mg, 6.81 mmol, 2 eq), 4-tert-butyl-2-(4-tert-butyl-2-pyridyl)pyridine (1.10 g, 4.09 mmol, 1.2 eq), and a 3 A molecular sieve (600 mg, 3.41 mmol) was reacted at 75° C. for 16 hours under the protection of nitrogen. The mixture was filtered to remove the solid, and the filtrate was diluted with dichloromethane (200 mL) and washed with saturated ammonium chloride (100 mL×2). The organic phase was dried with anhydrous sulfuric acid, spin-dried and purified by a silica gel column to obtain the compound WX049-1. ESI m/z: [M+H]$^+$=217.1.

Step 2: Synthesis of Compound WX049-2

The synthesis of the compound WX049-2 referred to the synthesis method of the step 3 of Example 1. $^1$H NMR (400 MHz, CHLOROFORM-d) δ=8.04 (d, J=8.7 Hz, 2H), 7.28 (s, 1H), 6.96 (d, J=8.5 Hz, 2H), 5.41 (s, 1H), 4.25 (tt, J=3.7, 7.5 Hz, 1H), 1.66-1.43 (m, 2H), 1.37-1.20 (m, 2H).

Step 3: Synthesis of Compound WX049-3

The synthesis of the compound WX049-3 referred to the step 4 of Example 1. ESI m/z: [M-tBu+H]$^+$=334.2.

Step 4: Synthesis of Compound WX049

The synthesis of the compound WX049 referred to the synthesis method of the step 5 in Example 1. $^1$H NMR (400 MHz, DMSO-d$_6$) δ=8.42 (br s, 3H), 7.99 (d, J=8.8 Hz, 2H), 7.48-7.13 (m, 3H), 4.74 (br d, J=3.1 Hz, 2H), 4.44 (tt, J=3.7, 7.4 Hz, 1H), 3.61 (br d, J=4.3 Hz, 2H), 1.43-1.20 (m, 4H).

Example 27: WX052

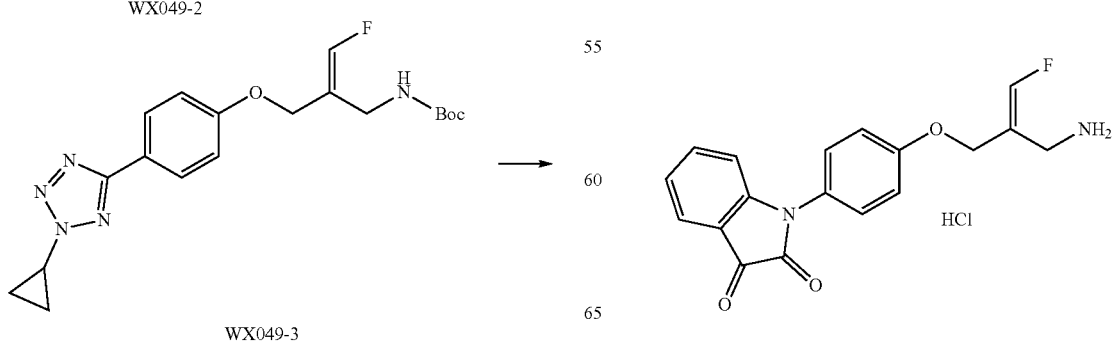

Synthesis Route:

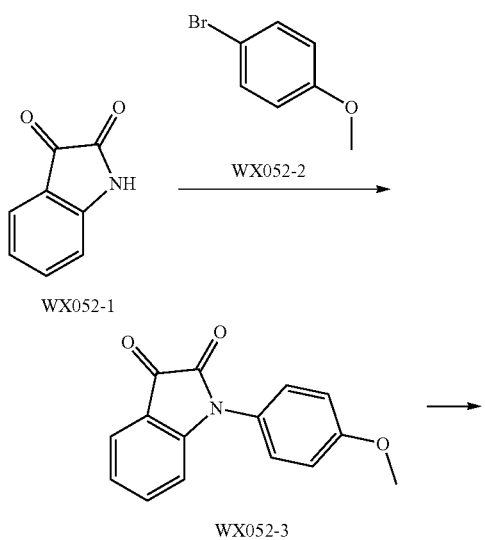

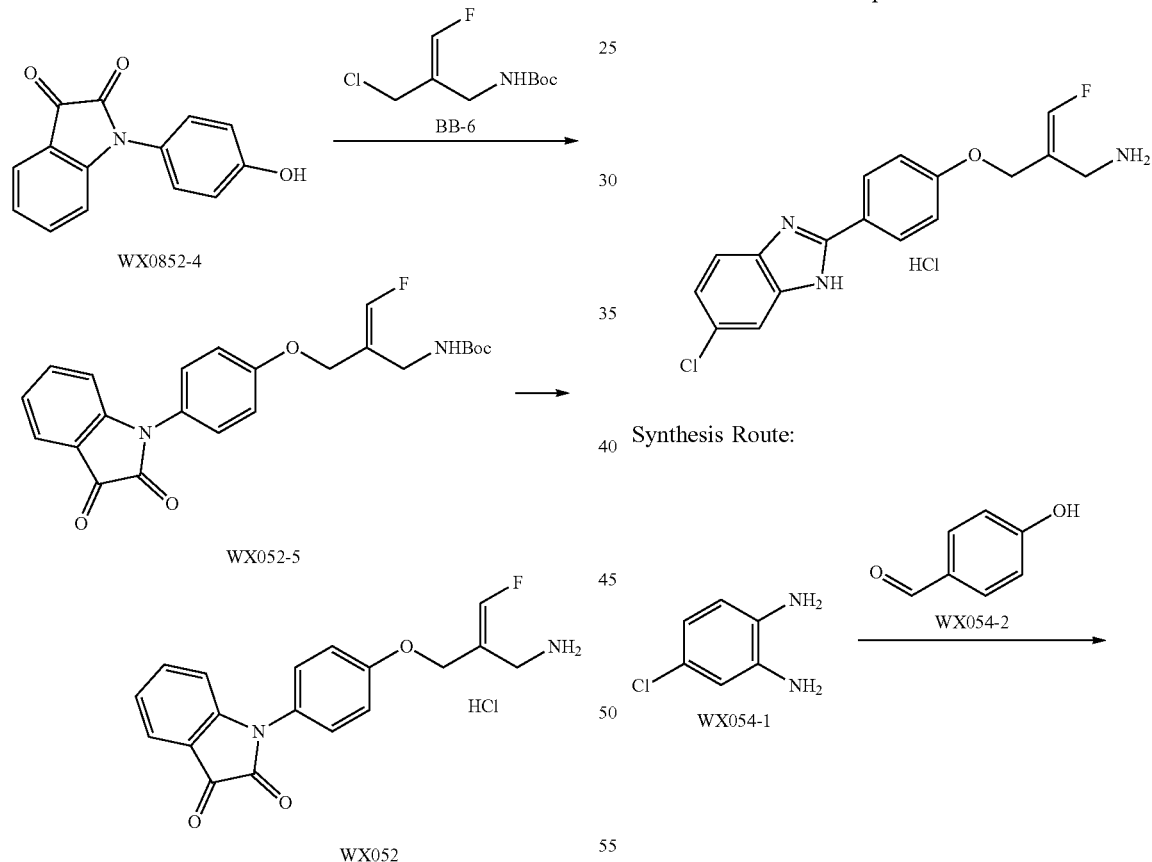

Step 1: Synthesis of Compound WX052-3

Sodium hydrogen (81.55 mg, 2.04 mmol, 33.98 μL, 60% purity, 1.2 eq) was added to a DMF solution (5 mL) of a compound WX052-1 (250 mg, 1.70 mmol, 1 eq). The resulting mixture was reacted at 25° C. for half an hour. A compound WX052-2 (317.80 mg, 1.70 mmol, 213.29 μL, 1 eq) and cuprous iodide (647.21 mg, 3.40 mmol, 2 eq) were added. The reaction was conducted at 145° C. for 12 hours under the protection of nitrogen. 100 mL of water was added into the reaction solution to quench the reaction at 0° C., and the reaction solution was extracted with ethyl acetate (80 mL×2). The organic phase was washed with salt water (80 mL×3), dried with anhydrous sodium sulfate, filtered and spin-dried, and the crude product was purified with a silica gel column to obtain the compound WX052-3. ESI m/z: [M+H]⁺=254.2.

Step 2: Synthesis of Compound WX052-4

The synthesis of the compound WX052-4 referred to the step 3 of Example 1. ESI m/z: [M−H]⁺=238.0.

Step 3: Synthesis of Compound WX052-5

The synthesis of the compound WX052-5 referred to the step 4 of Example 1. ESI m/z: [M+H]⁺=427.3.

Step 4: Synthesis of Compound WX052

The synthesis of the compound WX052 referred to the synthesis method of the step 5 in Example 1. $^1$H NMR (400 MHz, DEUTERIUM OXIDE) δ=7.71-7.48 (m, 2H), 7.41-7.30 (m, 2H), 7.25-6.99 (m, 4H), 6.87-6.78 (m, 1H), 3.94-3.65 (m, 4H).

Example 28: WX054

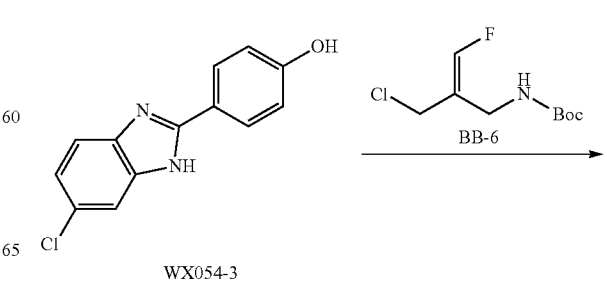

Synthesis Route:

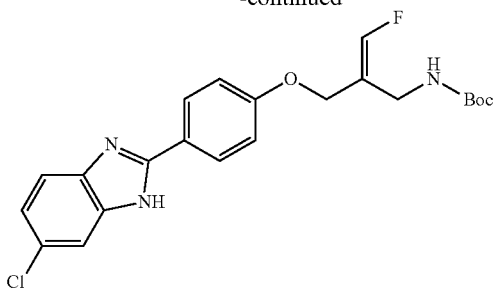

WX054-4

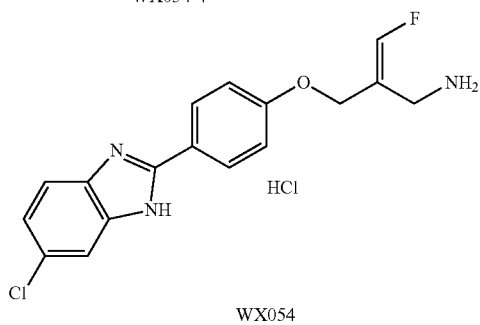

WX054

Step 1: Synthesis of Compound WX054-3

Sodium metabisulfite (399.98 mg, 2.10 mmol, 333.32 μL, 0.3 eq) was added to a N,N-dimethylformamide solution of a compound WX054-1 (1 g, 7.01 mmol, 1 eq) and a compound WX054-2 (856.47 mg, 7.01 mmol, 1 eq). The mixture was reacted at 140° C. for 6 hours. The reaction solution was poured into 30 mL of ice water, and then stirred for 30 minutes. The mixture was filtered to collect the solid, and the filter cake was washed with petroleum ether PE (2 mL×2), and dried to obtain the compound WX054-3. ESI m/z: [M+H]$^+$=245.2.

Step 2: Synthesis of Compound WX054-4

The synthesis of the compound WX054-4 referred to the step 4 of Example 1. $^1$H NMR (400 MHz, DMSO-d$_6$) δ=13.11-12.85 (m, 1H), 8.10 (br d, J=8.7 Hz, 2H), 7.80-7.54 (m, 2H), 7.22-7.08 (m, 4H), 4.60- 4.49 (m, 2H), 3.86-3.73 (m, 2H), 2.00 (s, 1H), 1.35 (s, 9H).

Step 3: Synthesis of Compound WX054

The synthesis of the compound WX054 referred to the synthesis method of the step 5 in Example 1. $^1$H NMR (400 MHz, DMSO-d6) Shift=8.40 (br dd, J=8.3, 13.3 Hz, 6H), 7.86-7.77 (m, 2H), 7.56-7.26 (m, 4H), 4.82 (br s, 2H), 3.75-3.52 (m, 2H).

Example 29: WX056

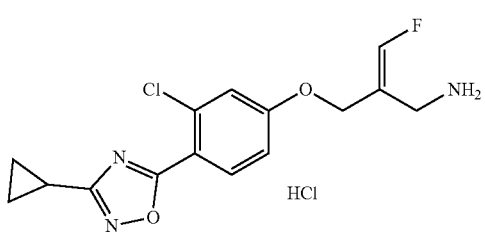 [SMILES: NC/C(=C\F)COc1ccc(-c2nc(C3CC3)no2)c(Cl)c1 ; Cl]

Synthesis Route:

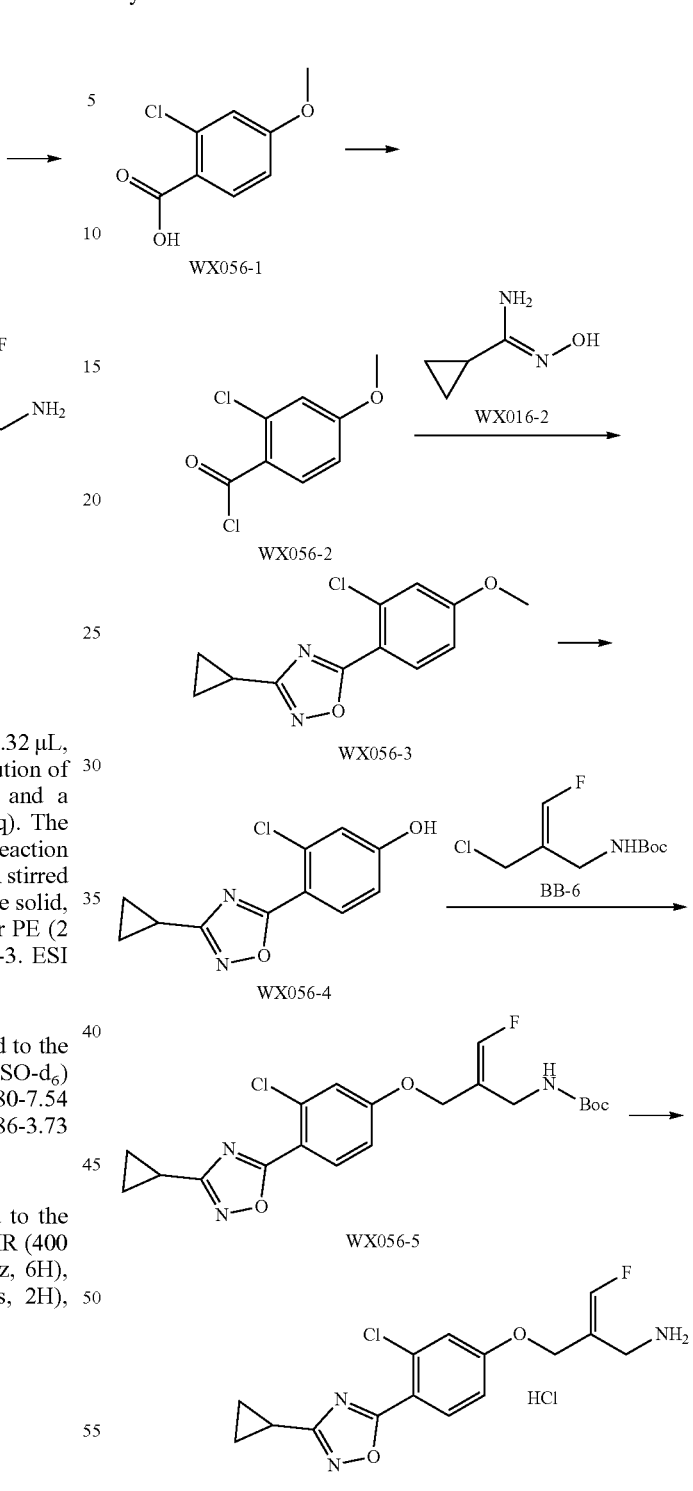

Step 1: Synthesis of Compound WX056-2

Oxalyl chloride (2.72 g, 21.44 mmol, 1.88 mL, 2 eq) and N,N-dimethylformamide (39.17 mg, 535.93 μmol, 41.23 μL, 0.05 eq) were added dropwise to a dichloromethane suspension of a compound WX056-1 (2 g, 10.72 mmol, 1 eq). The mixture was reacted for 3 hours at 20° C. The reaction solution was spin-dried to obtain the compound WX056-2.

Step 2: Synthesis of Compound WX056-3

The synthesis of the compound WX056-3 referred to the step 2 of Example 5. $^1$H NMR (400 MHz, CHLOROFORM-d) δ=7.99 (d, J=8.9 Hz, 1H), 7.06 (d, J=2.5 Hz, 1H), 6.93 (dd, J=2.5, 8.9 Hz, 1H), 3.89 (s, 3H), 2.22-2.13 (m, 1H), 1.18-1.01 (m, 4H).

Step 3: Synthesis of Compound WX056-4

The synthesis of the compound WX056-4 referred to the step 3 of Example 1. ESI m/z: [M+H]$^+$=237.2.

Step 4: Synthesis of Compound WX056-5

The synthesis of the compound WX056-5 referred to the step 4 of Example 1. ESI m/z: [M+H]$^+$=424.4.

Step 5: Synthesis of Compound WX056

The synthesis of the compound WX056 referred to the synthesis method of the step 5 in Example 1. $^1$H NMR (400 MHz, DMSO-d6) δ=8.39 (br s, 3H), 8.03 (d, J=8.8 Hz, 1H), 7.49-7.25 (m, 2H), 7.21 (dd, J=2.4, 8.8 Hz, 1H), 4.81 (br s, 2H), 3.61 (br s, 2H), 2.26-2.05 (m, 1H), 1.18-1.05 (m, 2H), 1.05-0.90 (m, 2H).

Example 30: WX062

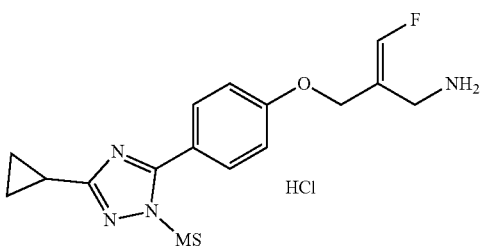

Synthesis Route:

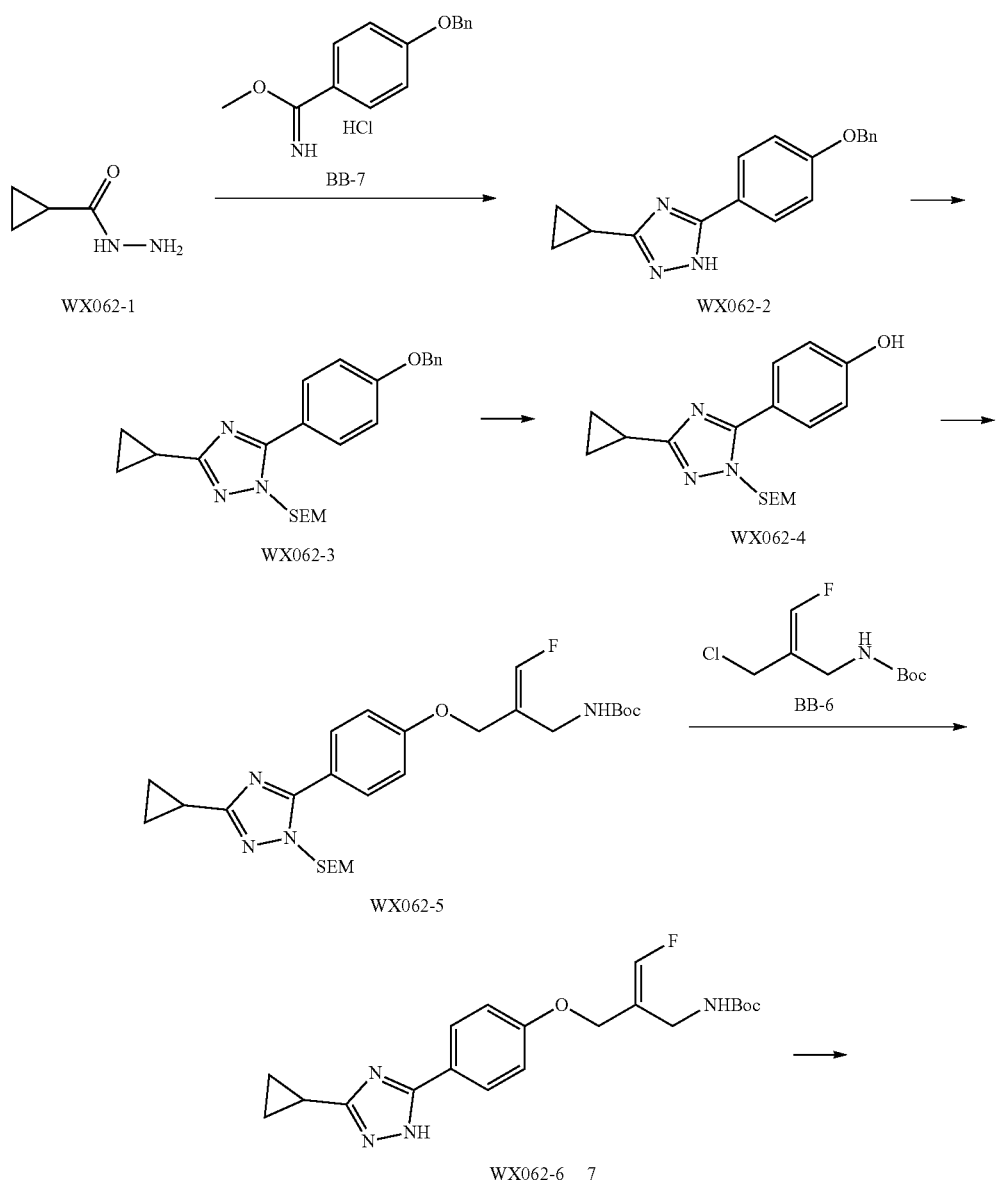

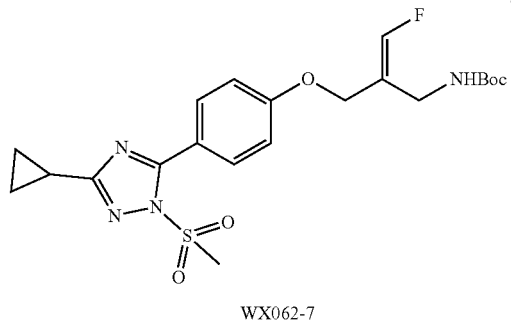

WX062-7

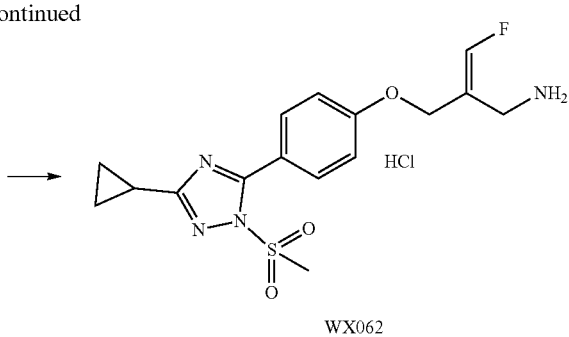

WX062

Step 1: Synthesis of Compound WX062-2

A compound WX062-1 (1.37 g, 13.68 mmol, 1.00 eq) was added to a methanol solution (3.00 mL) of a compound BB-7 (3.30 g, 13.68 mmol, 1.00 eq) and triethylamine (1.38 g, 13.68 mmol, 1.90 mL, 1.00 eq). The resulting mixture was reacted at 85° C. for 12 hours. The reaction solution was spin-dried, and the crude product was separated by a column (petroleum ether:ethyl acetate=5:1 to 1:1) to obtain the compound WX062-2. $^1$H NMR (400 MHz, METHANOL-$d_4$) δ ppm 7.86 (br d, J=8.00 Hz, 2H) 7.41-7.48 (d, J=8 Hz, 2H) 7.37 (t, J=8 Hz, 2H) 7.31 (d, J=8 Hz, 1H) 7.07 (d, J=8.00 Hz, 2H) 5.13 (s, 2H) 1.97-2.13 (m, 1H) 1.03 (m, 4H).

Step 2: Synthesis of Compound WX062-3

Sodium hydrogen (219.65 mg, 5.49 mmol, 60% purity, 1.00 eq) was added to a N,N-dimethylformamide solution (20.00 mL) of the compound WX062-2 (1.60 g, 5.49 mmol, 1.00 eq) at 0° C., and the resulting mixture was reacted at 25° C. for half an hour. SEMCl (915.59 mg, 5.49 mmol, 971.96 μL, 1.00 eq) was added and the reaction was continued to be carried out to be complete. The reaction solution was poured into water (80 ml) and extracted with ethyl acetate (40 ml×3), dried and spin-dried to obtain the target compound WX062-3.

Step 3: Synthesis of Compound WX062-4

Wet palladium-carbon (0.75 g, 2.85 mmol, 5% purity) was added to a methanol solution of the compound WX062-3 (1.2 g, 2.85 mmol, 1 eq), and the resulting mixture was reacted at the pressure of $H_2$ (15 psi) at 40° C. for 8 hours. The reaction solution was filtered and spin-dried to obtain the target compound WX062-4. ESI m/z: [M+H]$^+$=332.

Step 4: Synthesis of Compound WX062-5

The synthesis of the compound WX062-5 referred to the step 4 of Example 1.

Step 5: Synthesis of Compound WX062-6

Tetrabutylammonium fluoride (1N in tetrahydrofuran, 403.26 mg, 1.54 mmol, 4.00 mL, 5.00 eq) was added to a tetrahydrofuran solution (10 mL) of the compound WX062-5 (0.16 g, 308.47 μmol, 1.00 eq), and the resulting mixture was reacted at 60° C. for 24 hours. The reaction solution was poured into water (10 ml) and extracted with ethyl acetate (5 ml×3). The reaction solution was dried and spin-dried to obtain the target compound WX062-6. $^1$H NMR (400 MHz, DMSO-$d_6$) δ ppm 8.38 (br s, 3H) 8.08 (d, J=8.8 Hz, 2H) 7.26-7.56 (m, 1H) 7.20 (d, J=8 Hz, 2H) 4.76 (br d, J=4 Hz, 2H) 3.65 (d, J=4.0 Hz, 2H) 2.25 (m, 1H) 1.11-1.23 (m, 4H).

Step 6: Synthesis of Compound WX062-7

Methyl sulfonyl chloride (94.37 mg, 823.82 μmol, 63.76 μL, 2.00 eq) was added to a pyridine solution of the compound WX062-6 (0.16 g, 411.91 μmol, 1 eq) at 0° C., and the resulting mixture was reacted at 25° C. for 16 hours. The reaction solution was poured into water (30 ml), extracted with ethyl acetate (15 ml×3), dried and spin-dried, and the crude product was purified with a column (petroleum ether:ethyl acetate=2/1 to 1/1) to obtain the target compound WX062-7.

Step 7: Synthesis of Compound WX062

The synthesis of the compound WX062 referred to the step 5 of Example 1. $^1$H NMR (400 MHz, DMSO-$d_6$) δ ppm 8.16 (br s, 3H) 7.96 (d, J=9.2 Hz, 2H) 7.22-7.49 (m, 1H) 7.12 (d, J=8.8 Hz, 2H) 4.68 (d, J=2.8 Hz, 2H) 3.76 (s, 3H) 3.64 (s, 2H) 2.59-2.70 (m, 1H) 1.10-1.27 (m, 4H).

Example 31: WX064

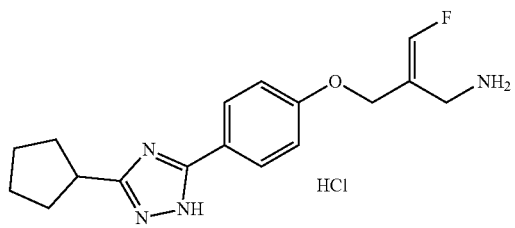 [SMILES: NC/C(=C\F)COc1ccc(-c2nc(C3CCCC3)n[nH]2)cc1 ; Cl]

Synthesis Route:

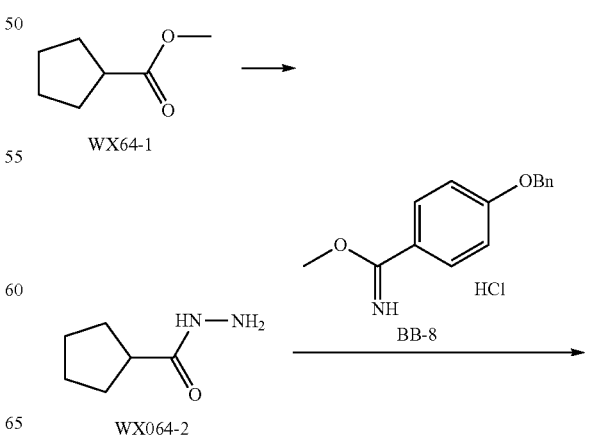

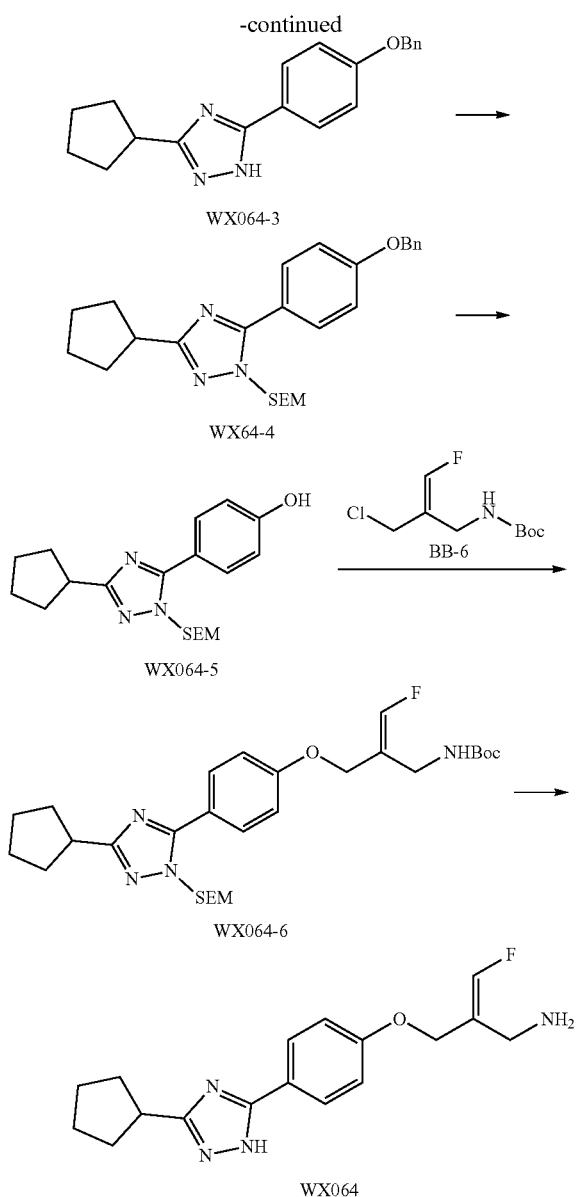

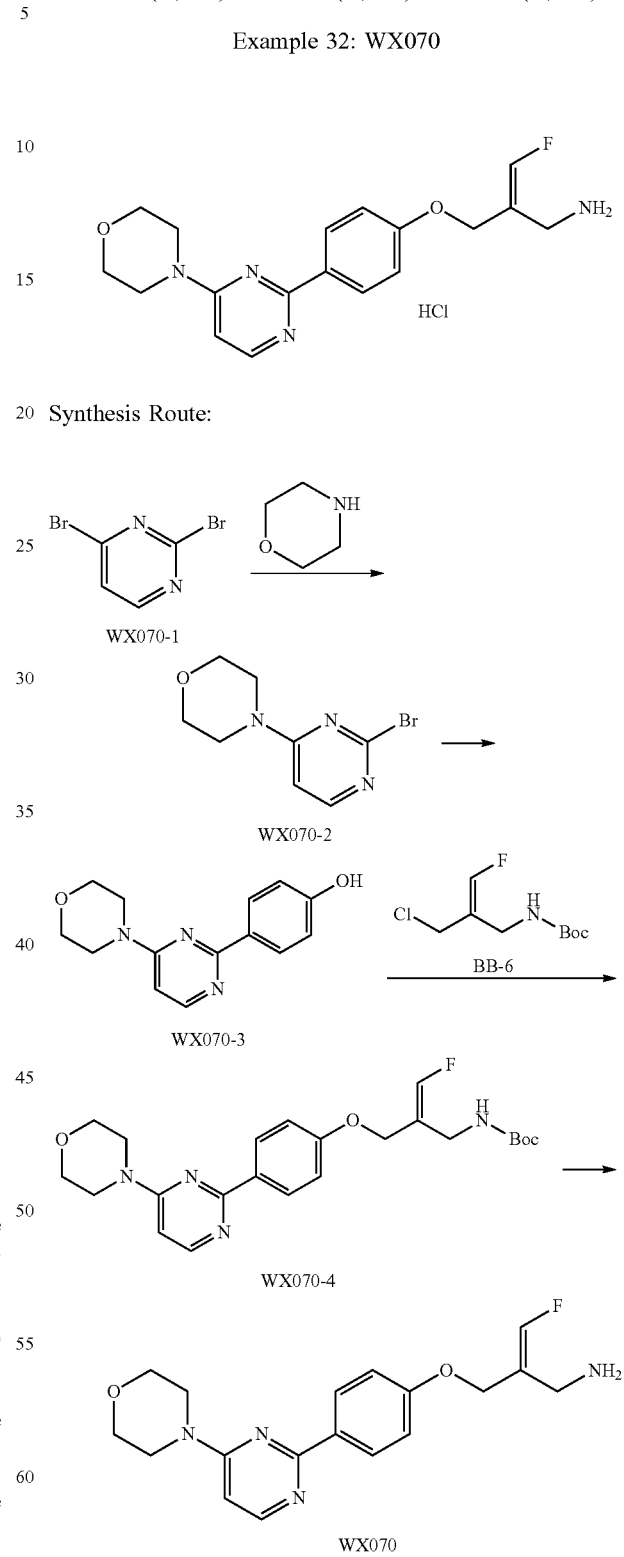

(400 MHz, DMSO-d$_6$) δ ppm 8.40 (br s, 3H) 8.15 (d, J=8.8 Hz, 2H) 7.26-7.49 (m, 1H) 7.21 (d, J=8 Hz, 2H) 4.77 (d, J=4 Hz, 2H) 3.63 (m, 2H) 3.37 (m, 1H) 2.08-2.19 (m, 2H) 1.86-1.96 (m, 2H) 1.77-1.85 (m, 2H) 1.65-1.74 (m, 2H).

Example 32: WX070

Synthesis Route:

Step 1: Synthesis of Compound WX064-2

A mixture of a compound WX064-1 (6.7 g, 52.27 mmol, 1 eq) and hydrazine hydrate (4.62 g, 78.41 mmol, 4.48 mL, 85% purity, 1.5 eq) was reacted at 90° C. for 3 hours. The reaction solution was spin-dried to obtain the target compound WX064-2. ESI m/z [M+1]$^+$=129.3.

Step 2: Synthesis of Compound WX064-3

The synthesis of compound WX064-3 referred to the step 1 of Example 30, ESI m/z [M+1]$^+$=320.3.

Step 3: Synthesis of Compound WX064-4

The synthesis of the compound WX064-4 referred to the step 2 of Example 30.

Step 4: Synthesis of Compound WX064-5

The synthesis of the compound WX064-5 referred to step 3 of Example 30.

Step 5: Synthesis of Compound WX064-6

The synthesis of the compound WX064-6 referred to the step 4 of Example 1.

Step 6: the synthesis of the compound WX064 referred to the synthesis method of the step 5 in Example 1. $^1$H NMR Step 1: Synthesis of Compound WX070-2

N,N-diisopropyl ethylamine (244.49 mg, 1.89 mmol, 329.50 μL, 1.5 eq) and 4-N,N-dimethylpyridine (7.70 mg, 63.06 μmol, 0.05 eq) were added into an ethanol solution of a compound WX070-1 (0.3 g, 1.26 mmol, 1 eq) and morpholine (109.87 mg, 1.26 mmol, 110.98 μL, 1 eq), and the resulting mixture was reacted at 20° C. for 2 hours. The reaction solution was diluted with water (20 ml), extracted with ethyl acetate (20 ml×2), dried and spin-dried to obtain the target compound WX070-2. $^1$H NMR (400 MHz, CHLOROFORM-d) δ=8.03-7.96 (m, 1H), 6.39 (d, J=6.2 Hz, 1H), 3.77-3.73 (m, 4H), 3.61 (br s, 4H).

Step 2: Synthesis of Compound WX070-3

The synthesis of the compound WX070-3 referred to the synthesis method of the step 1 of Example 8. ESI m/z [M+1]$^+$=258.3

Step 3: Synthesis of Compound WX070-4

The synthesis of the compound WX070-4 referred to the synthesis method of the step 4 in Example 1. ESI m/z [M+1]$^+$=445.5.

Step 4: Synthesis of Compound WX070

The synthesis of the compound WX070 referred to the synthesis method of the step 5 in Example 1. $^1$H NMR (400 MHz, DMSO-d$_6$) δ=8.41 (d, J=5.5 Hz, 1H), 8.34 (br s, 3H), 8.18 (d, J=8.9 Hz, 2H), 7.48-7.23 (m, 2H), 7.14 (d, J=8.9 Hz, 2H), 4.74 (d, J=2.9 Hz, 2H), 3.88-3.77 (m, 4H), 3.74-3.69 (m, 4H), 3.62 (br s, 2H).

Example 33: WX072

Synthesis Route:

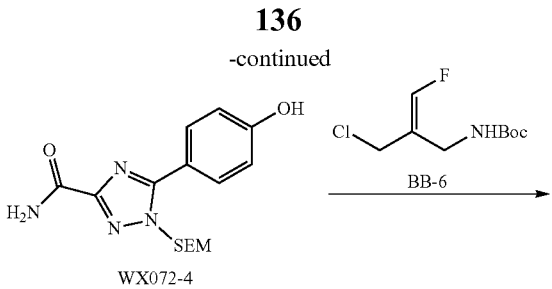

Step 1: Synthesis of Compound WX072-2

The synthesis of the compound WX072-2 referred to the step 1 of Example 30, [M−99]$^+$=340.3. $^1$H NMR (400 MHz, DMSO-d$_6$) δ ppm 14.47-14.97 (m, 1H) 7.97 (d, J=8.00 Hz, 3H) 7.31-7.56 (m, 6H) 7.18 (br s, 2H) 5.18 (s, 2H).

Step 2: Synthesis of Compound WX072-3

The synthesis of the compound WX072-3 referred to the synthesis method of the step 2 in Example 30, [M+H]$^+$=424.2.

Step 3: Synthesis of Compound WX072-4

The synthesis of the compound WX072-4 referred to the synthesis method of the step 3 in Example 30, $^1$H NMR (400 MHz, DMSO-d$_6$) δ=9.90 (br s, 1H), 8.37-8.25 (m, 1H), 8.12 (br s, 1H), 8.02 (s, 2H), 7.97-7.91 (m, 2H), 6.96-6.90 (m, 2H), 5.99-5.88 (m, 2H), 3.71 (t, J=8.0 Hz, 2H), 0.99-0.84 (m, 2H), 0.07-0.04 (m, 8H).

Step 4: Synthesis of Compound WX072-5

The synthesis of the compound WX072-5 referred to the synthesis method of the step 4 of Example 1, ESI m/z: [M+Na]$^+$=344.5.

Step 5: Synthesis of Compound WX072

The synthesis of the compound WX072 referred to the synthesis method of the step 5 of Example 1, $^1$H NMR (400 MHz, DMSO-d$_6$) δ=8.30 (br s, 3H), 8.09-7.92 (m, 3H), 7.76 (br s, 1H), 7.46-7.22 (m, 1H), 7.16 (br d, J=8.9 Hz, 2H), 4.78-4.64 (m, 2H), 3.62 (br d, J=4.4 Hz, 2H).

Example 34: WX073

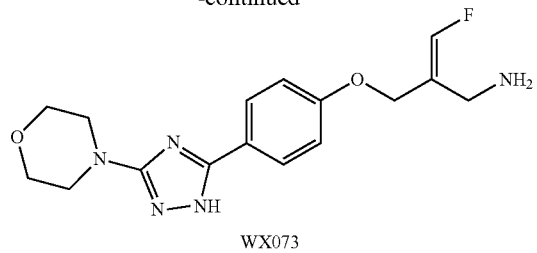

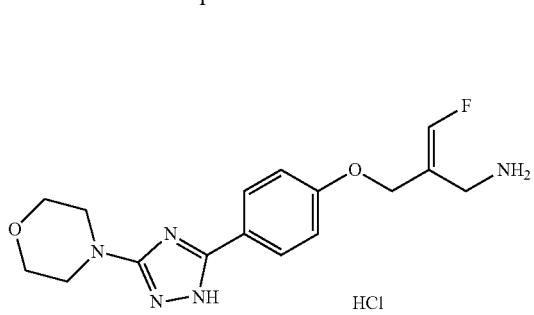

Synthesis Route:

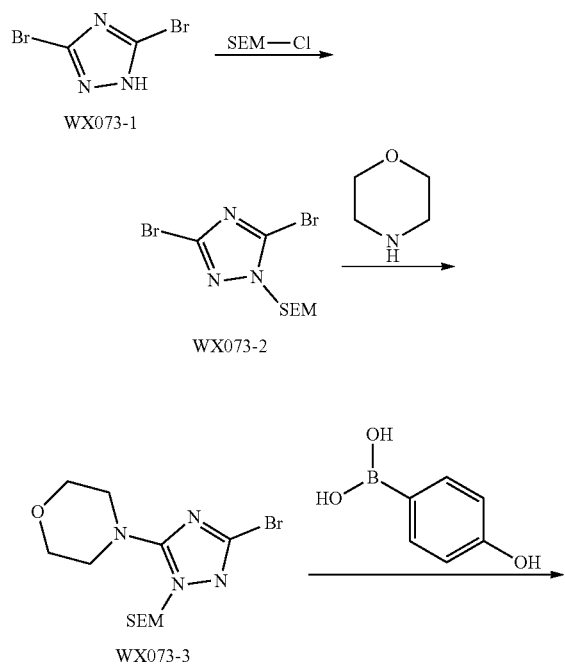

Step 1: Synthesis of Compound WX073-2

SEM-Cl (808.41 mg, 4.85 mmol, 858.18 μL, 1 eq) was added to a dichloromethane solution (10 mL) of a compound WX073-1 (1.1 g, 4.85 mmol, 1 eq) and triethylamine (727.00 mg, 7.18 mmol, 1 mL, 1.48 eq), and the resulting mixture was reacted 25° C. for 1 hour. The reaction solution was spin-dried to obtain the target compound WX073-2. ESI m/z: [M−TMS+O]⁻=300.1.

Step 2: Synthesis of Compound WX073-3

A N,N-dimethylformamide solution (2 mL) of the compound WX073-2 (400 mg, 1.12 mmol, 1 eq) and morpholine (107.34 mg, 1.23 mmol, 108.42 μL, 1.1 eq) was reacted at 110° C. for 1 hour under microwave. The reaction solution was diluted with ethyl acetate (50 ml) and washed with salt water (30 ml×2), dried with anhydrous sodium sulfate, and spin-dried to obtain the target compound WX073-3. ESI m/z: [M+H]⁺=363.3.

Step 3: Synthesis of Compound WX073-4

The synthesis of the compound WX073-4 referred to the step 1 of Example 8, ESI m/z: [M−H]⁻=375.1

Step 4: Synthesis of Compound WX073-5

The synthesis of the compound WX073-5 referred to the step 4 of Example 1, ESI m/z: [M+H]⁺=564.6.

Step 5: Synthesis of Compound WX073

The synthesis of the compound WX073 referred to the synthesis method of the step 5 in Example 1. ¹H NMR (400 MHz, DMSO-d₆) δ=8.42 (br s, 3H), 8.07 (br d, J=7.4 Hz, 2H), 7.50-7.22 (m, 1H), 7.15 (br d, J=7.4 Hz, 2H), 4.74 (br s, 2H), 3.74 (br s, 6H), 3.59 (br s, 7H), 3.65-3.55 (m, 1H), 3.65-3.55 (m, 1H).

Example 35: WX074

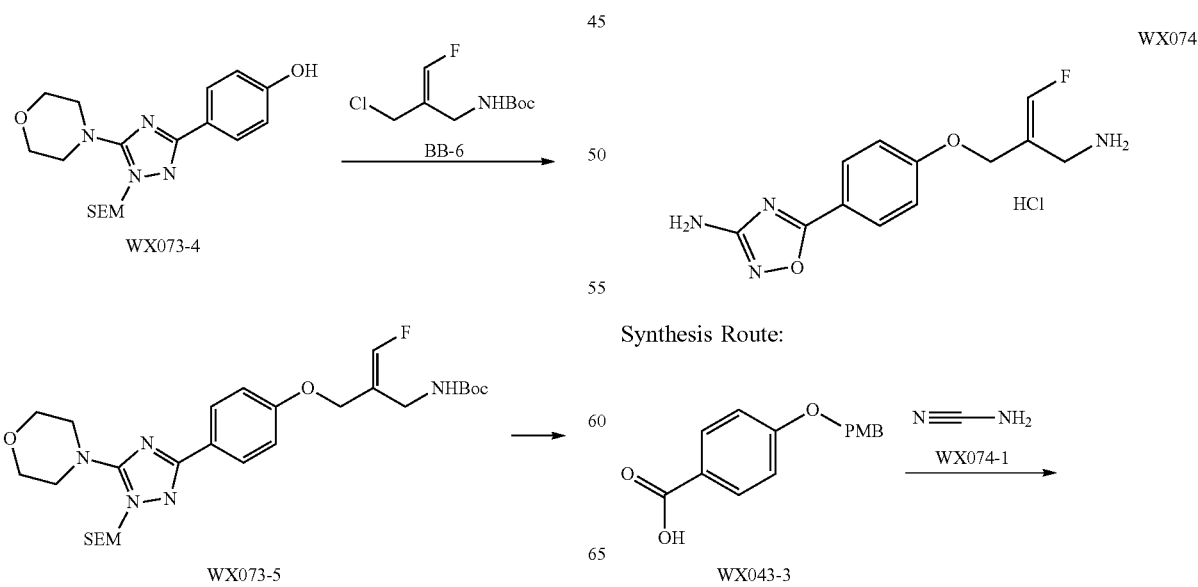

Synthesis Route:

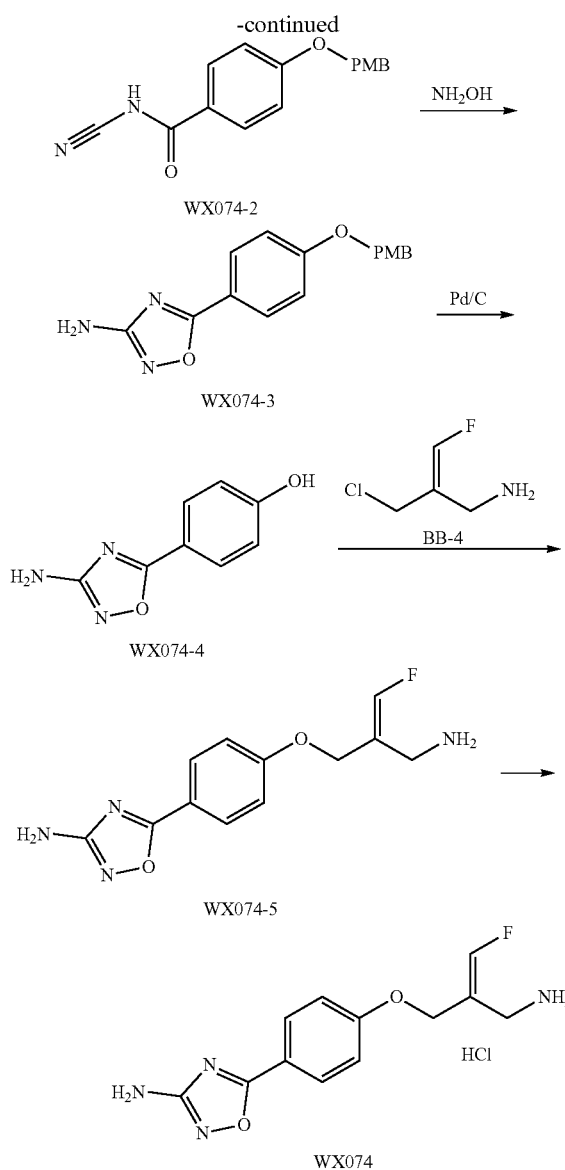

purified by a silica gel column (petroleum ether/ethyl acetate 10:1 to 1:1) to obtain the compound WX074-3. $^1$H NMR (400 MHz, DMSO-$d_6$) δ=7.92-7.84 (m, 2H), 7.41-7.33 (m, 2H), 7.19-7.12 (m, 2H), 6.95-6.89 (m, 2H), 6.29 (br s, 2H), 5.18-5.03 (m, 2H), 3.72 (s, 3H), 3.31 (s, 3H).

Step 3: Synthesis of Compound WX074-4

The synthesis of the compound WX074-4 referred to the synthesis method of the step 3 in Example 30. ESI m/z [M+H]$^+$=178.2.

Step 4: Synthesis of Compound WX074-5

The synthesis of the compound WX074-5 referred to the synthesis method of the step 4 in Example 1. ESI m/z [M-tBu+H]$^+$=309.

Step 5: Synthesis of Compound WX074

The synthesis of the compound WX074 referred to the synthesis method of the step 5 in Example 1. $^1$H NMR (400 MHz, DMSO-$d_6$) δ=8.33 (br s, 1H), 7.96 (d, J=8.9 Hz, 1H), 7.53-7.23 (m, 1H), 7.20 (d, J=9.0 Hz, 1H), 6.34 (br s, 1H), 4.75 (br d, J=3.0 Hz, 1H), 3.62 (br s, 1H).

Example 36: WX075

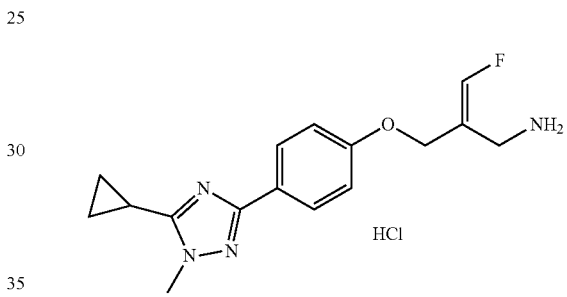

Synthesis Route:

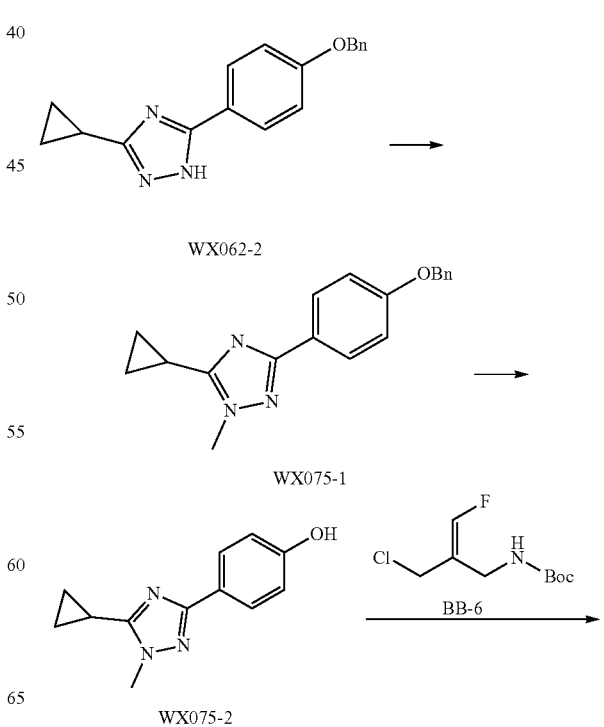

Step 1: Synthesis of Compound WX074-2

HATU (8.39 g, 22.07 mmol, 1.5 eq) was added to a N,N-dimethylamine (40 mL) solution of the compound WX043-3 (3.8 g, 14.71 mmol, 1 eq), triethylamine (2.98 g, 29.43 mmol, 4.10 mL, 2 eq) and a compound WX074-1 (927.82 mg, 22.07 mmol, 927.82 μL, 1.5 eq), and the resulting mixture was reacted at 25° C. for 12 hours. The reaction solution was diluted with 150 mL of water, and extracted with ethyl acetate (100 mL×3), and the organic phase was washed with saturated salt water (100 mL×3), dried and spin-dried to obtain the compound WX074-2. $^1$H NMR (400 MHz, DMSO-$d_6$) δ=7.88-7.80 (m, 2H), 7.40-7.30 (m, 2H), 7.05-6.96 (m, 2H), 6.95-6.85 (m, 2H), 5.04 (s, 2H), 3.72 (s, 3H).

Step 2: Synthesis of Compound WX074-3

A pyridine solution (20 mL) of the compound WX074-2 (2.3 g, 8.15 mmol, 1 eq) and hydroxylamine hydrochloride (849.27 mg, 12.22 mmol, 1.5 eq) was reacted at 110° C. for 1 hour. The reaction solution was adjusted to a pH of 2 with 1 N hydrochloric acid, extracted with ethyl acetate (50 mL×2), dried, and spin-dried, and the crude product was

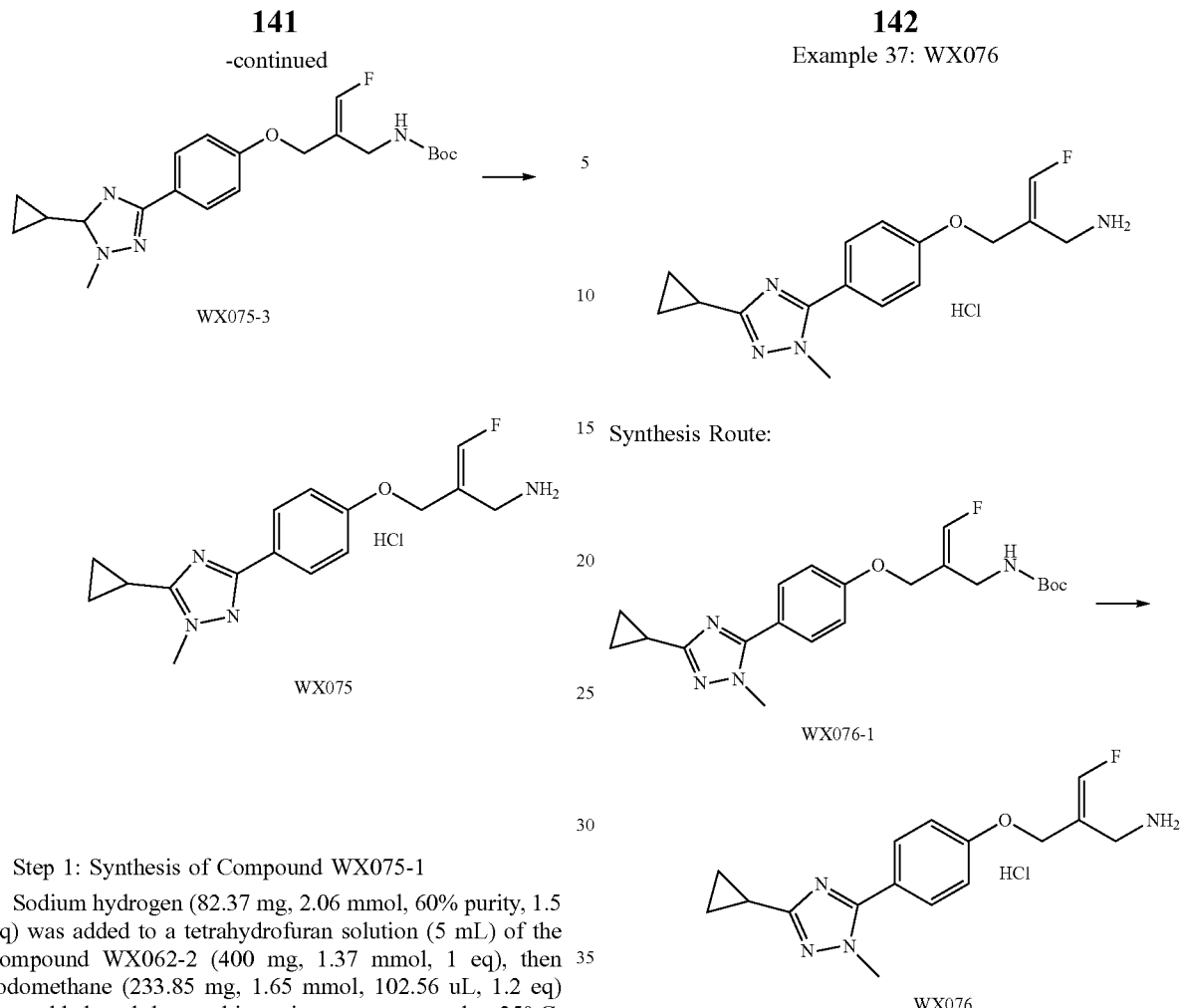

Step 1: Synthesis of Compound WX075-1

Sodium hydrogen (82.37 mg, 2.06 mmol, 60% purity, 1.5 eq) was added to a tetrahydrofuran solution (5 mL) of the compound WX062-2 (400 mg, 1.37 mmol, 1 eq), then iodomethane (233.85 mg, 1.65 mmol, 102.56 uL, 1.2 eq) was added, and the resulting mixture was reacted at 25° C. for 12 hours. The reaction solution was quenched with 1 mL of water, diluted with ethyl acetate (20 mL), washed with salt water (10 mL×2), dried with anhydrous sodium sulfate and spin-dried, and the crude product was purified by a column to obtain the target compound WX075-1. $^1$H NMR (400 MHz, CHLOROFORM-d) δ=7.97 (d, J=7.8 Hz, 1H), 7.99-7.56 (m, 1H), 7.58 (d, J=7.7 Hz, 1H), 7.49-7.28 (m, 5H), 7.11-7.00 (m, 2H), 5.16-5.10 (m, 2H), 4.00-3.83 (m, 3H), 1.91-1.84 (m, 1H), 1.19-0.95 (m, 4H).

Step 2: Synthesis of Compound WX075-2

The synthesis of the compound WX075-2 referred to the synthesis method of the step 3 in Example 30. ESI m/z [M+H]$^+$=216.3.

Step 3: Synthesis of Compound WX075-3

The synthesis of the compound WX075-3 referred to the synthesis method of the step 4 in Example 1. $^1$H NMR (400 MHz, DMSO-d$_6$) δ=7.82 (d, J=8.0 Hz, 2H), 7.19-6.92 (m, 4H), 4.46 (d, J=3.3 Hz, 2H), 3.93-3.83 (m, 3H), 3.77 (br d, J=4.6 Hz, 2H), 2.58-2.52 (m, 2H), 2.19-2.11 (m, 1H), 1.34 (s, 9H), 1.12- 0.90 (m, 4H).

Step 4: Synthesis of Compound WX075

The synthesis of the compound WX075 referred to the synthesis method of the step 5 in Example 1. $^1$H NMR (400 MHz, DMSO-d$_6$) δ=8.31 (br s, 3H), 7.90 (br d, J=8.5 Hz, 2H), 7.28 (br s, 1H), 7.07 (d, J=8.8 Hz, 2H), 5.36 (br s, 2H), 4.68 (br s, 2H), 3.92 (s, 3H), 3.61 (br d, J=4.6 Hz, 2H), 2.30-2.10 (m, 1H), 1.15-0.97 (m, 4H).

Step 1: Synthesis of Compound WX076-1

The isomer compound WX076-1 was separated from the synthetic compound WX075-3. $^1$H NMR (400 MHz, DMSO-d$_6$) δ=7.69-7.62 (m, 2H), 6.98 (s, 4H), 4.51 (d, J=3.0 Hz, 2H), 3.83 (s, 3H), 3.78 (br d, J=4.8 Hz, 2H), 1.99-1.91 (m, 1H), 1.35 (s, 9H), 0.95-0.77 (m, 4H).

Step 2: Synthesis of Compound WX076

The synthesis of the compound WX076 referred to the synthesis method of the step 5 in Example 1. $^1$H NMR (400 MHz, DMSO-d$_6$) δ=8.42 (br s, 3H), 7.74 (br d, J=8.7 Hz, 2H), 7.32 (br s, 4H), 4.76 (br s, 2H), 3.87 (s, 3H), 3.61 (br d, J=4.5 Hz, 2H), 2.11-1.99 (m, 1H), 1.05-0.86 (m, 4H).

Example 38: WX077

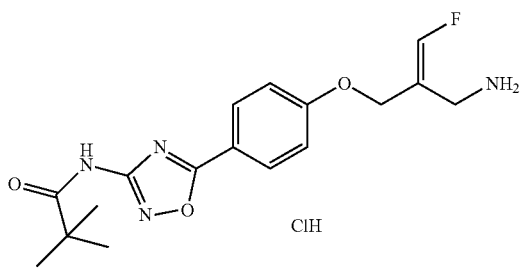 [SMILES: CC(C)(C)C(=O)Nc1noc(-c2ccc(OC/C(=C/F)CN)cc2)n1 ; Cl]

Synthesis Route:

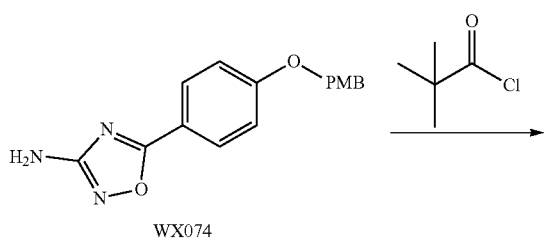

Step 1: Synthesis of Compound WX077-1

A toluene mixture (2.00 ml) of the compound WX0074 (50 mg), pyridine (19.95 mg) and pivaloyl chloride (30.42 mg) was reacted at 80° C. for 12 hours under the protection of nitrogen. The reaction solution was spin-dried, and the resulting residue was purified by a silica gel column (petroleum ether/ethyl acetate 10:1→5:1→1:1) to obtain the compound WX077-1, ESI m/z: [M+1]=382.2.

Step 2: Synthesis of Compound WX077-2

The synthesis of the compound WX077-2 referred to the synthesis method of the step 3 in Example 30. ESI m/z: [M+1]=262.3.

Step 3: Synthesis of Compound WX077-3

The synthesis of the compound WX077-3 referred to the step 4 of Example 1. ESI m/z: [M−56]=393.2.

Step 4: Synthesis of Compound WX077

The synthesis of the compound WX077 referred to the synthesis method of the step 5 in Example 1. 1H NMR (400 MHz, DMSO-d6). ppm: 1.41 (9H); 3.62 (2H,); 4.69-4.79 (2H); 7.11 (2H, J=8.8 Hz); 7.25-7.47 (1H); 7.98-8.11 (2H); 8.27 (3H,); 11.35 (1H,).

Example 39: WX100

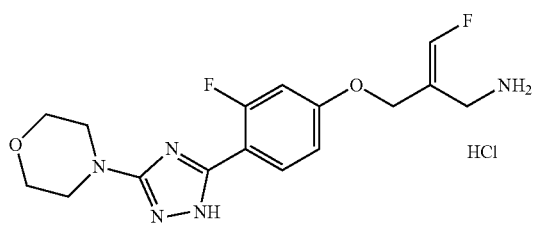 [SMILES: NC/C(=C\F)COc1ccc(-c2nc(N3CCOCC3)n[nH]2)c(F)c1 ; Cl]

Synthesis Route:

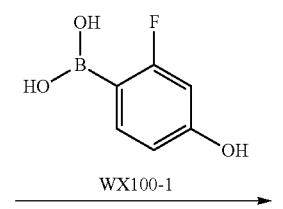

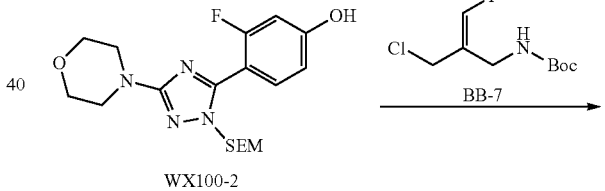

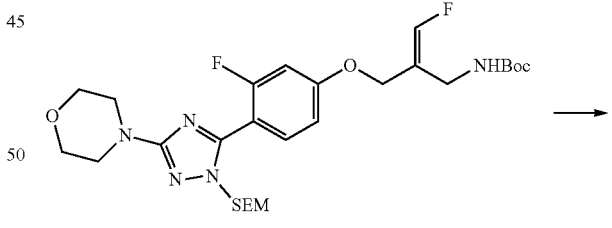

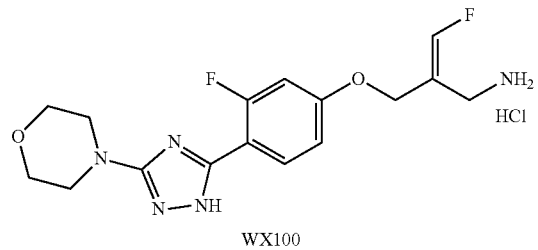

Step 1: Synthesis of Compound WX100-2

The synthesis of the compound WX100-2 referred to the step 1 of Example 16, ESI m/z: [M+H]+=395.3.

Step 2: Synthesis of Compound WX100-3

The synthesis of the compound WX100-3 referred to the step 4 of Example 1, ESI m/z: [M+H]⁺=582.3.

Step 3: Synthesis of Compound WX100

The synthesis of the compound WX100 referred to the step 5 of Example 1, ¹H NMR (400 MHz, DMSO-$d_6$) δ ppm 3.20-3.37 (m, 2H) 3.75-3.92 (m, 8H) 4.72 (d, J=3.01 Hz, 2H) 6.98 (dd, J=8.72, 2.32 Hz, 1H) 7.08 (d, J=2.26 Hz, 1H) 7.22-7.45 (m, 1H) 7.89 (t, J=8.72 Hz, 1H) 8.29 (br s, 2H).

Example 40: WX079

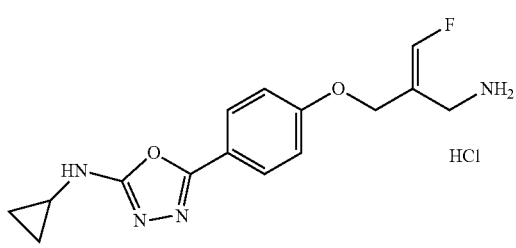 [SMILES: NC/C(=C\F)COc1ccc(-c2nnc(NC3CC3)o2)cc1 ; Cl]

Synthesis Route:

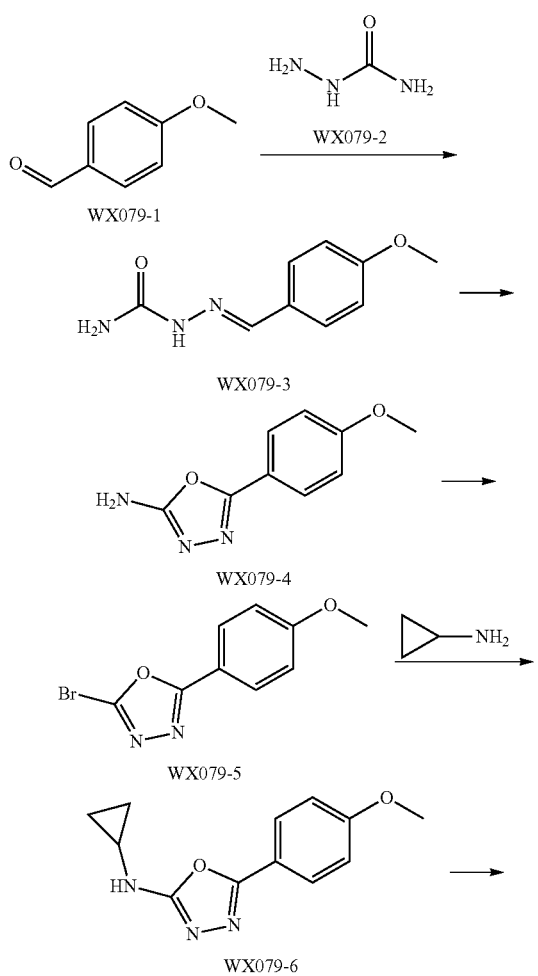

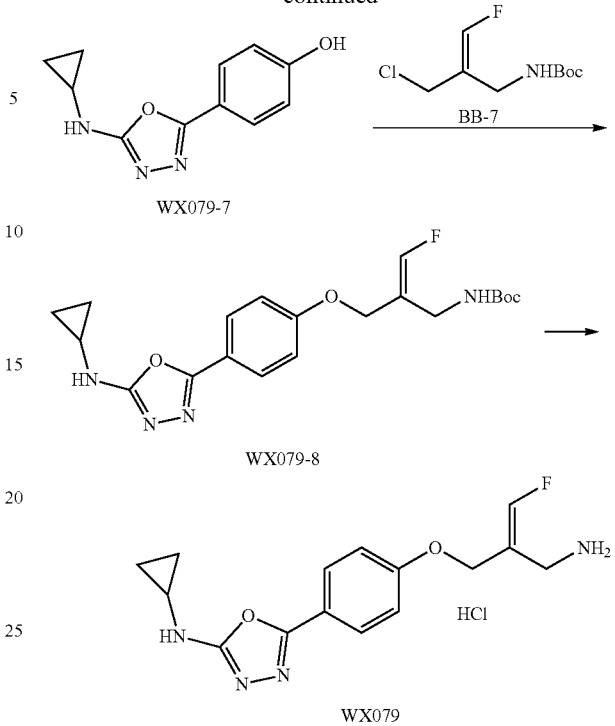

Step 1: Synthesis of Compound WX079-3

Acetic acid (600.52 mg) and a compound WX079-1 (1.36 g) were added to a methanol (10 ml) solution of a compound WX079-2 (1.12 g). The resulting mixture was stirred at 25° C. for 2 hours. The reaction solution was concentrated under reduced pressure and spin-dried to obtain the compound WX079-3. 1H NMR (400 MHz, CHLOROFORM-d) δ ppm 9.90 (s, 1H), 7.90-7.82 (m, 2H), 3.91 (s, 3H), 2.59 (br s, 2H).

Step 2: Synthesis of Compound WX079-4

Bromine (2.16 g) and sodium acetate (1.64 g) were added dropwise into an acetic acid (10 ml) solution of the compound WX079-3 (1.93 g) at 0° C. The resulting mixture was stirred at 25° C. for 2 hours. The reaction solution was diluted with water (60 ml) and extracted with ethyl acetate (30 ml×2). The organic phases were mixed and washed with 10% $Na_2S_2O_3$ (30 ml×2), dried with anhydrous sodium sulfate, filtered and spin-dried to obtain the compound WX079-4. ¹H NMR (400 MHz, CHLOROFORM-d) δ=7.85 (br d, J=8.4 Hz, 2H), 7.00 (br d, J=8.4 Hz, 2H), 3.90-3.88 (m, 2H), 3.52 (s, 1H).

Step 3: Synthesis of Compound WX079-5

The compound WX0079-4 (500 mg) was dissolved in acetonitrile (5.00 ml) at 0° C., isoamyl nitrite (919.1 mg) and copper bromide (1.75 g) were added, and the reaction solution was reacted at 25° C. for 2 hours. The reaction solution was poured into water (20 ml), extracted with ethyl acetate (20 ml) for three times, dried with anhydrous sodium sulfate, filtered, and spin-dried, and the resulting residue was purified by a silica gel column (petroleum ether/ethyl acetate 10:1→5:1→1:1) to obtain the compound WX079-5, ESI m/z: [M+1]=255.2.

Step 4: Synthesis of Compound WX079-6

The compound WX0079-5 (300 mg), cyclopropylamine (671.52 mg) and ethyl acetate (760.05 mg) were dissolved in tetrahydrofuran (5.00 ml), and the mixture was reacted at 70° C. for 12 hours. The reaction solution was spin-dried to obtain the compound WX079-6, ESI m/z: [M+1]=232.2.

Step 5: Synthesis of Compound WX079-7

The synthesis of the compound WX079-7 referred to the step 3 of Example 1. WX079-7, ESI m/z: [M+1]=218.1.

Step 6: Synthesis of Compound WX079-8

The synthesis of the compound WX079-8 referred to the step 4 of Example 1. WX079-8, ESI m/z: [M+1]=405.3.

Step 7: Synthesis of Compound WX079

The synthesis of the compound WX079 was described in step 5 in Example 1. WX079, 1H NMR (400 MHz, DMSO-d6) ppm: 0.58-0.67 (m, 2H); 0.72-0.80 (m, 2H); 2.70 (dd, 1H, J=3.5, 6.7 Hz); 3.59 (d, 2H, J=4.6 Hz); 4.75 (d, 2H, J=2.6 Hz); 7.18 (d, 2H, J=8.8 Hz); 7.22-7.47 (m, 1H); 7.77 (d, 2H, J=8.9 Hz); 8.45 (s, 3H); 9.03 (s, 1H).

Example 41: WX080

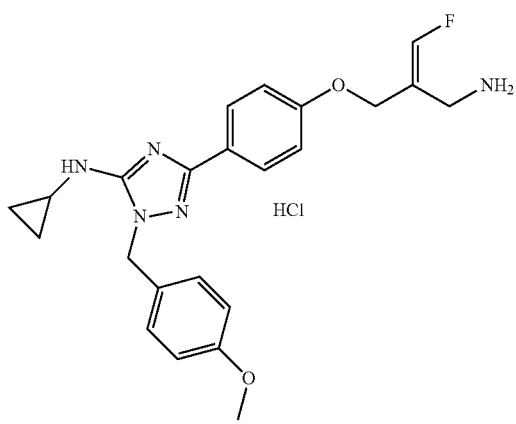 [SMILES: COc1ccc(Cn2nc(-c3ccc(OC/C(=C/F)CN)cc3)nc2NC2CC2)cc1 ; Cl]

Synthesis Route:

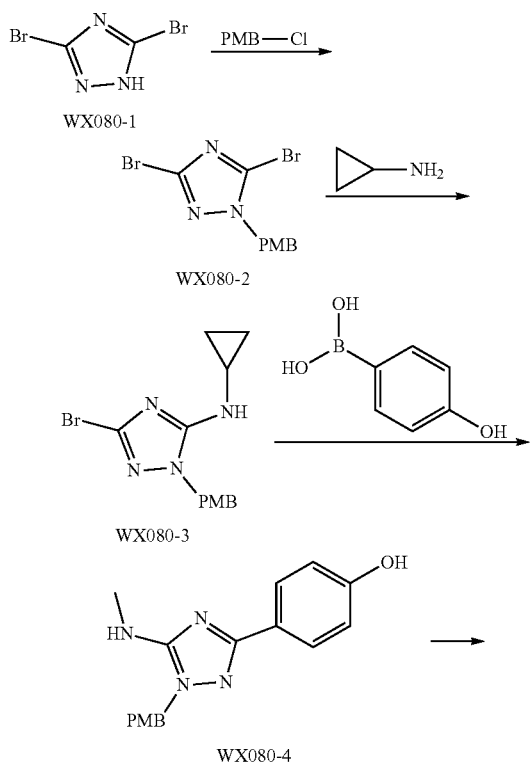

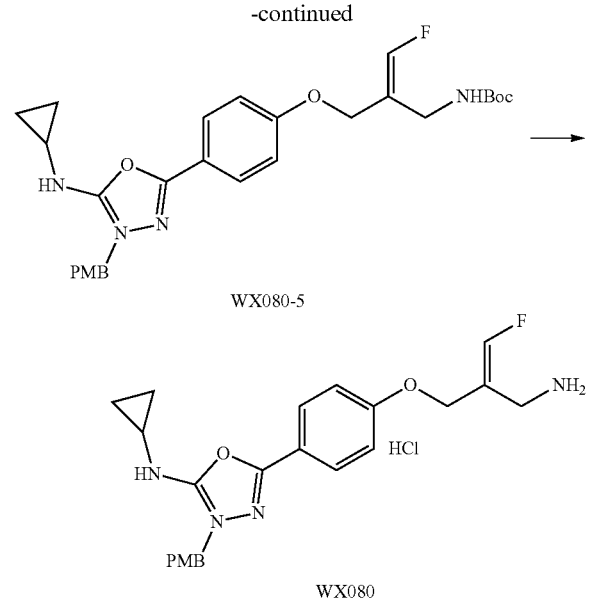

Step 1: Synthesis of Compound WX080-2

P-methoxybenzyl chloride (759.55 mg) was added to an acetonitrile mixture (10 ml) of a compound WX080-1 (1.1 g), N,N-diisopropyl ethylamine (1.25 g) and potassium iodide (402.55 mg). The resulting mixture was reacted at 80° C. for 2 hours. The reaction solution was spin-dried, and the resulting product was diluted with 100 ml of ethyl acetate and washed with water (20 ml×2). The organic phase was dried with anhydrous sodium sulfate, filtered and spin-dried to obtain the compound WX080-2. ESI m/z: [M−H]$^+$=348.1.

Step 2: Synthesis of Compound WX080-3

The synthesis of the compound WX080-3 referred to the step 4 of Example 40. [M−H]$^+$=335.2 ESI m/z: [M+H]+=325.2.

Step 3: Synthesis of Compound WX080-4

The synthesis of the compound WX080-4 referred to the step 1 of Example 16. ESI m/z: [M+H]$^+$=335.1.

Step 4: Synthesis of Compound WX080-5

The synthesis of compound WX080-5 referred to the synthesis method of step 4 in Example 1. ESI m/z: [M+H]$^+$=524.4.

Step 5: Synthesis of Compound WX080

The synthesis of the compound WX080 referred to the synthesis method of the step 5 in Example 1. $^1$H NMR (400 MHz, DMSO-d$_6$) δ=8.86 (br s, 1H), 8.38 (br s, 3H), 7.98 (br d, J=7.8 Hz, 2H), 7.44 (br s, 3H), 7.19-7.08 (m, J=7.8 Hz, 2H), 6.93 (br d, J=7.8 Hz, 2H), 5.23 (br s, 2H), 4.72 (br s, 2H), 3.98-3.70 (m, 2H), 2.93 (br s, 1H), 0.83 (br s, 2H), 0.71 (br s, 2H).

Example 42: WX081

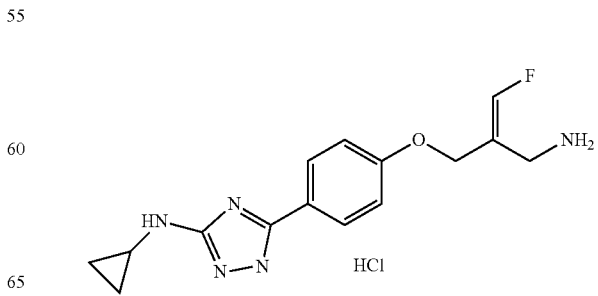

Synthesis Route:

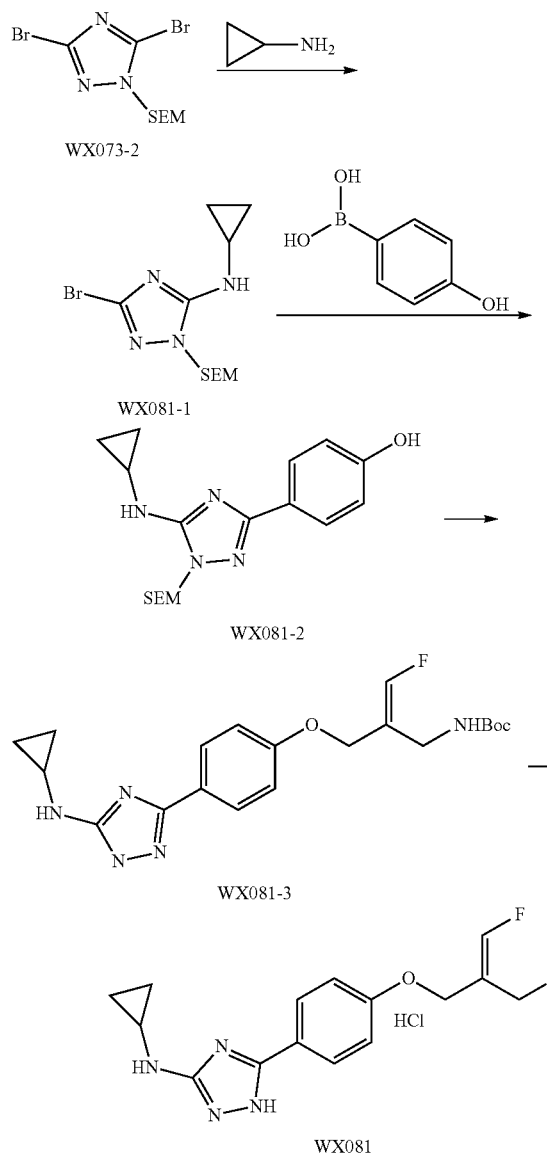

Example 43: WX082

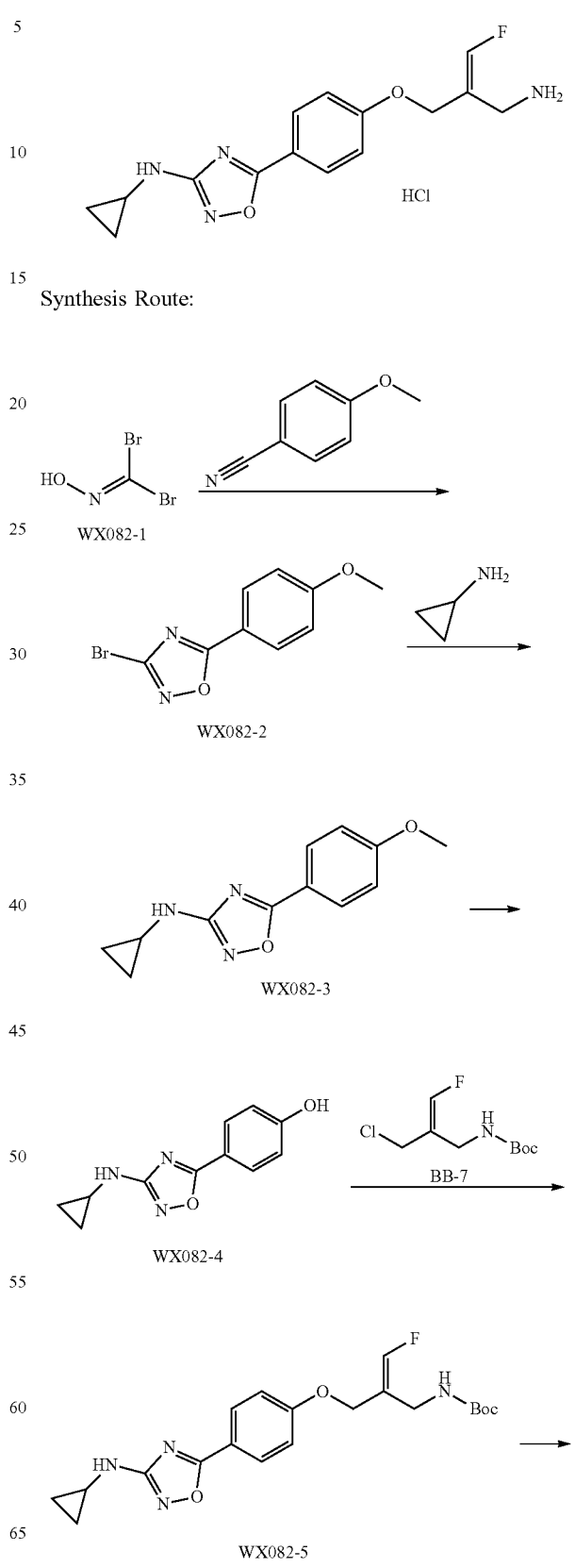

Step 1: Synthesis of Compound WX081-1

The synthesis of the compound WX081-1 referred to the step 4 of Example 40. ESI m/z: [M+H]⁺=335.2.

Step 2: Synthesis of Compound WX081-2

The synthesis of the compound WX081-2 referred to the step 1 of Example 16. [M−H]⁻=345.1.

Step 3: Synthesis of Compound WX081-3

Synthesis of the compound WX081-3 referred to the step 4 of Example 1. ESI m/z: [M+H]⁺=534.5

Step 4: Synthesis of Compound WX081

The synthesis of the compound WX081 referred to the step 5 of Example 1. $^1$H NMR (400 MHz, DEUTERIUM OXIDE) δ=7.71 (d, J=8.9 Hz, 2H), 7.21-6.97 (m, 1H), 4.63 (d, J=3.3 Hz, 2H), 4.64-4.62 (m, 1H), 4.64-4.62 (m, 1H), 4.64-4.62 (m, 1H), 3.82 (s, 2H), 2.69-2.62 (m, 1H), 0.87-0.76 (m, 2H), 0.71-0.58 (m, 2H).

-continued

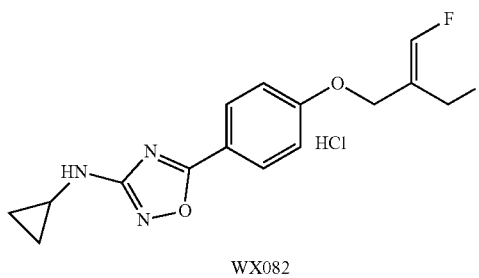

WX082

Step 1: Synthesis of Compound WX082-2

A toluene solution (2 ml) of compound WX082-1 (608.50 mg) was added to a toluene mixture (2 ml) of p-methoxybenzonitrile (798.88 mg) and sodium bicarbonate (756.06 mg) at 90° C. The resulting mixture was reacted at 90° C. for 12 hours. The reaction solution was filtered and spin-dried, and the crude product was purified by a silica gel column (petroleum ether/ethyl acetate 20:1→15:1→10:1) to obtain the compound WX082-2. ESI m/z: [M+H]$^+$=255.2.

Step 2: Synthesis of Compound WX082-3

The compound WX082-2 (0.15 g) was dissolved in cyclopropylamine (2.5 ml), and the resulting solution was reacted under microwave at 120° C. for 2 hours. The reaction solution was evaporated to be dry and the crude product was purified by a silica gel column (petroleum ether/ethyl acetate 20:1→15:1→10:1) to obtain the compound WX082-3. ESI m/z: [M+H]$^+$=232.3

Step 3: Synthesis of Compound WX082-4

The synthesis of the compound WX082-4 referred to the synthesis method of the step 3 in Example 1. ESI m/z: [M+H]$^{3o}$=218.3.

Step 4: Synthesis of Compound WX082-5

The synthesis of the compound WX082-5 referred to the synthesis method of the step 4 in Example 1. ESI m/z: [M+H]$^{3o}$=405.4.

Step 5: Synthesis of Compound WX082

The synthesis of the compound WX082 referred to the synthesis method of the step 5 in Example 1. $^1$H NMR (400 MHz, DMSO-d6). ppm: 0.45-0.55 (m, 2H); 0.57-0.76 (m, 2H); 2.40-2.45 (m, 1H,); 3.65 (s, 2H,); 4.74 (d, 2H, J=3.1 Hz); 7.21 (d, 2H, J=8.9 Hz); 7.24 (d, 1H, J=2.4 Hz); 7.26-7.49 (m, 1H); 7.97 (d, 2H, J=8.9 Hz); 8.18 (brs, 3H,)

Example 44: WX083

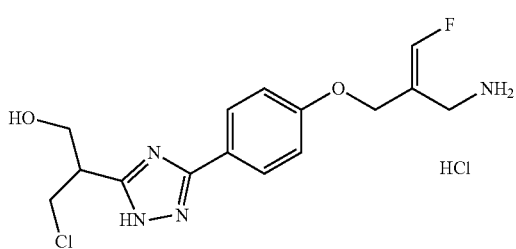 [SMILES: NC/C(=C\F)COc1ccc(-c2n[nH]c(C(CO)CCl)n2)cc1 ; Cl]

Synthesis Route:

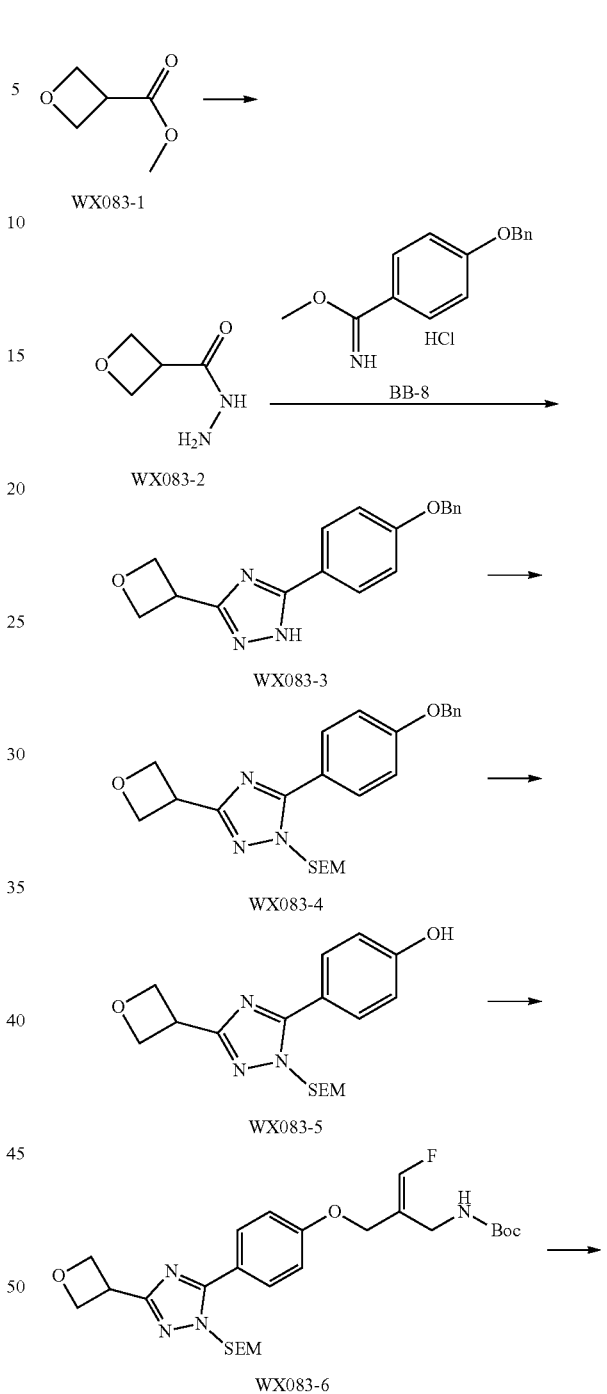

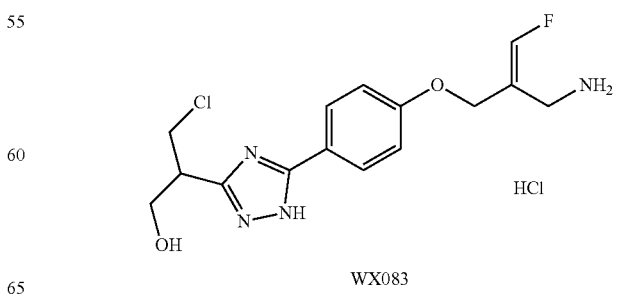

WX083

Step 1: Synthesis of Compound WX083-2

A compound WX083-1 (500 mg) was dissolved in hydrazine hydrate (1.52 g) and the resulting solution was reacted at 70° C. for 12 hours. The reaction solution was evaporated to be dry to obtain the compound WX083-2. ESI m/z: [M+H]$^+$=117.2.

Step 2: Synthesis of Compound WX083-3

The synthesis of the compound WX083-3 referred to the step 1 of Example 22. ESI m/z: [M+H]$^+$=308.1.

Step 3: Synthesis of Compound WX083-4

The synthesis of the compound WX083-4 referred to the step 2 of Example 22. ESI m/z: [M+H]$^+$=438.4

Step 4: Synthesis of Compound WX083-5

The synthesis of the compound WX083-5 referred to the synthesis method of the step 3 in Example 22. ESI m/z: [M+H]$^+$=348.3.

Step 5: Synthesis of Compound WX083-6

The synthesis of the compound WX083-6 referred to the synthesis method of the step 4 in Example 1. ESI m/z: [M+H]$^+$=535.3.

Step 6: Synthesis of Compound WX083

The synthesis of the compound WX083 referred to the synthesis method of the step 5 in Example 1. $^1$HNMR (400 MHz, DMSO-d6) ppm: 3.36-3.47 (1H); 3.63 (2H, J=4.8 Hz); 3.74-3.87 (2H); 4.00-4.15 (2H); 4.72 (3H, J=2.9 Hz); 7.16 (2H, J=8.9 Hz); 7.22-7.56 (1H); 8.04 (2H, J=8.7 Hz); 8.30 (3H).

Example 45: WX122

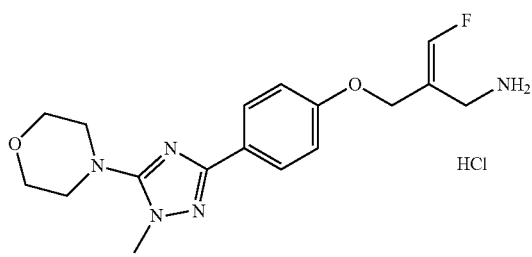 [SMILES: Cn1nc(-c2ccc(OC/C(=C/F)CN)cc2)nc1N1CCOCC1 ; Cl]

Synthesis Route:

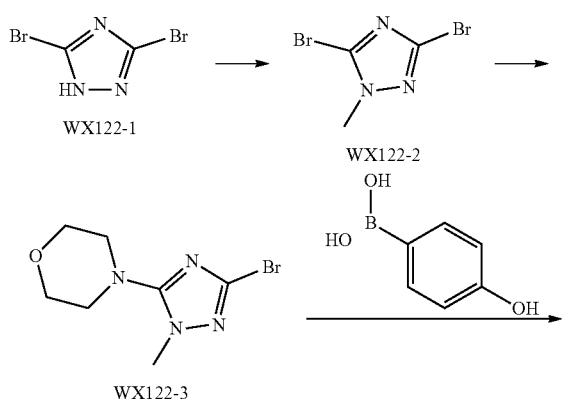

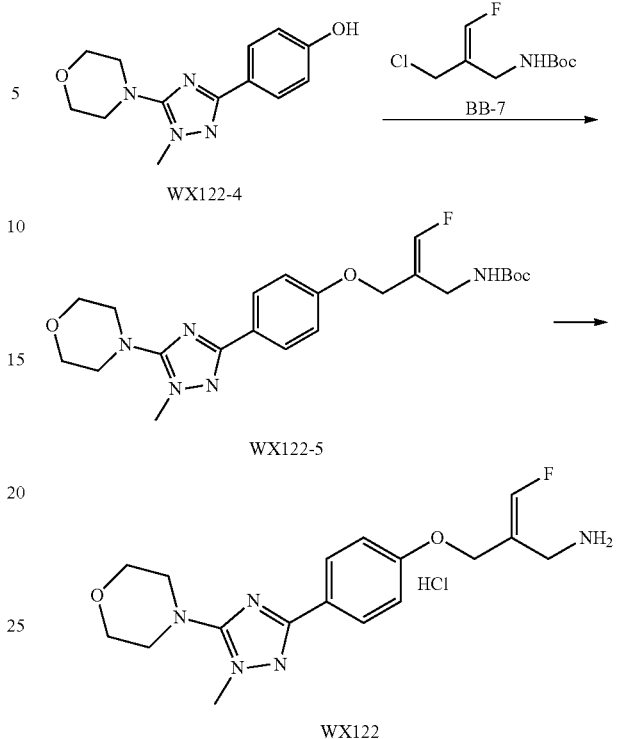

Step 1: Synthesis of Compound WX122-2

A Compound WX122-1 (4 g) was dissolved in DMF (100 ml) and the resulting solution was cooled down to 0° C. NaH (846.3 mg) was added in batch. Gas was generated during the process, and after 0.5 hour, MeI (2.6 grams) was added dropwise into the reaction solution which was slowly heated to 25° C. namely room temperature and stirred for 12 hours. The reaction solution was poured into a saturated ammonium chloride solution (300 ml), and extracted with ethyl acetate (50 ml×3), and the organic phase was washed with a saturated sodium chloride solution (100 ml). The organic phases were mixed and dried with anhydrous sodium sulfate, filtered, and concentrated under the reduced pressure. This compound was used directly in the next step and did not require purification. ESI m/z: [M+H]$^+$=242.

Step 2: Synthesis of Compound WX122-3

The synthesis of the compound WX122-3 referred to the step 2 of Example 34. 1H NMR (400 MHz, CHLOROFORM-d) δ ppm 3.83 (m, 4H), 3.69 (s, 3H), 3.20 (m, 4H).

Step 3: Synthesis of Compound WX122-4

The synthesis of the compound WX122-4 referred to the synthesis method of the step 1 in Example 16. ESI m/z: [M+H]$^+$=261.

Step 4: Synthesis of Compound WX122-5

The synthesis of the compound WX122-5 referred to the synthesis method of the step 4 in Example 1. ESI m/z: [M+H]$^+$=448. $^1$HNMR (400 MHz, CHLOROFORM-d) δ ppm 7.87-7.89 (m, 2H) 6.85-6.88 (m, 2H) 6.59-6.79 (m, 1H) 4.40-4.41 (br d, J=4 Hz, 2H) 3.94 (br d, J=8 Hz, 2H) 3.79-3.80 (m, 4H) 3.68 (s, 3H) 3.16-3.18 (m, 4H) 1.35 (s, 9H).

Step 5: Synthesis of Compound WX122

The synthesis of the compound WX122 referred to the synthesis method of the step 5 in Example 1. ESI m/z: [M+H]$^+$=348. $^1$H NMR (400 MHz, DMSO-d$_6$) δ=8.33 (br s, 3H), 7.88-7.91 (d, J=8.8 Hz, 2H), 7.23-7.44 (d, J=82.4 Hz, 1H), 7.06 (d, J=8.8 Hz, 2H), 4.68 (br s, 2H), 3.76 (m, 1H), 3.73 (s, 3H), 3.61 (m, 2H), 3.21 (m, 4H).

Example 46: WX085

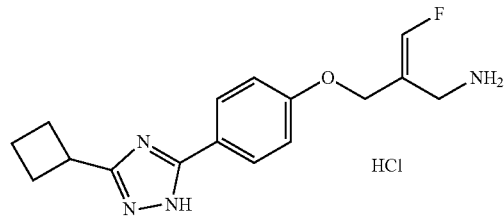 [SMILES: NC/C(=C\F)COc1ccc(-c2nc(C3CCC3)n[nH]2)cc1 ; Cl]

Synthesis Route:

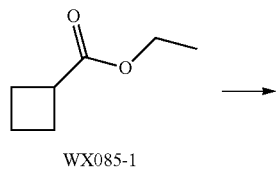
WX085-1

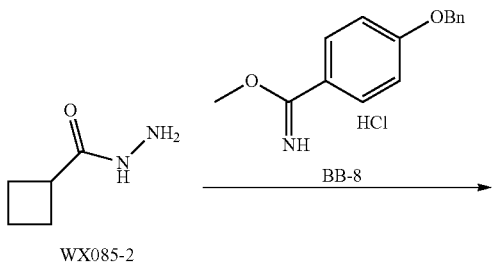

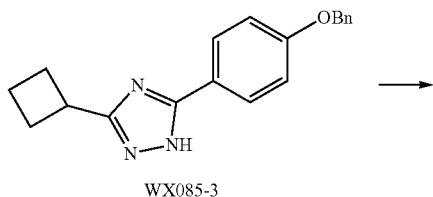
WX085-3

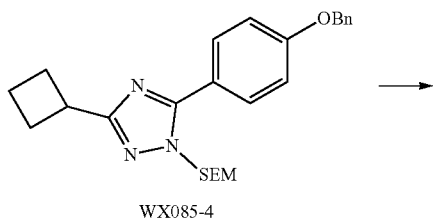
WX085-4

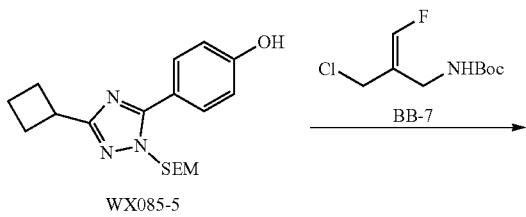
WX085-5

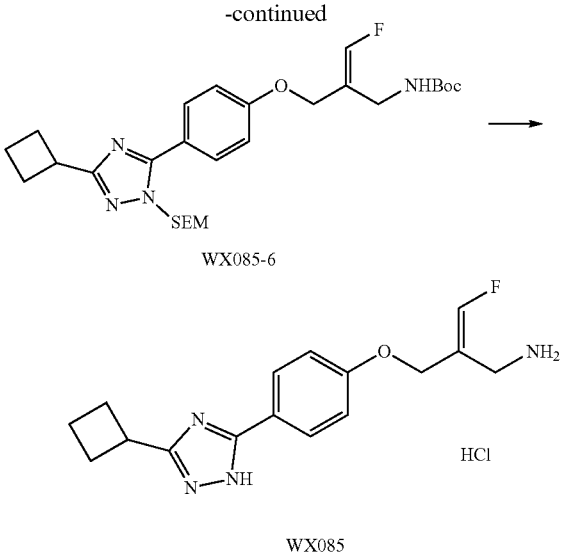
WX085-6

WX085

Step 1: Synthesis of Compound WX085-2

Ethyl cyclobutanecarboxylate (10 g) and hydrazine hydrate (11.96 g, 98% purity) were dissolved in anhydrous ethanol (15 ml) and the reaction solution was heated and stirred at 78° C. for 10 hours. The solvent was removed under reduced pressure, and the residue was pulped with a small amount of ethyl acetate, and filtered, and the filter cake was dried to obtain a crude product compound WX085-2. No further purification was required.

Step 2: Synthesis of Compound WX085-3

Compound BB-8 (2.78 g) and ethyl acetate (1.01 g) were dissolved in methanol (20 ml), the compound WX085-2 (1.14 g) was added at room temperature, and a reaction was performed for 12 hours at 70° C. The solvent was removed under reduced pressure, and the residue was suspended with 30 ml of ethyl acetate, a solid occurred, filtering was performed, and the filter cake was washed with a small amount of ethyl acetate and dried to obtain the compound WX085-3. $^1$H NMR (400 MHz, DMSO-d6) δ ppm 1.83-2.16 (m, 3H) 2.29-2.39 (m, 4H) 5.18 (s, 2H) 7.16 (d, J=8.53 Hz, 2H) 7.32-7.37 (m, 1H) 7.41 (t, J=7.28 Hz, 2H) 7.46-7.50 (m, 2H) 7.96 (d, J=8.53 Hz, 2H).

Step 3: Synthesis of Compound WX085-4

The compound WX085-3 (2.2 g) was dissolved in anhydrous DMF (20 ml), and sodium hydrogen (317 mg) was added at 0° C., and the mixture was reacted at 25° C. for 0.5 hour. The system was cooled to 0° C. and 2-(trimethylsilyl) ethoxymethyl chloride (1.55 g) was added. The mixture was reacted at room temperature for 12 hours. The reaction solution was poured into 30 ml of water and extracted with ethyl acetate (2×50 ml). The organic phase was dried, decompressed to remove the solvent, and the resulting residue was purified by column chromatography to obtain the compound WX085-4. $^1$H NMR (400 MHz, CHLOROFORM-d) δ ppm −0.02 (s, 8H) 0.88-0.93 (m, 2H) 1.94-2.18 (m, 2H) 2.34-2.46 (m, 2H) 2.49-2.64 (m, 2H) 3.58-3.64 (m, 2H) 3.71 (t, J=8.53 Hz, 1H) 5.11 (s, 2H) 5.38 (s, 2H) 7.03 (d, J=8.53 Hz, 2H) 7.32-7.47 (m, 5H) 8.04 (d, J=9.03 Hz, 2H).

Step 4: Synthesis of Compound WX085-5

The compound WX085-4 (760 mg) and a palladium-carbon catalyst (583.43 mg, purity 5%) were added to methanol (20 ml) and stirred at 45° C. under a hydrogen (15 psi) atmosphere for 12 hours. After the reaction was completed, the mixture was filtered, and the filtrate was decompressed to remove the solvent to obtain the compound WX085-5. ¹H NMR (400 MHz, CHLOROFORM-d) δ ppm 7.92-7.97 (m, 2H) 6.85 (d, J=8.53 Hz, 2H) 5.37-5.40 (m, 2H) 3.75-3.82 (m, 1H) 3.58-3.64 (m, 2H) 2.51-2.60 (m, 2H) 2.38-2.44 (m, 2H) 2.03-2.14 (m, 2H) 0.86-0.93 (m, 2H) −0.03 (s, 8H).

Step 5: Synthesis of Compound WX085-6

The compound WX085-5 (580 mg) and the compound BB-7 (375.47 mg) were dissolved in N,N-dimethylformamide (20 ml), and cesium carbonate (546.95 mg) was added at room temperature, and the reaction mixture was stirred for a reaction at 25° C. for 12 hours. The reaction mixture was poured into 30 ml of water and extracted with 60 ml of ethyl acetate. The solvent was removed from the organic phase to obtain a crude product WX085-6, directly used for the next reaction step without further purification. ESI m/z [M+H]⁺=533.2.

Step 6: Synthesis of Compound WX085

The compound WX085-6 (845 mg) was added to an ethyl acetate hydrogen chloride solution (10 ml, concentration 4M) at 0° C. and the reaction mixture was stirred at 25° C. for 2 hours. A large number of white solids appeared, and then were filtered, and the filter cake was dried, and to purified by preparative chromatography to obtain the compound WX085. ¹H NMR (400 MHz, DMSO-d6) δ ppm 8.41 (br s, 3H) 8.07 (br d, J=8.03 Hz, 2H) 7.22-7.47 (m, 1H) 7.15 (br d, J=8.53 Hz, 2H) 4.73 (br s, 2H) 3.75 (dt, J=16.94, 8.34 Hz, 1H) 3.60 (br d, J=3.51 Hz, 2H) 2.39-2.46 (m, 2H) 2.34 (br d, J=8.53 Hz, 2H) 1.84-2.12 (m, 2H).

Example 47: WX086

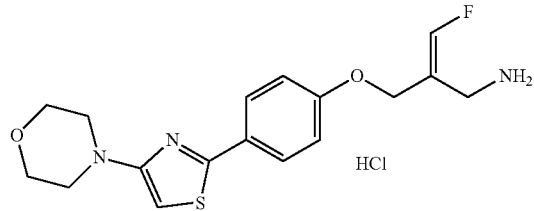 [SMILES: NC/C(=C\F)COc1ccc(-c2nc(N3CCOCC3)cs2)cc1 ; Cl]

Synthesis Route:

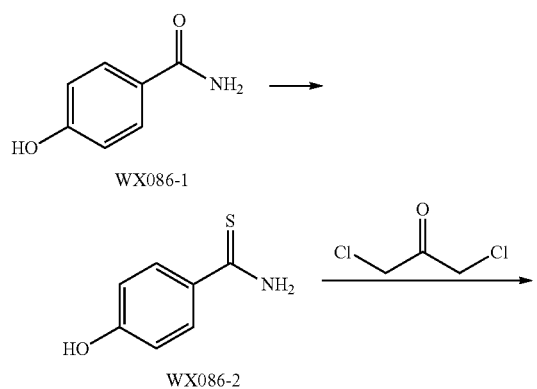

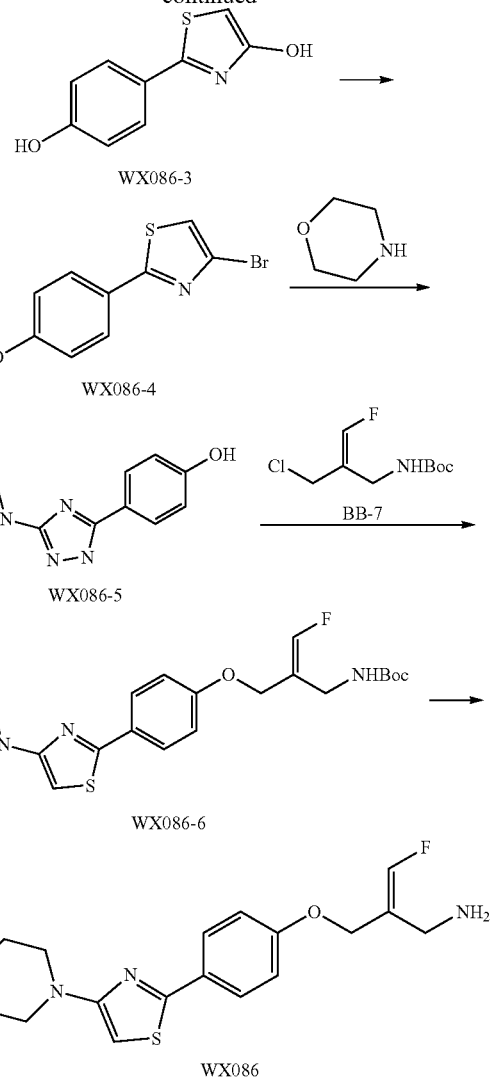

Step 1: Synthesis of Compound WX086-2

A compound WX086-1 (2 g) was dissolved in 2-methyltetrahydrofuran (40 ml) and was cooled to 0° C. Lawesson reagent (6.49 g) was added in batches, the mixture was naturally heated to 30° C., and a reaction is performed for 12 hours. The reaction solution was poured into water (100 ml), and a sodium bicarbonate solid was added to adjust PH=8, the solution was extracted with ethyl acetate (100 ml) for three times, and the organic layers were mixed, dried with anhydrous sodium sulfate, filtered and evaporated to be dry to obtain a crude product. The cruder product was separated by an automatic column passing machine (gradient elution: mobile phase petroleum ether:mobile phase ethyl acetate=0:1 to 2:3), and purified to obtain the compound WX086-2. ESI m/z [M+H]⁺=154.2.

Step 2: Synthesis of Compound WX086-3

The compound WX086-2 (1 g) was added to a liquid mixture of a sodium bicarbonate solution (20 ml) and DCM (40 ml), the mixture was cooled down to 0° C., and chloroacetyl chloride (1.11 g) was added dropwise. The reaction was naturally heated to 30° C. and stirred for 12 hours. The reaction solution was poured into water (100 ml), and extracted with ethyl acetate (100 ml) for three times, the organic phases were mixed, washed with saturated salt water (100 ml) for one time, dried with anhydrous sodium sulfate, and spin-dried to obtain a crude product. The crude product was pulped by ethyl acetate (30 ml) and petroleum ether (30 ml), and purified to obtain the compound WX086-3. ESI m/z [M+H]⁺=194.3.

Step 3: Synthesis of Compound WX086-4

The compound WX086-3 (1.00 g) and tetrabutyl ammonium bromide (4.00 g) were dissolved in acetonitrile (20 ml). The reaction solution was cooled to 0° C., phosphorus oxychloride (2.89 ml) was added dropwise, stirring was conducted for 0.5 hour, and the reaction was conducted at 80° C. for 4 hours. The reaction solution was poured into ice water (80 ml), and extracted with ethyl acetate (80 ml) for three times, and the organic phases were mixed, dried with anhydrous sodium sulfate, and evaporated to be dry to obtain a crude product. The crude product was separated by an automatic column passing machine (gradient elution:petroleum ether/ethyl acetate=0:1 to 2:1), and purified to obtain compound WX086-4. ESI m/z [M+H]⁺=256.1/258.1.

Step 4: Synthesis of Compound WX086-5

A DMF (5 ml) solution of the compound WX086-4, BINAP (145.87 mg), morpholine (204.09 mg), palladium acetate (52.59 mg), and potassium carbonate (323.77 mg) was added to a microwave tube, and reacted at 110° C. for 2 hours. The reaction solution was poured into water (30 ml), and extracted with ethyl acetate (30 ml) for three times, and the organic layers were mixed, dried with anhydrous sodium sulfate, and filtered and evaporated to be dry to obtain a crude product. The crude product was separated by an automatic column passing machine (gradient elution: petroleum ether/ethyl acetate=0:1 to 1:5) to obtain the compound WX086-5. ESI m/z [M+H]⁺=263.3.

Step 5: Synthesis of Compound WX086-6

The synthesis of the compound WX086-6 referred to the synthesis method of the step 4 in Example 1. ESI m/z [M+H]⁺=450.4.

Step 6: Synthesis of Compound WX086

The synthesis of the compound WX086 referred to the synthesis method of step 5 in Example 1. ¹H NMR (400 MHz, DMSO-d₆) δ=7.86-7.72 (m, 2H), 7.39-7.14 (m, 2H), 7.12-7.01 (m, 2H), 4.60 (br d, J=2.8 Hz, 2H), 3.78-3.68 (m, 4H), 3.62 (s, 3H), 3.22-3.15 (m, 2H), 3.24-3.01 (m, 1H), 3.11-3.00 (m, 1H). ¹⁹F NMR (376 MHz, DMSO-d₆) δ=121.677.

Example 48 WX087

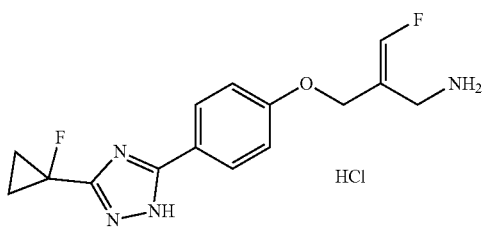 [SMILES: NC/C(=C\F)COc1ccc(-c2nc(C3(F)CC3)n[nH]2)cc1 ; Cl]

Synthesis Route:

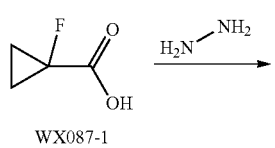

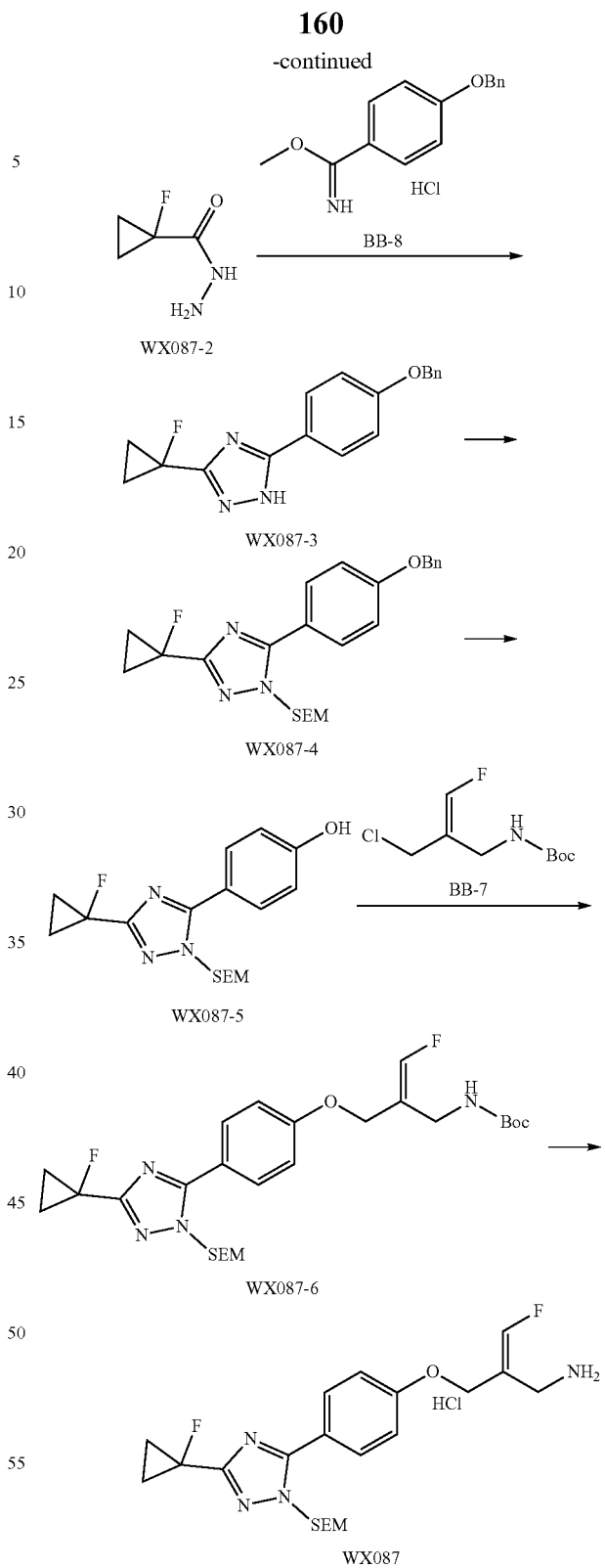

Step 1: Synthesis of Compound WX087-2

At 25° C., the substrate WX087-1 (300.0 mg), 1-(3-dimethylaminopropyl)-3-ethylcarbodiimide hydrochloride (663.1 mg) and 1-hydroxybenzotriazole (467.4 mg) were dissolved in DMF (6 ml) and stirred at 25° C. for 2 hours. At 0° C., the reaction solution was poured into a mixed solution of NH₂NH₂·H₂O (144.3 mg) and MeCN (6 ml), continuously stirred at 0° C. for one hour, then heated to 25° C. and stirred again for another hour. The reaction product was slowly poured into a NaHCO₃ saturated solution (20 ml), and extracted with ethyl acetate (10 ml×3), and the organic phase was washed with a saturated sodium chloride solution (20 ml), the organic phases were mixed, dried with anhydrous sodium sulfate, filtered, and concentrated under reduced pressure. The resulting crude product was directly used for the next reaction step without purification.

Step 2: Synthesis of Compound WX087-3

The synthesis of the compound WX087-3 referred to the step 1 of Example 22.

Step 3: Synthesis of Compound WX087-4

The synthesis of the compound WX087-4 referred to the step 2 of Example 22. ESI m/z [M+1]⁺=440.

Step 4: Synthesis of Compound WX087-5

The synthesis of the compound WX087-5 referred to the step 3 of Example 22.

Step 5: Synthesis of Compound WX087-6

The synthesis of the compound WX087-6 referred to the step 4 of Example 1. ESI m/z [M+1]+=537.

Step 6: the synthesis of the compound WX087 referred to the synthesis method of the step 5 in Example 1. ¹H NMR (400 MHz, DMSO-d₆) δ ppm 8.36 (br s, 2H) 7.97 (d, J=8.0 Hz, 2H) 7.22-7.46 (d, J=80.0 Hz, 1H) 7.13 (d, J=8.0 Hz, 2H) 4.71 (d, J=4.0 Hz, 2H) 3.61 (d, J=4.0 Hz, 2H) 1.46-1.57 (m, 2H) 1.21-1.31 (m, 2H).

Example 49: WX088

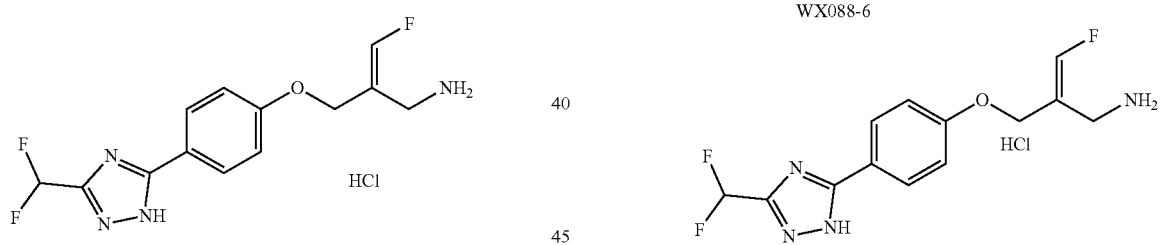

Synthesis Route:

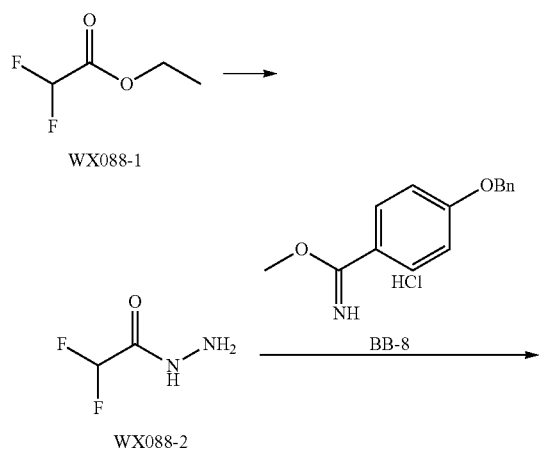

Step 1: Synthesis of Compound WX088-2

The synthesis of the compound WX088-2 referred to the step 1 of Example 46.

Step 2: Synthesis of Compound WX088-3

The compound BB-8 (2.78 g) and N,N-diisopropyl ethylamine (1.29 g) were dissolved in methanol (20 ml), the compound WX088-2 (1.14 g) was added at room temperature, and a reaction was performed at 70° C. for 12 hours. The solvent was removed under reduced pressure and the residue was purified by rapid column chromatography to obtain the compound WX088-3. ¹H NMR (400 MHz, CHLOROFORM-d) δ ppm 7.86 (d, J=9.03 Hz, 2H) 7.31-7.47 (m, 5H) 7.05 (d, J=8.53 Hz, 2H) 6.76 (t, J=53.21 Hz, 1H) 5.34 (br s, 1H) 5.11 (s, 2H).

Step 3: Synthesis of Compound WX088-4

The synthesis of the compound WX088-4 referred to the step 3 of Example 46. ¹H NMR (400 MHz, CHLOROFORM-d) δ ppm 8.00-8.03 (m, 1H) 7.85-7.90 (m, 1H) 7.43-7.45 (m, 1H) 7.30-7.45 (m, 4H) 6.99-7.08 (m, 2H)

6.56-6.90 (m, 1H) 5.45-5.63 (m, 2H) 5.10 (d, J=8.03 Hz, 2H) 3.57-3.84 (m, 2H) 0.89-0.99 (m, 2H) −0.03 (d, J=11.04 Hz, 9H).

Step 4: Synthesis of Compound WX088-5

The synthesis of the compound WX088-5 referred to the step 4 of Example 46. ESI m/z [M+1]$^+$=342.

Step 5: Synthesis of Compound WX088-6

The synthesis of the compound WX088-6 referred to the step 5 of Example 46. ESI m/z [M+1]$^+$=529 and 551.

Step 6: Synthesis of Compound WX088

The synthesis of the compound WX088 referred to the step 6 of Example 46. $^1$H NMR (400 MHz, DMSO-d6) δ ppm 8.45 (br s, 3H) 8.04 (d, J=8.53 Hz, 2H) 6.93-7.47 (m, 4H) 4.74 (d, J=3.01 Hz, 2H) 3.60 (br d, J=5.02 Hz, 2H).

Example 50: WX089

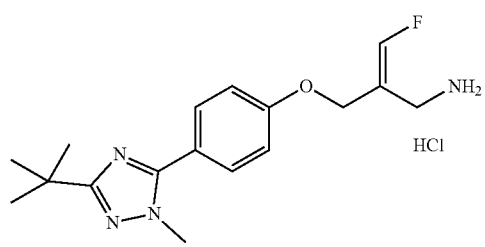 [SMILES: Cn1nc(C(C)(C)C)nc1-c1ccc(OC/C(=C/F)CN)cc1 ; Cl]

Synthesis Route:

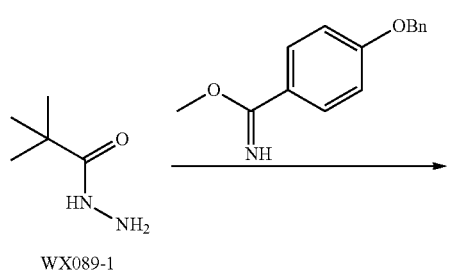

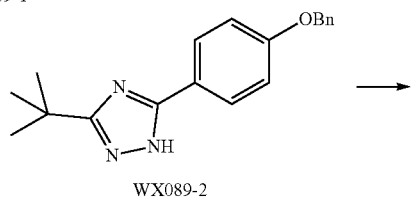

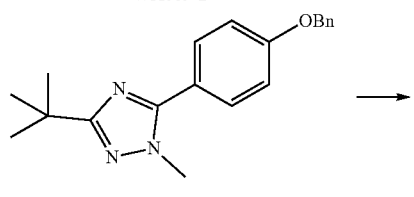

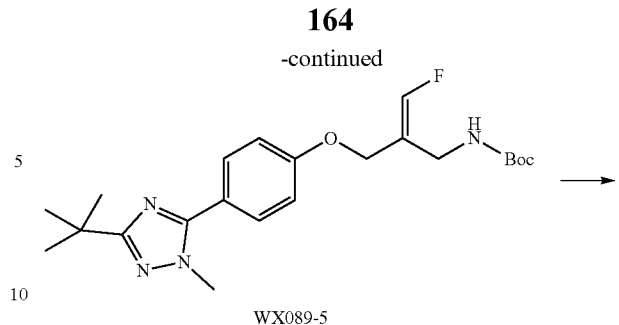

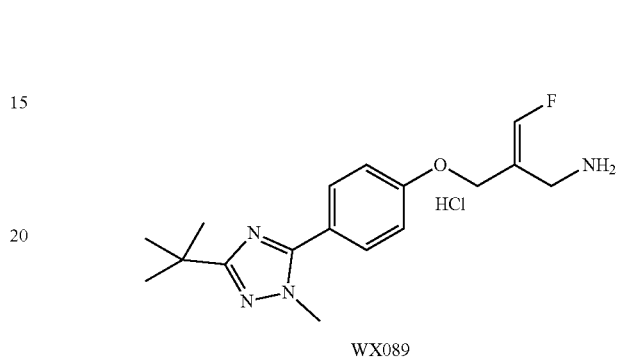

Step 1: Synthesis of Compound WX089-2

The synthesis of the compound WX089-2 referred to the step 1 of Example 22, ESI m/z [M+1]$^+$=308.4.

Step 2: Synthesis of Compound WX089-3

The synthesis of the compound WX089-3 referred to the synthesis method of the step 1 in Example 37, ESI m/z [M+1]$^+$=322.4.

Step 3: Synthesis of Compound WX089-4

The synthesis of the compound WX089-4 referred to the step 3 of Example 22, ESI m/z [M+1]$^+$=232.4.

Step 4: Synthesis of Compound WX089-5

The synthesis of the compound WX089-5 referred to the step 4 of Example 1, ESI m/z [M+1]$^+$=419.

Step 5: Synthesis of Compound WX089

The synthesis of the compound WX089 referred to the synthesis method of the step 5 of Example 1 $^1$H NMR (400 MHz, DMSO-d$_6$) δ=8.30 (br s, 3H), 7.75 (d, J=8.9 Hz, 2H), 7.48-7.23 (m, 1H), 7.19 (d, J=8.9 Hz, 2H), 4.73 (d, J=3.1 Hz, 2H), 3.89 (s, 3H), 3.63 (br s, 2H), 1.34 (s, 9H). $^{19}$F NMR (376 MHz, DMSO-d$_6$) δ=122.505.

Example 51: WX090

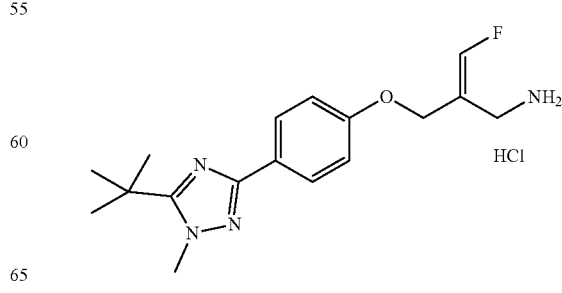

Synthesis Route:

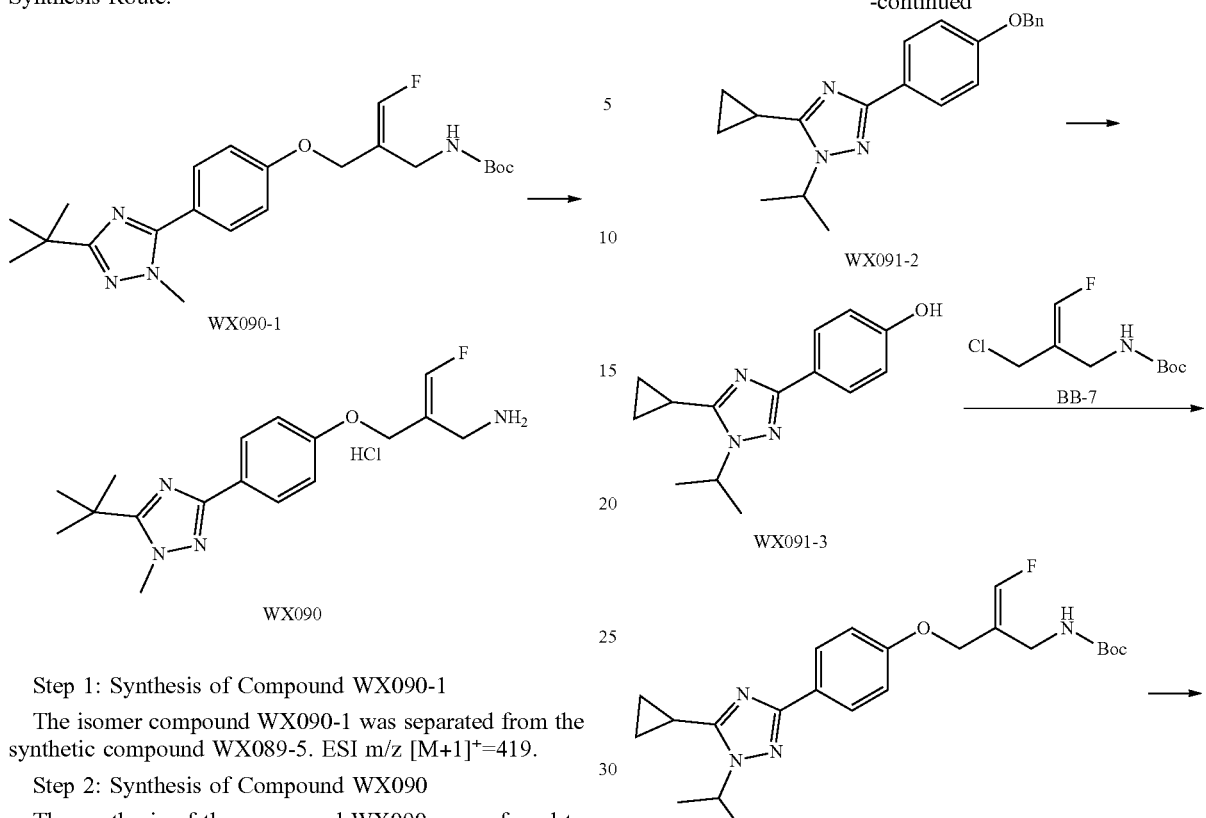

Step 1: Synthesis of Compound WX090-1

The isomer compound WX090-1 was separated from the synthetic compound WX089-5. ESI m/z [M+1]$^+$=419.

Step 2: Synthesis of Compound WX090

The synthesis of the compound WX090 was referred to the synthesis method of step 5 in Example 1. $^1$H NMR (400 MHz, DMSO-d$_6$) δ=8.27 (br s, 3H), 7.90 (d, J=8.8 Hz, 2H), 7.48-7.19 (m, 1H), 7.06 (d, J=8.8 Hz, 2H), 4.66 (d, J=3.3 Hz, 2H), 4.07-3.90 (m, 4H), 3.63-3.62 (m, 2H), 1.52-1.33 (m, 9H).

Example 52: WX091

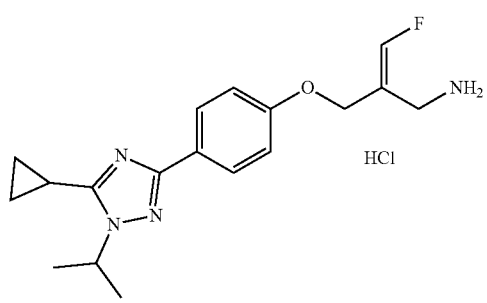 [SMILES: CC(C)n1nc(-c2ccc(OC/C(=C/F)CN)cc2)nc1C1CC1 ; Cl]

Synthesis Route:

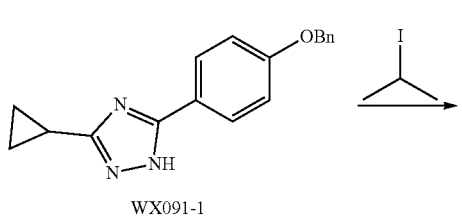

Step 1: Synthesis of Compound WX091-2

The synthesis of the compound WX091-2 referred to the step 1 of Example 27, ESI m/z: [M+H]$^+$=334.4.

Step 2: Synthesis of Compound WX091-3

The synthesis of the compound WX091-3 referred to the step 3 of Example 22, ESI m/z: [M+H]$^+$=244.3.

Step 3: Synthesis of Compound WX091-4

The synthesis of the compound WX091-4 referred to the step 4 of Example 1, $^1$H NMR (400 MHz, DMSO-d$_6$) δ ppm 0.97-1.13 (m, 4H) 1.33 (s, 9H) 1.46 (d, J=6.53 Hz, 6H) 2.33 (d, J=1.76 Hz, 1H) 3.76 (br d, J=4.02 Hz, 2H) 4.46 (d, J=3.14 Hz, 2H) 4.86 (dt, J=13.14, 6.54 Hz, 1H) 6.98-7.04 (m, 2H) 7.82-7.91 (m, 2H).

Step 4: Synthesis of Compound WX091

The synthesis of the compound WX091 referred to the step 5 of Example 1, $^1$H NMR (400 MHz, DMSO-d$_6$) δ ppm 1.09-1.19 (m, 4H) 1.48 (d, J=6.53 Hz, 6H) 2.22-2.32 (m, 1H) 3.61 (br d, J=4.39 Hz, 2H) 4.69 (d, J=3.01 Hz, 2H) 4.91 (dt, J=13.11, 6.49 Hz, 1H) 7.09 (d, J=8.91 Hz, 2H) 7.19-7.50 (m, 1H) 7.96 (d, J=8.66 Hz, 2H) 8.37 (br s, 3H) 8.29-8.49 (m, 1H).

Example 53: WX092

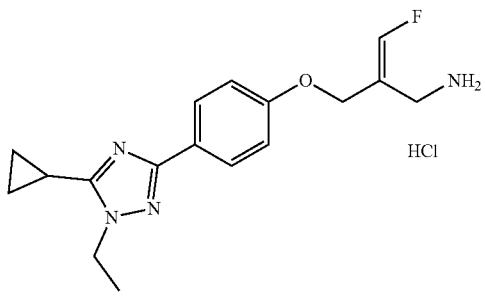 [SMILES: CCn1nc(-c2ccc(OC/C(=C/F)CN)cc2)nc1C1CC1 ; Cl]

Synthesis Route:

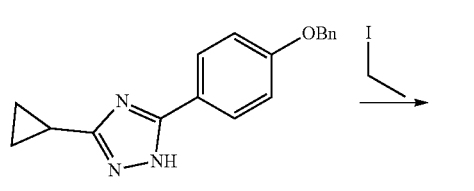

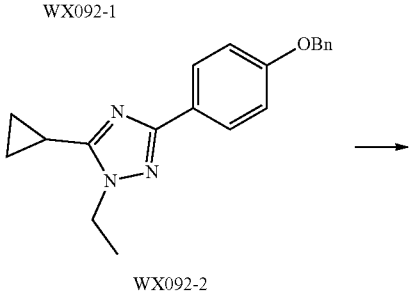

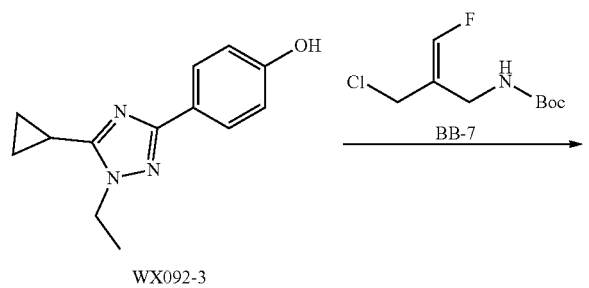

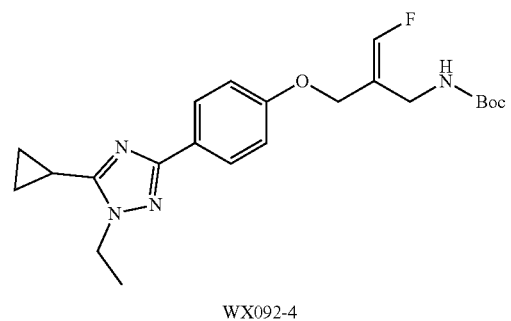

-continued

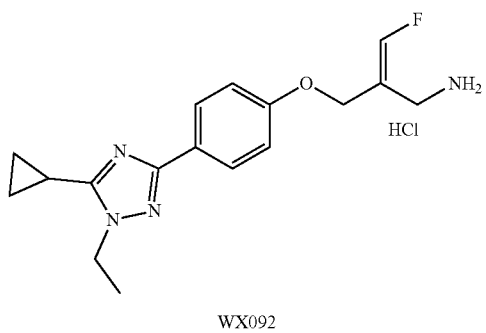

WX092

Step 1: Synthesis of Compound WX092-2

The synthesis of the compound WX092-2 referred to the step 1 of Example 22, ESI m/z: [M−H]⁻=320.3.

Step 2: Synthesis of Compound WX092-3

The synthesis of the compound WX092-3 referred to the step 3 of Example 22, ESI m/z: [M+H]⁺=230.3.

Step 3: Synthesis of Compound WX092-4

The synthesis of the compound WX092-4 referred to the step 4 of Example 1, $^1$H NMR (400 MHz, DMSO-d$_6$) δ ppm 1.01-1.08 (m, 3H) 1.34 (s, 9H) 1.37-1.46 (m, 1H) 1.37-1.46 (m, 1H) 1.37-1.46 (m, 1H) 1.41 (t, J=7.22 Hz, 4H) 2.17-2.23 (m, 1H) 3.77 (br d, J=3.89 Hz, 2H) 4.29 (q, J=7.28 Hz, 2H) 4.47 (d, J=3.14 Hz, 2H) 7.01 (d, J=8.78 Hz, 2H) 7.84-7.89 (m, 1H) 7.84-7.89 (m, 1H) 8.23 (br s, 1H).

Step 4: Synthesis of Compound WX092

The synthesis of the compound WX092 referred to the step 5 of Example 1, $^1$H NMR (400 MHz, DMSO-d6) δ ppm 0.98-1.13 (m, 4H) 1.41 (t, J=7.22 Hz, 3H) 2.21 (br s, 1H) 3.57-3.59 (m, 2H) 4.29 (q, J=7.45 Hz, 2H) 4.66 (br s, 2H) 7.06 (d, J=8.53 Hz, 2H) 7.21-7.46 (m, 1H) 7.90 (br d, J=8.28 Hz, 2H) 8.23 (br s, 3H).

Example 54: WX093

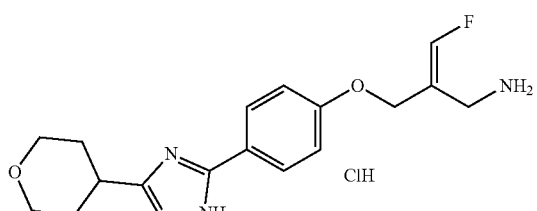

Synthesis Route:

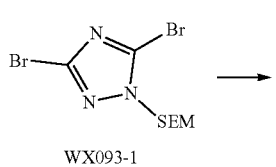

WX093-1

-continued

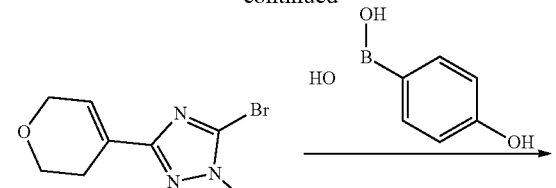
WX093-2

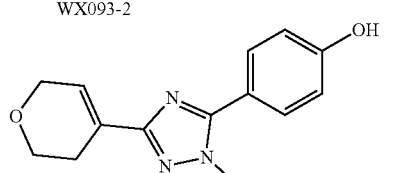
WX093-3

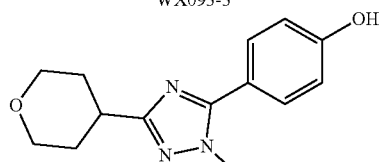
WX093-4

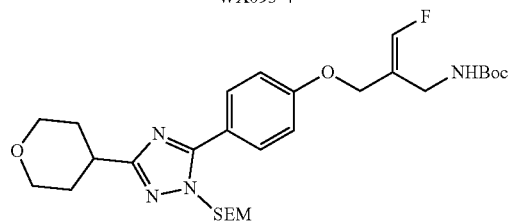
WX093-5

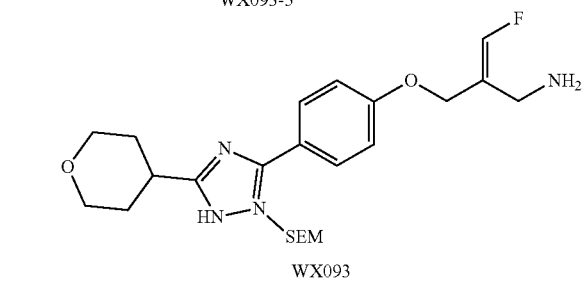
WX093

Step 1: Synthesis of Compound WX093-2

The synthesis of the compound WX093-2 referred to the step 1 of Example 16. ESI m/z [M+1]⁺=360.3, 362.3.

Step 2: Synthesis of Compound WX093-3

The synthesis of the compound WX093-3 referred to the step 1 of Example 16. ESI m/z [M+1]⁺=374.3.

Step 3: Synthesis of Compound WX093-4

The synthesis of the compound WX093-4 referred to the synthesis method of the step 3 in Example 22. ESI m/z [M+1]⁺=376.4.

Step 4: Synthesis of Compound WX093-5

The synthesis of the compound WX093-5 referred to the synthesis method of the step 4 in Example 1. ESI m/z [M+1]⁺=563.5.

Step 5: Synthesis of Compound WX093

The synthesis of the compound WX093 referred to the step 5 of Example 1. ¹H NMR (400 MHz, DMSO-d6) ppm: 1.73-2.02 (4H); 3.18 (1H,); 3.47 (2H, J=11.4 Hz); 3.63 (2H,); 3.93 (2H, J=10.7 Hz); 4.69 (2H,); 7.17 (2H, J=7.8 Hz); 7.21-7.46 (1H); 8.01 (2H, J=8.0 Hz).

Example 55: WX094

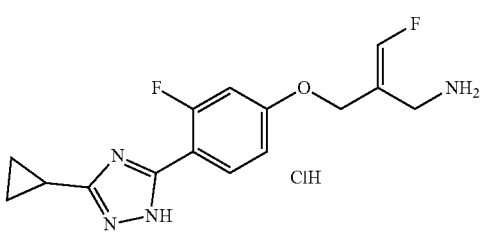 [SMILES: NC/C(=C\F)COc1ccc(-c2nc(C3CC3)n[nH]2)c(F)c1 ; Cl]

Synthesis Route:

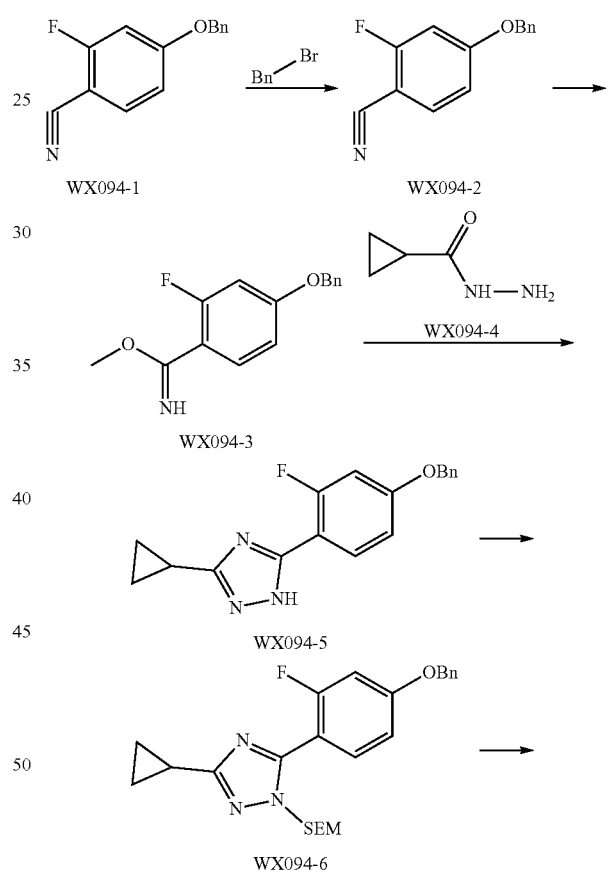

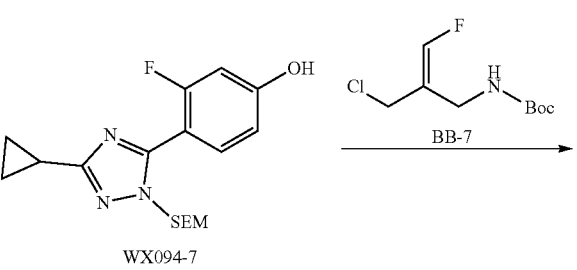
WX094-7

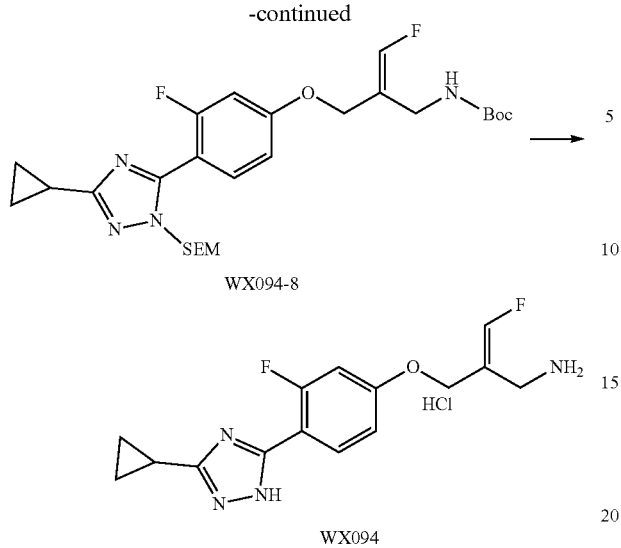

Step 1: Synthesis of Compound WX094-2

The synthesis of the compound WX094-2 referred to the synthesis method in the step 1 of the Fragment BB-7. ESI m/z: [M+H]$^+$=228.2.

Step 2: Synthesis of Compound WX094-3

The synthesis of the compound WX094-3 referred to the synthesis method in the step 2 of the Fragment BB-7. ESI m/z [M+H]$^+$=261.1.

Step 3: Synthesis of Compound WX094-4

The synthesis of the compound WX094-4 referred to the step 1 of Example 22, ESI m/z[M+H]$^+$=310.34.

Step 4: Synthesis of Compound WX094-5

The synthesis of the compound WX094-5 referred to the step 2 of Example 22, ESI m/z [M+H]$^+$=440.3.

Step 5: Synthesis of Compound WX094-6

The synthesis of the compound WX094-6 referred to the step 3 of Example 22, ESI m/z [M+H]$^+$=350.2.

Step 6: Synthesis of Compound WX094-7

The synthesis of the compound WX094-7 referred to the step 4 of Example 1, ESI m/z [M+H]$^+$=537.3.

Step 7: Synthesis of Compound WX094

The synthesis of the compound WX094 referred to the synthesis method of the step 5 of Example 1. $^1$H NMR (400 MHz, DMSO-d6) δ ppm 0.96-1.23 (m, 4H) 2.06-2.25 (m, 1H) 3.60 (br d, J=4.89 Hz, 2H) 4.75 (d, J=3.01 Hz, 2H) 7.00 (dd, J=8.72, 2.32 Hz, 1H) 7.10 (dd, J=12.67, 2.26 Hz, 1H) 7.23-7.48 (m, 1H) 7.95 (t, J=8.72 Hz, 1H) 8.40 (br s, 3H).

Example 56: WX095

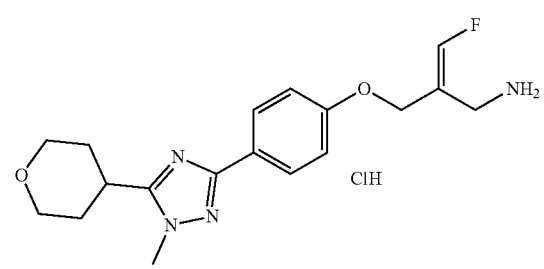 [SMILES: Cn1nc(-c2ccc(OC/C(=C/F)CN)cc2)nc1C1CCOCC1 ; Cl]

Synthesis Route:

Step 1: Synthesis of Compound WX095-1

The synthesis of the compound WX095-1 referred to the synthesis method of the step 1 synthesis in Example 16. ESI m/z [M+1]$^+$=246.2

Step 2: Synthesis of Compound WX095-2

The synthesis of compound WX095-2 referred to the synthesis method of the step 1 of Example 16. ESI m/z [M+1]$^+$=258.4.

Step 3: Synthesis of Compound WX095-3

The synthesis of the compound WX095-3 referred to the synthesis method of the step 3 in Example 22. ESI m/z [M+1]⁺=260.4.

Step 4: Synthesis of Compound WX095-4

The synthesis of the compound WX095-4 referred to the synthesis method of the step 4 in Example 1. ESI m/z [M+1]⁺=447.4.

Step 5: Synthesis of Compound WX095

The synthesis of the compound WX095 referred to the synthesis method of the step 5 of Example 1. $^1$H NMR (400 MHz, DEUTERIUM OXIDE) δ=7.81 (br d, J=8.8 Hz, 2H), 7.24-6.95 (m, 3H), 4.65 (br d, J=2.9 Hz, 2H), 4.05 (br d, J=11.4 Hz, 2H), 3.96 (s, 3H), 3.83 (s, 2H), 3.66-3.43 (m, 3H), 1.91 (br d, J=2.5 Hz, 4H).

Example 57: WX096

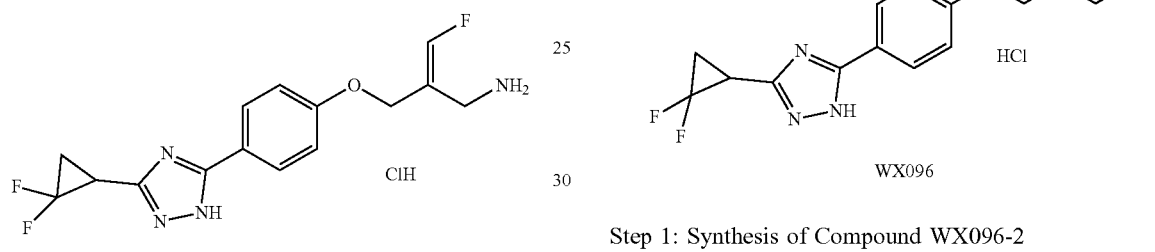

Synthesis Route:

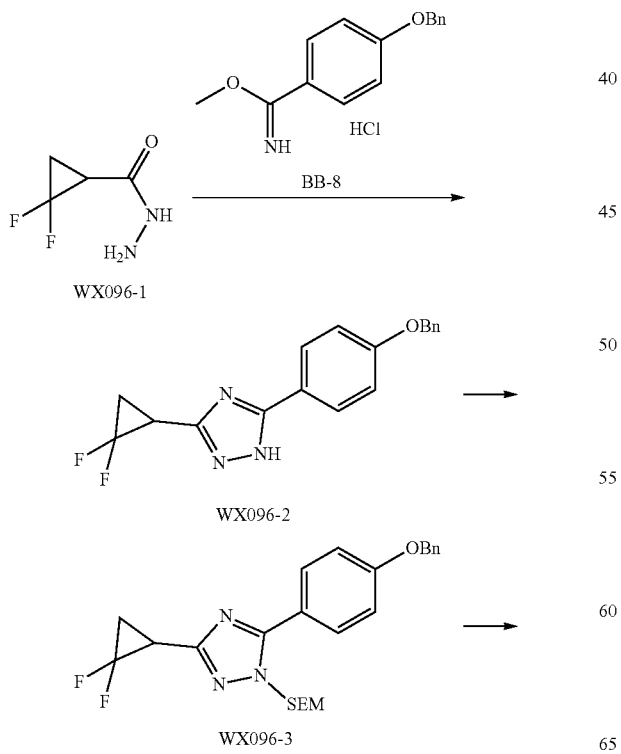

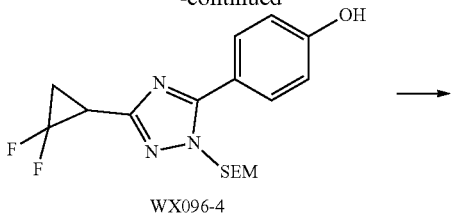

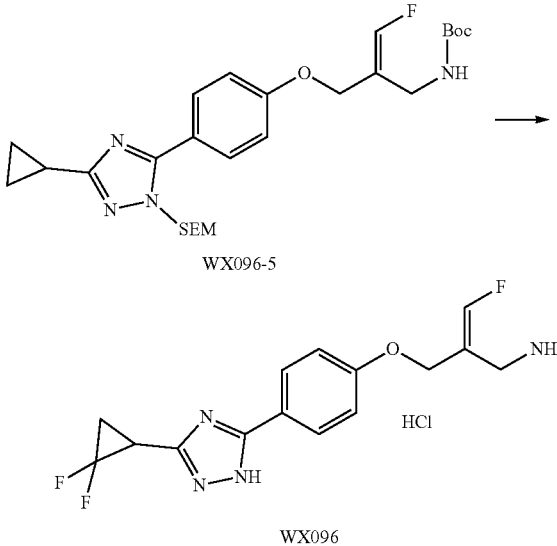

Step 1: Synthesis of Compound WX096-2

The synthesis of the compound WX096-2 referred to the step 1 of Example 22, ESI m/z: [M+H]⁺=328.3.

Step 2: Synthesis of Compound WX096-3

The synthesis of the compound WX096-3 referred to the synthesis method of the step 2 of Example 22, ESI m/z [M+H]⁺=458.4.

Step 3: Synthesis of Compound WX096-4

The synthesis of the compound WX096-4 referred to the synthesis method of the step 3 of Example 22, ESI m/z [M+H]⁺=368.4

Step 4: Synthesis of Compound WX096-5

The synthesis of the compound WX096-5 referred to the synthesis method of the step 4 of Example 1, ESI m/z [M+H]⁺=555.5.

Step 5: Synthesis of Compound WX096

The synthesis of the compound WX096 referred to the synthesis method of the step 5 of Example 1. $^1$HNMR (400 MHz, METHANOL-d4) δ=7.98 (d, J=8.9 Hz, 2H), 7.42-7.16 (m, 3H), 4.74 (d, J=3.3 Hz, 2H), 3.86 (s, 2H), 3.16 (dt, J=8.0, 11.1 Hz, 1H), 2.36-2.14 (m, 2H).

Example 58: WX097

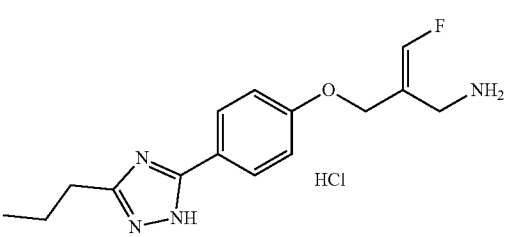 [SMILES: CCCc1n[nH]c(-c2ccc(OC/C(=C/F)CN)cc2)n1 ; Cl]

Synthesis Route:

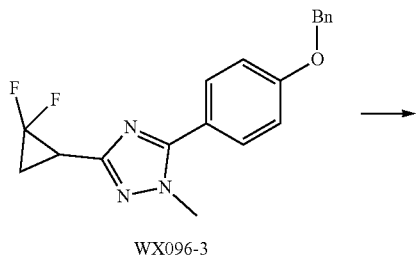

WX096-3

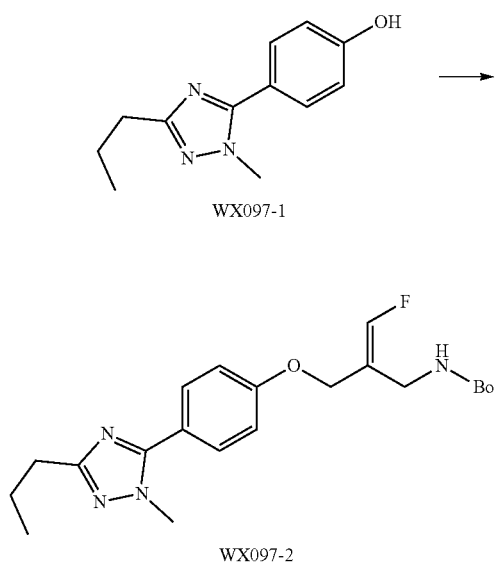

WX097-1

WX097-2

WX097

Step 1: Synthesis of Compound WX097-1

The compound WX097-1 was obtained when the compound WX096-4 was synthesized. ESI m/z [M+H]$^+$=334.4.

Step 2: Synthesis of Compound WX097-2

The synthesis of the compound WX097-2 referred to the synthesis method of the step 4 in Example 1. ESI m/z [M+H]$^+$=539.6.

Step 3: Synthesis of Compound WX097

The synthesis of the compound WX097 referred to the synthesis method of the step 5 in Example 1. $^1$H NMR (400 MHz, METHANOL-d4) δ=7.99 (d, J=8.9 Hz, 2H), 7.39-7.16 (m, 3H), 4.74 (d, J=3.3 Hz, 2H), 3.85 (s, 2H), 3.01 (t, J=7.6 Hz, 2H), 1.96-1.85 (m, 2H), 1.08 (t, J=7.3 Hz, 3H).

Example 59: WX098

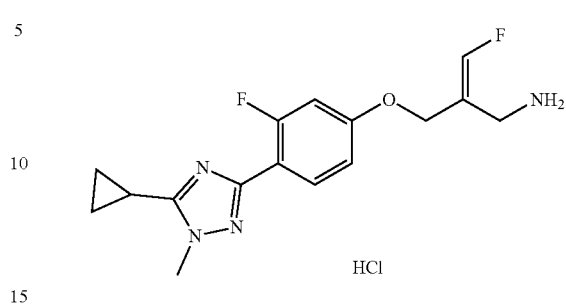

Synthesis Route:

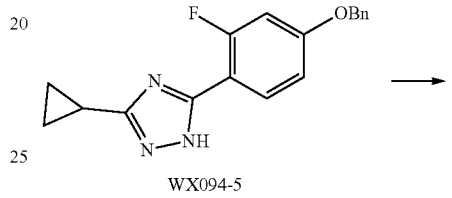

WX094-5

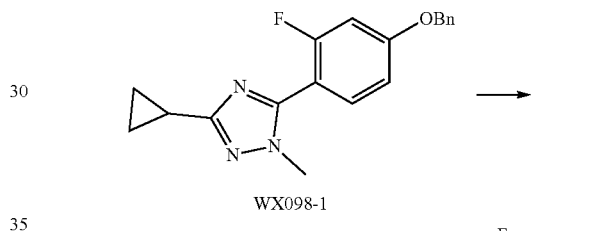

WX098-1

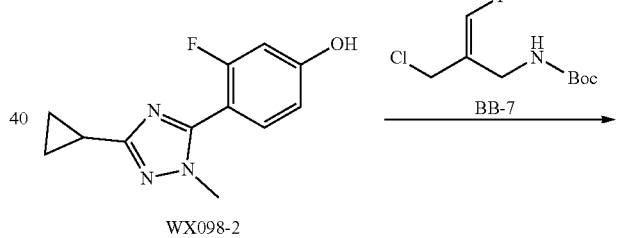

WX098-2

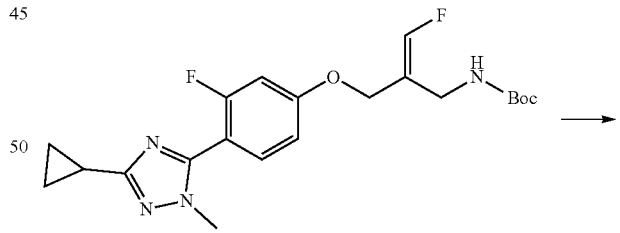

WX098-3

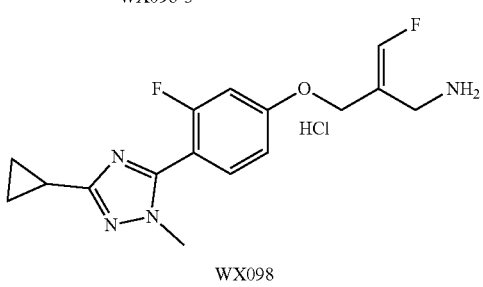

WX098

Step 1: Synthesis of Compound WX098-1

The synthesis of the compound WX098-1 referred to the step 1 of Example 27, ESI m/z: [M+H]$^+$=324.2.

Step 2: Synthesis of Compound WX098-2

The synthesis of the compound WX098-2 referred to the step 3 of Example 22, ESI m/z: [M+H]$^+$=234.1

Step 3: Synthesis of Compound WX098-3

The synthesis of the compound WX098-3 referred to the step 4 of Example 1, [M+H]$^+$=421.3

Step 4: Synthesis of Compound WX098

The synthesis of the compound WX098 referred to the step 5 of Example 1, 1H NMR (400 MHz, DMSO-d6) δ ppm 0.75-1.14 (m, 4H) 2.10-2.26 (m, 1H) 3.60 (br d, J=4.39 Hz, 2H) 3.68-3.69 (m, 1H) 3.68 (s, 1H) 3.68-3.68 (m, 1H) 3.92 (s, 1H) 3.89-3.89 (m, 1H) 3.92-3.94 (m, 1H) 3.92-3.93 (m, 1H) 4.59-4.87 (m, 2H) 6.86-7.08 (m, 2H) 7.20-7.47 (m, 1H) 7.85 (t, J=8.72 Hz, 1H) 8.33 (br s, 3H).

Example 60: WX099

Synthesis Route:

Step 1: Synthesis of Compound WX099-2

The synthesis of the compound WX099-2 referred to the step 1 of Example 16, ESI m/z: [M+H]$^+$=413.2.

Step 2: Synthesis of Compound WX099-3

The synthesis of the compound WX099-3 referred to the step 4 of Example 1, ESI m/z: [M+H]$^+$=600.4.

Step 3: Synthesis of Compound WX099

The synthesis of the compound WX099 referred to the step 5 of Example 1, $^1$H NMR (400 MHz, DMSO-d$_6$) δ ppm 3.29-3.44 (m, 2H) 3.82 (br s, 8H) 4.75 (br s, 2H) 6.98 (br d, J=9.70 Hz, 2H) 7.23-7.51 (m, 1H) 8.32 (br s, 2H).

Example 61: WX101

Synthesis Route:

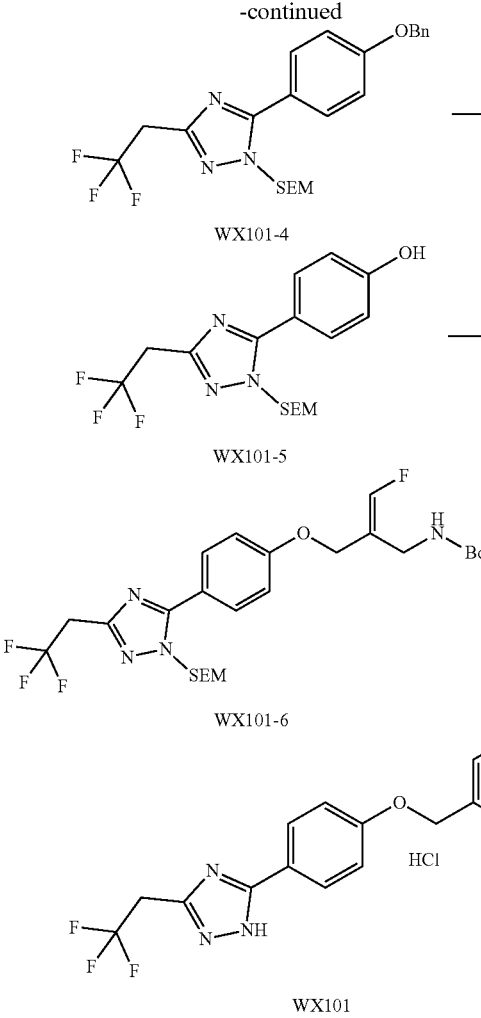

Step 1: Synthesis of Compound WX101-2

A compound WX101-1 was dissolved in MeOH (5 ml), and hydrazine hydrate (510.20 mg) was added at 0° C. The reaction was stirred at 30° C. for 25 hours. The reaction solution was concentrated under reduced pressure to obtain a crude product. The crude product was pulped by petroleum ether:methyl tert-butyl ether 1:1 (10 ml), and purified to obtain the target compound WX101-2. ESI m/z: [M+H]$^+$=141.1.

Step 2: Synthesis of Compound WX101-3

The synthesis of the compound WX101-3 referred to the step 1 of Example 22, ESI m/z: [M+H]$^+$=334.4.

Step 3: Synthesis of Compound WX101-4

The synthesis of the compound WX101-4 referred to the step 2 of Example 22, ESI m/z [M+H]$^+$=464.4.4.

Step 4: Synthesis of Compound WX101-5

The synthesis of the compound WX101-5 referred to the step 3 of Example 22, ESI m/z [M+H]$^+$=374.3.

Step 4: Synthesis of Compound WX101-6

The synthesis of the compound WX101-6 referred to the step 4 of Example 1, ESI m/z [M+H]$^+$=561.5.

Step 5: Synthesis of Compound WX101

The synthesis of the compound WX101 referred to the step 5 of Example 1. $^1$H NMR (400 MHz, DMSO-d6) δ=8.05 (br s, 3H), 7.96 (d, J=8.8 Hz, 2H), 7.47 (s, 1H), 7.28-7.13 (m, 2H), 4.67 (br s, 2H), 3.85 (br s, 3H), 3.66 (br s, 3H).

Example 62: WX102

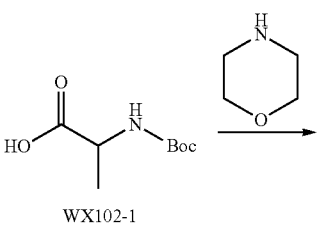

Synthesis Route:

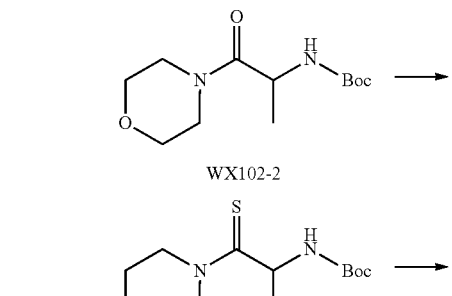

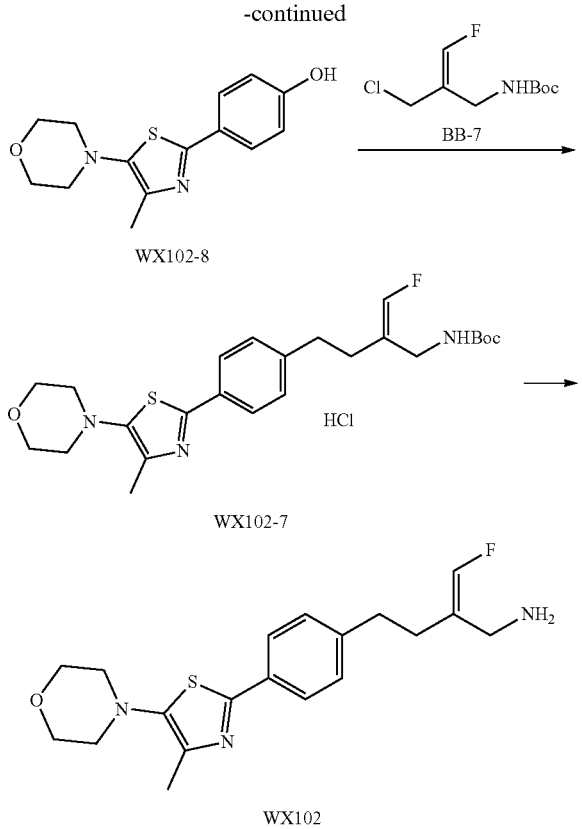

Step 1: Synthesis of Compound WX102-2

O-(7-azabenzotriazole)-N,N,N,N-tetramethyl urea hexafluorophosphate (7.23 g) was added to a N, N-dimethylformamide (25 ml) solution of a compound WX102-1 (3 g), N,N-diisopropyl ethylamine (2.46 g) and morpholine (2.07 g). The resulting mixture was reacted at 25° C. for 1 hour. The reaction solution was poured into water (50 ml), and extracted with ethyl acetate (50 ml) twice. The organic phases were mixed and washed with saturated salt water (50 ml) for three times, dried with anhydrous sodium sulfate, filtered and spin-dried to obtain the compound WX102-2. ESI m/z [M−56]$^+$=203.3.

Step 2: Synthesis of Compound WX102-3

The compound WX102-2 was dissolved in tetrahydrofuran (10 ml) and Lawesson reagent (7.83 g) was added. The obtained mixture was reacted at 25° C. for 2 hours. The reaction solution was poured into water (50 ml), adjusted with sodium carbonate to PH=8, and extracted with ethyl acetate (50 ml) twice, the organic layers were mixed, dried with anhydrous sodium sulfate, and then filtered and evaporated to be dry to obtain the compound WX102-3. ESI m/z [M−1]$^+$=219.3.

Step 3: Synthesis of Compound WX102-4

The synthesis of the compound WX102-4 referred to the synthesis method of the step 5 of Example 1. ESI m/z [M+1]$^+$=175.4.

Step 4: Synthesis of Compound WX102-5

The compound WX102-4 (0.6 g) was dissolved in dichloromethane (15 ml), triethylamine (1.19 ml) was added, a reaction was conducted for 0.2 hour, and p-methoxybenzoyl chloride (587.58 μL) was added dropwise. The resulting mixture was reacted at 25° C. for 1 hour. The reaction solution was poured into water (50 ml), and extracted with ethyl acetate (50 ml) twice, and the organic phases were mixed, dried with anhydrous sodium sulfate, filtered and evaporated to be dry to obtain the compound WX102-5. ESI m/z [M+1]$^+$=309.4.

Step 5: Synthesis of Compound WX102-6

A PPA (30 g) mixture of the compound WX102-5 (0.6 g) was reacted at 140° C. for 1 hour. The reaction solution was poured into water (100 ml), adjusted with sodium carbonate to PH=8, extracted with ethyl acetate (100 ml) twice, dried with anhydrous sodium sulfate, filtered and evaporated to be dry. The crude product was separated by an automatic column passing machine (gradient elution:petroleum ether/ethyl acetate=1:0 to 1:5) and purified to obtain the compound WX102-6. ESI m/z [M+1]$^+$=291.4.

Step 6: Synthesis of Compound WX102-7

The synthesis of the compound WX102-7 referred to the synthesis method of the step 3 of Example 1, ESI m/z [M+1]$^+$=277.4.

Step 7: Synthesis of Compound WX102-8

The synthesis of the compound WX102-8 referred to the synthesis method of the step 4 of Example 1, ESI m/z [M+1]$^+$=464.4.

Step 8: Synthesis of Compound WX102

The synthesis of the compound WX102 referred to the synthesis method of the step 5 of Example 1. $^1$H NMR (400 MHz, D2O) δ=7.77 (br d, J=8.4 Hz, 2H), 7.29-6.98 (m, 3H), 4.68 (br s, 2H), 3.85 (br s, 6H), 3.00 (br s, 4H), 2.35 (br s, 3H). ($^{19}$F NMR (376 MHz, D2O) δ=120.189.

Example 63: WX103

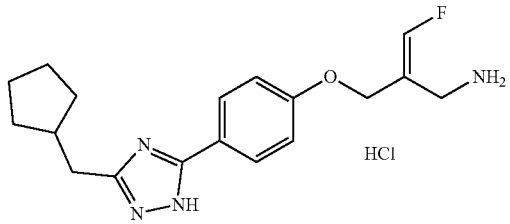 [SMILES: NC/C(=C\F)COc1ccc(-c2nc(CC3CCCC3)n[nH]2)cc1 ; Cl]

Synthesis Route:

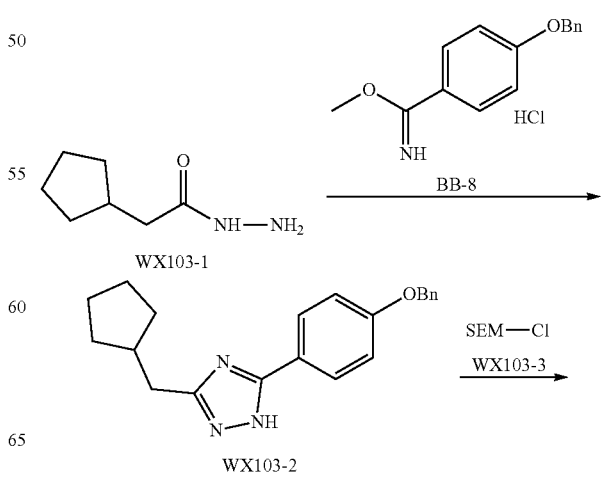

183
-continued

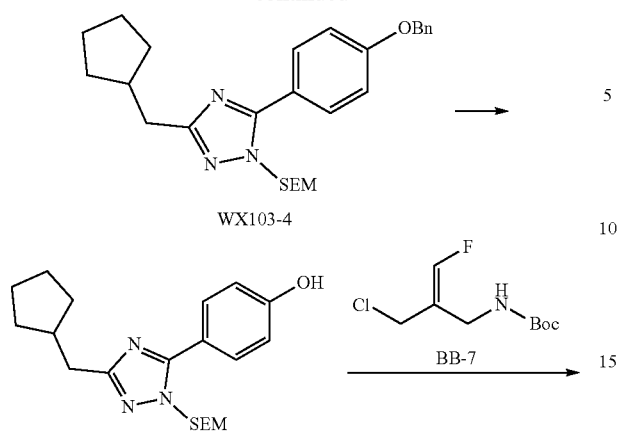

WX103-4, WX103-5, WX103-6, WX103

Step 1: Synthesis of Compound WX103-2

The synthesis of the compound WX103-2 referred to the step 1 of Example 22. ESI m/z [M+H]⁺=334.2.

Step 2: Synthesis of Compound WX103-4

The synthesis of the compound WX103-4 referred to the step 2 of Example 22. ESI m/z [M+H]⁺=464.3.

Step 3: Synthesis of Compound WX103-5

The synthesis of the compound WX103-5 referred to the step 3 of Example 22. ESI m/z [M+H]⁺=374.2.

Step 4: Synthesis of Compound WX103-6

The synthesis of the compound WX103-6 referred to the step 4 of Example 1. ESI m/z [M+H]⁺=561.4.

Step 5: Synthesis of Compound WX103

The synthesis of the compound WX103 referred to the step 5 of Example 1. $^1$H NMR (400 MHz, DMSO-$d_6$) δ ppm 1.13-1.31 (m, 2H) 1.44-1.79 (m, 6H) 2.80 (d, J=7.40 Hz, 2H) 3.17 (br s, 2H) 4.70 (br d, J=3.01 Hz, 2H) 7.15 (d, J=8.78 Hz, 2H) 7.24-7.49 (m, 1H) 8.02 (d, J=8.66 Hz, 2H) 8.24 (br s, 3H).

184

Example 64: WX104

Synthesis Route:

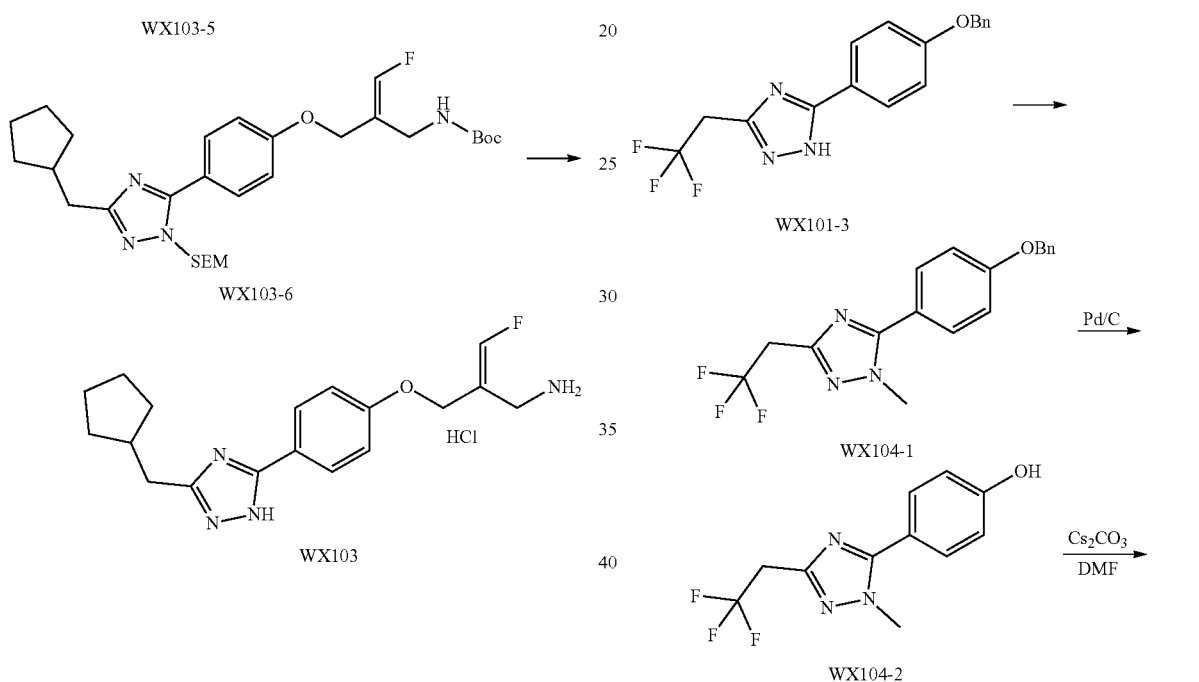

WX101-3, WX104-1, WX104-2, WX104-3, WX104

Step 1: Synthesis of Compound WX104-1

The synthesis of the compound WX104-1 referred to the step 1 of Example 27, ESI m/z: [M+H]$^+$=348.3.

Step 2: Synthesis of Compound WX104-2

The synthesis of the compound WX104-2 referred to the step 3 of Example 22, ESI m/z: [M+H]$^+$=258.3

Step 3: Synthesis of Compound WX104-3

The synthesis of the compound WX104-3 referred to the step 4 of Example 1, [M+H]$^+$=445.4

Step 4: Synthesis of Compound WX104

The synthesis of the compound WX104 referred to the step 5 of Example 1, $^1$H NMR (400 MHz, DMSO-d6) δ=8.05 (br s, 3H), 7.96 (d, J=8.8 Hz, 2H), 7.47 (s, 1H), 7.28-7.13 (m, 2H), 4.67 (br s, 2H), 3.85 (br s, 3H), 3.66 (br s, 3H).

Example 65: WX105

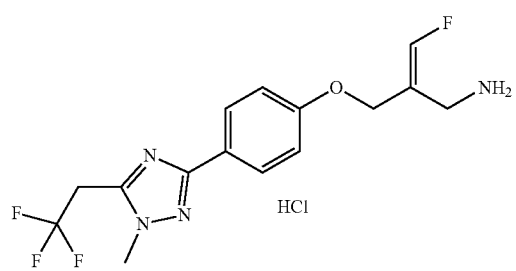 [SMILES: Cn1nc(-c2ccc(OC/C(=C/F)CN)cc2)nc1CC(F)(F)F ; Cl]

Synthesis Route:

WX104-3

WX105

Step 1: Synthesis of Compound WX105

The separation of the compound WX104 resulted in the isomer compound WX105. $^1$H NMR (400 MHz, METHANOL-d$_4$) δ=7.73 (d, J=8.8 Hz, 2H), 7.40-7.13 (m, 3H), 4.72 (d, J=3.5 Hz, 2H), 3.99 (s, 3H), 3.85 (s, 2H), 3.73 (q, J=10.5 Hz, 2H).

Example 66: WX106

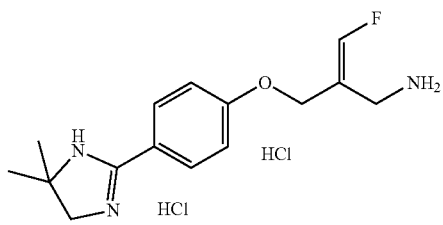 [SMILES: CC1(C)CN=C(c2ccc(OC/C(=C/F)CN)cc2)N1 ; Cl ; Cl]

Synthesis Route:

WX106-1

WX106-2

WX106-4

WX106

Step 1: Synthesis of Compound WX106-2

The synthesis of the compound WX106-2 referred to the step 4 of Example 1, ESI m/z [M−56]$^+$=254.3.

Step 2: Synthesis of Compound WX106-4

A DMF (5 ml) mixture of the compound WX106-2 (0.17 g), a compound WX106-3 (58.13 mg) and NaHSO$_3$ (68.63 mg) was reacted at 100° C. for 3 hours. The reaction solution was spin-dried and the crude product was purified by preparative high pressure liquid chromatography (chromatography column: Waters Xbridge 150×25 mm 5 μm; mobile phase: [water (0.05% HCl)-acetonitrile]; B %: 5%-30%, 12 min) to obtain the compound WX106-4. ESI m/z [M+1]$^+$=378

Step 3: Synthesis of Compound WX106

The synthesis of the compound WX106 referred to the step 5 of Example 1, $^1$H NMR (400 MHz, DMSO-$d_6$) δ=10.91 (s, 1H), 10.60 (br s, 1H), 8.40 (br s, 3H), 8.08 (d, J=8.9 Hz, 2H), 7.52-7.17 (m, 3H), 4.80 (d, J=2.9 Hz, 2H), 3.72 (s, 2H), 3.59 (br s, 2H), 3.35 (s, 21H), 1.44 (s, 6H).

Example 67: Compound WX107

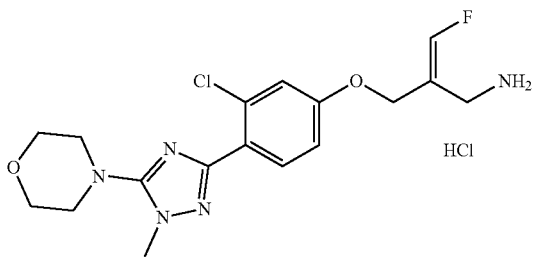 [SMILES: Cn1nc(-c2ccc(OC/C(=C/F)CN)cc2Cl)nc1N1CCOCC1 ; Cl]

Synthesis Route:

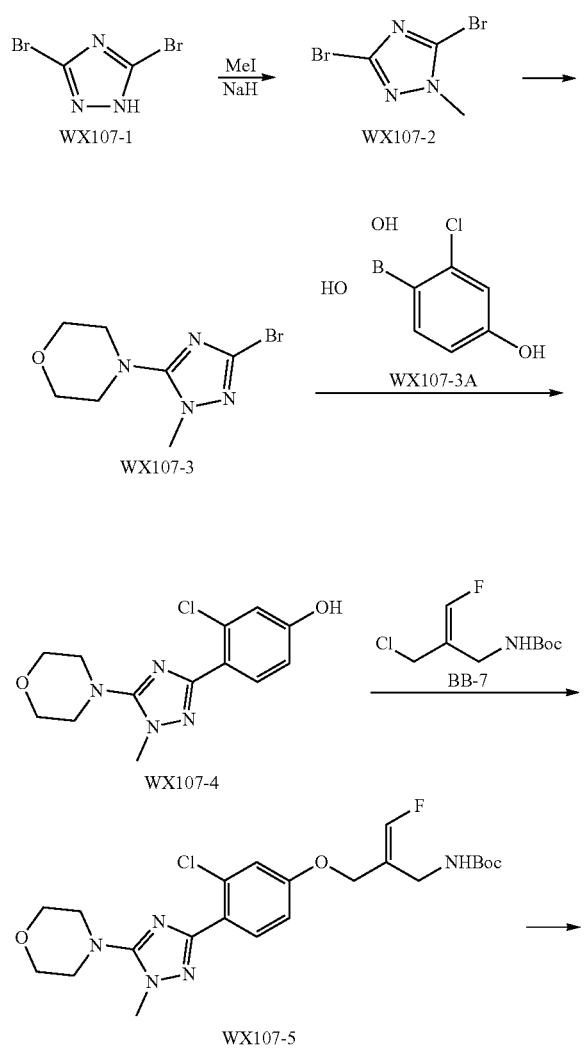

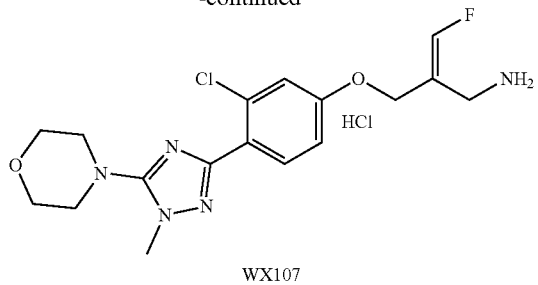

WX107

Step 1: Sodium hydride (423.17 mg, 60% purity) was added to a N,N-dimethylformamide solution (10 ml) of a compound WX107-1 (2.0 g) at 0° C., and the reaction was stirred for 0.5 hour at 0° C. Iodomethane (1.57 g) was added to the reaction solution and the reaction was stirred at 25° C. for 14 hours. After the reaction was completed, water (10 ml) was added to quench the reaction, and then water (20 ml) was added, the mixture was extracted with ethyl acetate (20 ml) for three times, and the organic phases were mixed, washed with water (20 ml) twice, dried with anhydrous sodium sulfate, then filtered and concentrated to obtain a crude product WX107-2. NMR (400 MHz, CHLOROFORM-d) δ=3.88-3.75 (m, 3H).

Step 2: Morpholine (1.59 g) was added to a N,N-dimethylformamide (20 ml) solution of the compound WX107-2 (2.0 g), and the reaction solution was stirred at 120° C. for 4 hours. After the reaction was completed, water (50 ml) was added, and the mixture was extracted with ethyl acetate (30 ml) for three times. The mixed organic phase was washed with saturated salt water (30 ml) and water (30 ml), respectively, and dried with anhydrous sodium sulfate, filtered and concentrated to obtain a crude product. The crude product was purified by a column to obtain the compound WX107-3. $^1$H NMR (400 MHz, CHLOROFORM-d) δ=3.88-3.79 (m, 4H), 3.71-3.66 (m, 3H), 3.26-3.15 (m, 4H).

Step 3: A 1,4-dioxane (6 ml) and water (2 ml) solution of the compound WX107-3 (0.2 g), a compound WX107-3A (418 mg), tetrakis(triphenylphosphine)palladium (140.30 mg) and potassium carbonate (335.60 mg) was replaced with nitrogen for three times, and the reaction solution was stirred at 120° C. for 2 hours. After the reaction was completed, the mixture was directly concentrated, and the cruder product was purified by a column to obtain the compound WX107-4. $^1$H NMR (400 MHz, CHLOROFORM-d) δ=7.54-7.50 (m, 1H), 7.05 (br s, 1H), 6.86 (d, J=2.5 Hz, 1H), 6.68 (dd, J=2.5, 8.5 Hz, 1H), 3.86-3.77 (m, 4H), 3.71 (s, 3H), 3.24-3.12 (m, 4H).

Step 4: Cesium carbonate (420.07 mg) and a compound WX107-4a (173.03 mg) were added to a N,N-dimethylformamide (8 ml) solution of the compound WX107-4 (190 mg, 645 μmol), and the reaction solution was stirred at 25° C. for 5 hours. After the reaction was completed, water (50 ml) was added and the mixture was extracted with ethyl acetate (50 ml) for three times. The mixed organic phase was washed with saturated salt water (50 ml) and water (50 ml), respectively, dried with anhydrous sodium sulfate, and filtered and concentrated to obtain a crude product WX107-5.

Step 5: Ethyl acetate-hydrochloride (20 ml) was added to an ethyl acetate solution (10 ml) of the compound WX107-5 (190 mg). The reaction solution was stirred at 25° C. for 2 hours. After the reaction was completed, the solution was directly concentrated to obtain a crude product. The crude product was separated by preparative high performance liquid chromatography to obtain the target compound WX107. ¹H NMR (400 MHz, DMSO-d₆) δ=8.42 (br s, 3H), 7.77 (d, J=8.5 Hz, 1H), 7.44 (s, 0.5H), 7.23 (s, 0.5H), 7.20 (d, J=2.5 Hz, 1H), 7.08 (dd, J=2.5, 9.0 Hz, 1H), 4.74 (br d, J=3.0 Hz, 2H), 3.76 (br d, J=4.5 Hz, 4H), 3.60 (br d, J=4.5 Hz, 2H), 3.26- 3.17 (m, 4H).

Example 68: Compound WX123

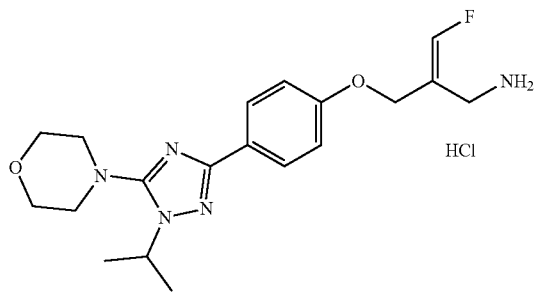 [SMILES: CC(C)n1nc(-c2ccc(OC/C(=C/F)CN)cc2)nc1N1CCOCC1 ; Cl]

Synthesis Route:

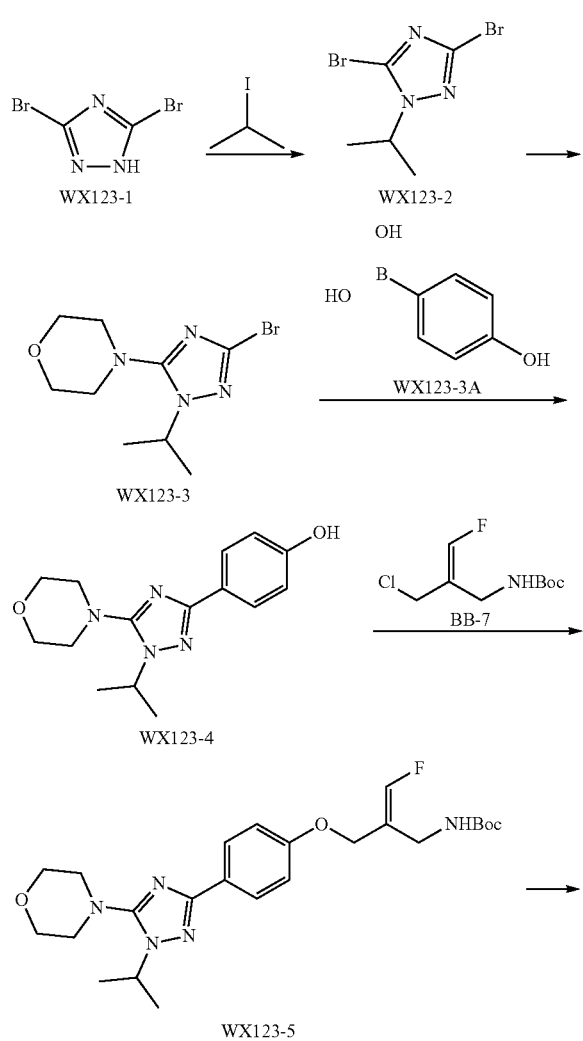

-continued

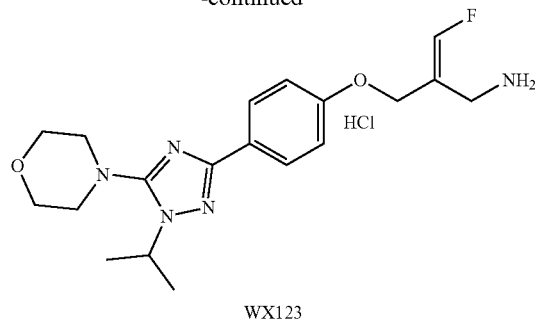

WX123

Step 1: Sodium hydrogen (423.17 mg) was added to a N,N-dimethylformamide solution (10 ml) of a compound WX123-1 (2.0 g) at 0° C., and the reaction was stirred for 0.5 hour at 0° C. Isopropane iodide (1.57 g) was added to the reaction solution and the reaction was stirred at 25° C. for 14 hours. After the reaction was completed, water (10 ml) was added to quench the reaction, and then water (20 ml) was added, and the solution was extracted with ethyl acetate (20 ml) for three times. The mixed organic phase was washed with water (20 ml) twice, dried with anhydrous sodium sulfate, and then filtered and concentrated to obtain a crude product WX123-2. ¹H NMR (400 MHz, CHLOROFORM-d) δ=3.88-3.75 (m, 3H).

Step 2: Morpholine (713 mg) was added to a N,N-dimethylformamide (20 ml) solution of the compound WX123-2 (1.0 g), and the reaction solution was stirred at 120° C. for 4 hours. After the reaction was completed, water (50 ml) was added, and the solution was extracted with ethyl acetate (30 ml) for three times. The mixed organic phase was washed with saturated salt water (30 ml) and water (30 ml), respectively, and dried with anhydrous sodium sulfate, filtered and concentrated to obtain a crude product. The crude product was purified by a column to obtain the compound WX123-3.

Step 3: A 1,4-dioxane (6 ml) and water (2 ml) solution of the compound WX123-3 (0.2 g), a compound WX123-3A (300 mg), tetrakis(triphenylphosphine)palladium (125.99 mg) and potassium carbonate (3.1.39 mg) was replaced with nitrogen for three times, and the reaction solution was stirred at 120° C. for 2 hours. After the reaction was completed, the mixture was directly concentrated, and the cruder product was purified by a column to obtain the compound WX123-4. ¹H NMR (400 MHz, CHLOROFORM-d) δ=7.93-7.66 (m, 2H), 6.77-6.64 (m, 2H), 4.42 (spt, J=6.6 Hz, 1H), 3.87-3.67 (m, 4H), 3.20-2.99 (m, 4H), 1.42 (d, J=6.5 Hz, 6H).

Step 4: Cesium carbonate (420.07 mg) and the compound BB-7 (173.03 mg) were added to a N,N-dimethylformamide (8 ml) solution of the compound WX123-4 (190 mg), and the reaction solution was stirred at 25° C. for 5 hours. After the reaction was completed, water (50 ml) was added and the mixture was extracted with ethyl acetate (50 ml) for three times. The mixed organic phase was washed with saturated salt water (50 ml) and water (50 ml), respectively, dried with anhydrous sodium sulfate, and filtered and concentrated to obtain a crude product WX123-5.

Step 5: Ethyl acetate hydrochloride (20 ml) was added to an ethyl acetate solution (10 ml) of the compound WX123-5 (190 mg). The reaction solution was stirred at 25° C. for 2 hours. After the reaction was completed, the solution was directly concentrated to obtain a crude product. The crude product was separated by preparative high performance liquid chromatography to obtain the target compound WX123. ¹H NMR (400 MHz, DMSO-d₆) δ=8.42 (br s, 3H), 7.77 (d, J=8.5 Hz, 1H), 7.44 (s, 0.5H), 7.23 (s, 0.5H), 7.20 (d, J=2.5 Hz, 1H), 7.08 (dd, J=2.5, 9.0 Hz, 1H), 4.74 (br d, J=3.0 Hz, 2H), 3.76 (br d, J=4.5 Hz, 4H), 3.60 (br d, J=4.5 Hz, 2H), 3.26- 3.17 (m, 4H).

Example 69: Compound WX109

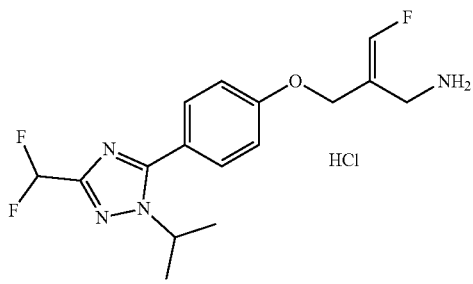 [SMILES: CC(C)n1nc(C(F)F)nc1-c1ccc(OC/C(=C/F)CN)cc1 ; Cl]

Synthesis Route:

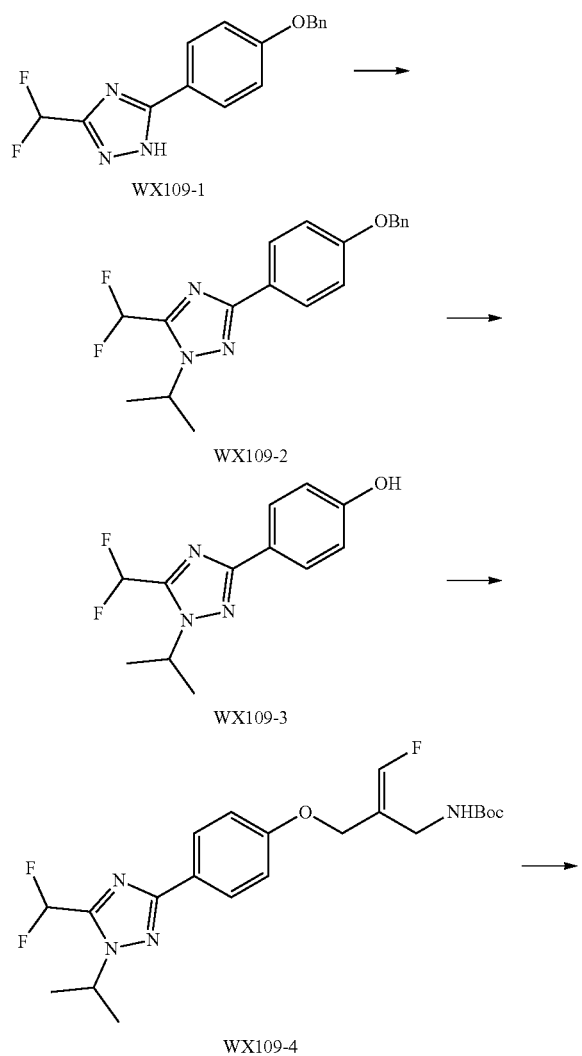

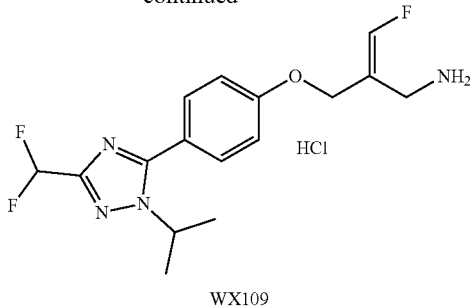

WX109

Step 1: Sodium hydrogen (95.6 mg, 60% purity) was added to a N,N-dimethylformamide solution (10 ml) of a compound WX109-1 (0.6 g) at 0° C., and the reaction was stirred for 1 hour at 25° C. Isopropane iodide (372 mg) was added to the reaction solution and the reaction was stirred at 25° C. for 13 hours. After the reaction was completed, water (10 ml) was added to quench the reaction, then water (20 ml) was added, and the solution was extracted with ethyl acetate (20 ml) for three times. The mixed organic phase was washed with water (20 ml) twice, dried with anhydrous sodium sulfate, and then filtered and concentrated to obtain a crude product WX109-2.

Step 2: Palladium-carbon (0.1 g, purity 10%) was added to a methanol solution (50 ml) of the compound WX109-2 (0.55 g), and the reaction solution was stirred at 45° C. under hydrogen (15 psi) for 1 hour. After the reaction was completed, the solution was filtered and concentrated to obtain a crude product WX109-3.

Step 3: Cesium carbonate (900.6 mg) and a compound WX109-3a (371 mg) were added to a N,N-dimethylformamide (15 ml) solution of the compound WX109-3 (0.35 g), and the reaction solution was stirred at 25° C. for 16 hours. After the reaction was completed, water (50 ml) was added and the mixture was extracted with ethyl acetate (50 ml) for three times. The mixed organic phase was washed with saturated salt water (50 ml) and water (50 ml), respectively, dried with anhydrous sodium sulfate, and filtered and concentrated to obtain a crude product WX109-4.

Step 4: Ethyl acetate hydrochloride (20 ml) was added to an ethyl acetate solution (10 ml) of the compound WX109-4 (0.5 g). The reaction solution was stirred at 25° C. for 2 hours. After the reaction, the solution was directly concentrated to obtain a crude product. The crude product was separated by preparative high performance liquid chromatography to obtain the target compound WX109. ¹H NMR (400 MHz, DMSO-d₆) δ=8.51 (br s, 3H), 7.63 (d, J=8.8 Hz, 2H), 7.46 (s, 0.5H), 7.25 (br d, J=3.8 Hz, 1H), 7.21 (d, J=8.8 Hz, 2H), 7.11 (s, 0.5H), 4.78 (br d, J=3.0 Hz, 2H), 4.70 (td, J=6.6, 13.2 Hz, 1H), 3.61 (br d, J=5.0 Hz, 2H), 1.44 (d, J=6.5 Hz, 6H).

193

Example 70: Compound WX124

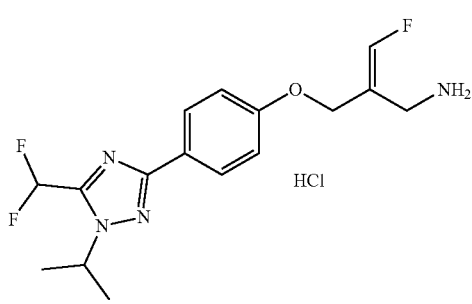 [SMILES: CC(C)n1nc(-c2ccc(OC/C(=C/F)CN)cc2)nc1C(F)F ; Cl]

Synthesis Route:

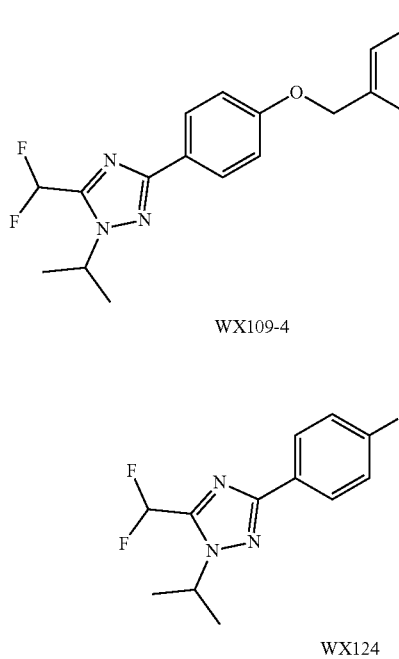

Step 1: the synthesized compound WX109 was separated to obtain the isomer WX124. $^1$H NMR (400 MHz, DMSO-d$_6$) δ=8.41 (br s, 3H), 7.96 (d, J=8.5 Hz, 2H), 7.66-7.21 (m, 2H), 7.11 (d, J=8.8 Hz, 2H), 4.85 (td, J=6.4, 13.0 Hz, 1H), 4.71 (br d, J=2.8 Hz, 2H), 3.61 (br d, J=4.8 Hz, 2H), 1.49 (d, J=6.3 Hz, 6H).

Example 71: WX111

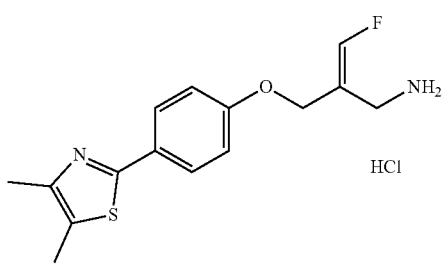 [SMILES: Cc1nc(-c2ccc(OC/C(=C/F)CN)cc2)sc1C ; Cl]

194

Synthesis Route:

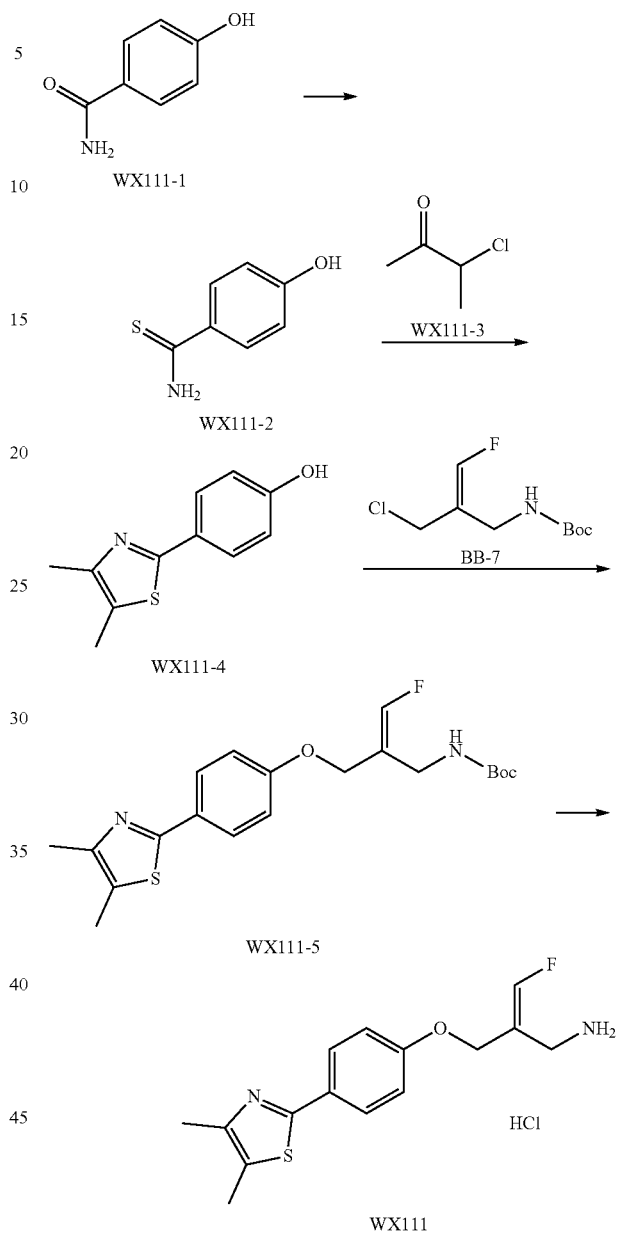

Step 1: Synthesis of Compound WX111-2

The synthesis of the compound WX111-2 referred to the synthesis method in the step 2 of Example 62. ESI m/z [M−1]$^+$=138.

Step 2: Synthesis of Compound WX111-4

The compound WX111-2 (0.5 g) and a compound WX111-3 (347.75 mg) were dissolved in ethanol (10 ml), and the mixture was stirred for a reaction at 80° C. for 4 hours. The reaction solution was concentrated under reduced pressure, the crude product was dissolved in ethyl acetate (15 ml), pulped with petroleum ether (15 ml), and filtered to obtain the target compound WX111-4. ESI m/z [M+H]$^+$=206.1.

Step 3: Synthesis of Compound WX111-5

The synthesis of the compound WX111-5 referred to the synthesis method of the step 4 in Example 1. ESI m/z [M+H]$^+$=393.2.

Step 4: Synthesis of Compound WX111

The synthesis of the compound WX111 referred to the synthesis method of the step 5 in Example 1. $^1$H NMR (400 MHz, METHANOL-d$_4$) δ ppm 2.49 (d, J=10.41 Hz, 6H) 3.86 (s, 2H) 4.75 (d, J=3.14 Hz, 2H) 7.16-7.41 (m, 3H) 7.94 (d, J=8.91 Hz, 2H).

Example 72: WX112

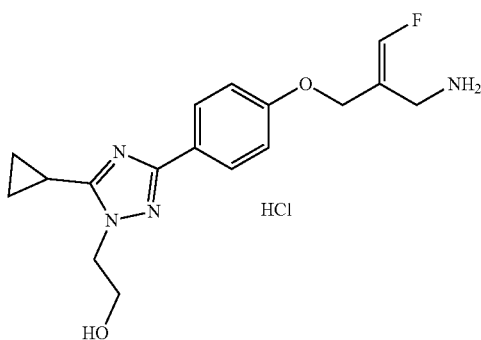 [SMILES: NC/C(=C\F)COc1ccc(-c2nc(C3CC3)n(CCO)n2)cc1 ; Cl]

Synthesis Route:

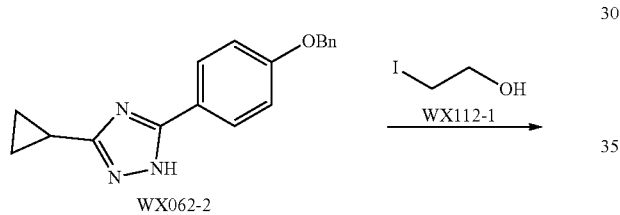

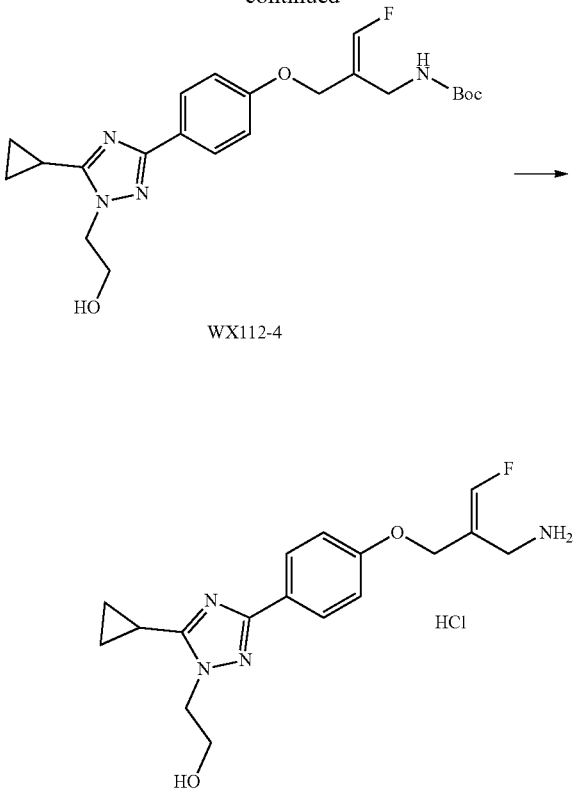

Step 1: Synthesis of Compound WX112-2

The compound WX062-2 was dissolved in DMF (3 ml) and iodoethanol was added, and K2CO3 (128.08 mg) was added. The reaction was stirred at 80° C. for 6 hours. The reaction solution was diluted with water (40 ml), and extracted with methyl tert-butyl ether (30 ml×2), and the organic phase was washed with saturated salt water (30 ml×3), then collected, dried with anhydrous sodium sulfate and filtered, and the filtrate was concentrated under reduced pressure to obtain the target compound WX112-2. ESI m/z [M+H]$^+$=336.3

Step 2: Synthesis of Compound WX112-3

The synthesis of the compound WX112-3 referred to the synthesis method in the step 3 of Example 22. ESI m/z [M+H]$^+$=245.

Step 3: Synthesis of Compound WX112-4 the synthesis of the compound WX112-4 referred to the synthesis method of the step 4 in Example 1. ESI m/z [M+H]$^+$=433.4.

Step 4: Synthesis of Compound WX112

The synthesis of the compound WX112 referred to the synthesis method of the step 5 in Example 1. $^1$H NMR (400 MHz, METHANOL-d$_4$) δ=8.01 (d, J=8.8 Hz, 2H), 7.42-7.15 (m, 3H), 4.74 (d, J=3.4 Hz, 2H), 4.56 (t, J=4.9 Hz, 2H), 4.06 (t, J=4.9 Hz, 2H), 3.85 (s, 2H), 2.55-2.45 (m, 1H), 1.51-1.35 (m, 4H).

Example 73: WX113

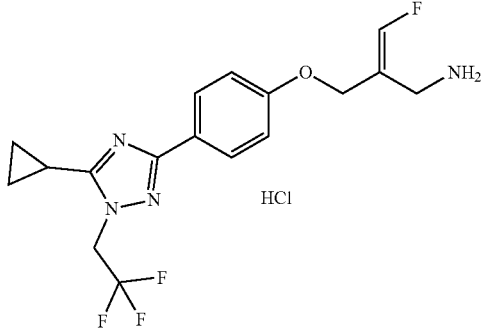 [SMILES: NC/C(=C\F)COc1ccc(-c2nc(C3CC3)n(CC(F)(F)F)n2)cc1 ; Cl]

Synthesis Route:

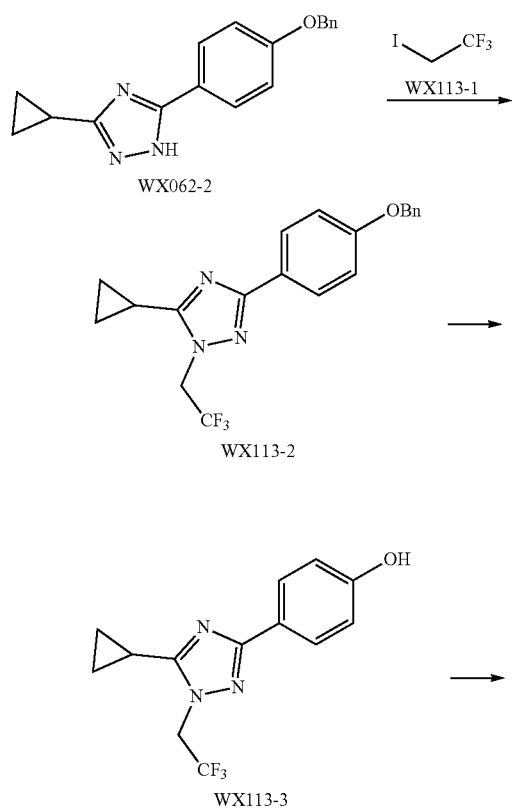

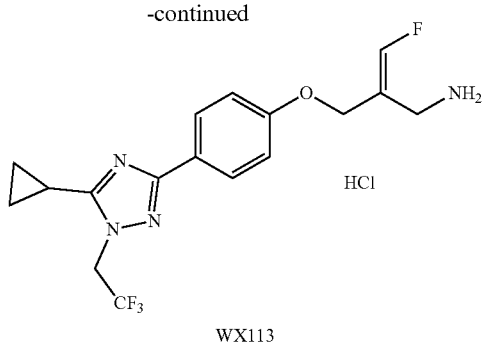

Step 1: Synthesis of Compound WX113-2

The synthesis of the compound WX113-2 referred to the synthesis method of the step 1 in Example 72. ESI m/z [M+H]$^+$=374.3

Step 2: Synthesis of Compound WX113-3

The synthesis of the compound WX113-3 referred to the synthesis method of the step 3 in Example 22. ESI m/z [M+H]$^+$=284.3.

Step 3: Synthesis of Compound WX113-4

The synthesis of the compound WX113-4 referred to the synthesis method of the step 4 in Example 1. ESI m/z [M+H]$^+$=471.4.

Step 4: Synthesis of Compound WX113

The synthesis of the compound WX113 referred to the synthesis method of the step 5 in Example 1. $^1$H NMR (400 MHz, METHANOL-d$_4$) δ=7.95 (d, J=8.9 Hz, 2H), 7.36-7.06 (m, 3H), 5.17 (q, J=8.1 Hz, 2H), 4.67 (d, J=3.5 Hz, 2H), 3.83 (s, 2H), 2.21 (br s, 1H), 1.35-1.12 (m, 6H).

Example 74: WX125

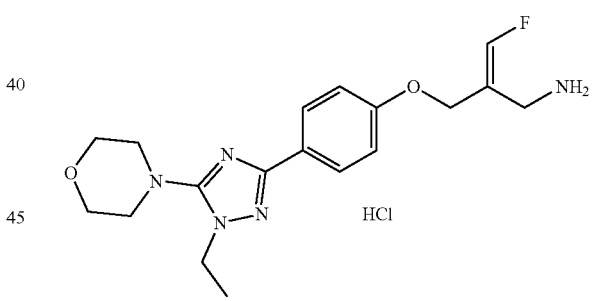

Synthesis Route:

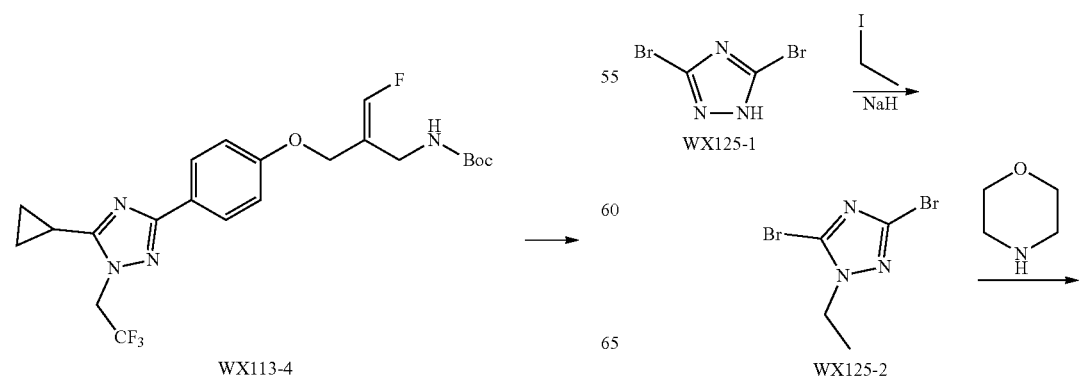

-continued

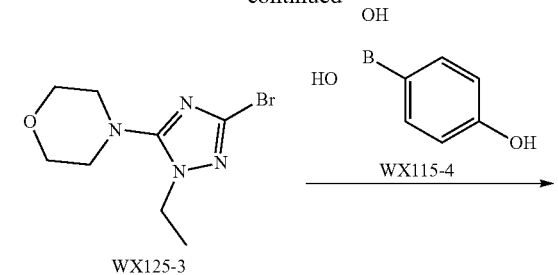
WX125-3

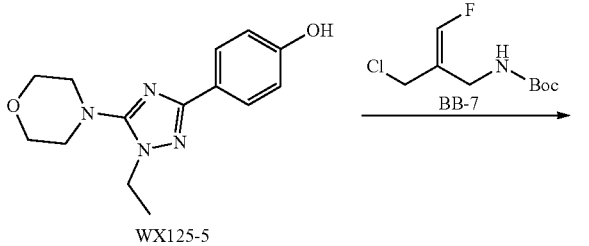
WX125-5

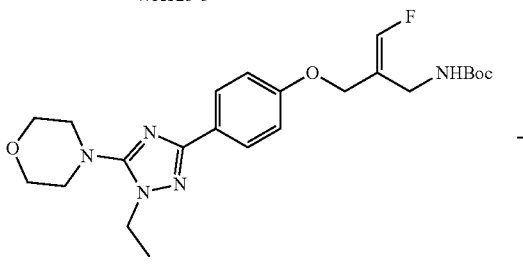
WX125-6

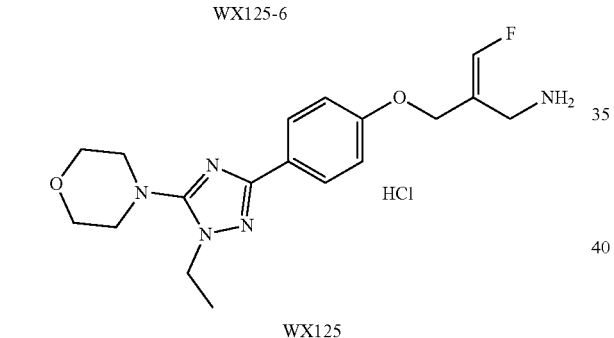
WX125

Step 1: Synthesis of Compound WX125-2

The synthesis of the compound WX125-2 referred to the synthesis method of the step 1 in Example 45. ESI m/z [M+H]$^+$=256.1

Step 2: Synthesis of Compound WX125-3

The synthesis of compound WX125-3 referred to the synthesis method in the step 2 of Example 34. ESI m/z [M+H]$^+$=263.0.

Step 3: Synthesis of Compound WX125-5

The synthesis of the compound WX125-5 referred to the synthesis method of the step 1 in Example 16. ESI m/z [M+H]$^+$=275.3.

Step 4: Synthesis of Compound WX125-6

The synthesis of the compound WX125-6 referred to the synthesis method of the step 4 in Example 1. ESI m/z [M+H]$^+$=462.5.

Step 5: Synthesis of Compound WX125

The synthesis of the compound WX125 referred to the synthesis method of the step 5 in Example 1. $^1$H NMR (400 MHz, METHANOL-d$_4$) δ ppm 1.59 (t, J=7.22 Hz, 3H) 3.33-3.34 (m, 2H) 3.55-3.62 (m, 4H) 3.81-3.84 (m, 1H) 3.85-3.91 (m, 4H) 4.25 (q, J=7.28 Hz, 2H) 4.74 (d, J=3.39 Hz, 2H) 7.17-7.37 (m, 1H) 7.23 (d, J=8.91 Hz, 1H) 7.38 (s, 1H) 7.99 (d, J=8.91 Hz, 2H).

Example 75: WX126

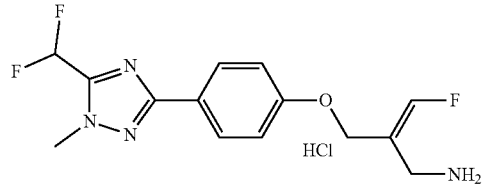 [SMILES: Cn1nc(-c2ccc(OC/C(=C/F)CN)cc2)nc1C(F)F ; Cl]

Synthesis Route:

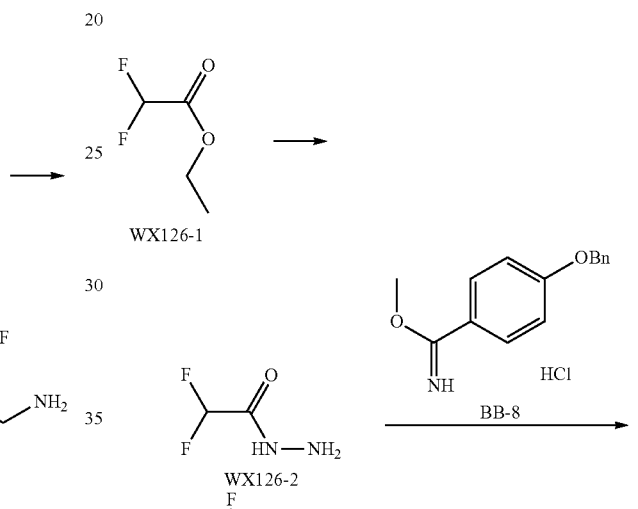

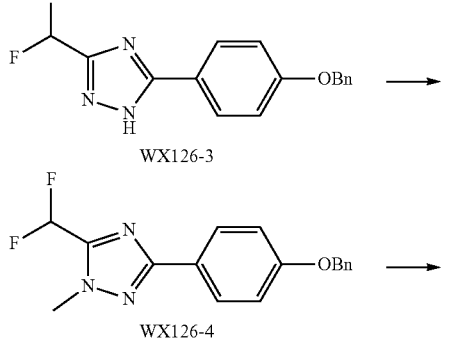

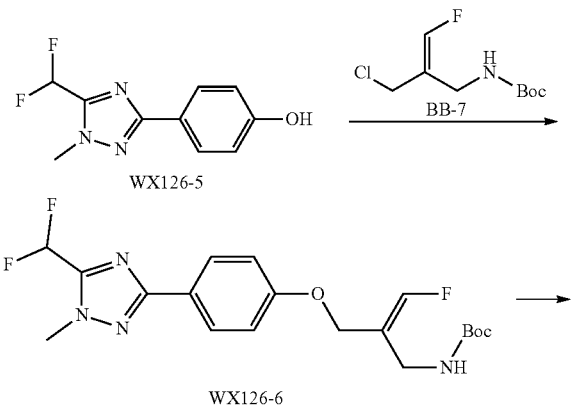

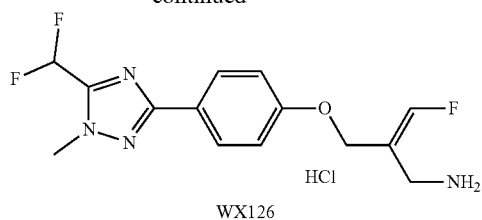

WX126

Step 1: Synthesis of Compound WX126-2

A compound WX126-1 (10 g) was put into a 50 ml pre-dried pear-shaped bottle. Hydrazine hydrate (8.07 g) was added dropwise at 0° C., and a reaction was conducted under reflux at 80° C. for 16 hours. The reaction solution was dissolved in 10 ml of a saturated sodium bicarbonate water solution, and the solution was extracted with ethyl acetate (20 ml×10), dried with anhydrous sodium sulfate, and filtered, and the filtrate was concentrated under reduced pressure to obtain the target compound WX126-2.

Step 2: Synthesis of Compound WX126-3

The synthesis of the compound WX126-3 referred to the synthesis method in the step 1 of Example 22. ESI m/z [M+H]$^+$=302.

Step 3: Synthesis of Compound WX126-4

The synthesis of the compound WX126-4 referred to the synthesis method of the step 1 in Example 27. ESI m/z [M+H]$^+$=316.3.

Step 4: Synthesis of Compound WX126-5

The synthesis of the compound WX126-5 referred to the synthesis method in the step 3 of Example 22. ESI m/z [M+H]$^+$=226.1.

Step 5: Synthesis of Compound WX126-6

The synthesis of the compound WX126-6 referred to the synthesis method of the step 4 in Example 1. ESI m/z [M+H]$^+$=413.

Step 6: Synthesis of Compound WX126

The synthesis of the compound WX126 referred to the synthesis method of the step 5 in Example 1. $^1$H NMR (400 MHz, DMSO-d$_6$) δ ppm 3.62 (s, 2H) 3.99 (s, 3H) 4.63 (br d, J=3.09 Hz, 2H) 7.08 (d, J=8.82 Hz, 2H) 7.27 (s, 1H) 7.53 (s, 1H) 7.94 (br s, 2H)

Example 76: WX127

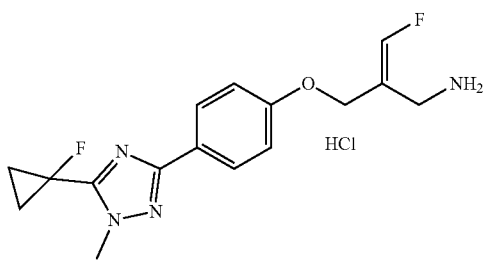 [SMILES: Cn1nc(-c2ccc(OC/C(=C/F)CN)cc2)nc1C1(F)CC1 ; Cl]

Synthesis Route:

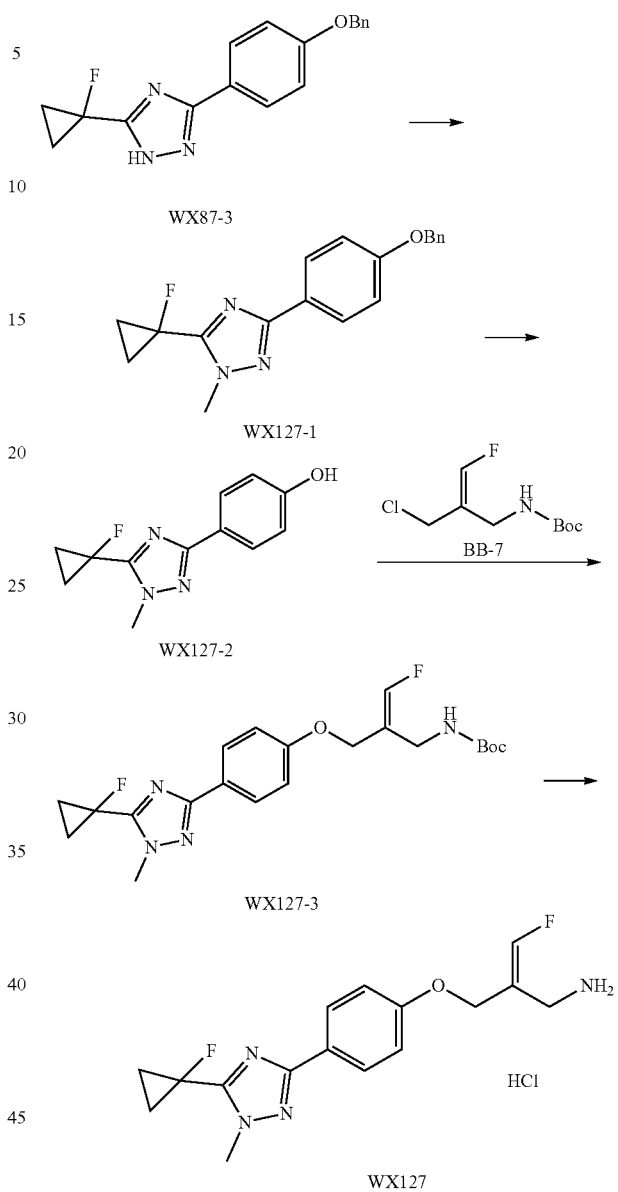

Step 1: Synthesis of Compound WX127-1

The synthesis of the compound WX127-1 referred to the synthesis method of the step 1 in Example 27. ESI m/z [M+H]$^+$=324.3.

Step 2: Synthesis of Compound WX127-2

The synthesis of the compound WX127-2 referred to the synthesis method in the step 3 of Example 22. ESI m/z [M+H]$^+$=234.1.

Step 3: Synthesis of Compound WX127-3

The synthesis of the compound WX127-3 referred to the synthesis method of the step 4 in Example 1. ESI m/z [M+H]$^+$=421.3.

Step 4: Synthesis of Compound WX127

The synthesis of the compound WX127 referred to the synthesis method of the step 5 in Example 1. $^1$H NMR (400 MHz, DMSO-d$_6$) δ ppm 1.27-1.40 (m, 2H) 1.52-1.68 (m, 2H) 3.62 (br d, J=4.14 Hz, 2H) 4.02 (d, J=1.25 Hz, 3H) 4.68

(br d, J=3.14 Hz, 2H) 7.09 (d, J=8.78 Hz, 2H) 7.21-7.46 (m, 1H) 7.92 (d, J=8.78 Hz, 1H) 7.91-7.92 (m, 1H) 8.27 (br s, 3H).

Example 77: WX117

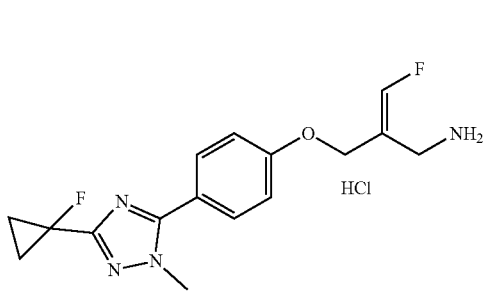 [SMILES: Cn1nc(C2(F)CC2)nc1-c1ccc(OC/C(=C/F)CN)cc1 ; Cl]

Synthesis Route:

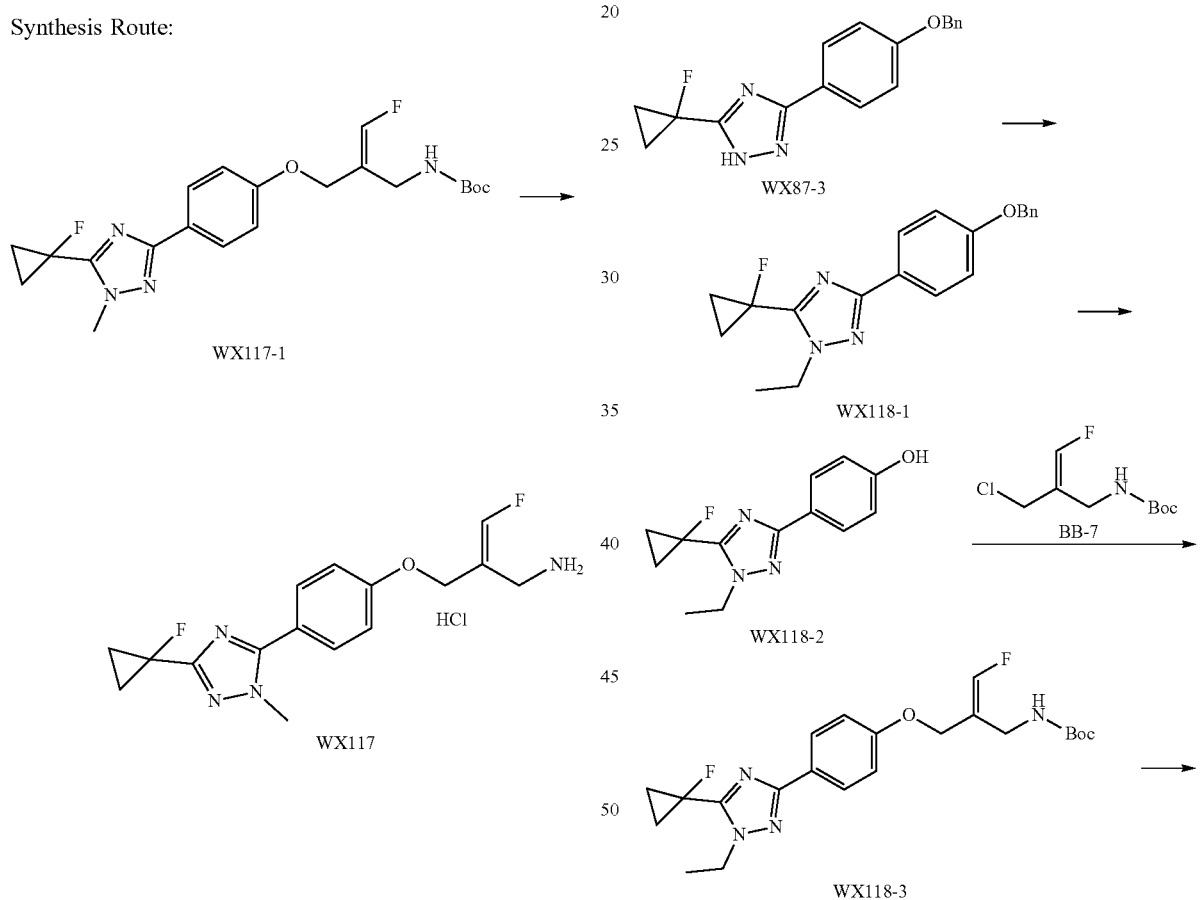

Step 1: Synthesis of Compound WX117-1

The isomer WX117-1 was separated from the synthetic compound WX116-3. ESI m/z [M+H]$^+$=421.3.

Step 2: Synthesis of Compound WX117

The synthesis of the compound WX117 referred to the synthesis method of the step 5 in Example 1. $^1$H NMR (400 MHz, DMSO-d$_6$) δ ppm 1.27-1.40 (m, 2H) 1.52-1.68 (m, 2H) 3.62 (br d, J=4.14 Hz, 2H) 4.02 (d, J=1.25 Hz, 3H) 4.68 (br d, J=3.14 Hz, 2H) 7.09 (d, J=8.78 Hz, 2H) 7.21-7.46 (m, 1H) 7.92 (d, J=8.78 Hz, 1H) 7.91-7.92 (m, 1H) 8.27 (br s, 3H).

Example 78: WX118

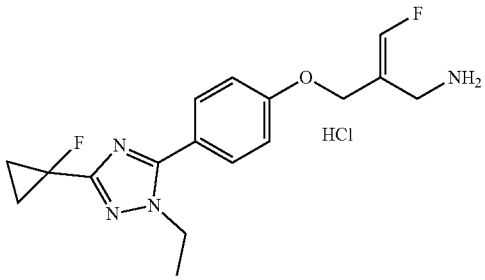 [SMILES: CCn1nc(C2(F)CC2)nc1-c1ccc(OC/C(=C/F)CN)cc1 ; Cl]

Synthesis Route:

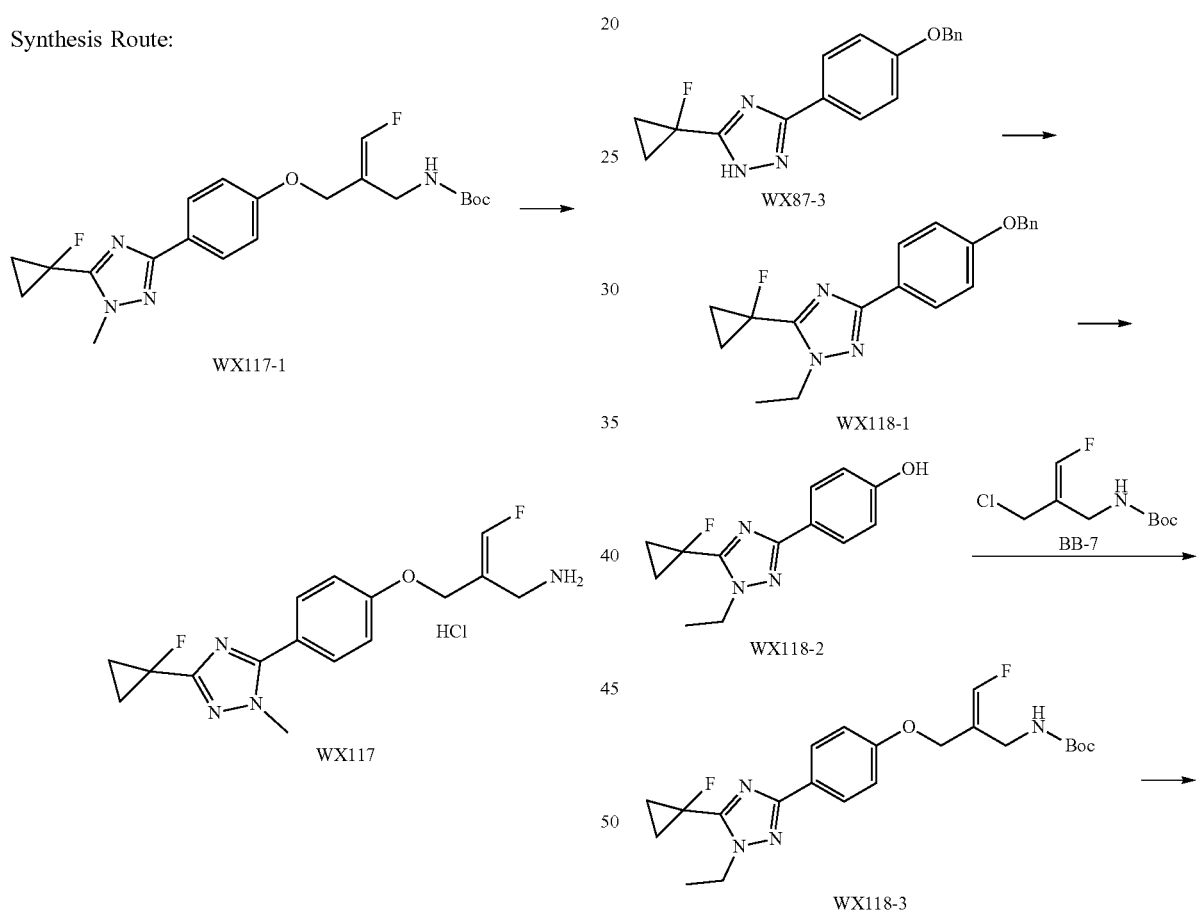

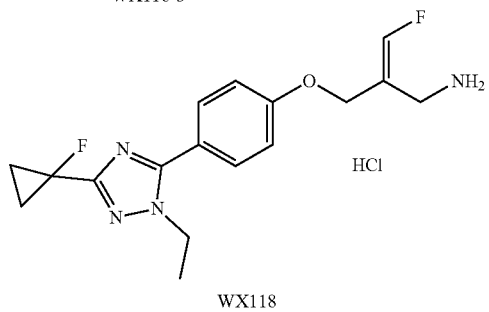

Step 1: Synthesis of Compound WX118-1

The synthesis of the compound WX118-1 referred to the synthesis method of the step 1 in Example 27. ESI m/z [M+H]$^+$=338.2.

Step 2: Synthesis of Compound WX118-2

The synthesis of the compound WX118-2 referred to the synthesis method in the step 3 of Example 22. ESI m/z [M+H]$^+$=247.3.

Step 3: Synthesis of Compound WX118-3

The synthesis of the compound WX118-3 referred to the synthesis method of the step 4 in Example 1. ESI m/z [M+H]$^+$=435.3.

Step 4: Synthesis of Compound WX118

The synthesis of the compound WX118 referred to the synthesis method of the step 5 in Example 1. $^1$H NMR (400 MHz, DMSO-d$_6$) δ ppm 1.27-1.40 (m, 2H) 1.52-1.68 (m, 2H) 3.62 (br d, J=4.14 Hz, 2H) 4.02 (d, J=1.25 Hz, 3H) 4.68 (br d, J=3.14 Hz, 2H) 7.09 (d, J=8.78 Hz, 2H) 7.21-7.46 (m, 1H) 7.92 (d, J=8.78 Hz, 1H) 7.91-7.92 (m, 1H) 8.27 (br s, 3H).

Example 79: WX128

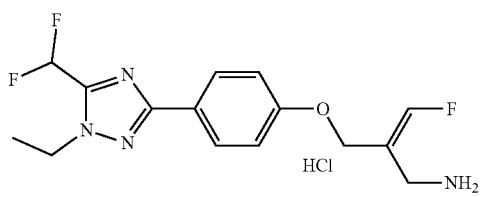 [SMILES: CCn1nc(-c2ccc(OC/C(=C/F)CN)cc2)nc1C(F)F ; Cl]

Synthesis Route:

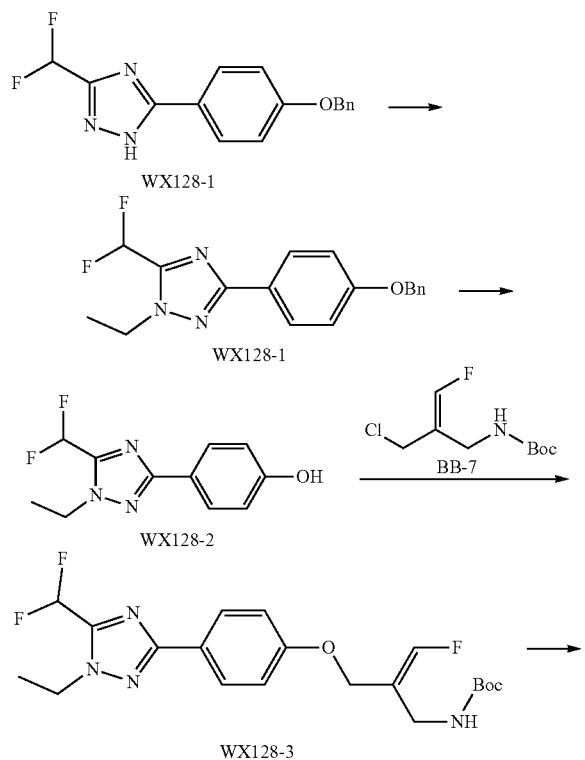

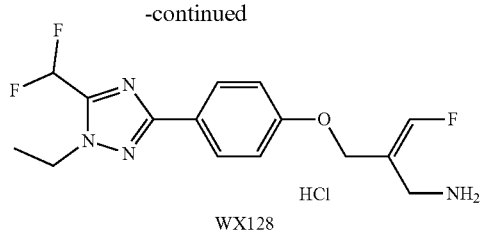

WX128

Step 1: Synthesis of Compound WX128-1

The synthesis of the compound WX128-1 referred to the synthesis method of the step 1 in Example 27. ESI m/z [M+H]$^+$=330.3.

Step 2: Synthesis of Compound WX128-2

The synthesis of compound WX128-2 referred to the synthesis method in the step 3 of Example 22. ESI m/z [M+H]$^+$=240.3.

Step 3: Synthesis of Compound WX128-3

The synthesis of the compound WX128-3 referred to the synthesis method of the step 4 in Example 1. $^1$H NMR (400 MHz, METHANOL-d$_4$) δ=7.99 (br d, J=8.8 Hz, 2H), 7.32-6.80 (m, 4H), 4.53 (d, J=3.4 Hz, 2H), 4.42 (q, J=7.2 Hz, 2H), 3.96 (br s, 2H), 1.54 (t, J=7.2 Hz, 3H), 1.47-1.38 (m, 9H).

Step 4: Synthesis of Compound WX128

The synthesis of the compound WX128 referred to the synthesis method of the step 5 in Example 1. $^1$H NMR (400 MHz, DMSO-d$_6$) δ=8.34 (br s, 3H), 7.92 (d, J=8.8 Hz, 2H), 7.46-7.21 (m, 1H), 7.09 (d, J=8.9 Hz, 2H), 4.69 (br d, J=3.0 Hz, 2H), 4.36 (q, J=7.2 Hz, 3H), 3.62 (br d, J=4.6 Hz, 2H), 1.66-1.51 (m, 2H), 1.46 (t, J=7.2 Hz, 3H), 1.40-1.30 (m, 2H).

Example 80: WX129

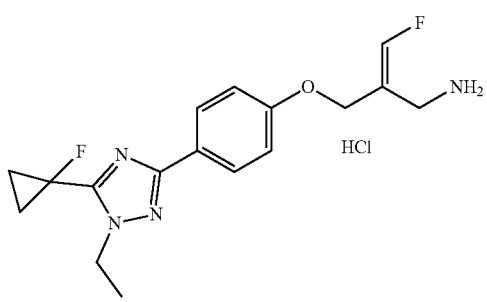 [SMILES: CCn1nc(-c2ccc(OC/C(=C/F)CN)cc2)nc1C1(F)CC1 ; Cl]

Synthesis Route:

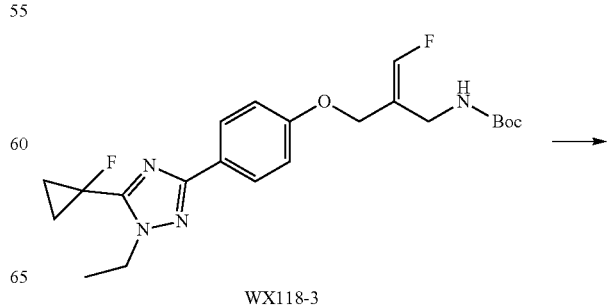

WX118-3

-continued

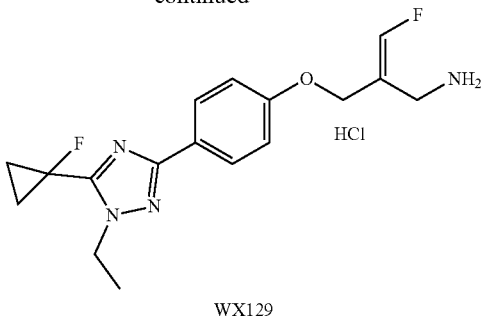

WX129

Step 1: Synthesis of Compound WX129

The synthetic compound WX118-3 was separated by preparative chromatography (HCl system) to obtain the isomer compound WX129. $^1$H NMR (400 MHz, DMSO-d$_6$) δ=8.34 (br s, 3H), 7.92 (d, J=8.8 Hz, 2H), 7.46-7.21 (m, 1H), 7.09 (d, J=8.9 Hz, 2H), 4.69 (br d, J=3.0 Hz, 2H), 4.36 (q, J=7.2 Hz, 3H), 3.62 (br d, J=4.6 Hz, 2H), 1.66-1.51 (m, 2H), 1.46 (t, J=7.2 Hz, 3H), 1.40-1.30 (m, 2H).

Example 81: WX130

Synthesis Route:

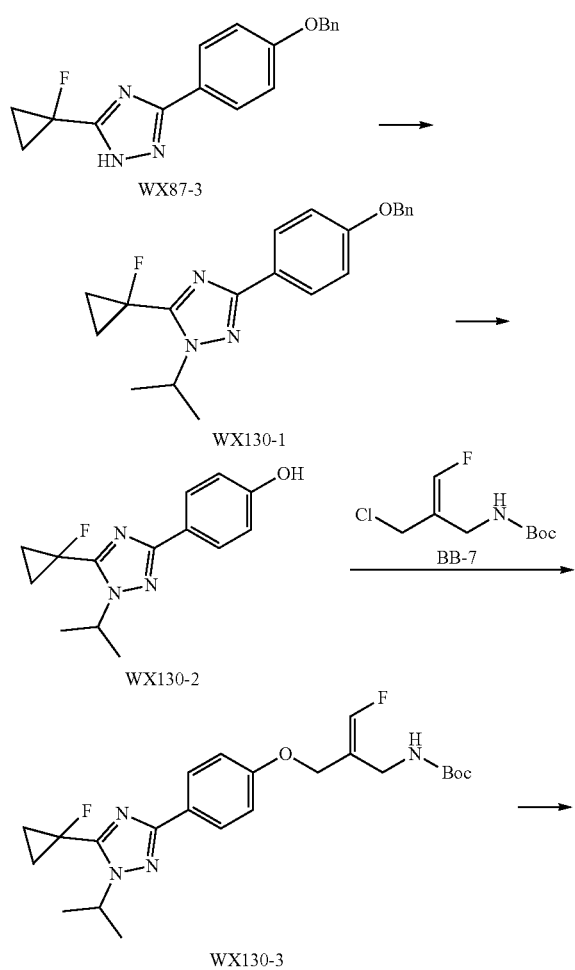

-continued

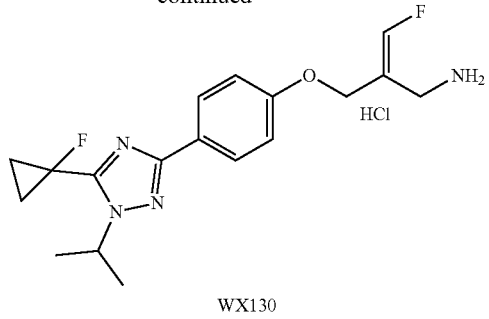

WX130

Step 1: Synthesis of Compound WX130-1

The synthesis of the compound WX130-1 referred to the synthesis method of the step 1 in Example 27. ESI m/z [M+H]$^+$=352.2.

Step 2: Synthesis of Compound WX130-2

The synthesis of the compound WX130-2 referred to the synthesis method in the step 3 of Example 22. ESI m/z [M+H]$^+$=262.3.

Step 3: Synthesis of Compound WX130-3

The synthesis of the compound WX130-3 referred to the synthesis method of the step 4 in Example 1. $^1$H NMR (400 MHz, METHANOL-d$_4$) δ=7.96 (d, J=8.8 Hz, 2H), 7.08-7.01 (m, 2H), 6.83 (s, 1H), 5.05 (td, J=6.5, 13.2 Hz, 1H), 4.53 (d, J=3.4 Hz, 2H), 3.96 (s, 2H), 1.66-1.54 (m, 7H), 1.46-1.35 (m, 11H).

Step 4: Synthesis of Compound WX130

The synthesis of the compound WX130 referred to the synthesis method of the step 5 in Example 1. $^1$H NMR (400 MHz, DMSO-d$_6$) δ=8.24 (br s, 3H), 7.94 (d, J=8.8 Hz, 2H), 7.36 (s, 1H), 7.09 (d, J=8.8 Hz, 2H), 4.93 (td, J=6.5, 12.9 Hz, 1H), 4.67 (br d, J=3.0 Hz, 2H), 3.63 (br d, J=4.6 Hz, 2H), 1.65-1.55 (m, 2H), 1.65- 1.55 (m, 1H), 1.65-1.55 (m, 1H), 1.51 (d, J=6.7 Hz, 6H), 1.44-1.26 (m, 2H).

Experimental Example 1: In Vitro Evaluation

Human VAP-1 Enzyme Activity Assay:

The inhibition of the sample on VAP-1 enzyme activity was measured by using an Amplex® Red Monoamine Oxidase kit (Invitrogen #A12214). 100 nL of the gradiently-diluted to-be-tested compound (solvent DMSO) was added to a 384-well plate. 25 μL of 10 nM VAP-1 enzyme solution was added and incubated for 30 minutes at room temperature. A substrate mixture of VAP-1 enzyme (200 μM Amplex Red, 1 U/mL HRP, 1 mM Benzylamine) was added and incubated for 60 minutes at room temperature. After the incubation, the fluorescent signal was read with a microplate reader Envision (excitation light wavelength 530-560 nm, emission light wavelength 590 nm). The fluorescence signal value after the background signal was removed was analyzed by Prism software, and the IC$_{50}$ of the sample against the VAP-1 enzyme was calculated.

TABLE 1

Results of in vitro screening test of the compounds of the present disclosure

| Compound | Human Recombinant VAP-1/SSAO Enzyme Inhibitory Activity IC$_{50}$ (nM) |
|---|---|
| WX004 | 2.5 |
| WX008 | 0.4 |

TABLE 1-continued

Results of in vitro screening test of the compounds of the present disclosure

| Compound | Human Recombinant VAP-1/SSAO Enzyme Inhibitory Activity $IC_{50}$ (nM) |
|---|---|
| WX009 | 3.7 |
| WX014 | 0.8 |
| WX016 | 1.0 |
| WX017 | 0.8 |
| WX019 | 2.0 |
| WX021 | 0.3 |
| WX022 | 0.3 |
| WX023 | 0.4 |
| WX024 | 0.3 |
| WX025 | 0.9 |
| WX026 | 0.3 |
| WX028 | 0.7 |
| WX033 | 0.3 |
| WX034 | 0.8 |
| WX035 | 2.3 |
| WX036 | 4.6 |
| WX039 | 0.5 |
| WX040 | 0.5 |
| WX041 | 0.6 |
| WX042 | 1.6 |
| WX044 | 0.5 |
| WX045 | 1.1 |
| WX048 | 0.6 |
| WX049 | 0.3 |
| WX052 | 1.3 |
| WX054 | 0.4 |
| WX056 | 1.7 |
| WX062 | 1.2 |
| WX064 | 0.8 |
| WX070 | 1.1 |
| WX072 | 0.7 |
| WX073 | 0.9 |
| WX074 | 1.0 |
| WX075 | 0.7 |
| WX076 | 2.1 |
| WX077 | 1.6 |
| WX079 | 0.2 |
| WX080 | 3.8 |
| WX081 | 0.5 |
| WX082 | 0.3 |
| WX083 | 0.4 |
| WX085 | 0.2 |
| WX086 | 9.9 |
| WX087 | 0.3 |
| WX088 | 0.4 |
| WX089 | 1.9 |
| WX090 | 1.1 |
| WX091 | 1.2 |
| WX092 | 1.4 |
| WX093 | 0.3 |
| WX094 | 0.3 |
| WX095 | 2.9 |
| WX096 | 0.8 |
| WX097 | 0.5 |
| WX098 | 1.8 |
| WX099 | 3.4 |
| WX100 | 1.1 |
| WX101 | 0.4 |
| WX102 | 0.4 |
| WX103 | 0.2 |
| WX104 | 0.3 |
| WX105 | 0.5 |
| WX106 | 1.1 |
| WX107 | 0.9 |
| WX109 | 2.8 |
| WX111 | 0.4 |
| WX112 | 1.7 |
| WX113 | 1.1 |
| WX117 | 0.7 |
| WX118 | 0.7 |
| WX122 | 1.0 |
| WX123 | 2.2 |
| WX124 | 1.4 |
| WX125 | 1.0 |
| WX126 | 0.2 |
| WX127 | 0.8 |
| WX128 | 1.0 |
| WX129 | 1.0 |
| WX130 | 1.4 |

Conclusion: The compounds of the present disclosure showed strong inhibition of human recombinant VAP-1/SSAO enzyme activity in in vitro assays.

Experimental Example 2: VAP-1 Cell Activity Assay

The inhibition of the sample on VAP-1 cell activity was measured by using an Amplex® Red Monoamine Oxidase kit (Invitrogen #A12214).

Cell Preparation

The cultured HUVEC or CHO cells were plated into a 6-well plate at a density of 0.8 M/well, placed in a 37° C., 5% $CO_2$ incubator for incubation for 24 hours, and then the cells was transferred with a Lipo2000 reagent and a VAP-1/pCDNA (3.1) plasmid, and liquid was changed for the cells after 5 hours (Lipo2000 was toxic to the cells); after 24 hours, the cells were digested and plated into 384-well plates with a density of 25 μl, 10000 cells/well, and liquid was replaced with medium without FBS for the cells after 6-7 hours, and the cell plates were incubated overnight at 37° C. in a 5% $CO_2$ incubator.

Compound Semi-Inhibitory Concentration Detection

1) Dilution of the compound: serial dilution in 4× gradient was carried out with 100% DMSO, 10 points were diluted, the starting concentration of the to-be-tested compound was 0.5 mM (final concentration was 1) μM); 100 nl of compound solution was transferred to a 384-well cell assay plate with ECHO. Negative control wells: 100 nl of DMSO; background control wells: 100 nl DMSO+25 μL medium.

2) The reaction was carried out in the dark at room temperature for 30 min.

3) Preparation of Amplex Red reagent+HRP+benzylamine substrate working solution: Amplex Red reagent+HRP+benzylamine substrate working solution (200 μM Amplex Red reagent+1 U/mL HRP+1 mM benzylamine): 45 μl of 20 mM Amplex Red reagent mother solution, 22.5 μl of 200 U/ml horseradish peroxidase (HRP) mother solution and 45 ul of 100 mM benzylamine were taken and added to 4.3875 ml of 1× reaction buffer.

4) After 30 min, 25 μl of the substrate working solution was added to a 384-well plate, and a final concentration was 100 μM Amplex Red reagent+0.5 U/mL HRP+0.5 mM benzylamine, respectively.

5) The reaction was carried out in the dark at room temperature for 60 minutes, and the fluorescence value was measured by Envision: the excitation wave was 535 nm, and the emission wave was 590 nm.

6) Inhibition rate calculation formula: % inhibition rate= (1−(test hole minus background−positive control well minus background)/(negative control well minus background-positive control well minus background))*100

7) The data were analyzed with Prism. The $IC_{50}$ of the sample against VAP-1 cells was calculated.

TABLE 2

In vitro screening test results of the compounds of the present disclosure

| Compound | VAP-1/SSAO Cellular Inhibitory Activity $IC_{50}$ (nM) |
|---|---|
| WX008 | 0.3 |
| WX014 | 0.3 |
| WX016 | 0.2 |
| WX034 | 0.4 |
| WX047 | 0.8 |
| WX058 | 0.6 |
| WX084 | 1.4 |
| WX087 | 0.8 |
| WX088 | 1.6 |
| WX091 | 1.3 |
| WX095 | 0.2 |
| WX097 | 0.3 |
| WX098 | 0.2 |
| WX101 | 0.4 |
| WX104 | 0.7 |
| WX107 | 1.5 |
| WX108 | 1.8 |
| WX109 | 0.7 |
| WX110 | 0.4 |
| WX112 | 0.9 |
| WX113 | 0.9 |
| WX114 | 0.8 |
| WX126 | 0.3 |
| WX116 | 0.3 |
| WX117 | 0.9 |
| WX118 | 0.7 |
| WX119 | 0.4 |
| WX120 | 0.5 |
| WX121 | 0.5 |

Conclusion: the compounds of the present disclosure showed strong inhibition of VAP-1/SSAO cell activity in in vitro assays.

Experimental Example 3: Determination of Kinetic Solubility

The test compound was dissolved in DMSO to prepare a 10 mmol/L stock solution. 980 µL of dissolution medium was pipetted into a 2 mL screw-capped glass vial by using a pipette (Eppendorf Research). 20 µL of the stock solution of each test compound and the QC sample were added to a buffer solution corresponding to a kinetic detection solution of pH 7.4. The final concentrations of the test compound and DMSO solution were 200 µM and 2%, respectively. The vial was screwed with a cover. The theoretical maximum concentration was 200 µM. The mixture was shaken at 880 rpm for 24 hours at room temperature. The vial was centrifuged for 30 minutes at 13,000 rpm. 200 µL of the supernatant was added to a 96-well plate by using a digital pipette. The solubility of the test compound was determined by high performance liquid chromatography.

TABLE 3

Kinetic Solubility

| Compound | Solubility (µM) pH 7.4 |
|---|---|
| WX084 | >200 |
| WX108 | >200 |

TABLE 3-continued

Kinetic Solubility

| Compound | Solubility (µM) pH 7.4 |
|---|---|
| WX0115 | >200 |
| WX0119 | >200 |

Conclusion: the compounds of the disclosure exhibited excellent water solubility (at pH=7.4). The compounds of the disclosure were readily soluble in water.

Experimental Example 4: Compound Pharmacokinetic Evaluation

Experimental purpose: compound pharmacokinetics were tested in SD rats

Experimental Material:

Sprague Dawley rats (male, 200-300 g, 7-9 weeks old, Shanghai Slack)

Experimental procedure: the pharmacological characteristics of the compound after intravenous and oral administration were tested in rodents by standard protocol, candidate compounds in the experiment was prepared into clear solutions to be administered to the rats in a single intravenous injection and orally. The intravenous and oral solvents were a certain proportion of an aqueous hydroxypropyl β-cyclodextrin solution or a physiological saline solution. Whole blood samples within 24 hours were collected, and centrifuged at 3000 g for 15 minutes, the supernatant was separated to obtain plasma samples, 4 times volume of acetonitrile solution containing internal standard was added to precipitate protein, centrifuging was conducted to take the supernatant, equal volume of water was added and centrifuging was conducted to the supernatant to be sampled. The LC-MS/MS analysis method was used to quantitatively analyze the plasma concentration, and the pharmacokinetic parameters such as peak concentration, peak time, clearance rate, half-life, area under the drug concentration-time curve, and bioavailability were calculated.

Experimental Results:

Table 4 pharmacokinetic test results

| Test Product (compound obtained from each Example) | Peak Concentration $C_{max}$ (nM) | Peak Time $T_{max}$ (h) | Concentration Integral AUC (nM · hr) | Bioavailability F (%) |
|---|---|---|---|---|
| WX084 | 1917 | 1.2 | 7454 | 95 |
| WX108 | 2820 | 1.3 | 16823 | 77 |
| WX126 | 2343 | 1.5 | 9309 | 99 |
| WX119 | 2760 | 1.7 | 11661 | 87 |

Conclusion: the compounds of the present disclosure had excellent bioavailability.

Experimental Example 5: Compound Pharmacokinetic Evaluation

Experimental purpose: compound pharmacokinetics were tested in CD-1 mice

Experimental Material:

CD-1 mouse (Male, 25-35 g, 6-9 weeks old, Shanghai Slack);

Experimental procedure: the pharmacological characteristics of the compound after intravenous and oral administration were tested in rodents by standard protocol, candidate compounds in the experiment was prepared into clear solutions to be administered to the mice in a single intravenous injection and orally. The intravenous and oral solvents were a certain proportion of an aqueous hydroxypropyl β-cyclodextrin solution or a physiological saline solution. Whole blood samples within 24 hours were collected, and centrifuged at 3000 g for 15 minutes, the supernatant was separated to obtain plasma samples, 4 times volume of acetonitrile solution containing internal standard was added to precipitate protein, centrifuging was conducted to take the supernatant, equal volume of water was added and centrifuging was conducted to take the supernatant to be sampled. The LC-MS/MS analysis method was used to quantitatively analyze the plasma concentration, and the pharmacokinetic parameters such as peak concentration, peak time, clearance rate, half-life, area under the drug concentration-time curve, and bioavailability were calculated.

Experimental Results:

Table 5 Pharmacokinetic Test Results

| Test Product (compound obtained from each Example) | Peak Concentration $C_{max}$ (nM) | Peak Time $T_{max}$ (h) | Concentration Integral AUC (nM · hr) | Bioavailability F (%) |
|---|---|---|---|---|
| WX084 | 3660 | 0.5 | 5237 | 76 |
| WX108 | 6493 | 0.7 | 17884 | 80 |
| WX126 | 3527 | 0.5 | 6490 | 102 |
| WX119 | 3410 | 0.5 | 8152 | 113 |

Conclusion: the compounds of the present disclosure had excellent bioavailability.

Experimental Example 6: Study on In Vitro Pharmacokinetic Properties

Experimental purpose: distribution of compounds in liver and blood of CD-1 mice was tested;

Experimental Material:

CD-1 Mice (male, 25-35 g, 6-9 weeks old, Shanghai Slack);

Experimental procedure: after oral administration, the drug was distributed in the liver and blood of rodents, candidate compounds in the experiment were formulated into a clear solution to be administered to mice in a single oral dose. The oral solvent was a certain proportion of an aqueous solution of hydroxypropyl β-cyclodextrin or a physiological saline solution. The concentration of the drug in the liver and blood was measured at 1 hour and 4 hours after administration.

Experimental Results:

TABLE 6

Results of distribution in liver and blood in vivo

| Test Product (compound obtained from each Example) | Liver Concentration/ Plasma Concentration (@1.0 hour) | Liver Concentration/ Plasma Concentration (@4.0 hour) |
|---|---|---|
| PXS-4728A | 13140/1470 = 10 | 2120/154 = 14 |
| WX084 | 13460/1483 = 10 | 2658/231 = 12 |
| WX108 | 13900/1170 = 12 | 3024/272 = 11 |
| WX126 | 13520/934 = 15 | 3364/190 = 17 |
| WX119 | 18660/1061 = 18 | 6342/310 = 20 |

Conclusion: compared with PXS-4728A, the compounds of the present disclosure had better liver distribution.

Experimental Example 7: In Vivo Study

The therapeutic effect of compounds on an oral $CCl_4$-induced chronic liver fibrosis male C57BL/6 model was tested.

Experimental Material:

Male C57BL/6 mice, 7-8 weeks old;

Experimental method: Male C57BL/6 mice were orally administered from the day $CCl_4$ was put for modeling, and administered daily. Continuous administration was conducted for 28 days. The animals were fasted for at least 6 hours on the next day after the last administration Animal weight was measured during euthanasia and all animals were euthanized under the guidance of the KCl Animal Euthanasia SOP. Non-anticoagulant venous blood of mice was collected from the ocular venous plexus. The whole blood was allowed to stand at room temperature for 30 minutes, and centrifuged at 5000 rpm for 5 minutes, and the serum was separated and placed in a 1.5 ml EP tube and stored at −80° C. After the whole body of the animal was perfused with hypothermic saline, the liver was taken and subjected to tissue gross image acquisition. The left lobe of the liver was divided into 4 equal parts and put into 4 tissue cryotubes for liquid nitrogen freezing, and then transferred to −80° C. for storage. The rest of the liver tissue was fixed in 10% neutral formalin fixative. The ratio of fixative volume to liver tissue volume was at least 1:10. The specimen was placed at room temperature for fixation for at least 72 hours for subsequent pathological examination. After hematoxylin-eosin staining (HE) and Sirius-Red staining, the sections were scanned by a Nanozoomer S210 digital section scanner. HE staining was subjected to double-blind score by two pathological readers, and the area of hepatic fibrosis was analyzed for sirius-red stained sections by digital pathology.

Figure 2:
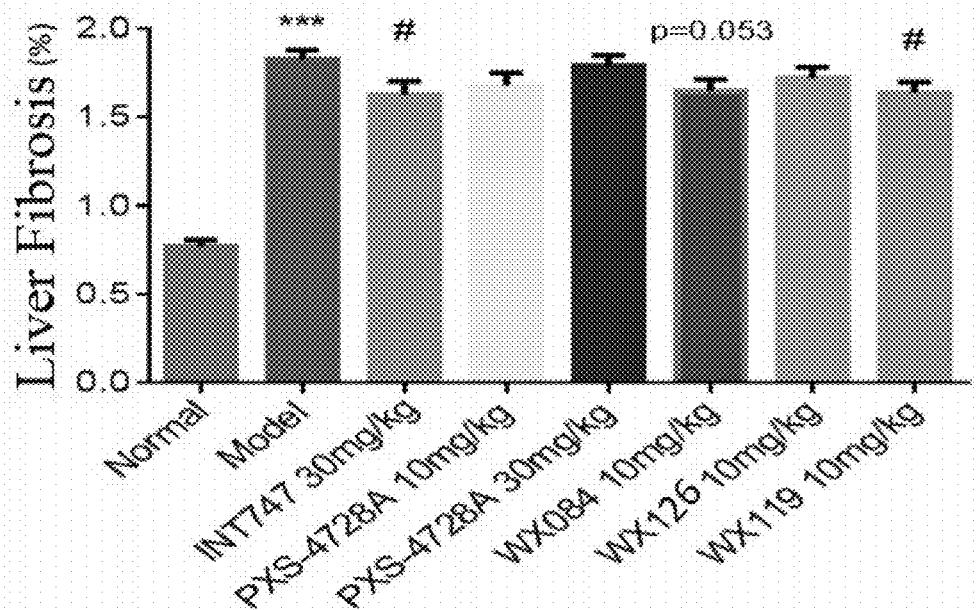
FIG. 2: Results of liver fibrosis.

Experimental results: The liver injury score result was shown in FIG. 1; the liver fibrosis score was shown in FIG. 2.

Conclusion: in in vivo efficacy, the compounds WX126 and WX119 of the present disclosure had an obvious improvement effect on liver injury and fibrosis, and the compounds were superior to the compound PXS-4728A in the same dosage.

Experimental Example 8: Human Liver Microsomal CYP Inhibition Assay

The purpose of the study was to evaluate the inhibition of the test sample on human liver microsomal cytochrome P450 isozymes (CYP1A2, CYP2C9, CYP2C19, CYP2D6, and CYP3A4) by using the CYP isozyme 5-in-1 probe substrate.

Mixed human liver microsomes (HLM) were purchased from Corning Inc. (Steuben, N.Y., USA) or XenoTech, LLC. (Lenexa, Kans., USA) or other suppliers, and stored at the temperature below −70° C. prior to use.

A series of diluted test sample working solution were added to an incubation system containing cofactors of human liver microsomes, a probe substrate and a circulation system, and the control without a test substance but containing a solvent was used as enzyme activity control (100%). The concentration of the metabolite produced by the probe sample in the sample was determined by liquid chromatography-tandem mass spectrometry (LC-MS/MS). Non-linear regression analysis was performed on the concentration of the average percent activity of the test sample by using SigmaPlot (V.11). The $IC_{50}$ value was calculated by a three-parameter or four-parameter recursive logarithmic equation. The test results were shown in Table 7:

TABLE 7

| Test Product (compound obtained from each Example) | CYP1A2, 2C9, 2C19, 2D6, 3A4 (IC50, µM) |
|---|---|
| PXS-4728A | 9/32/76/38/>50 |
| WX084 | >50/>50/>50/>50/>50 |
| WX108 | 25/>50/7/>50/>50 |
| WX126 | 5/24/17/36/>50 |
| WX119 | 4/15/11/35/>50 |

Conclusion: the compounds WX084, WX108, WX126, and WX119 of the present disclosure had weaker inhibition on five CYP isozymes.

Experimental Example 9: Inhibition Test of hERG Potassium Ion Channel

1. Experimental Purpose:
The effect of the to-be-tested compound on the potassium ion channel of hERG was detected by a fully automatic patch clamp method.
2. Experimental Method
2.1. Cell Culture
The cells stably expressing hERG potassium channel used in the experiment were obtained from CHO-hERE of Aviva Biosciences, and CHO-hERG was cultured in 5% $CO_2$ at 37° C. The CHO hERG culture solution is shown in Table 8.

TABLE 8

CHO hERG culture solution

| Reagent | Supplier | Batch Number | Volume (mL) |
|---|---|---|---|
| F12 Hams | Invitrogen | 31765-092 | 500 |
| FBS | Invitrogen | 10099-141 | 50 |
| G418/Geneticin | Invitrogen | 10131-027 | 1 |
| Hygromycin B | Invitrogen | 10687-010 | 1 |

2.2. Early-Stage Preparation of Cells;
CHO-hERG cells prepared for the experiment were cultured for at least two days, and the cell density reached 75% or more. Prior to the start of the experiment, cells were digested with TrypLE and then resuspended in extracellular fluid to collect the cells.
2.3. Preparation of Intracellular and Extracellular Fluids
Extracellular fluids need to be prepared once a month. The intracellular fluid need to be subpackaged and frozen at −20° C. The internal and external fluid components are shown in Table 9.

TABLE 9

Intracellular and extracellular components

| Components | Extracellular Fluid (mM) | Intracellular Fluid (mM) |
|---|---|---|
| NaCl | 145 | — |
| KCl | 4 | 120 |
| KOH | — | 31.25 |
| $CaCl_2$ | 2 | 5.374 |
| $MgCl_2$ | 1 | 1.75 |
| Glucose | 10 | — |
| $Na_2ATP$ | — | 4 |
| HEPES | 10 | 10 |
| EGTA | — | 10 |
| pH | 7.4 (NaOH) | 7.2 (KOH) |
| Osmotic Pressure | 295 mOsm | 285 mOsm |

2.4. Preparation of the Compound
The to-be-tested compound and the positive control Amitriptyline were dissolved in DMSO to a certain concentration of the stock solution, and then diluted according to different gradients, and finally added to the extracellular fluid in a certain ratio, and diluted to a concentration to be measured. Visual inspection was performed to see if there was any precipitation before the start of the experiment. Finally, the concentration of DMSO in the to-be-tested solution and the positive control Amitriptyline should not exceed 0.3%.
2.5. Voltage Stimulation Protocol
The clamping potential was kept at −80 mv, first a voltage stimulation of −50 mv was given for 80 ms to record the cell leakage current value, and then was depolarized to +20 mv to be maintained for 4800 ms, the channel of hERG was open, and then repolarized to −50 mv to be maintained 5000 ms, hERG tail current was led out and recorded, and finally, the voltage was returned to the clamping potential of −80 mv to be maintained for 3100 ms. The above voltage stimulation was repeated once every 15000 ms.
2.6. QPatch$^{HTX}$ Whole Cell Patch Clamp Recording
hERG QPatch$^{HTX}$ experiment was performed at room temperature. A whole cell protocol, a voltage stimulation protocol and a compound detection protocol were established on the software of QPatch Assay Software 5.2 (Sophion Bioscience).
First, 30 repeated set voltage stimulations were performed, which was the baseline area for subsequent analysis, followed by the addition of 5 µl of extracellular fluid, repeated for three times. The concentration of each compound added in sequence was repeated three times in a volume of 5 µl. The cells were incubated for at least 5 min at each test concentration. During the entire recording process, the indicators needed to meet the data analysis acceptance criteria. If the standard was not met, the cells would not be included in the analysis scope, and the compounds would be retested. The above recording process was automatically operated by Qpatch analysis software. The test concentration of each compound was 0.24 µM, 1.20 µM, 6.00 µM, and 30.00 µM, and at least two cells were repeated for each concentration.
2.7. Data Analysis
In each complete current record, based on the percentage of peak current in the negative control, the percent inhibition of the concentration of each compound can be calculated. The dose-effect relationship curve was obtained by fitting with the standard Xi's equation. The specific equation was as follows:

$$I_{(C)} = I_b + (I_f - I_b) * c^n / (IC_{50}^n + c^n)$$

C is the compound test concentration, n is the slope
The curve fitting and inhibition rate calculations were all completed by Qpatch analysis software. If the inhibition rate exceeds half of the inhibition at the lowest concentration or the inhibition rate does not reach half of the inhibition at the highest concentration, the corresponding $IC_{50}$ of the compound is lower than the lowest concentration or the IC$_{50}$ value is greater than the highest concentration.

2.8. Test Results

The results of the hERG IC$_{50}$ values for the Example Compounds were shown in Table 10

TABLE 10

Example Compound hERG IC$_{50}$ value results

| Test Sample | hERG IC$_{50}$ (μM) | Test Number |
|---|---|---|
| WX008 | >30 | N = 6 |
| WX126 | >30 | N = 3 |

Conclusion: the compounds of the present disclosure WX008 and WX126 had a weak inhibition of hERG potassium current.

The invention claimed is:

1. A compound of a formula (IV) or a pharmaceutically acceptable salt thereof,

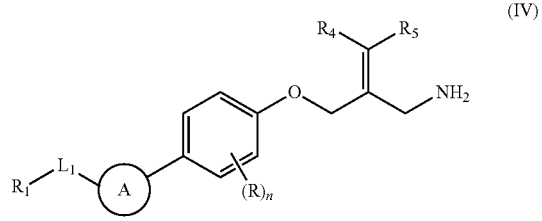

wherein,
one of R$_4$ and R$_5$ is H, and the other is selected from the group consisting of F, Cl, Br and I;
the ring A is 5-6 membered heterocycloalkyl optionally substituted by a R group;
R$_1$ is selected from the group consisting of H, halogen, OH, NH$_2$, CN, COOH, and —C(═O)NH$_2$; or is selected from the group consisting of C$_{1-6}$ alkyl, C$_{1-6}$ heteroalkyl, C$_{3-6}$ cycloalkyl, 5-6 membered heterocycloalkyl, phenyl and 5-6 membered heteroaryl, wherein each is optionally substituted by one, two or three R groups;
L$_1$ is selected from the group consisting of a single bond, —(CRR)$_{1-3}$—,

and —NH—;
n is selected from 0, 1, 2 or 3;
R is selected from the group consisting of H, F, Cl, Br, I, OH, NH$_2$, and C(═O)NH$_2$; or is selected from the group consisting of C$_{1-6}$ alkyl, C$_{1-6}$ heteroalkyl, C$_{3-6}$ cycloalkyl and C$_{3-6}$ cycloalkyl-NH—, wherein each is optionally substituted by one, two or three R' groups;
R' is selected from the group consisting of H, F, Cl, Br, I, OH, CN, NH$_2$, COOH, Me, Et, CF$_3$, CHF$_2$, CH$_2$F, NHCH$_3$ and N(CH$_3$)$_2$;
the "hetero" of the C$_{1-6}$ heteroalkyl, 5-6 membered heterocycloalkyl and 5-6 membered heteroaryl represents a heteroatom or a heteroatom group, and is selected from the group consisting of —C(═O)NH—, —NH—, —C(═NH)—, —S(═O)$_2$NH—, —S(═O)NH—, —O—, —S—, N, ═O, ═S, —C(═O)O—, —C(═O)—, —S(═O)— and —S(═O)$_2$—; and
in any one of the above cases, the number of the heteroatom or the heteroatom group is independently selected from 1, 2 or 3.

2. The compound or the pharmaceutically acceptable salt thereof according to claim 1, wherein R is selected from the group consisting of H, F, Cl, Br, I, OH, NH$_2$, and C(═O)NH$_2$; or is selected from the group consisting of Me, Et,

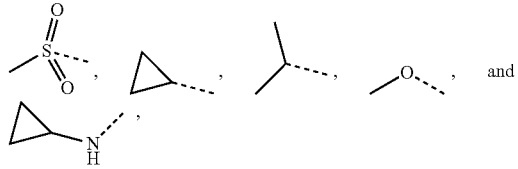

wherein each is optionally substituted by one, two or three R' groups.

3. The compound or the pharmaceutically acceptable salt thereof according to claim 2, wherein R is selected from the group consisting of H, F, Cl, Br, I, OH, NH$_2$, Me, Et, CF$_3$, C(═O)NH$_2$,

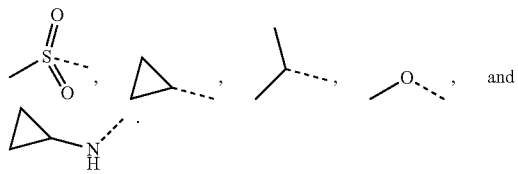

4. The compound or the pharmaceutically acceptable salt thereof according to claim 1, wherein R$_1$ is selected from the group consisting of H, halogen, OH, NH$_2$, CN, COOH, and —C(═O)NH$_2$; or is selected from the group consisting of C$_{1-3}$ alkyl, C$_{1-3}$ heteroalkyl, phenyl, cyclopropyl, cyclopentyl, cyclohexyl, morpholinyl, cyclobutyl and tetrahydro-2H-pyranyl, wherein each is optionally substituted by one, two or three R groups.

5. The compound or the pharmaceutically acceptable salt thereof according to claim 4, wherein R$_1$ is selected from the group consisting of H, F, Cl, Br, I, OH, NH$_2$, CN, COOH, —C(═O)NH$_2$, Me, CF$_3$, Et,

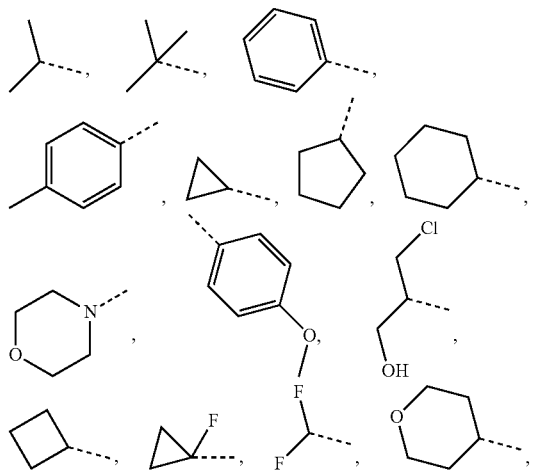

-continued

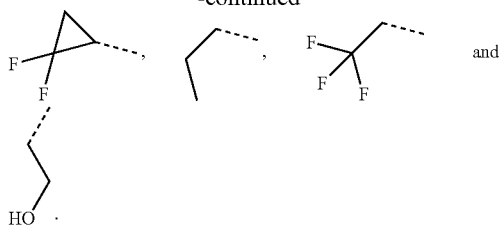

6. The compound or the pharmaceutically acceptable salt thereof according to claim 1, wherein $L_1$ is selected from the group consisting of a single bond, —CH₂—, —CH₂CH₂—,

and —NH—.

7. The compound or the pharmaceutically acceptable salt thereof according to claim 5, wherein the structural unit

is selected from the group consisting of H, NH₂, COOH, —C(═O)NH₂, Me, CF₃, Et,

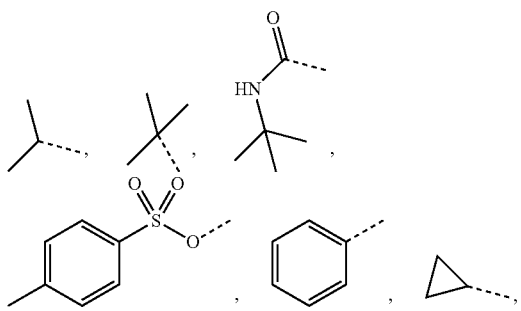

-continued

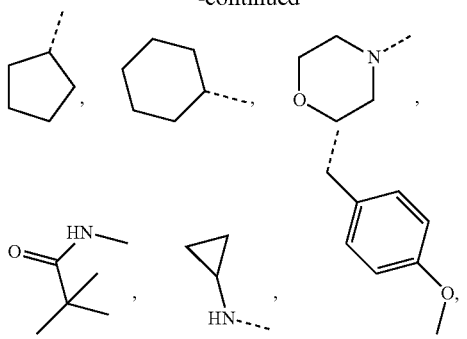

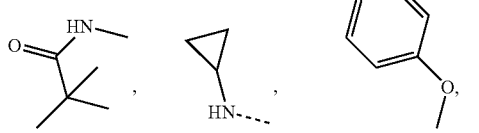

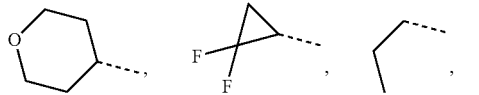

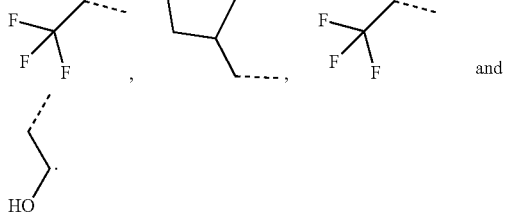

8. A method for the treatment of a disease related to SSAO, comprising a step of administering the compound or the pharmaceutically acceptable salt thereof according to claim 1 or a tautomer thereof to a subject in need.

9. The method according to claim 8, wherein the disease related to SSAO is nonalcoholic steatohepatitis.

\* \* \* \* \*